US011739377B2

(12) United States Patent
Jayasinghe et al.

(10) Patent No.: US 11,739,377 B2

(45) Date of Patent: *Aug. 29, 2023

(54) METHOD OF IMPROVING THE MOVEMENT OF A TARGET POLYNUCLEOTIDE WITH RESPECT TO A TRANSMEMBRANE PORE

(71) Applicant: Oxford Nanopore Technologies PLC, Oxford (GB)

(72) Inventors: Lakmal Nishantha Jayasinghe, Oxford (GB); Elizabeth Jayne Wallace, Oxford (GB); Jonathan Bankes Pugh, Oxford (GB); Richard George Hambley, Oxford (GB); Neil Roger Wood, Oxford (GB); Clive Gavin Brown, Cambridge (GB); James White, Oxford (GB); Andrew John Heron, Oxford (GB); Mark Bruce, Oxford (GB); Christopher Peter Youd, Oxford (GB); Rebecca Victoria Bowen, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 347 days.

This patent is subject to a terminal disclaimer.

(21) Appl. No.: 17/075,017

(22) Filed: Oct. 20, 2020

(65) Prior Publication Data

US 2021/0139972 A1 May 13, 2021

Related U.S. Application Data

(63) Continuation of application No. 16/572,869, filed on Sep. 17, 2019, now Pat. No. 10,844,432, which is a continuation of application No. 15/308,252, filed as application No. PCT/GB2015/051291 on May 1, 2015, now Pat. No. 10,443,097.

(30) Foreign Application Priority Data

May 2, 2014 (GB) ..................................... 1407809
Oct. 7, 2014 (GB) ..................................... 1417708
Oct. 7, 2014 (GB) ..................................... 1417712

(51) Int. Cl.
*C07K 14/35* (2006.01)
*C12Q 1/68* (2018.01)
*C12Q 1/6869* (2018.01)

(52) U.S. Cl.
CPC ............ *C12Q 1/6869* (2013.01); *C07K 14/35* (2013.01)

(58) Field of Classification Search
CPC ......... C12Q 1/68; C12Q 1/6869; C07K 14/35
See application file for complete search history.

(56) References Cited

U.S. PATENT DOCUMENTS 5,795,782 A 8/1998 Church et al.
6,015,714 A 1/2000 Baldarelli et al.
6,150,112 A 11/2000 Weissman et al.
6,362,002 B1 3/2002 Denison et al.
6,426,231 B1 7/2002 Bayley et al.
6,627,067 B1 9/2003 Branton et al.
6,824,659 B2 11/2004 Bayley et al.
6,863,833 B1 3/2005 Bloom et al.
6,916,665 B2 7/2005 Bayley et al.
6,927,070 B1 8/2005 Bayley et al.
7,189,503 B2 3/2007 Akeson et al.
8,105,846 B2 1/2012 Bayley et al.
8,785,211 B2 7/2014 Bayley et al.
8,822,160 B2 9/2014 Bayley et al.
8,828,208 B2 9/2014 Canas et al.
9,073,990 B2 7/2015 Paas et al.
9,127,313 B2 9/2015 Brown et al.
9,222,082 B2 12/2015 Jayasinghe et al.
9,447,152 B2 9/2016 Clarke et al.
9,562,887 B2 2/2017 Maglia et al.
9,580,480 B2 2/2017 Lu et al.
9,588,079 B2 3/2017 Gundlach et al.
9,732,381 B2 8/2017 Stoddart et al.
9,751,915 B2 9/2017 Clarke et al.
9,777,049 B2 10/2017 Bruce et al.
10,006,905 B2 6/2018 Maglia et al.
10,167,503 B2 1/2019 Clarke et al.
10,266,885 B2 4/2019 Jayasinghe et al.
10,385,389 B2 8/2019 Heron et al.
10,400,014 B2 9/2019 Howorka et al.
10,443,097 B2 * 10/2019 Jayasinghe .......... C12Q 1/6869

(Continued)

FOREIGN PATENT DOCUMENTS

CA 2381139 A1 3/2001
CN 102116783 A 7/2011

(Continued)

OTHER PUBLICATIONS

Butler et al.; 2008; Single-molecule DNA detection with an engineered MspA protein nanopore. PNAS 105(52): 20647-20652.*
International Search Report and Written Opinion for Application NW. PCT/GB2015/051291, dated Oct. 14, 2015.
International Preliminary Report on Patentability for Application NW. PCT/GB2015/051291, dated Nov. 17, 2016.
[No Author Listed] EBI Accession No. GSP:AXX09397. May 13, 2010.
[No Author Listed] Enterobacteria phage vB_EcoM-ACG-C40, complete genome. Genbank Acc. No. NC 019399.1. 2 pages.

(Continued)

*Primary Examiner* — Karen Cochrane Carlson

(74) *Attorney, Agent, or Firm* — Wolf, Greenfield & Sacks, P.C.

(57) ABSTRACT

The invention relates to improving the movement of a target polynucleotide with respect to a transmembrane pore when the movement is controlled by a polynucleotide binding protein. The invention also relates to improved transmembrane pores and polynucleotide binding proteins.

15 Claims, 37 Drawing Sheets

Specification includes a Sequence Listing.

(56) References Cited

U.S. PATENT DOCUMENTS 10,472,673 B2 11/2019 Maglia et al.
10,514,378 B2 12/2019 Maglia et al.
10,669,581 B2 6/2020 Stoddart et al.
10,802,015 B2 10/2020 Maglia et al.
10,844,432 B2 * 11/2020 Jayasinghe .......... C12Q 1/6869
10,882,889 B2 1/2021 Bruce et al.
10,975,428 B2 4/2021 Jayasinghe et al.
10,976,300 B2 4/2021 Maglia et al.
10,976,311 B2 4/2021 Maglia et al.
10,995,372 B2 5/2021 Jayasinghe et al.
11,034,734 B2 6/2021 Howorka et al.
11,104,709 B2 8/2021 Maglia et al.
11,169,138 B2 11/2021 Maglia et al.
11,186,868 B2 11/2021 Jayasinghe et al.
11,307,192 B2 4/2022 Jayasinghe et al.
11,572,387 B2 2/2023 Remaut et al.
11,597,970 B2 3/2023 Jayasinghe et al.
2001/0044137 A1 11/2001 Heyman et al.
2002/0028458 A1 3/2002 Lexow
2002/0094526 A1 7/2002 Bayley et al.
2002/0197614 A1 12/2002 Mosaic
2003/0044816 A1 3/2003 Denison et al.
2003/0099951 A1 5/2003 Akeson et al.
2003/0165936 A1 9/2003 Rabbani et al.
2003/0211502 A1 11/2003 Sauer et al.
2003/0215881 A1 11/2003 Bayley et al.
2004/0209299 A1 10/2004 Pinter et al.
2004/0214177 A1 10/2004 Bension
2005/0053961 A1 3/2005 Akeson et al.
2006/0063171 A1 3/2006 Akeson et al.
2006/0105461 A1 5/2006 Tom-Moy et al.
2007/0218471 A1 9/2007 Kim et al.
2008/0121534 A1 5/2008 White et al.
2008/0311582 A1 12/2008 Bayley et al.
2009/0111115 A1 4/2009 Drmanac et al.
2009/0256116 A1 10/2009 Shumaker-Parry et al.
2009/0283412 A1 11/2009 Sansinena et al.
2009/0298075 A1 12/2009 Travers et al.
2009/0298188 A1 12/2009 Peti-Peterdi
2010/0120098 A1 5/2010 Grunenwald et al.
2010/0196203 A1 8/2010 Sanghera et al.
2010/0297638 A1 11/2010 Bayley et al.
2011/0120871 A1 5/2011 Reid et al.
2011/0121840 A1 5/2011 Sanghera et al.
2011/0177498 A1 7/2011 Clarke et al.
2011/0229877 A1 9/2011 Jayasinghe et al.
2011/0311965 A1 12/2011 Maglia et al.
2012/0058468 A1 3/2012 Mckeown
2012/0064599 A1 3/2012 Jayasinghe et al.
2012/0100530 A1 4/2012 Moysey et al.
2012/0107802 A1 5/2012 Stoddart et al.
2012/0322679 A1 12/2012 Brown et al.
2014/0051069 A1 2/2014 Jayasinghe et al.
2014/0186823 A1 7/2014 Clarke et al.
2014/0194324 A1 7/2014 Gormley et al.
2014/0262784 A1 9/2014 Clarke et al.
2014/0296083 A1 10/2014 Brown et al.
2015/0008126 A1 1/2015 Maglia et al.
2015/0031020 A1 1/2015 Jayasinghe et al.
2015/0068904 A1 3/2015 Bruce et al.
2015/0152495 A1 6/2015 Stava et al.
2015/0175663 A1 6/2015 Yokoi et al.
2015/0191709 A1 7/2015 Heron et al.
2015/0218629 A1 8/2015 Heron et al.
2015/0346149 A1 12/2015 Brown et al.
2016/0005330 A1 1/2016 Maglia et al.
2016/0010147 A1 1/2016 Heron et al.
2016/0053300 A1 2/2016 Maglia et al.
2016/0370358 A1 12/2016 Maglia et al.
2017/0058337 A1 3/2017 Clarke et al.
2017/0058338 A1 3/2017 Jayasinghe et al.
2017/0107569 A1 4/2017 Heron et al.
2017/0233803 A1 8/2017 Stoddart et al.
2017/0306398 A1 10/2017 Jayasinghe et al.
2018/0030526 A1 2/2018 Brown et al.
2018/0095066 A1 4/2018 Jayasinghe et al.
2018/0148481 A2 5/2018 Howorka et al.
2018/0208632 A1 7/2018 Bruce et al.
2018/0209952 A1 7/2018 Maglia et al.
2019/0071721 A1 3/2019 Jayasinghe et al.
2019/0202876 A1 7/2019 Jayasinghe et al.
2019/0300582 A1 10/2019 Jayasinghe et al.
2019/0330282 A1 10/2019 Jayasinghe et al.
2019/0346431 A1 11/2019 Maglia et al.
2020/0017556 A1 1/2020 Howorka et al.
2020/0072824 A1 3/2020 Maglia et al.
2020/0087724 A1 3/2020 Heron et al.
2020/0224262 A1 7/2020 Jayasinghe et al.
2020/0299336 A9 9/2020 Jayasinghe et al.
2020/0299337 A9 9/2020 Jayasinghe et al.
2020/0407785 A1 12/2020 Stoddart et al.
2021/0147486 A1 5/2021 Remaut et al.
2021/0269872 A1 9/2021 Jayasinghe et al.
2021/0284696 A1 9/2021 Remaut et al.
2021/0292376 A1 9/2021 Howorka et al.
2021/0317520 A1 10/2021 Jayasinghe et al.
2021/0324020 A1 10/2021 Bruce et al.
2021/0405039 A1 12/2021 Maglia et al.
2022/0024985 A9 1/2022 Remaut et al.
2022/0064230 A1 3/2022 Jayasinghe et al.
2022/0091096 A1 3/2022 Maglia et al.
2022/0119879 A1 4/2022 Jayasinghe et al.
2022/0154269 A9 5/2022 Jayasinghe et al.
2022/0162264 A9 5/2022 Remaut et al.
2022/0283141 A1 9/2022 Jayasinghe et al.

FOREIGN PATENT DOCUMENTS

CN 102174554 A 9/2011
CN 102317310 A 1/2012
CN 103460040 A 12/2013
EP 2194123 B1 8/2012
EP 2682460 A1 1/2014
GB 2453377 A 4/2009
GB 1314695.6 8/2013
JP 2015-514128 A 5/2015
WO WO 1999/005167 A1 2/1999
WO WO 2000/028312 A1 5/2000
WO WO 2001/042782 A1 6/2001
WO WO 2001/059453 A2 8/2001
WO WO 2002/042496 A2 5/2002
WO WO 2003/095669 A1 11/2003
WO WO 2005/013666 A2 2/2005
WO WO 2005/076010 A2 8/2005
WO WO 2006/028508 A2 3/2006
WO WO 2006/100484 A2 9/2006
WO WO 2007/057668 A1 5/2007
WO WO 2007/075987 A2 7/2007
WO WO 2007/084103 A2 7/2007
WO WO 2008/102120 A1 8/2008
WO WO 2008/102121 A1 8/2008
WO WO 2008/124107 A1 10/2008
WO WO 2009/024775 A1 2/2009
WO WO 2009/035647 A1 3/2009
WO WO 2009/044170 A1 4/2009
WO WO 2009/077734 A2 6/2009
WO WO 2009/143425 A1 11/2009
WO WO 2010/004265 A1 1/2010
WO WO 2010/004273 A1 1/2010
WO WO 2010/034018 A2 3/2010
WO WO 2010/055307 A1 5/2010
WO WO 2010/086602 A1 8/2010
WO WO 2010/086603 A1 8/2010
WO WO 2010/086622 A1 8/2010
WO WO 2010/122293 A1 10/2010
WO WO 2011/067559 A1 6/2011
WO WO 2012/042226 A1 4/2012
WO WO 2012/042226 A2 4/2012
WO WO 2012/107778 A2 8/2012
WO WO 2012/164270 A1 12/2012
WO WO 2013/014451 A1 1/2013
WO WO 2013/041878 A1 3/2013
WO WO 2013/057495 A1 4/2013
WO WO 2013/057495 A2 4/2013

(56) References Cited

FOREIGN PATENT DOCUMENTS

| | | |
|---|---|---|
| WO | WO 2013/098561 A1 | 7/2013 |
| WO | WO 2013/098562 A1 | 7/2013 |
| WO | WO 2013/098562 A2 | 7/2013 |
| WO | WO 2013/153359 A1 | 10/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/064443 A1 | 5/2014 |
| WO | WO 2014/064443 A2 | 5/2014 |
| WO | WO 2014/064444 A1 | 5/2014 |
| WO | WO 2014/122654 A2 | 8/2014 |
| WO | WO 2014/135838 A1 | 9/2014 |
| WO | WO 2014/142850 A1 | 9/2014 |
| WO | WO 2014/153047 A1 | 9/2014 |
| WO | WO 2014/153625 A1 | 10/2014 |
| WO | WO 2014/187924 A1 | 11/2014 |
| WO | WO 2015/022544 A1 | 2/2015 |
| WO | WO 2015/051378 A1 | 4/2015 |
| WO | WO 2015/055981 A1 | 4/2015 |
| WO | WO 2015/055981 A2 | 4/2015 |
| WO | WO 2015/097289 A1 | 7/2015 |
| WO | WO 2015/110777 A1 | 7/2015 |
| WO | WO 2015/124935 A1 | 8/2015 |
| WO | WO 2015/150786 A1 | 10/2015 |
| WO | WO 2015/150787 A1 | 10/2015 |
| WO | WO 2015/166275 A1 | 11/2015 |
| WO | WO 2015/166276 A1 | 11/2015 |
| WO | WO 2016/034591 A2 | 3/2016 |
| WO | WO 2016/055778 A1 | 4/2016 |
| WO | WO 2016/166232 A1 | 10/2016 |
| WO | WO 2017/149316 A1 | 9/2017 |
| WO | WO 2017/149317 A1 | 9/2017 |
| WO | WO 2017/149318 A1 | 9/2017 |
| WO | WO 2018/211241 A1 | 11/2018 |

OTHER PUBLICATIONS

[No Author Listed] Helicos BioSciences Corporation, "Helicos Genetic Analysis System," Specification Sheet retrieved online at: www.helicosbio.com/Portals/O/Documents/Helicos_SalesSpec.pdf, 4 pages (2008).

[No Author Listed] Uniprot Accession No. A0A081NL13. Oct. 29, 2014. 4 pages.

[No Author Listed] Uniprot Accession No. A0A0P7DN88. Jan. 20, 2016. 4 pages.

[No Author Listed] Uniprot Accession No. Q8Z727. Oct. 24, 2003. 6 pages.

Ahern, Biochemical, reagents kits offer scientists good return on investment. The Scientist. Jul. 24, 1995;9(15):20.

Akeson et al., Microsecond time-scale discrimination among polycytidylic acid, polyadenylic acid, and polyuridylic acid as homopolymers or as segments within single RNA molecules. Biophys J. Dec. 1999;77(6):3227-33.

Aoki et al., Single channel properties of lysenin measured in artificial lipid bilayers and their applications to biomolecule detection. Proc Jpn Acad Ser B Phys Biol Sci. 2010;86(9):920-5.

Aravind et al., The DNA-Repair Protein AlkB, EGL-9, and Leprecan Define New Families of 2-oxoglutarate-andIron-Dependent Dioxygenases. Genome Biology. 2001;2:1-8.

Ashkenasy et al., Recognizing a single base in an individual DNA strand: a step toward DNA sequencing in nanopores. Angew Chem Int Ed Engl. Feb. 18, 2005;44(9): 1401-4.

Ashkenasy et al., Single Nucleobase Sensitivity of a-Hemolysin (a-HL) Transmembrane Protein Pore: Toward Single DNA Sequencing. ACS National Meeting. 2005;45(13), Abstract No. 74.

Ashton et al., MinION Nanopore Sequencing Identifies the Position and Structure of a Bacterial antibiotic Resistance Island. Nat Biotechnol. Mar. 2015;33(3):296-302.

Astier et al., Stochastic detection of motor protein-RNA complexes by single-channel current recording. Chemphyschem. Oct. 22, 2007;8(15):2189-94.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Atkins et al., Structure-function relationships of a novel bacterial toxin, hemolysin E. The role of alpha G. J Biol Chem. Dec. 29, 2000;275(52):41150-5.

Avrameas, Coupling of enzymes to proteins with glutaraldehyde. Use of the conjugates for the detection of antigens and antibodies. Immunochemistry. Jan. 1969;6(1):43-52.

Bayley, Nanopore Sequencing: From Imagination to Reality. Clin Chem. 2015;61(1):25-31.

Bayley et al., Stochastic sensors inspired by biology. Nature. Sep. 13, 2001;413(6852):226-30.

Bayley et al., Wrestling with native chemical ligation. ACS Chem Biol. Dec. 18, 2009;4(12):983-5. doi: 10.1021/cb900304p.

Bayley, Membrane-protein structure: Piercing insights. Nature. Jun. 4, 2009;459(7247):651-2. doi: 10.1038/459651a.

Bayley, Sequencing single molecules of DNA. Curr Opin Chem Biol. Dec. 2006;10(6):628-37. Epub Nov. 20, 2006.

Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.

Bezrukov et al., Counting Polymers Moving Through a Single Ion Channel. Nature. Jul. 28, 1994;370:279-81.

Bleijlevens et al., Changes in Protein Dynamics of the DNA Repair Dioxygenase AlkB Upon Binding of FE2+ and 2-Oxoglutarate. Biochemistry. Mar. 26, 2012;51:3334-41.

Bleijlevens et al., Dynamic States of the DNA Repair Enzyme AlkB regulate Product Release. Eur Mol Biol Org. Jul. 11, 2008;9(9):872-77.

Braha et al., Carriers versus adapters in stochastic sensing. Chemphyschem. May 2005;6(5):889-92.

Braha et al., Designed protein pores as components for biosensors. Chem Biol. Jul. 1997;4(7):497-505.

Branton et al., The potential and challenges of nanopore sequencing. Nat Biotechnol. Oct. 2008;26(10):1146-53. doi:10.1038/nbt.1495.

Braslavsky et al., Sequence information can be obtained from single DNA molecules. Proc Natl Acad Sci U S A. Apr. 1, 2003;100(7):3960-4. Epub Mar. 21, 2003.

Butler et al., Determination of RNA orientation during translocation through a biological nanopore. Biophys J. Jan. 1, 2006;90(1):190-9. Epub Oct. 7, 2005.

Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.

Chan, Advances in sequencing technology. Mutat Res. Jun. 3, 2005;573(1-2): 13-40.

Cheley et al., A functional protein pore with a "retro" transmembrane domain. Protein Sci. Jun. 1999;8(6):1257-67.

Cheley et al., A genetically encoded pore for the stochastic detection of a protein kinase. Chembiochem. Dec. 2006;7(12):1923-7.

Cheley et al., Spontaneous oligomerization of a staphylococcal alpha-hemolysin conformationally constrained by removal of residues that form the transmembrane beta-barrel. Protein Eng. Dec. 1997;10(12):1433-43.

Chen et al., Atomic Layer Deposition to Fine-Tune the Surface Properties and Diameters of Fabricated Nanopores. Nano Lett. Jun. 25, 2004;4(7):1333-1337.

Chen et al., Outer membrane protein G: Engineering a quiet pore for biosensing. Proc Natl Acad Sci U S A. Apr. 29, 2008; 105(17):6272-7. doi: 10.1073/pnas.0711561105. Epub Apr. 28, 2008.

Chin et al., The Metabolite alpha-Ketoglutarate Extends Lifespan by Inhibiting ATP Synthase and TOR. Nature. Jul. 19, 2014;510:397-401.

Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.

(56) References Cited

OTHER PUBLICATIONS

Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.
Comai et al., Protein engineering modulates the transport properties and ion selectivity of the pores formed by staphylococcal gamma-haemolysins in lipid membranes. Mol Microbiol. Jun. 2002;44(5):1251-67.
Dani et al., MspA Porin-Gold Nanoparticle Assemblies: Enhanced Binding through a Controlled Cysteine Mutation. Nano Lett. Apr. 2008;8(4):1229-36. doi: 10.1021/n1072658h. Epub Mar. 5, 2008.
Deamer et al., Characterization of nucleic acids by nanopore analysis. Acc Chem Res. Oct. 2002;35(10):817-25.
Deamer et al., Nanopores and nucleic acids: prospects for ultrarapid sequencing. Trends Biotechnol. Apr. 2000;18(4):147-51.
Derrington et al., A Novel DNA Sensing Technique Using Nanopore MSPA. 54th Annual Meeting of the Biophysical Society, Poster 2182-Plat, 2 pages (2010).
Derrington et al., Nanopore DNA sequencing with MspA. Proc Natl Acad Sci U S A. Sep. 14, 2010; 107(37):16060-5. doi: 10.1073/pnas.1001831107. Epub Aug. 26, 2010.
Dorre et al., Techniques for single molecule sequencing. Bioimaging, vol. 5:139-152 (1997).
Eid et al., Real-time DNA sequencing from single polymerase molecules. Science. Jan. 2, 2009;323(5910):133-8. doi: 10.1126/science.1162986. Epub Nov. 20, 2008.
Eifier et al., Cytotoxin ClyA from *Escherichia coli* assembles to a 13-meric pore independent of its redox-state. EMBO J. Jun. 7, 2006;25(11):2652-61. doi: 10.1038/sj.emboj.7601130. Epub May 11, 2006.
Eliseev et al., Aminocyclodextrins as Selective Hosts with Several Binding Sites for Nucleotides. Angew. Chem. Int. Ed. Engl., vol. 32(9):1331-1333 (1993).
Eliseev et al., Molecular Recognition of Nucleotides, Nucleosides, and Sugars by Aminocyclodextrins. J. Am. Chem. Soc., vol. 116:6081-6088 (1994).
Engelhardt et al., A tetrameric porin limits the cell wall permeability of Mycobacterium smegmatis. J Biol Chem. Oct. 4, 2002;277(40):37567-72. Epub Jul. 18, 2002.
Ergel et al., Protein Dynamics Control the Progression and Efficiency of the Catalytic Reaction Cycle of the *Escherichia coli* DNA-Repair Enzyme AlkB. J Biol Chem. Oct. 24, 2014;289(43):29584-601.
Fahie et al., Resolved Single-Molecule Detection of Individual Species Within a Mixture of Anti-Biotin Antibodies Using an Engineered Monometric Nanopore. Am Chem Soc. Jan. 9, 2015;9(2):1089-98.
Flomenbom et al., Single stranded DNA translocation through a nanopore: a master equation approach. Phys Rev E Stat Nonlin Soft Matter Phys. Oct. 2003;68(4 Pt 1):041910. Epub Oct. 14, 2003.
Flusberg et al., Direct detection of DNA methylation during single-molecule, real-time sequencing. Nat Methods. Jun. 2010;7(6):461-5. doi: 10.1038/nmeth.1459. Epub May 9, 2010.
Fologea et al., Potential analytical applications of lysenin channels for detection of multivalent ions. Anal Bioanal Chem. Oct. 2011;401(6):1871-9. doi: 10.1007/s00216-011-5277-8. Epub Aug. 5, 2011.
Franceschini et al., A nanopore machine promotes the vectorial transport of DNA across membranes. Sep. 2013; Nat Commun. 2013;4:2415. doi: 10.1038/ncomms3415.
Franceschini et al., DNA Translocation through Nanopores at Physiological Ionic Strengths Requires Precise Nanoscale Engineering. ACS Nano. Sep. 27, 2016;10(9):8394-402. doi: 10.1021/acsnano.6b03159. Epub Aug. 15, 2016.
Freedman et al., Single Molecule Unfolding and Stretching of Protein Domains Inside a Solid-State Nanopore by Electric Field. Scientific Reports. Apr. 10, 2013;3(1638):1-8.
Galenkamp et al., Direct electrical quantification of glucose and asparagine from bodily fluids using nanopores. Nat Commun. 2018;9(1):4085. Published Oct. 5, 2018. doi:10.1038/s41467-018-06534-1.
Genschel et al., Interaction of *E. coli* single-stranded DNA binding protein (SSB) with exonuclease I. The carboxy-terminus of SSB is the recognition site for the nuclease. Biol Chem. Mar. 2000;381(3):183-92.
Gershow et al., Recapturing and trapping single molecules with a solid-state nanopore. Nat Nanotechnol. Dec. 2007;2(12):775-9. doi:10.1038/nnano.2007.381. Epub Dec. 2, 2007.
Ghosal, Electrokinetic-flow-induced viscous drag on a tethered DNA inside a nanopore. Phys Rev E Stat Nonlin Soft Matter Phys. Dec. 2007;76(6 Pt 1):061916. Epub Dec. 26, 2007.
Gilbert et al., Two Structural Transitions in Membrane Pore Formation by Pneumolysin, the Pore-Forming Toxin of Streptococcus Pneumoniae. Cell. May 28, 1999;97:647-655.
Gouridis et al., Conformational Dynamics in Substrate-Binding Domains Influences Transport in the ABC Importer GinPQ. Nat Stuct Mol Biol. Dec. 8, 2014;22(1):57-66.
Gu et al., Capture of a single molecule in a nanocavity. Science. Jan. 26, 2001;291(5504):636-40.
Gu et al., Electroosmotic enhancement of the binding of a neutral molecule to a transmembrane pore. Proc Natl Acad Sci U S A. Dec. 23, 2003;100(26):15498-503. Epub Dec. 15, 2003.
Gu et al., Interaction of the noncovalent molecular adapter, beta-cyclodextrin, with the staphylococcal alpha-hemolysin pore. Biophys J. Oct. 2000;79(4):1967-75.
Gu et al., Prolonged residence time of a noncovalent molecular adapter, beta-cyclodextrin, within the lumen of mutant alpha-hemolysin pores. J Gen Physiol. Nov. 2001;118(5):481-94.
Gu et al., Reversal of charge selectivity in transmembrane protein pores by using noncovalent molecular adapters. Proc Natl Acad Sci U S A. Apr. 11, 2000;97(8):3959-64.
Gu et al., Stochastic sensing of organic analytes by a pore-forming protein containing a molecular adapter. Nature. Apr. 22, 1999;398(6729):686-90.
Guan et al., Stochastic sensing of TNT with a genetically engineered pore. Chembiochem. Oct. 2005;6(10):1875-81.
Guasch et al., Detailed architecture of a DNA translocating machine: the high-resolution structure of the bacteriophage phi29 connector particle. J Mol Biol. Jan. 25, 2002;315(4):663-76.
Hall et al., Hybrid pore formation by directed insertion of ?-haemolysin into solid-state nanopores. Nat Nanotechnol. Dec. 2010;5(12):874-7. doi: 10.1038/nnano.2010.237. Epub Nov. 28, 2010.
Han et al., Characterization and optimization of an entropic trap for DNA separation. Anal Chem. Jan. 15, 2002;74(2):394-401.
Han et al., RecJ exonuclease: substrates, products and interaction with SSB. Nucleic Acids Res. Feb. 18, 2006;34(4):1084-91. Print 2006.
Haque et al., Solid-State and Biological Nanopore for Real-Time Sensing of Single Chemical and Sequencing of DNA. Nano Today. Feb. 2013;8(1):56-74.
He et al. 2012; The T4 phage SF1 B helicase dda is structurally optimized to perform DNA strand separation. Structure. 20:1189-1200.
Henrickson et al., Driven DNA transport into an asymmetric nanometer-scale pore. Phys Rev Lett. Oct. 2, 2000;85(14):3057-60.
Heron et al., Direct detection of membrane channels from gels using water-in-oil droplet bilayers. J Am Chem Soc. Dec. 26, 2007; 129(51):16042-7. Epub Dec. 1, 2007.
Holden et al., Direct introduction of single protein channels and pores into lipid bilayers. J Am Chem Soc. May 11, 2005;127(18):6502-3.
Holden et al., Functional bionetworks from nanoliter water droplets. J Am Chem Soc. Jul. 11, 2007;129(27):8650-5. Epub Jun. 16, 2007.
Hornblower et al., Single-molecule analysis of DNA-protein complexes using nanopores. Nat Methods. Apr. 2007;4(4):315-7. Epub Mar. 4, 2007.
Howorka et al., DNA Duplex Formation of Individual DNA Strands within a Single Protein Pore. Biophysical Journal, vol. 82{ 1, pt. 2):508a, No. 2482-Plat (2002).

(56) References Cited

OTHER PUBLICATIONS

Howorka et al., Kinetics of duplex formation for individual DNA strands within a single protein nanopore. Proc Natl Acad Sci U S A. Nov. 6, 2001;98(23):12996-3001. Epub Oct. 23, 2001.
Howorka et al., Nanopore Analytics: Sensing of Single Molecules. The Royal Society of Chemistry. Jun. 15, 2009;38:2360-84.
Howorka et al., Nanopores as protein sensors. Nat Biotechnol. Jun. 7, 2012;30(6):506-7. doi: 10.1038/nbt.2264.
Howorka et al., Probing distance and electrical potential within a protein pore with tethered DNA. Biophys J. Dec. 2002;83(6):3202-10.
Howorka et al., Sequence-specific detection of individual DNA strands using engineered nanopores. Nat Biotechnol. Jul. 2001;19(7):636-9.
Hu et al., Theory of DNA translocation through narrow ion channels and nanopores with charged walls. Phys Rev E Stat Nonlin Soft Matter Phys. Sep. 2008;78(3 Pt 1):032901. Epub Sep. 10, 2008.
Huff et al., Functions of the periplasmic loop of the porin MspA from Mycobacterium smegmatis. J Biol Chem. Apr. 10, 2009;284(15):10223-31. doi: 10.1074/jbc.M808599200. Epub Feb. 10, 2009.
Hwang et al., Electrical behavior of droplet interface bilayer networks: experimental analysis and modeling. J Am Chem Soc. Sep. 26, 2007;129(38): 11854-64. Epub Sep. 1, 2007.
Iacovache et al., Structure and assembly of pore-forming proteins. Curr Opin Struct Biol. Apr. 2010;20(2):241-6. doi:10.1016/j.sbi.2010.01.013. Epub Feb. 19, 2010.
Ide et al., Lysenin forms a voltage-dependent channel in artificial lipid bilayer membranes. Biochem Biophys Res Commun. Jul. 21, 2006;346(1):288-92. Epub May 26, 2006.
Ivanov et al., DNA tunneling detector embedded in a nanopore. Nano Lett. Jan. 12, 2011;11(1):279-85. doi: 10.1021/n1103873a. Epub Dec. 6, 2010.
Jayasinghe et al., The leukocidin pore: evidence for an octamer with four LukF subunits and four LukS subunits alternating around a central axis. Protein Sci. Oct. 2005;14(10):2550-61.
Jung et al., The internal cavity of the staphylococcal alpha-hemolysin pore accommodates approximately 175 exogenous amino acid residues. Biochemistry. Jun. 28, 2005;44(25):8919-29.
Kalli et al., Conformational changes in talin on binding to anionic phospholipid membranes facilitate signaling by integrin transmembrane helices. PLoS Comput Biol. Oct. 2013;9(10):e1003316. doi:10.1371/journal.pcbi.1003316.
Kang et al., Single protein pores containing molecular adapters at high temperatures. Angew Chem Int Ed Engl. Feb. 25, 2005;44(10):1495-9.
Kasianowicz et al., Characterization of individual polynucleotide molecules using a membrane channel. Proc Natl Acad Sci U S A. Nov. 26, 1996;93(24):13770-3.
Khulbe et al., DNA translocation through a-hemolysin nanopores with potential application to macromolecular data storage. Journal Applied Physics, vol. 97(104317):1-7 (2005).
Kobayashi et al., Comparative Physiology and Biochemistry, 2005, vol. 22, No. 3-4, pp. 139-148.
Kolinko et al., Single-cell genomics reveals potential for magnetite and greigite biomineralization in an uncultivated multicellular magnetotactic prokaryote. Environ Microbiol Rep. Oct. 2014;6(5):524-31. doi: 10.1111/1758-2229.12198. Epub Aug. 28, 2014. Abstract Only.
Krylova et al., DNA aptamers for as analytical tools for the quantitative analysis of DNA-dealkylating enzymes. Anal Biochem. 2011;414(2):261-265. doi:10.1016/j.ab.2011.03.010.
Kumar et al., PEG-labeled nucleotides and nanopore detection for single molecule DNA sequencing by synthesis. Sci Rep. 2012;2:684. Epub Sep. 21, 2012.
Langecker et al., Synthetic lipid membrane channels formed by designed DNA nanostructures. Science. Nov. 16, 2012;338(6109):932-6. doi: 10.1126/science.1225624.
Li et al., Different Anomeric Sugar Bound States of Maltose Binding Protein Resolved by a Cytolysin A Nanopore Tweezer. ACS Nano. 2020;14(2):1727-1737. doi:10.1021/acsnano.9b07385.
Li et al., DNA molecules and configurations in a solid-state nanopore microscope. Nat Mater. Sep. 2003;2(9):611-5. Epub Aug. 24, 2003.
Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.
Lu et al., Protein Motion and Configurations in a Form-Fitting Nanopore: Avidin in ClyA. Biophys J. Sep. 4, 2018; 115(5): 801-808. Epub Aug. 4, 2018. doi: 10.1016/j.bpj.2018.07.024.
Luchian et al., Single-Molecule Covalent Chemistry with Spatially Separated Reactants. Angew. Chem. Int. Ed. 2003;42:3766-771.
Ludwig et al., Analysis of the SlyA-Controlled Expression, Subcellular Localization and Pore-Forming Activity of a 34 kDa Haemolysin (ClyA) from *Escherichia coli* K-12. Mol Microbiol. 1999;31(2):557-67.
Luo et al., Influence of polymer-pore interactions on translocation. Phys Rev Lett. Oct. 5, 2007;99(14):148102. Epub Oct. 1, 2007.
Maglia et al., DNA strands from denatured duplexes are translocated through engineered protein nanopores at alkaline pH. Nano Lett. Nov. 2009;9(11):3831-6. doi: 10.1021/n19020232.
Maglia et al., Engineering a Biomimetic Biological Nanopore to Selectively Capture Folded Target Proteins. Biophysical J. Feb. 5, 2013;104(2):518a.
Maglia et al., Enhanced translocation of single DNA molecules through alpha-hemolysin nanopores by manipulation of internal charge. Proc Natl Acad Sci U S A. Dec. 16, 2008; 105(50):19720-5. doi:10.1073/pnas.0808296105. Epub Dec. 5, 2008.
Makaram et al., Trends in Nanomaterial-Based Non-Invasive Diabetes Sensing Technologies. Diagnostics. Apr. 21, 2014;4:27-46.
Manrao et al., Nucleotide Discrimination with DNA Immobilized in the MspA Nanopore. PLoS One, vol. 6(10):e25723, 7 pages (2011).
Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.
Manrao et al., Single Nucleotide Discrimination in Single Stranded DNA Immobilized within Biological Nanopre MSPA. 54th Annual Meeting of the Biophysical Society, 3 pages (2010).
Martin et al., Nanoscale protein pores modified with PAMAM dendrimers. J Am Chem Soc. Aug. 8, 2007;129(31):9640-9. Epub Jul. 18, 2007.
Marziali et al., New DNA sequencing methods. Annu Rev Biomed Eng. 2001;3:195-223.
Mathé et al., Orientation discrimination of single-stranded DNA inside the alpha-hemolysin membrane channel. Proc Natl Acad Sci USA. Aug. 30, 2005; 102(35):12377-82. Epub Aug. 19, 2005.
Matsuura et al., Real-time observation of a single DNA digestion by lambda exonuclease under a fluorescence microscope field. Nucleic Acids Res. Aug. 15, 2001;29(16):E79.
Meller et al., Rapid nanopore discrimination between single polynucleotide molecules. Proc Natl Acad Sci U S A. Feb. 1, 2000;97(3):1079-84.
Meller et al., Single molecule measurements of DNA transport through a nanopore. Electrophoresis. Aug. 2002;23(16):2583-91.
Meller, Dynamics of polynucleotide transport through nanometre-scale pores. Journal Physics: Condensed Matter, vol. 15:R581-R607 (2003).
Merzlyak et al., Conductance and ion selectivity of a mesoscopic protein nanopore probed with cysteine scanning mutagenesis. Biophys J. Nov. 2005;89(5):3059-70. Epub Aug. 5, 2005.
Mikheyev et al., A First Look at the Oxford Nanopore MinION Sequencer. Mol Ecol Res. 2014;14:1097-1102.
Miles et al., The Staphylococcal Leukocidin Bicomponent Toxin Forms Large Ionic Channels. Biochemistry. Jun. 28, 2001;40:8514-522.
Mitchell et al., Chemical tags facilitate the sensing of individual DNA strands with nanopores. Angew Chem Int Ed Engl. 2008;47(30):5565-8. doi: 10.1002/anie.200800183.
Miyazaki et al., MEGAWHOP Cloning: A Method of Creating Random Mutagenesis Libraries via Megaprimer PCR of Whole Plasmids. Methods in Enzymology. 2011 ;498:399-406.

(56) References Cited

OTHER PUBLICATIONS

Mohammad et al., Controlling a single protein in a nanopore through electrostatic traps. J Am Chem Soc. Mar. 26, 2008;130(12):4081-8. doi: 10.1021/ja710787a. Epub Mar. 6, 2008.
Moreau et al., Coupling ion channels to receptors for biomolecule sensing. Nat Nanotechnol. Oct. 2008;3(10):620-5. doi: 10.1038/nnano.2008.242. Epub Sep. 7, 2008.
Movileanu et al., Detecting protein analytes that modulate transmembrane movement of a polymer chain within a single protein pore. Nat Biotechnol. Oct. 2000;18(10):1091-5.
Movileanu et al., Location of a constriction in the lumen of a transmembrane pore by targeted covalent attachment of polymer molecules. J Gen Physiol. Mar. 2001;117(3):239-52.
Moyer et al., Correlation Between Sweat Glucose and Blood Glucose in Subjects with Diabetes. Diabetes Technol Ther. 2012:14(5):398-402.
Mueller et al., RCSB Protein Data Bank No. 2WCD. Mar. 11, 2009. doi: 10.2210/pdb2WCD/pdb. 5 pages.
Mueller et al., The Structure of Cytolytic alpha-Helical Toxin Pore Reveals its Assembly Mechanism. Nature. Jun. 4, 2009;459:726-731.
Mueller et al., The Structure of Cytolytic alpha-Helical Toxin Pore Reveals its Assembly Mechanism. Nature. Jun. 4, 2009;459:Supplemental Information.
Muller et al., DNA-directed assembly of artificial multienzyme complexes. Biochem Biophys Res Commun. Dec. 5, 2008;377(1):62-7. doi:10.1016/j.bbrc.2008.09.078. Epub Sep. 25, 2008.
Nakane et al., A nanosensor for transmembrane capture and identification of single nucleic Acid molecules. Biophys J. Jul. 2004;87(1):615-21. Erratum in: Biophys J. Nov. 2004;87(5):3618.
Nakane et al., Nanopore sensors for nucleic acid analysis. J. Phys.: Condens. Matter, vol. 15: R 1365-R1393 (2003).
Niedzwiecki et al., Inspection of the Engineered FhuA deltaC/delta4L Protein Nanopore by Polymer Exclusion. Biophys J. Nov. 2012; 103:2115-124.
Nikolaidou et al., alpha-Ketoglutarate: Biological Effects of a Novel Biomarker of Heart Failure. Heart. Sep. 2010;96(17). 2 pages.
Ogasawara et al., Determination of Reduced Nicotinamide Adenine Dinucleotid Phosphate Concentration Using High-Performance Liquid Chromatography with Fluorescence Detection: Ratio of the Reduced Form as a Biomarker of Oxidative Stress. Biol Pharm Bull. Nov. 2009;32(11):1819-18223.
Oukhaled et al., Dynamics of Completely Unfolded and Native Proteins through Solid-State Nanopores as a Function of Electric Driving Force. Am Chem Soc. 2011 Arp 8;5(5):3628-38.
Pfeiffer et al., Bivalent cholesterol-based coupling of oligonucleotides to lipid membrane assemblies. J Am Chem Soc. Aug. 25, 2004;126(33):10224-5.
Plesa et al., Fast Translocation of Proteins through Solid State Nanopores. Nano Lett. Jan. 23, 2013:13:658-663.
Purnell et al., Nucleotide identification and orientation discrimination of DNA homopolymers immobilized in a protein nanopore. Nano Lett. Sep. 2008;8(9):3029-34. doi: 10.1021/n1802312f. Epub Aug. 13, 2008.
Quick et al., A reference Bacterial Genome Dataset Generated on the MinION Portable Single-Molecule Nanopore Sequencer. GigaScience. 2014;3(22):1-6.
Rajagopalan et al., Interaction of Dihydrofolate Reductase with Methotrexate: Ensemble and Single-Molecule Kinetics. PNAS. Oct. 15, 2002:99(21):13481 -6.
Rhee et al., Nanopore sequencing technology: research trends and applications. Trends Biotechnol. Dec. 2006;24(12):580-6. Epub Oct. 19, 2006.
Rodriguez-Gallego et al., Mapping of the Circulating Metabolome Reveals alpha-Ketoglutarate as a Predictor of Morbid Obesity-Associated Non-Alcoholic Fatty Liver Disease. Int J of Obesity. 2015;39:279-287.
Rotem et al., Protein detection by nanopores equipped with aptamers. J Am Chem Soc. Feb. 8, 2012;134(5):2781-7. doi:10.1021/ja2105653. Epub Jan. 26, 2012.
Rucker et al., Recombinant ferritin: modulation of subunit stoichiometry in bacterial expression systems. Protein Eng. 1997;10(8):967-973. doi:10.1093/protein/10.8.967.
Russo et al., Reversible permeabilization of plasma membranes with an engineered switchable pore. Nat Biotechnol. Mar. 1997;15(3):278-82.
Saariaho et al., Characteristics of MuA transposase-catalyzed processing of model transposon end DNA hairpin substrates. Nucleic Acids Res. Jun. 6, 2006;34(10):3139-49.
Sanchez-Quesada et al., Cyclic Peptides as Molecular Adapters for a Pore-Forming Protein. Journal American Chemical Society, vol. 122(48):11757-11766 (2000).
Sanchez-Quesada et al., Single DNA rotaxanes of a transmembrane pore protein. Angew Chem Int Ed Engl. Jun. 7, 2004;43(23):3063-7.
Sanderson, Personal genomes: Standard and pores. Nature. Nov. 6, 2008;456(7218):23-5. doi: 10.1038/456023a.
Sauer-Budge et al., Unzipping kinetics of double-stranded DNA in a nanopore. Phys Rev Lett. Jun. 13, 2003;90(23):238101. Epub Jun. 9, 2003.
Smeets et al., Salt dependence of ion transport and DNA translocation through solid-state nanopores. Nano Lett. Jan. 2006;6(1):89-95.
Skocaj et al., The sensing of membrane microdomains based on pore-forming toxins. Curr Med Chem. 2013;20(4):491-501.
Soni et al., Synchronous optical and electrical detection of biomolecules traversing through solid-state nanopores. Rev Sci Instrum. Jan. 2010;81(1):014301. doi: 10.1063/1.3277116.
Soskine et al., An engineered ClyA nanopore detects folded target proteins by selective external association and pore entry. Nano Lett. Sep. 12, 2012;12(9):4895-900. doi:10.1021/n13024438. Epub Aug. 6, 2012.
Soskine et al., Single-Molecule Analyte Recognition with ClyA Nanopores Equipped with Internal Protein Adaptors. J Am Chem Soc. 2015;137:5793-97.
Soskine et al., Tuning the size and properties of ClyA nanopores assisted by directed evolution. J Am Chem Soc. Sep. 11, 2013;135(36):13456-63. doi: 10.1021/ja4053398. Epub Aug. 27, 2013.
Stoddart et al., Multiple base-recognition sites in a biological nanopore: two heads are better than one. Angew Chem Int Ed Engl. 2010;49(3):556-9. doi: 10.1002/anie.200905483.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Sutherland et al., An analysis of mismatched duplex DNA unzipping through a bacterial nanopore. Biochem Cell Biol. Jun. 2004;82(3):407-12.
Trewick et al., Oxidative Demethylation by *Escherichia coli* AlkB Directly Reverts DNA Base Damage. Nature. Sep. 12, 2002:419:174-78.
Van De Goor, Nanopore Detection: Threading DNA Through a Tiny Hole. PharmaGenomics, vol. 4 (3):28-30 (2004).
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/1a904822f.
Van Meervelt et al., Detection of Two Isomeric Binding Configurations in a Protein-Aptamer Complex with a Biological Nanopore. Am Chem Soc. Dec. 10, 2014;8(12):12826-35.
Van Meervelt et al., Real-Time Conformational Changes and Controlled Orientation of Native Proteins Inside a Protein Nanoreactor. J Am Chem Soc. Dec. 27, 2017; 139(51): 18640-18646. EPub Dec. 5, 2017. doi: 10.1021/jacs.7b10106.
Walker et al., Key residues for membrane binding, oligomerization, and pore forming activity of staphylococcal alpha-hemolysin identified by cysteine scanning mutagenesis and targeted chemical modification. J Biol Chem. Sep. 29, 1995;270(39):23065-71.
Wallace et al., *E. coli* hemolysin E (HlyE, ClyA, She A): X-ray crystal structure of the toxin and observation of membrane pores by electron microscopy. Cell. Jan. 21, 2000;100(2):265-76.
Wang et al., Nanopores with a spark for single-molecule detection. Nat Biotechnol. Jul. 2001;19(7):622-3.

(56) References Cited

OTHER PUBLICATIONS

Wanunu et al., DNA translocation governed by interactions with solid-state nanopores. Biophys J. Nov. 15, 2008;95(10):4716-25. doi: 10.1529/biophysj.108.140475. Epub Aug. 15, 2008.
Wanunu, Nanopores: A journey towards DNA sequencing. Phys Life Rev. Jun. 2012;9(2):125-58. doi:10.1016/j.plrev.2012.05.010. Epub May 18, 2012.
Welford et al., The Selectivity and Inhibition of AlkB. J. Biol. Chem. Mar. 21, 2003;278(12):10157-161.
Wendell et al., Translocation of double-stranded DNA through membrane-adapted phi29 motor protein nanopores. Nat Nanotechnol. 2009;4(11):765-772. doi:10.1038/nnano.2009.259.
White et al., Single Ion-Channel Recordings Using Glass Nanopore Membranes. J Am Chem Soc. 2007;129:11766-775.
Wolfe et al., Catalyzing the translocation of polypeptides through attractive interactions. J Am Chem Soc. Nov. 14, 2007;129(45):14034-41. Epub Oct. 19, 2007.
Wong et al., Polymer capture by electro-osmotic flow of oppositely charged nanopores. J Chem Phys. Apr. 28, 2007;126(16):164903.
Wu et al., Protein nanopores with covalently attached molecular adapters. J Am Chem Soc. Dec. 26, 2007;129(51):16142-8. Epub Nov. 30, 2007.
Yoo et al., Glucose Biosensors: An Overview of Use in Clinical Practice. Sensores. May 4, 2010;10:4558-4576.
Zernia et al., Current Blockades of Proteins inside Nanopores for Real-Time Metabolome Analysis. ACS Nano. Feb. 25, 2020; 14(2): 2296-2307. EPub Jan. 31, 2020. doi: 10.1021/acsnano.9b09434.
Zernia et al., Current Blockades of Proteins inside Nanopores for Real-Time Metabolome Analysis. ACS Nano. Feb. 25, 2020; 14(Supplemental Information). EPub Jan. 31, 2020. doi: 10.1021/acsnano.9b09434. 19 pages.
Zhou et al., Ion Channel Probes for Scanning Ion Conductance Microscopy. Langmuir. Nov. 25, 2014;30:15351-355.
[No Author Listed] NCBI Genbank Accession No. ABV05494. Jan. 31, 2014, 1 page.
[No Author Listed] Nextera™ DNA Sample Preparation Kits (Illumina) Oct. 2011. (2 pages).
[No Author Listed] Oxford Nanopore "Product" brochure (2020) https://nanoporetech.com/sites/default/files/s3/literature/product-brochure.Pdf (36 pages).
[No Author Listed] Protein Databank entries of AlphaFold structure prediction for POAE98 and POA202, 2 pages.
[No Author Listed] Uniprot Accession No. POAE98 and POA202 search results, last accessed Mar. 29, 2022. 4 pages.
[No Author Listed] UniProt, "SubName: Full=Curli production assembly/transport component {ECO:0000313:EMBL:CTR43957.1};", XP002783536, retrieved from EBI accession No. UNIPROT:A0A0K3UZP3, Nov. 11, 2015.
[No Author Listed] UniprotKB Accession No. N2DXIO, Jun. 26, 2013, 1 page.
Afonine et al., Real-space refinement in PHENIX for cryo-EM and crystallography. Acta Crystallogr D Struct Biol. 2018;74(Pt 6):531-544. doi:10.1107/S2059798318006551.
Altschul et al. Basic local alignment search tool. J Mol Biol. Oct. 5, 1990;215(3):403-10. doi: 10.1016/S0022-2836(05)80360-2.
Altschul, A protein alignment scoring system sensitive at all evolutionary distances. J Mol Evol. Mar. 1993;36(3):290-300. doi: 10.1007/BF00160485.
Ayub et al., Engineered transmembrane pores. Curr Opin Chem Biol. 2016;34:117-126. doi:10.1016/j.cbpa.2016.08.005. Author Manuscript, 16 pages.
Boersma et al., Continuous stochastic detection of amino acid enantiomers with a protein nanopore. Angew Chem Int Ed Engl. Sep. 17, 2012;51(38):9606-9. doi: 10.1002/anie.201205687. Epub Aug. 29, 2012.
Brown et al., Tools for macromolecular model building and refinement into electron cryo-microscopy reconstructions. Acta Crystallogr D Biol Crystallogr. 2015;71(Pt 1):136-153. doi:10.1107/S1399004714021683.
Burton et al., ClpX-mediated remodeling of mu transpososomes: selective unfolding of subunits destabilizes the entire complex. Mol Cell. Aug. 2001;8(2):449-54. doi: 10.1016/s1097-2765(01)00307-0.
Caruccio, Preparation of next-generation sequencing libraries using Nextera™ technology: simultaneous DNA fragmentation and adaptor tagging by in vitro transposition. Methods Mol Biol. 2011;733:241-55. doi: 10.1007/978-1-61779-089-8_17.
Chapman et al., Role of *Escherichia coli* curli operons in directing amyloid fiber formation. Science. 2002;295(5556):851-855. doi:10.1126/science.1067484. Author Manuscript, 9 pages.
Chin et al., Addition of a photocrosslinking amino acid to the genetic code of *Escherichia coli*. Proc Natl Acad Sci U S A. Aug. 20, 2002;99(17):11020-4. doi: 10.1073/pnas.172226299. Epub Aug. 1, 2002.
De Vlaminck et al., Mechanism of homology recognition in DNA recombination from dual-molecule experiments. Mol Cell. Jun. 8, 2012;46(5):616-24. doi: 10.1016/j.molcel.2012.03.029. Epub May 3, 2012.
Devereux et al., A comprehensive set of sequence analysis programs for the VAX. Nucleic Acids Res. Jan. 11, 1984;12(1 Pt 1):387-95. doi: 10.1093/nar/12.1part1.387.
Epst Ein, Assembly, Spatial Distribution, and Secretion Activity of the Curlin Secretion Lipoprotein, CsgG. Dissertation. The University of Michigan. 2008. 167 pages.
Fiume et al., Savant: genome browser for high-throughput sequencing data. Bioinformatics. Aug. 15, 2010;26(16):1938-44. doi: 10.1093/bioinformatics/btq332. Epub Jun. 20, 2010.
Fleckenstein et al., "UPI0002CA1AFE" Uniprot Accession No. https://www.uniprot.org/uniparc/UPI0002CA1AFE, Jun. 26, 2013 (Jun. 26, 2013).
Gibson et al., AgfC and AgfE facilitate extracellular thin aggregative fimbriae synthesis in Salmonella enteritidis. Microbiology. Apr. 2007;153(Pt 4):1131-1140. doi: 10.1099/mic.0.2006/000935-0.
Goedhart et al., Quantitative co-expression of proteins at the single cell level—application to a multimeric FRET sensor. PLoS One. 2011;6(11):e27321. doi: 10.1371/journal.pone.0027321. Epub Nov. 17, 2011.
Goryshin et al., Tn5 in vitro transposition. J Biol Chem. Mar. 27, 1998;273(13):7367-74. doi: 10.1074/jbc.273.13.7367.
Goyal et al., Crystallization and preliminary X-ray crystallographic analysis of the curli transporter CsgG. Acta Crystallographica Section F: Structural Biology and Crystallization Communications. Dec. 1, 2013;69(12):1349-53.
Guo et al., Nanopore sensor for copper ion detection using a polyamine decorated β-cyclodextrin as the recognition element. RSC Adv. 2017;7:15315. doi: 10.1039/c7ra00454k. 6 pages.
Hammar et al., Expression of two csg operons is required for production of fibronectin- and congo red-binding curli polymers in *Escherichia coli* K-12. Mol Microbiol. Nov. 1995;18(4):661-70. doi: 10.1111/j.1365-2958.1995.mmi_18040661.x.
Haque et al., DNA-associated click chemistry. Science China Chemistry. Feb. 2014;57(2):215-231. doi:10.1007/s11426-013-5035-1.
Heng et al., Sizing DNA using a nanometer-diameter pore. Biophys J. Oct. 2004;87(4):2905-11. doi: 10.1529/biophysi.104.041814. Epub Aug. 23, 2004.
Higgins et al., DNA-joining enzymes: a review. Methods Enzymol. 1979;68:50-71. doi: 10.1016/0076-6879(79)68006-0.
Jain et al., The Oxford Nanopore MinION: delivery of nanopore sequencing to the genomics community. Genome Biol. Nov. 25, 2016;17(1):239. doi: 10.1186/s13059-016-1103-0. Erratum in: Genome Biol. Dec. 13, 2016; 17 (1):256.
Juncker et al., Prediction of lipoprotein signal peptides in Gram-negative bacteria. Protein Sci. 2003; 12(8):1652-1662. doi:10.1110/ps.0303703.
Kanaan et al., UPF1-like helicase grip on nucleic acids dictates processivity. Nat Commun. Sep. 14, 2018;9(1):3752. doi: 10.1038/s41467-018-06313-y.
Kimanius et al., Accelerated cryo-EM structure determination with parallelisation using GPUs in RELION-2. Elife. 2016;5:e18722. Published Nov. 15, 2016. doi:10.7554/eLife.18722. 21 pages.

(56) References Cited

OTHER PUBLICATIONS

Klenchin et al., Phosphate coordination and movement of DNA in the Tn5 synaptic complex: role of the (R)YREK motif. Nucleic Acids Res. Oct. 2008;36(18):5855-62. doi: 10.1093/nar/gkn577. Epub Sep. 12, 2008.
Le et al., Thermostable DNA ligase-mediated PCR production of circular plasmid (PPCP) and its application in directed evolution via in situ error-prone PCR. DNA Res. Aug. 2013;20(4):375-82. doi: 10.1093/dnares/dst016. Epub Apr. 30, 2013.
Li et al., ChIA-PET tool for comprehensive chromatin interaction analysis with paired-end tag sequencing. Genome Biol. 2010;11(2):R22. doi: 10.1186/GB-2010-11-2-r22. Epub Feb. 25, 2010.
Li, Minimap2: pairwise alignment for nucleotide sequences. Bioinformatics. 2018;34(18):3094-3100. doi:10.1093/bioinformatics/bty191.
Loferer et al., Availability of the fibre subunit CsgA and the nucleator protein CsgB during assembly of fibronectin-binding curli is limited by the intracellular concentration of the novel lipoprotein CsgG. Mol Microbiol. 1997;26(1):11-23. doi: 10.1046/j.1365-2958.1997.5231883.x.
Lovett, The DNA Exonucleases of *Escherichia coli*. EcoSal Plus. Dec. 2011;4(2):10.1128/ecosalplus.4.4.7. doi: 10.1128/ecosalplus.4.4.7. Author Manuscript, 45 pages.
Lu et al., Expression, purification and structural analysis of csgF gene of curli systems from *Escherichia coli* CFT073. Microbiol China. 2016, 43(9):2063-2071. doi: 10.13344/j.microbiol.china.150752.
Ludtke, Single-Particle Refinement and Variability Analysis in EMAN2.1. Methods Enzymol. 2016;579:159-89. doi: 10.1016/bs.mie.2016.05.001. Epub Jul. 1, 2016.
Nivala et al., Unfoldase-mediated protein translocation through an α-hemolysin nanopore. Nat Biotechnol. Mar. 2013;31(3):247-50. doi: 10.1038/nbt.2503. Epub Feb. 3, 2013. Author Manuscript, 10 pages.
Notice of Opposition for European Patent No. EP3097210 dated Aug. 12, 2019.
Peabody et al., Type II protein secretion and its relationship to bacterial type IV pili and archaeal flagella. Microbiology. Nov. 2003;149(Pt 11):3051-3072. doi: 10.1099/mic.0.26364-0.
Pud et al., Mechanical Trapping of DNA in a Double-Nanopore System. Nano Lett. 2016;16(12):8021-8028. doi:10.1021/acs.nanolett.6b04642. Author Manuscript, 17 pages.
Reznikoff, Tn5 as a model for understanding DNA transposition. Mol Microbiol. Mar. 2003;47(5):1199-206. doi: 10.1046/j.1365-2958.2003.03382.x.
Rhee et al., Comprehensive genome-wide protein-DNA interactions detected at single-nucleotide resolution. Cell. Dec. 9, 2011;147(6):1408-19. doi: 10.1016/j.cell.2011.11.013.
Rohou et al., CTFFIND4: Fast and accurate defocus estimation from electron micrographs. J Struct Biol. Nov. 2015;192(2):216-21. doi: 10.1016/j.jsb.2015.08.008. Epub Aug. 13, 2015.
Scheres, Relion: implementation of a Bayesian approach to cryo-EM structure determination. J Struct Biol. Dec. 2012;180(3):519-30. doi: 10.1016/j.jsb.2012.09.006. Epub Sep. 19, 2012.
Shelbourne et al., Fast copper-free click DNA ligation by the ring-strain promoted alkyne-azide cycloaddition reaction. Chem Commun (Camb). Jun. 14, 2011;47(22):6257-9. doi: 10.1039/c1cc10743g. Epub May 6, 2011.
Sivanathan et al., Generating extracellular amyloid aggregates using *E. coli* cells. Genes Dev. Dec. 1, 2012;26(23):2659-67. doi: 10.1101/gad.205310.112. Epub Nov. 19, 2012.
Sternberg et al., DNA interrogation by the CRISPR RNA-guided endonuclease Cas9. Nature. Mar. 6, 2014;507(7490):62-7. doi: 10.1038/nature13011. Epub Jan. 29, 2014. Author Manuscript, 16 pages.
Taylor et al., New insight into the molecular control of bacterial functional amyloids. Front Cell Infect Microbiol. Apr. 8, 2015;5:33. doi: 10.3389/fcimb.2015.00033.
Third Party Observation for Application No. EP 15759438.3, mailed Oct. 20, 2022. 11 pages.
Third Party Observation for Application No. EP 15759438.3, mailed Sep. 17, 2021. 21 pages.
Third Party Observation for Application No. EP 18734933.7, mailed Apr. 11, 2022. 14 pages.
Third Party Observation for European Application No. EP18734933.7, mailed Sep. 27, 2021.
Tuteja et al., Helicases as molecular motors: An insight. Physica A. Dec. 1, 2006;372(1):70-83. doi: 10.1016/j.physa.2006.05.014. Epub Jun. 5, 2006.
Van Der Verren et al., A dual-constriction biological nanopore resolves homonucleotide sequences with high fidelity. Nat Biotechnol. Dec. 2020;38(12):1415-1420. doi: 10.1038/s41587-020-0570-8. Epub Jul. 6, 2020. Author Manuscript, 25 pages.
Van Gerven et al., Bacterial amyloid formation: structural insights into curli biogenesis. Trends Microbiol. Nov. 2015; 23(11): 693-706. EPub Oct. 1, 2015. doi: 10.1016/j.tim.2015.07.010. Author Manuscript, 24 pages.
Wang et al., Engineering of protein nanopores for sequencing, chemical or protein sensing and disease diagnosis. Curr Opin Biotechnol. Jun. 2018;51:80-89. doi: 10.1016/j.copbio.2017.11.006. Epub Dec. 10, 2017.
Wang et al., Measuring and modeling the kinetics of individual DNA-DNA polymerase complexes on a nanopore. ACS Nano. May 28, 2013;7(5):3876-86. doi: 10.1021/nn401180j. Epub Apr. 16, 2013.
Wang et al., Protein engineering with non-natural amino acids. InTechOpen; Feb. 24, 2012. DOI: 10.5772/28719.
Wiedmann et al., Ligase chain reaction (LCR)—overview and applications. PCR Methods Appl. Feb. 1994;3(4):S51-64. doi: 10.1101/gr.3.4.s51.
Wilkinson et al., Bacterial DNA ligases. Mol Microbiol. Jun. 2001;40(6):1241-8. doi: 10.1046/j.1365-2958.2001.02479.x.
Wu et al., Sequence-specific capture of protein-DNA complexes for mass spectrometric protein identification. PLoS One. 2011;6(10):e26217. doi: 10.1371/journal.pone.0026217. Epub Oct. 20, 2011.
Wu et al., Single-molecule detection of nitrogen mustards by covalent reaction within a protein nanopore. J Am Chem Soc. May 28, 2008;130(21):6813-9. doi: 10.1021/ja8004607. Epub Apr. 30, 2008.
Yen et al., SWR-C and INO80 chromatin remodelers recognize nucleosome-free regions near +1 nucleosomes. Cell. Sep. 12, 2013; 154(6):1246-56. doi: 10.1016/j.cell.2013.08.043.
Zheng et al., MotionCor2: anisotropic correction of beam-induced motion for improved cryo-electron microscopy. Nat Methods. Apr. 2017; 14(4):331-332. doi: 10.1038/nmeth.4193. Epub Feb. 27, 2017.

* cited by examiner

Run 3

Run 2

Run 1

Run 1
Run 2
Run 3
0-10 ns
10-20 ns
20-30 ns
30-40 ns
N180
D202
K199
T2
R216
K255
0
100
200
300
400
1000
2000
3000
4000
5000
6000

0-10 ns
10-20 ns
20-30 ns
30-40 ns
Run 1
Run 2
Run 3
W195
D198
R207
E258
Y350
Y438
D202
Y197
K199
F223
D185
Y304
9000
6000
3000
0
100
200
300
400

(A)
250
200
150
100
50
0
3550 3600 3650 3700 3750 3800 3850 3900
(B)
250
200
150
100
50
0
3510 3515 3520 3525 3530 3535
(C)
60
50
40
30
3512.4 3512.6 3512.8 3513 3513.2 3513.4 3513.5

(A)
250
200
150
100
50
0
200 210 220 230 240 250 260 270 280 290 300 310
(B)
200
150
100
50
200 205 210 215 220 225
(C)
70
60
50
40
30
206.5 207 207.5 208 208.5 209 209.5 run 3 run 2 run 1

0-10 ns
10-20 ns
20-30 ns
30-40 ns
Run 1
Run 2
Run 3
E318
E268
R304
10000
8000
6000
4000
2000
0
100
200
300
400
500

A)

B)

METHOD OF IMPROVING THE MOVEMENT OF A TARGET POLYNUCLEOTIDE WITH RESPECT TO A TRANSMEMBRANE PORE

FIELD OF THE INVENTION

The invention relates to improving the movement of a target polynucleotide with respect to a transmembrane pore when the movement is controlled by a polynucleotide binding protein. The invention also relates to improved transmembrane pores and polynucleotide binding proteins.

BACKGROUND OF THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the strand sequencing method, a single polynucleotide strand is passed through the pore and the identities of the nucleotides are derived. Strand sequencing can involve the use of a polynucleotide binding protein to control the movement of the polynucleotide through the pore.

The different forms of Msp are porins from *Mycobacterium smegmatis*. MspA is a 157 kDa octameric porin from *Mycobacterium smegmatis*. Wild-type MspA does not interact with DNA in a manner that allows the DNA to be characterised or sequenced. The structure of MspA and the modifications required for it to interact with and characterise DNA have been well documented (Butler, 2007, Nanopore Analysis of Nucleic Acids, Doctor of Philosophy Dissertation, University of Washington; Gundlach, Proc Natl Acad Sci USA. 2010 Sep. 14; 107(37):16060-5. Epub 2010 Aug. 26; and International Application No. PCT/GB2012/050301 (published as WO/2012/107778).

SUMMARY OF THE INVENTION

The inventors have surprisingly demonstrated that polynucleotide binding protein-controlled movement of a target polynucleotide with respect to a transmembrane pore is improved by modifying a part of the transmembrane pore which interacts with the polynucleotide binding protein and/or a part of the polynucleotide binding protein which interacts with the transmembrane pore.

Accordingly, the invention provides a method of improving the movement of a target polynucleotide with respect to a transmembrane pore when the movement is controlled by a polynucleotide binding protein, comprising modifying a part of the transmembrane pore which interacts with the polynucleotide binding protein and/or a part of the polynucleotide binding protein which interacts with the transmembrane pore and thereby improving the movement of the target polynucleotide with respect to the transmembrane pore.

The invention also provides:

a method of moving a target polynucleotide with respect to a transmembrane pore using a polynucleotide binding protein, comprising a) providing a transmembrane pore and a polynucleotide binding protein in which a part of the transmembrane pore which interacts with the polynucleotide binding protein and/or a part of the polynucleotide binding protein which interacts with the transmembrane pore has been modified; and b) contacting the transmembrane pore and polynucleotide binding protein provided in a) with the target polynucleotide such that the protein controls the movement of the polynucleotide with respect to the transmembrane pore;

a method of characterising a target polynucleotide, comprising:

a) providing a transmembrane pore and a polynucleotide binding protein in which a part of the transmembrane pore which interacts with the polynucleotide binding protein and/or a part of the polynucleotide binding protein which interacts with the transmembrane pore has been modified;

b) contacting the transmembrane pore and polynucleotide binding protein provided in (a) with the target polynucleotide such that the protein controls the movement of the polynucleotide with respect to the transmembrane pore; and c) taking one or more measurements as the polynucleotide moves with respect to the transmembrane pore, wherein the measurements are indicative of one or more characteristics of the polynucleotide, and thereby characterising the target polynucleotide;

a transmembrane pore in which a part of the transmembrane pore which interacts with a polynucleotide binding protein has been modified;

a mutant Msp monomer comprising a variant of SEQ ID NO: 2 in which a part of the monomer which interacts with a polynucleotide binding protein has been modified;

a construct comprising two or more covalently attached MspA monomers, wherein at least one of the monomers is a mutant monomer of the invention;

a homo-oligomeric pore derived from Msp comprising identical mutant monomers of the invention or identical constructs of the invention;

a hetero-oligomeric pore derived from Msp comprising at least one mutant monomer of the invention or at least one construct of the invention;

a polynucleotide binding protein in which a part of the protein which interacts with a transmembrane pore has been modified;

a combination of a transmembrane pore and a polynucleotide binding protein in which a part of the transmembrane pore which interacts with the polynucleotide binding protein and/or a part of the polynucleotide binding protein which interacts with the transmembrane pore has been modified;

a kit for characterising a target polynucleotide comprising (a) a transmembrane pore of the invention and (b) the components of a membrane;

a kit for characterising a target polynucleotide comprising (a) a polynucleotide binding protein of the invention and (b) a polynucleotide adaptor to which the polynucleotide binding protein is optionally bound;

an apparatus for characterising target polynucleotides in a sample, comprising (a) a plurality of transmembrane pores of the invention or a plurality of combinations of the invention and (b) a plurality of membranes; and a method of characterising a target polynucleotide, comprising:

a) providing a transmembrane pore and a polymerase in which a part of the transmembrane pore which interacts with the polymerase and/or a part of the polymerase which interacts with the transmembrane pore has been modified;

b) contacting the target polynucleotide with the transmembrane pore and polymerase provided in a) and labelled nucleotides such that phosphate labelled species are sequentially added to the target polynucleotide by the polymerase, wherein the phosphate species contain a label specific for each nucleotide; and c) detecting the phosphate labelled species using the transmembrane pore and thereby characterising the polynucleotide.

E139K)8 (SEQ ID NO: 2 with mutations D56N/E59R/L88N/D90N/D91N/Q126R/D134R/E139K and deletion of the amino acids L74/G75/D118/L119). Sections B and C show zoomed in regions of current trace A.

Figure 12:
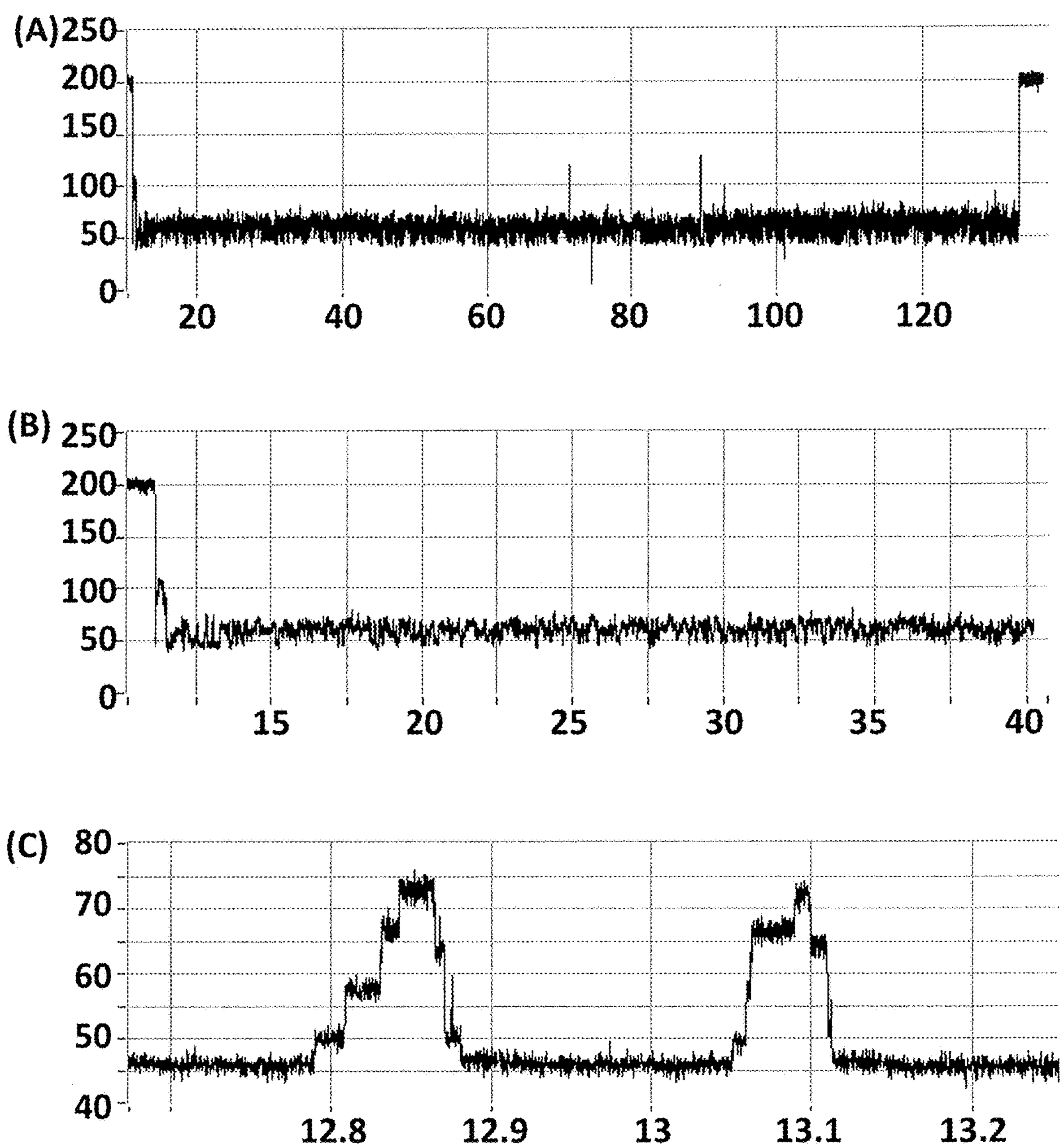

FIG. 12 shows example current traces (y-axis label=Current (pA), x-axis label=Time (s) for all three traces) of when a helicase (T4 Dda—E94C/C109A/C136A/A360C) controlled the translocation of the DNA construct X through the MspA nanopore MspA—((Del-L74/G75/D118/L119)D56Y/E59R/L88N/D90N/D91N/Q126R/D134R/E139K)8 (SEQ ID NO: 2 with mutations)D56Y/E59R/L88N/D90N/D91N/Q126R/D134R/E139K and deletion of the amino acids L74/G75/D118/L119). Sections B and C show zoomed in regions of current trace A.

Figure 13:
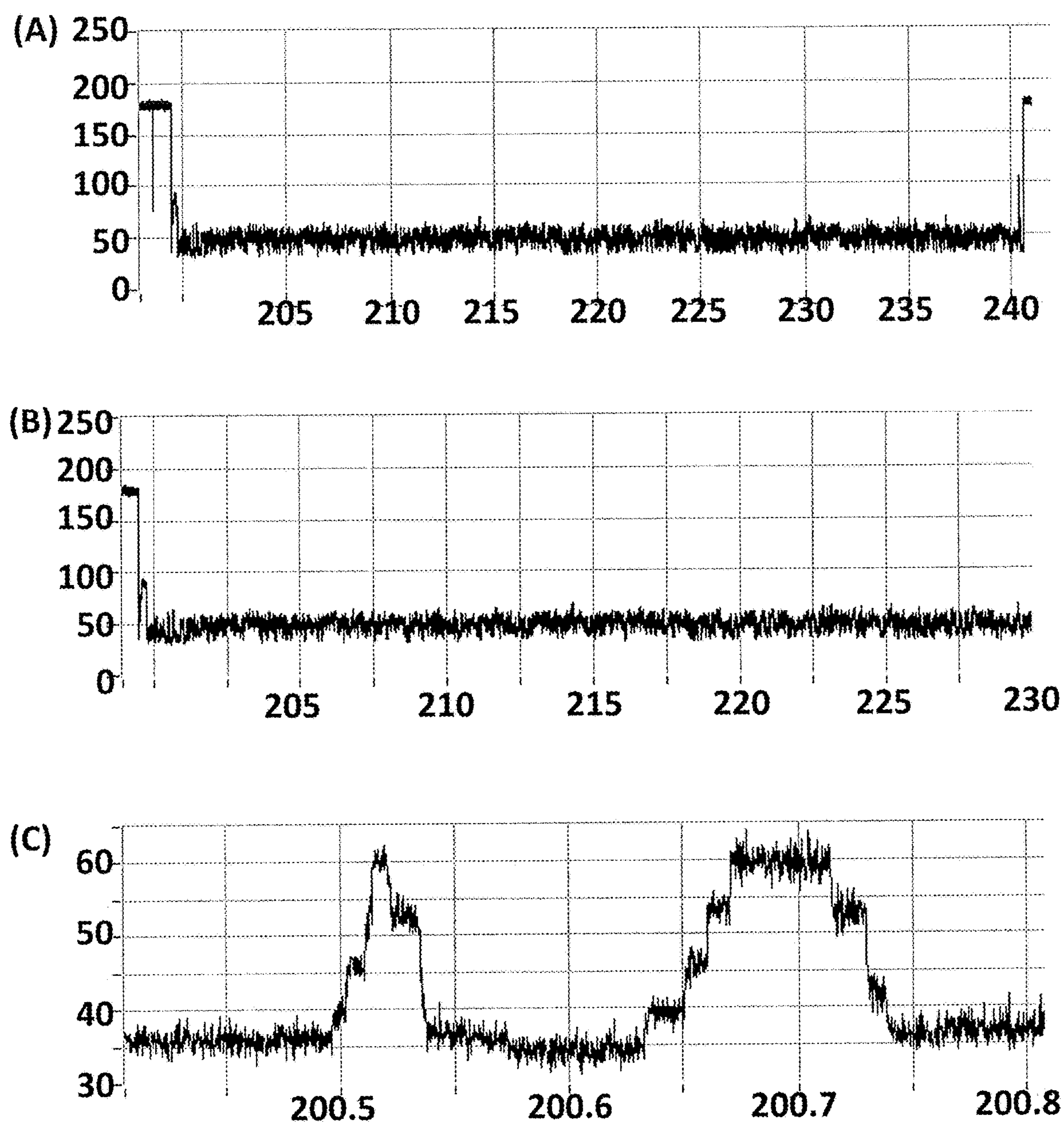

FIG. 13 shows example current traces (y-axis label=Current (pA), x-axis label=Time (s) for all three traces) of when a helicase (T4 Dda—E94C/C109A/C136A/A360C) controlled the translocation of the DNA construct X through the MspA nanopore MspA—((Del-L74/G75/D118/L119)D56N/E57D/E59R/L88N/D90N/D91N/Q126R/D134R/E139K)8 (SEQ ID NO: 2 with mutations D56N/E57D/E59R/L88N/D90N/D91N/Q126R/D134R/E139K and deletion of the amino acids L74/G75/D118/L119). Sections B and C show zoomed in regions of current trace A.

Figure 14:
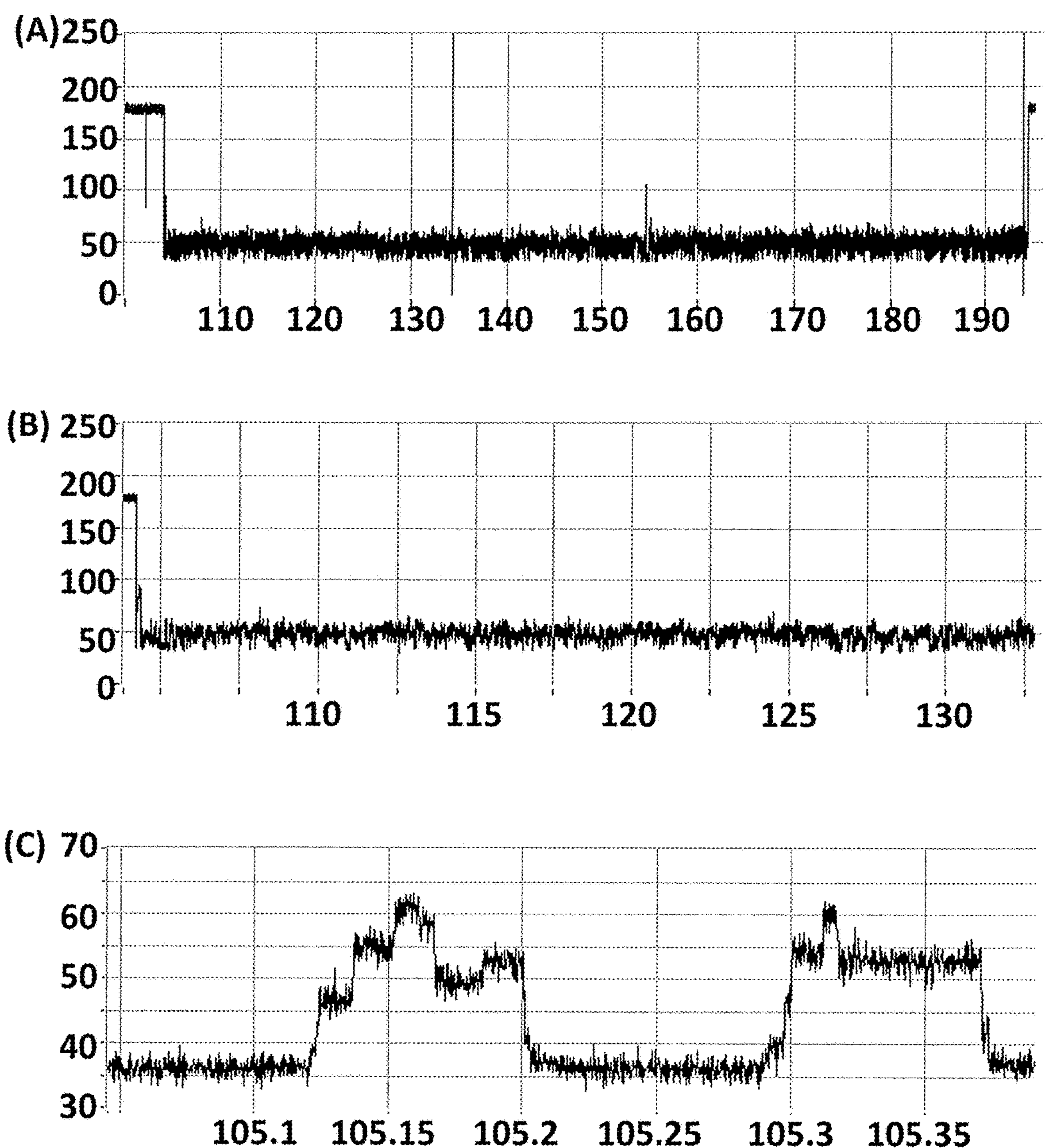

FIG. 14 shows example current traces (y-axis label=Current (pA), x-axis label=Time (s) for all three traces) of when a helicase (T4 Dda—E94C/C109A/C136A/A360C) controlled the translocation of the DNA construct X through the MspA nanopore MspA—((Del-L74/G75/D118/L119)D56N/E59T/L88N/D90N/D91N/Q126R/D134R/E139K)8 (SEQ ID NO: 2 with mutations D56N/E59T/L88N/D90N/D91N/Q126R/D134R/E139K and deletion of the amino acids L74/G75/D118/L119). Sections B and C show zoomed in regions of current trace A.

Figure 15:
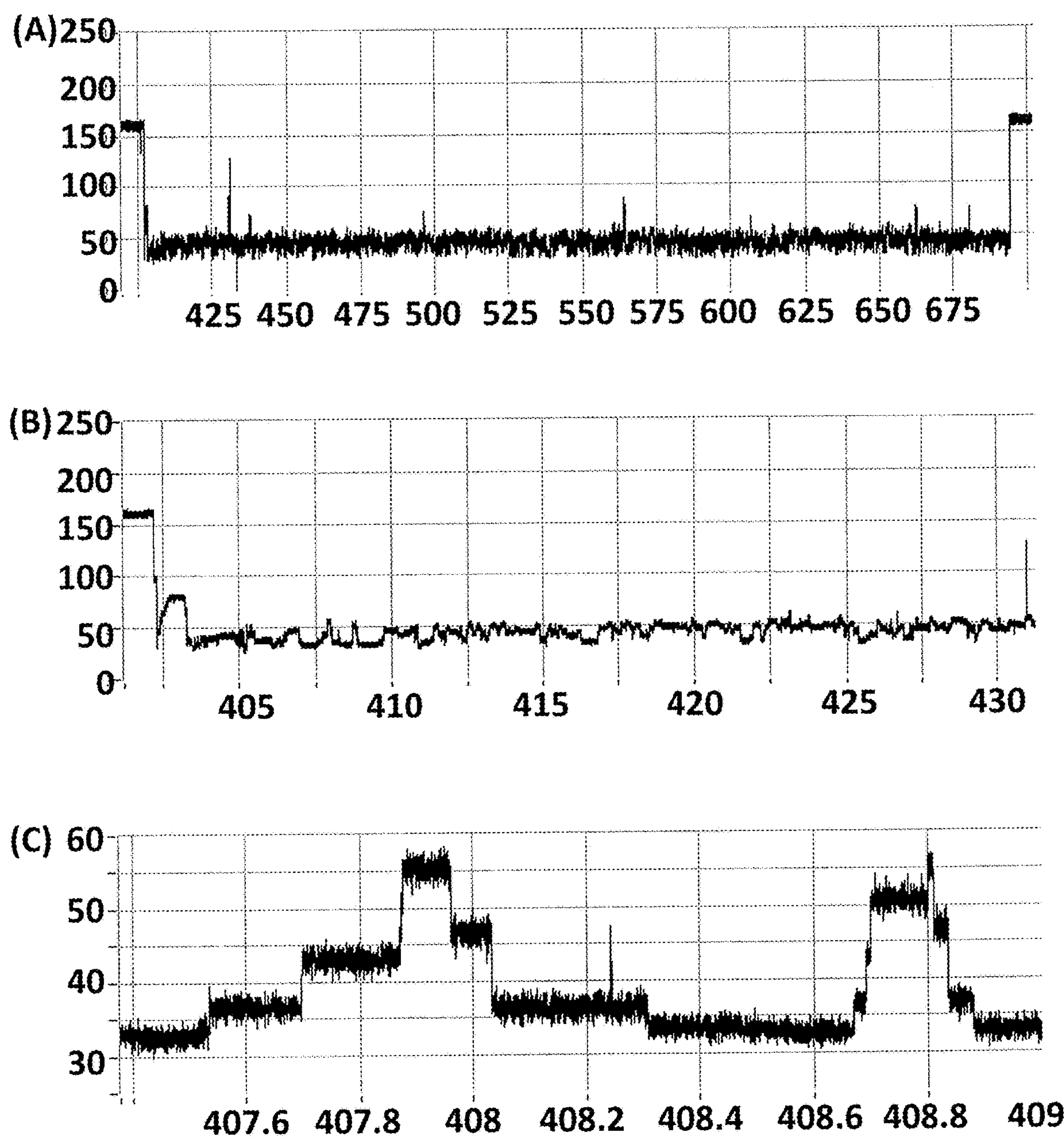

FIG. 15 shows example current traces (y-axis label=Current (pA), x-axis label=Time (s) for all three traces) of when a helicase (T4 Dda—E94C/C109A/C136A/A360C) controlled the translocation of the DNA construct X through the MspA nanopore MspA—((Del-L74/G75/D118/L119)D56N/E59Q/L88N/D90N/D91N/Q126R/D134R/E139K)8 (SEQ ID NO: 2 with mutations D56N/E59Q/L88N/D90N/D91N/Q126R/D134R/E139K and deletion of the amino acids L74/G75/D118/L119). Sections B and C show zoomed in regions of current trace A.

Figure 16:
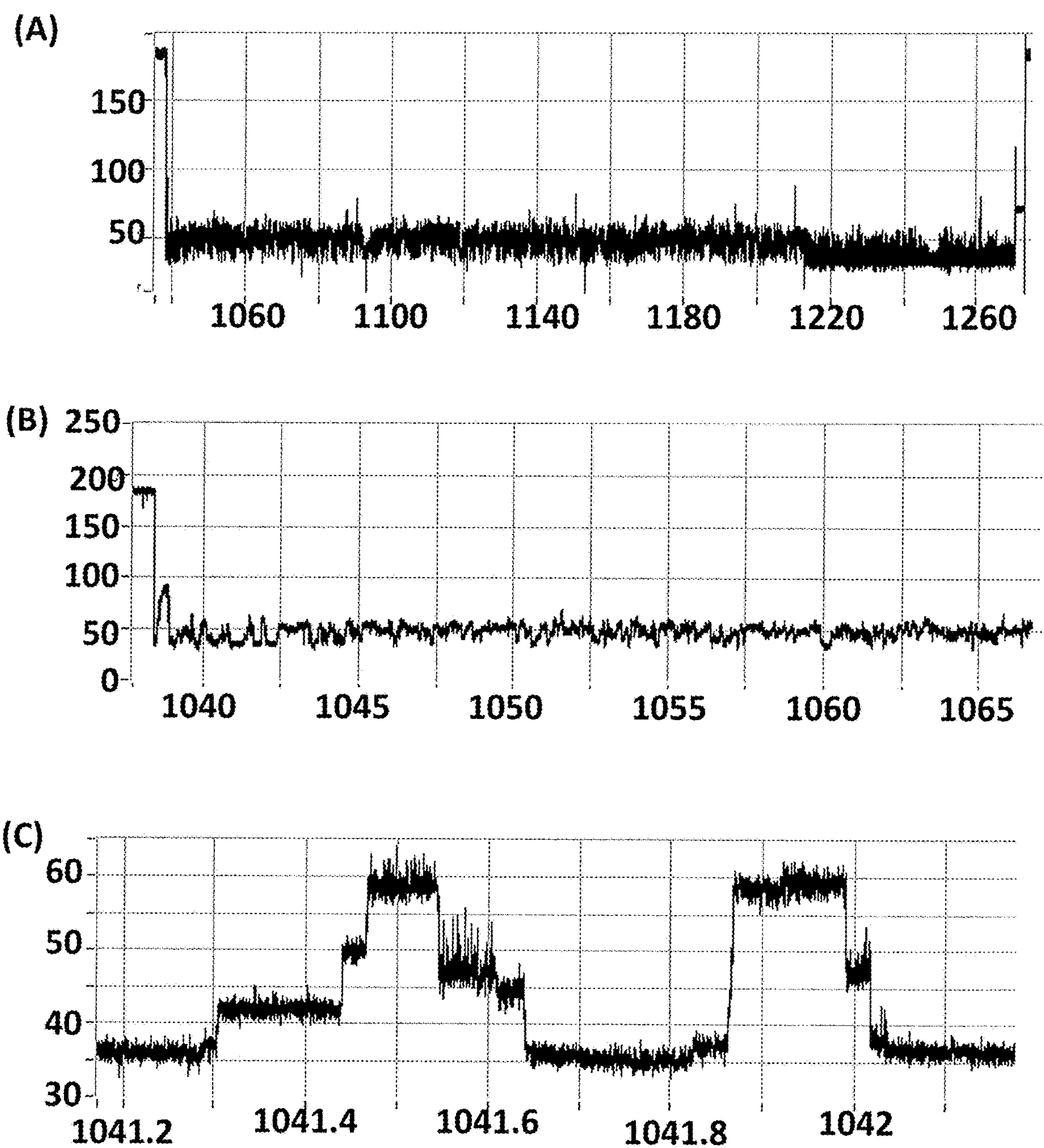

FIG. 16 shows example current traces (y-axis label=Current (pA), x-axis label=Time (s) for all three traces) of when a helicase (T4 Dda—E94C/C109A/C136A/A360C) controlled the translocation of the DNA construct X through the MspA nanopore MspA—((Del-L74/G75/D118/L119)E59F/L88N/D90N/D91N/Q126R/D134R/E139K)8 (SEQ ID NO: 2 with mutations E59F/L88N/D90N/D91N/Q126R/D134R/E139K and deletion of the amino acids L74/G75/D118/L119). Sections B and C show zoomed in regions of current trace A.

Figure 17:
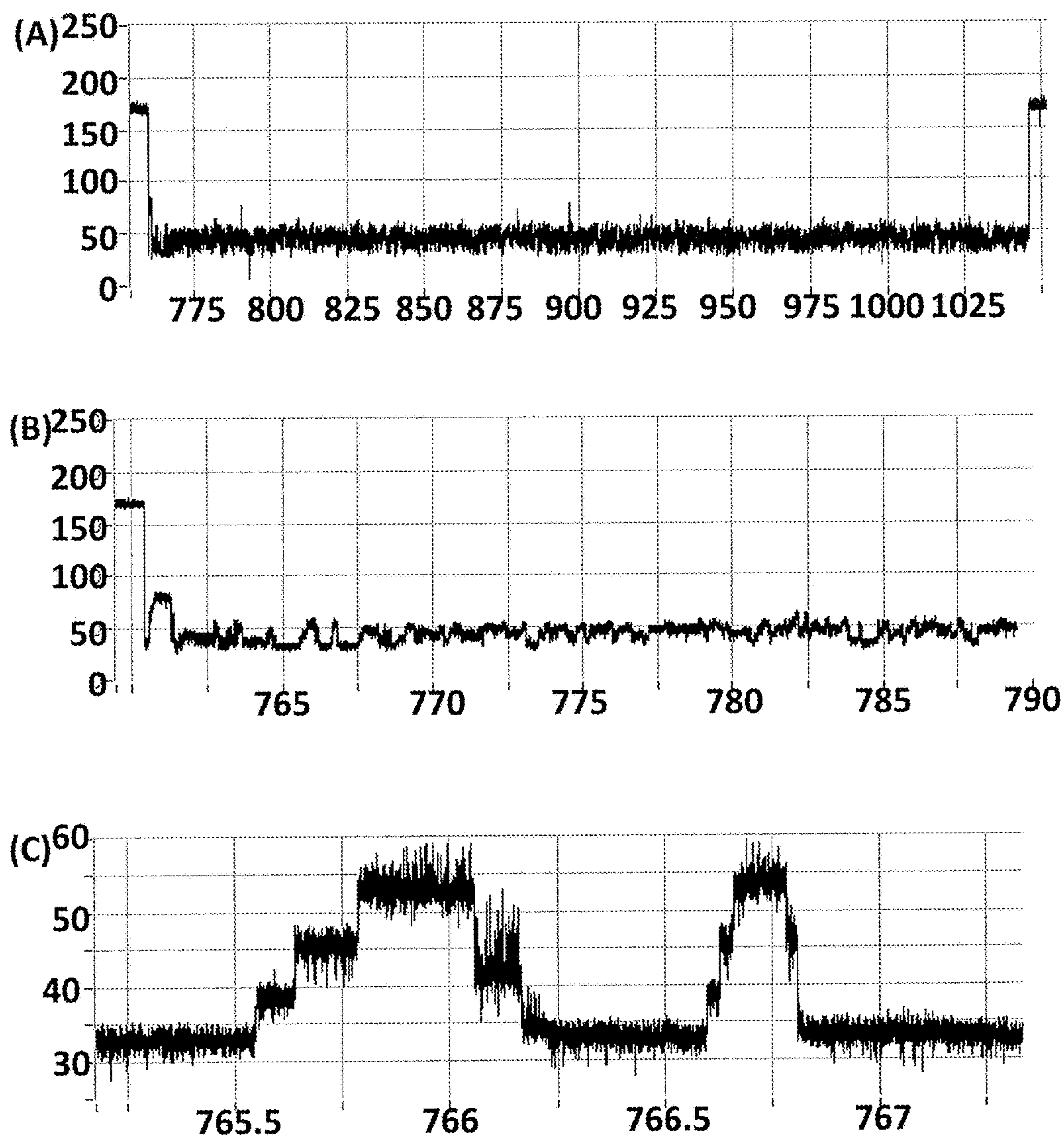

FIG. 17 shows example current traces (y-axis label=Current (pA), x-axis label=Time (s) for all three traces) of when a helicase (T4 Dda—E94C/C109A/C136A/A360C) controlled the translocation of the DNA construct X through the MspA nanopore MspA—((Del-L74/G75/D118/L119)D56N/E59F/L88N/D90N/D91N/Q126R/D134R/E139K)8 (SEQ ID NO: 2 with mutations D56N/E59F/L88N/D90N/D91N/Q126R/D134R/E139K and deletion of the amino acids L74/G75/D118/L119). Sections B and C show zoomed in regions of current trace A.

Figure 18:
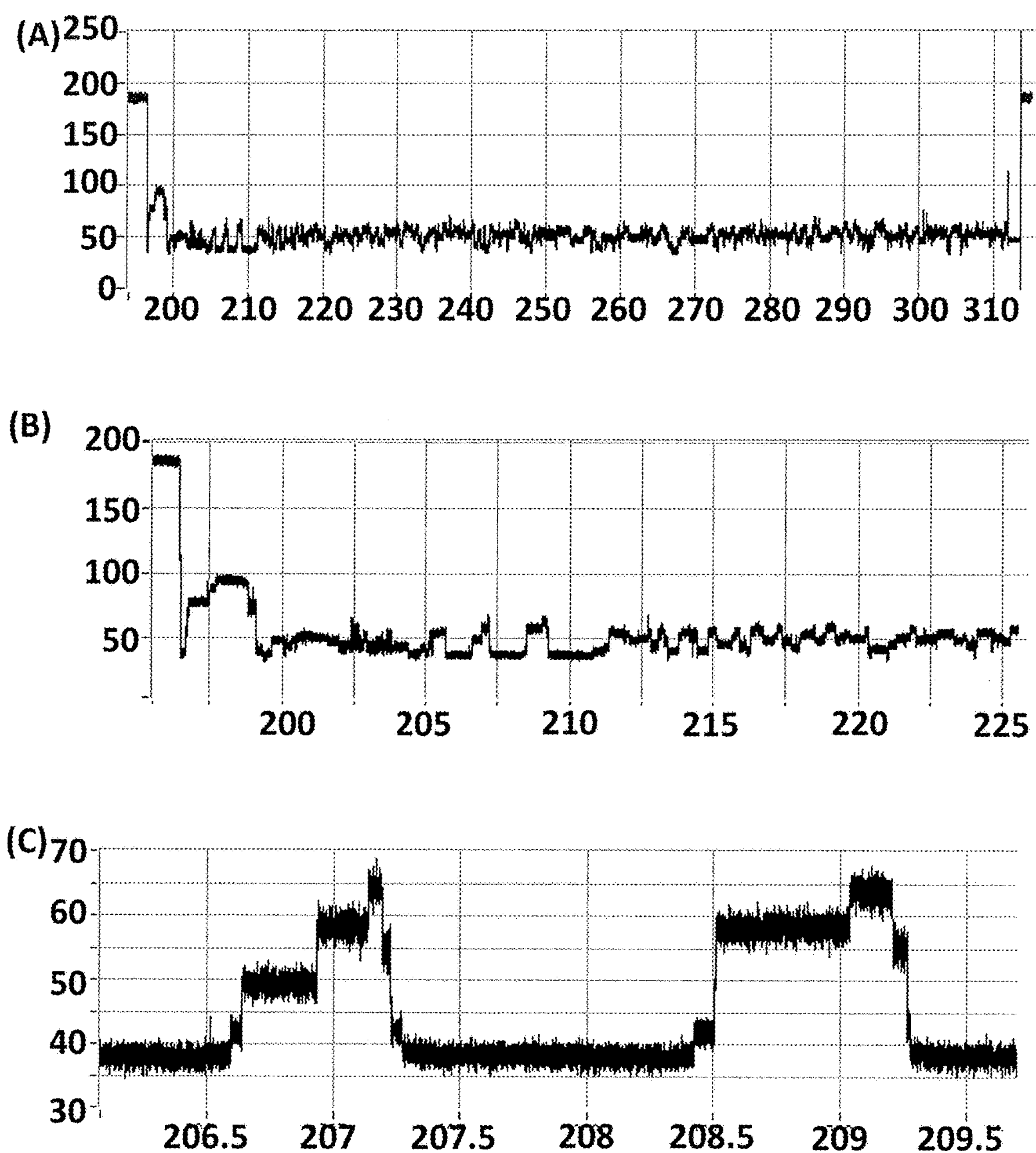

FIG. 18 shows example current traces (y-axis label=Current (pA), x-axis label=Time (s) for all three traces) of when a helicase (T4 Dda—E94C/C109A/C136A/A360C) controlled the translocation of the DNA construct X through the MspA nanopore MspA—((Del-L74/G75/D118/L119)D56F/E59R/L88N/D90N/D91N/Q126R/D134R/E139K)8 (SEQ ID NO: 2 with mutations D56F/E59R/L88N/D90N/D91N/Q126R/D134R/E139K and deletion of the amino acids L74/G75/D118/L119). Sections B and C show zoomed in regions of current trace A.

Figure 19:
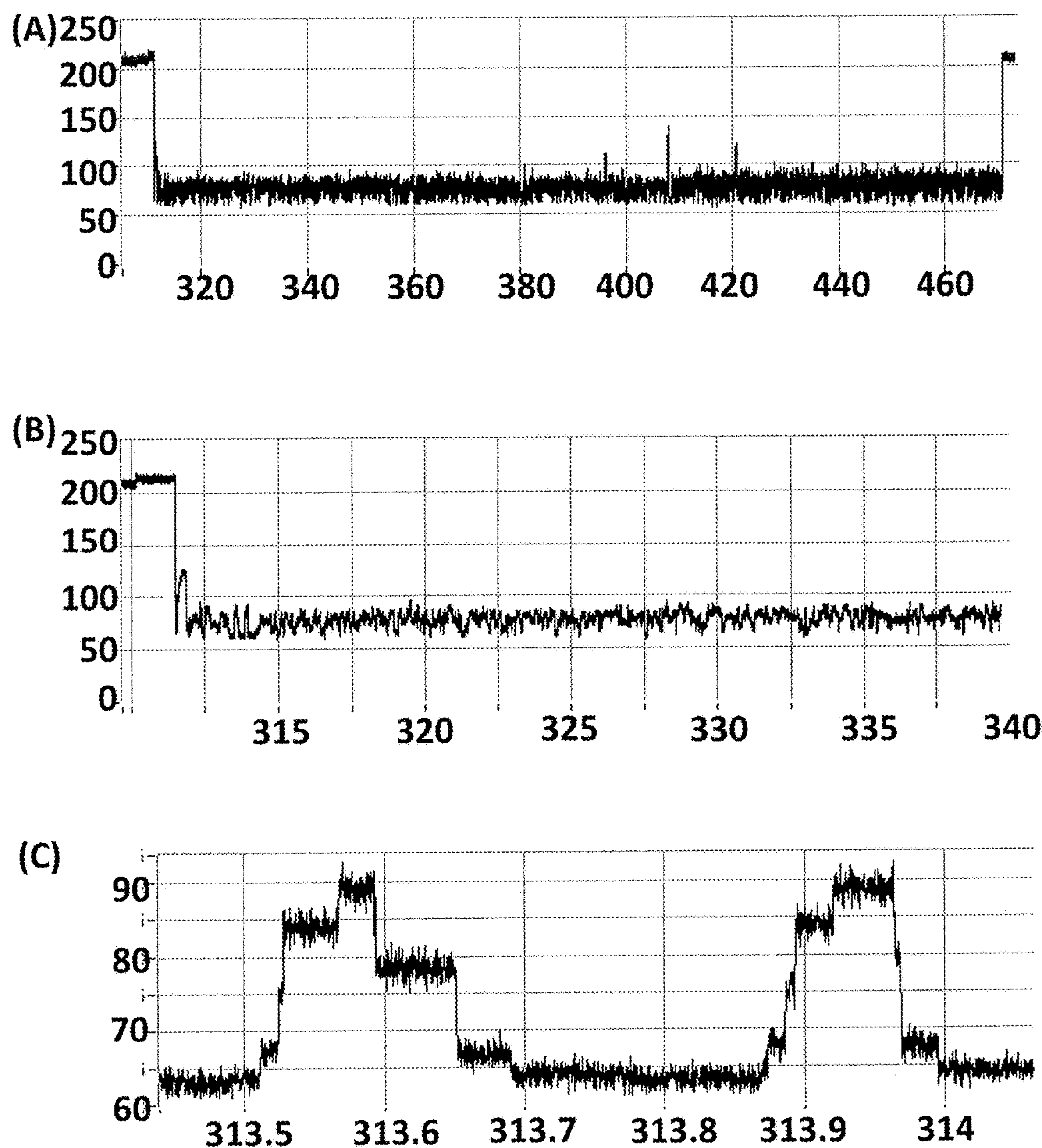

FIG. 19 shows example current traces (y-axis label=Current (pA), x-axis label=Time (s) for all three traces) of when a helicase (T4 Dda—E94C/C109A/C136A/A360C) controlled the translocation of the DNA construct X through the MspA nanopore MspA—((Del-L74/G75/D118/L119)D56N/E59R/L88N/D90N/D91N/Q126R/D134N/E139K)8 (SEQ ID NO: 2 with mutations D56N/E59R/L88N/D90N/D91N/Q126R/D134N/E139K and deletion of the amino acids L74/G75/D118/L119). Sections B and C show zoomed in regions of current trace A.

Figure 20:
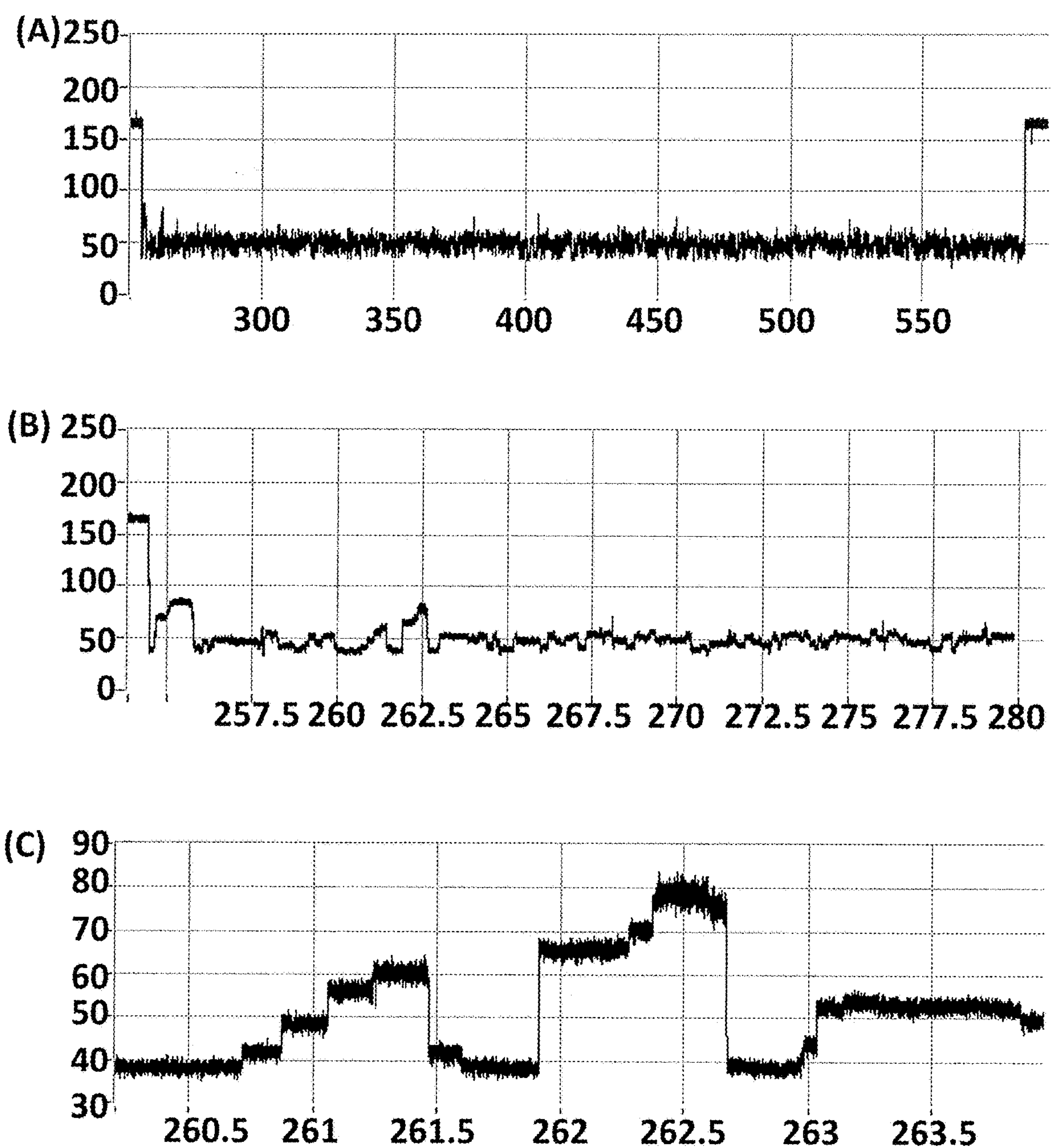

FIG. 20 shows example current traces (y-axis label=Current (pA), x-axis label=Time (s) for all three traces) of when a helicase (T4 Dda—E94C/C109A/C136A/A360C) controlled the translocation of the DNA construct X through the MspA nanopore MspA—((Del-L74/G75/D118/L119)D56N/E59W/L88N/D90N/D91N/Q126R/D134R/E139K)8 (SEQ ID NO: 2 with mutations D56N/E59W/L88N/D90N/D91N/Q126R/D134R/E139K and deletion of the amino acids L74/G75/D118/L119). Sections B and C show zoomed in regions of current trace A.

Figure 21:
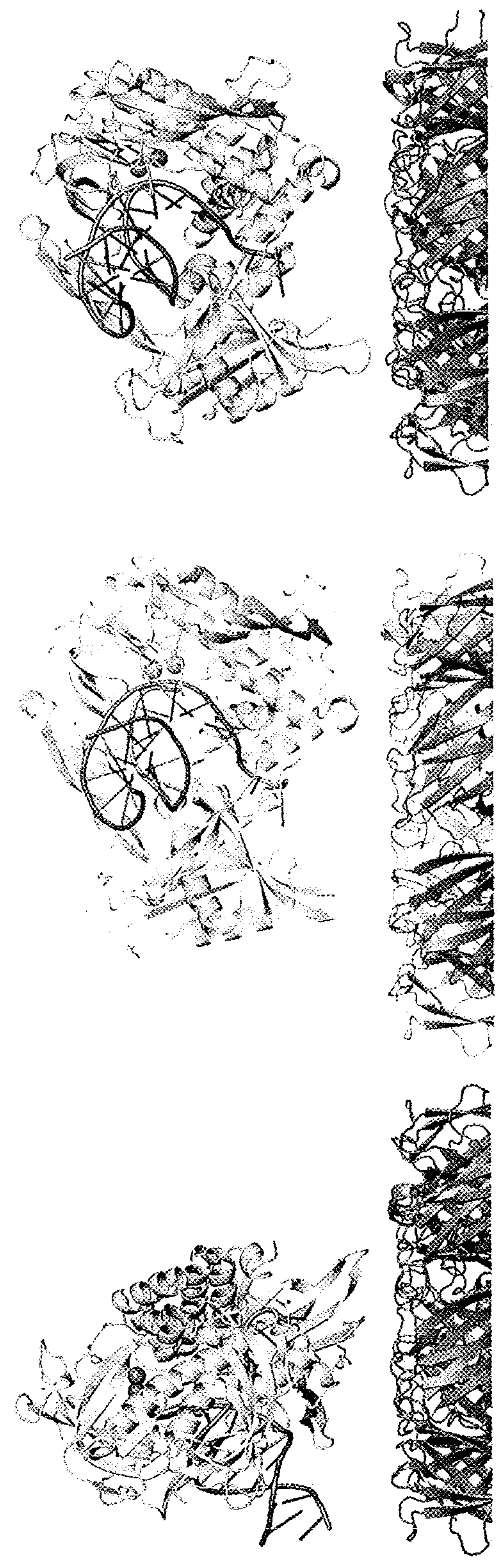

FIG. 21 shows the three different initial simulation orientations of Phi29 DNA polymerase-(D12A/D66A) (SEQ ID NO: 9 with mutations D12A/D66A) with respect to αHL—(E111N/K147N)8 (SEQ ID NO: 4). The difference between run 2 and run 3 was that both the enzyme and pore had different side chain conformations despite the pore and enzyme being in the same position. In run one the enzyme has been tilted slightly with respect to the nanopore.

Figure 22:
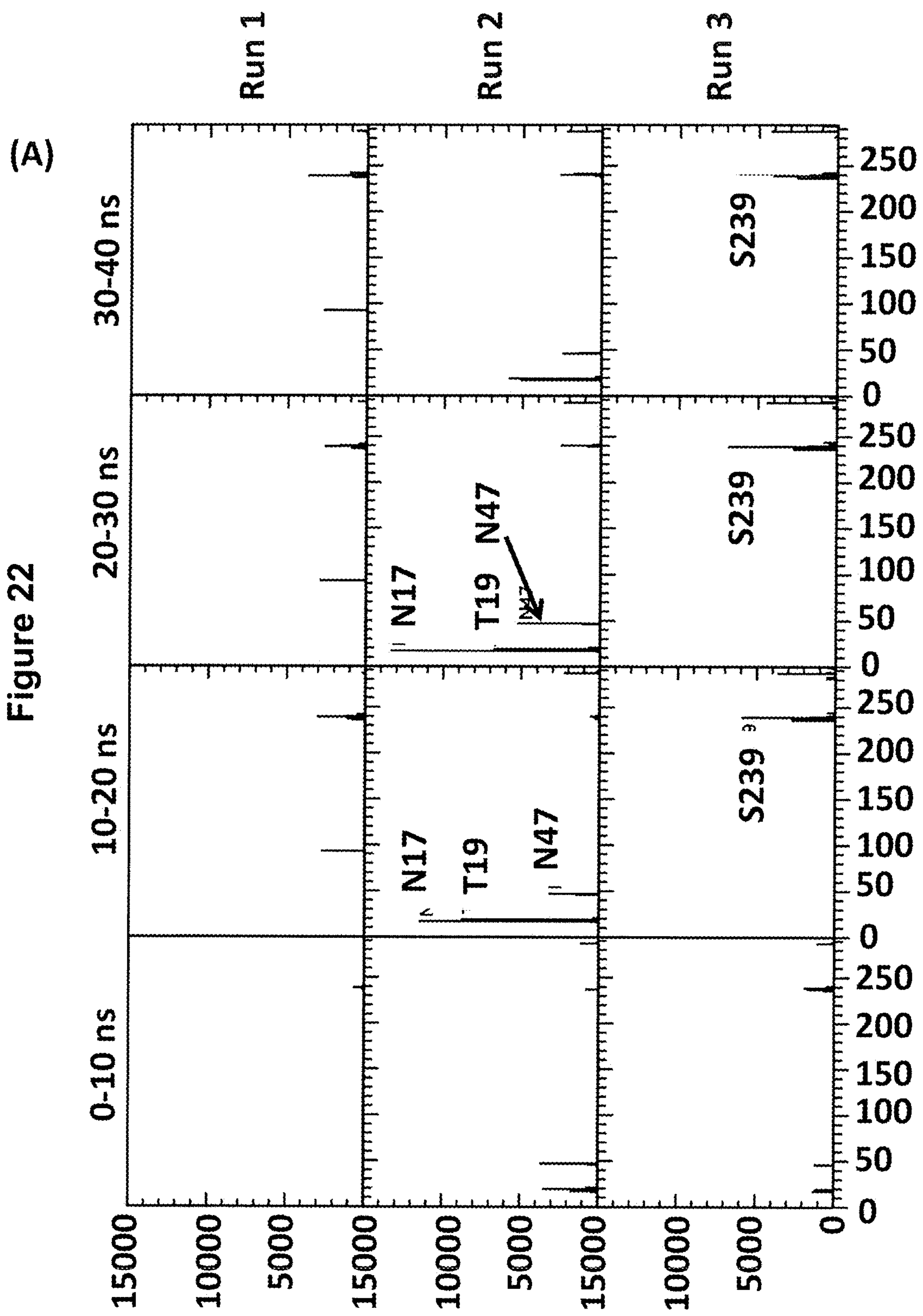

FIG. 22 shows a plot (y-axis label=number of pore/enzyme contacts, x-axis label=pore amino acid residue number) of the interaction points of the nanopore αHL—(E111N/K147N)8 with Phi29 DNA polymerase-(D12A/D66A). Each row of the plot shows the interaction points for the different enzyme/nanopore orientations e.g. runs 1-3.

Figure 23:
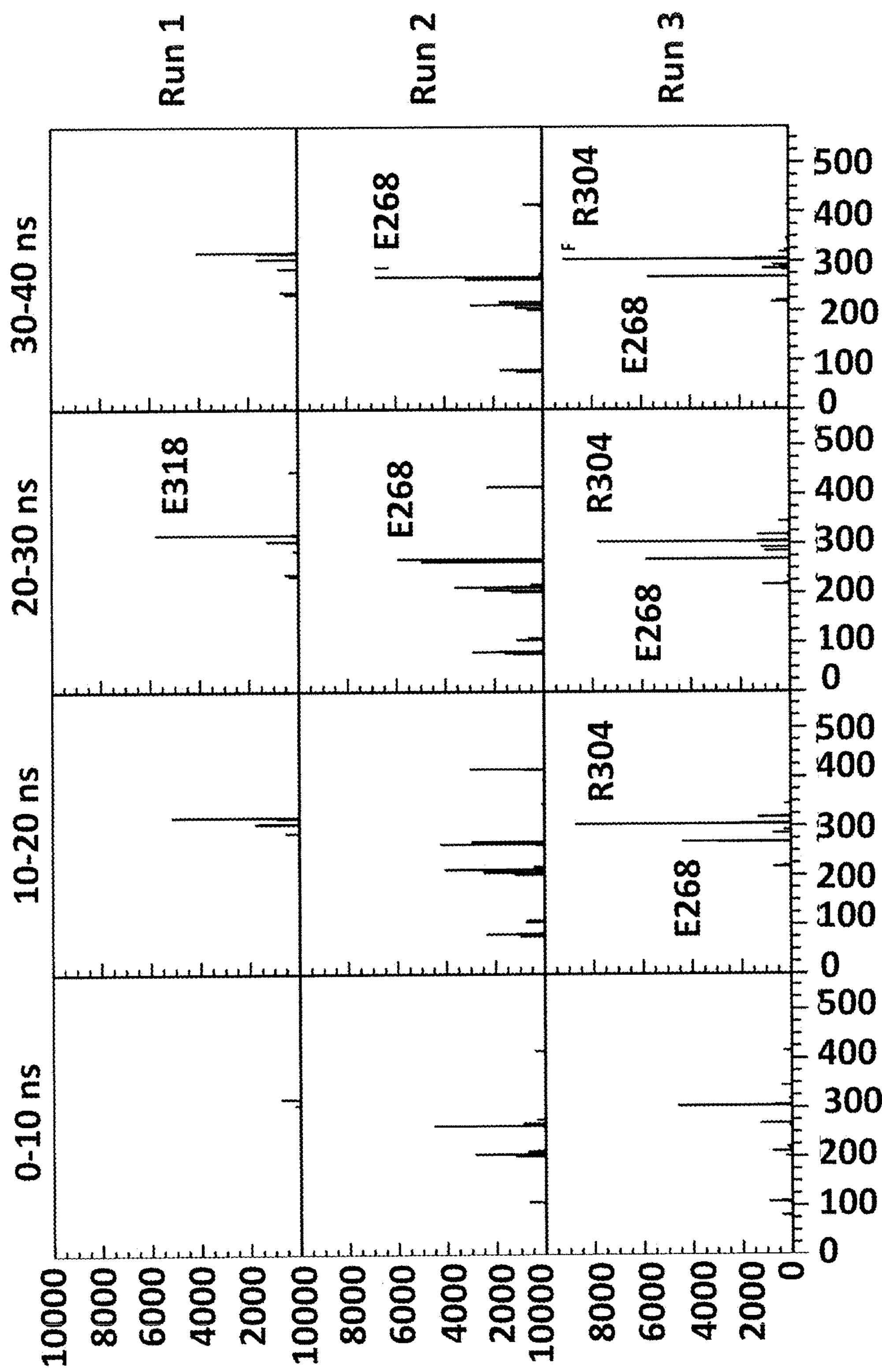

FIG. 23 shows a plot (y-axis label=number of pore/enzyme contacts, x-axis label=enzyme amino acid residue number) of the interaction points of the enzyme Phi29 DNA polymerase-(D12A/D66A) with αHL—(E111N/K147N)8. Each row of the plot shows the interaction points for the different enzyme/nanopore orientations e.g. runs 1-3.

Figure 24:
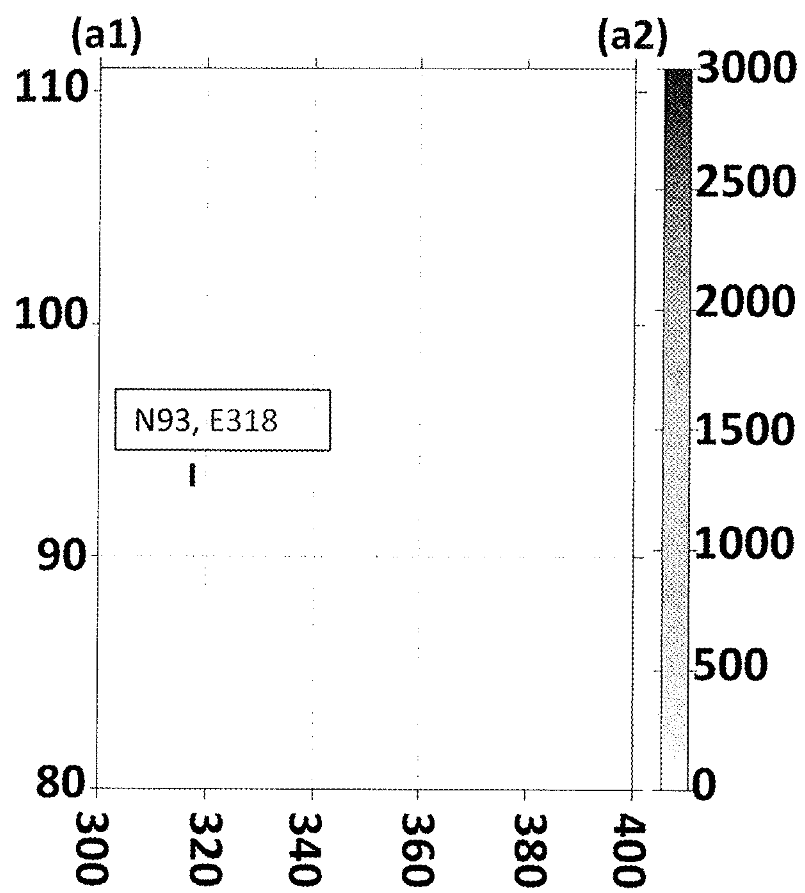

FIG. 24 shows a zoomed in region of a plot (y-axis label (a1)=pore amino acid residue number, y-axis label (a2)=number of pore/enzyme contacts, x-axis label=enzyme amino acid residue number) which shows which amino acids in the pore (αHL—(E111N/K147N)8) interact with particular amino acids in the enzyme (Phi29 DNA polymerase-(D12A/D66A)) from run 1. The grey bands in the plot indicate an interaction between amino acids. The darkness of the grey band corresponds to the number of interactions between enzyme/pore, with dark grey=many interactions and light grey=fewer interactions. The first amino acid in each box corresponds to the interacting amino acid in the αHL—(E111N/K147N)8 and the second amino acid corresponds to the interacting amino acids in Phi29 DNA polymerase-(D12A/D66A).

Figure 25:
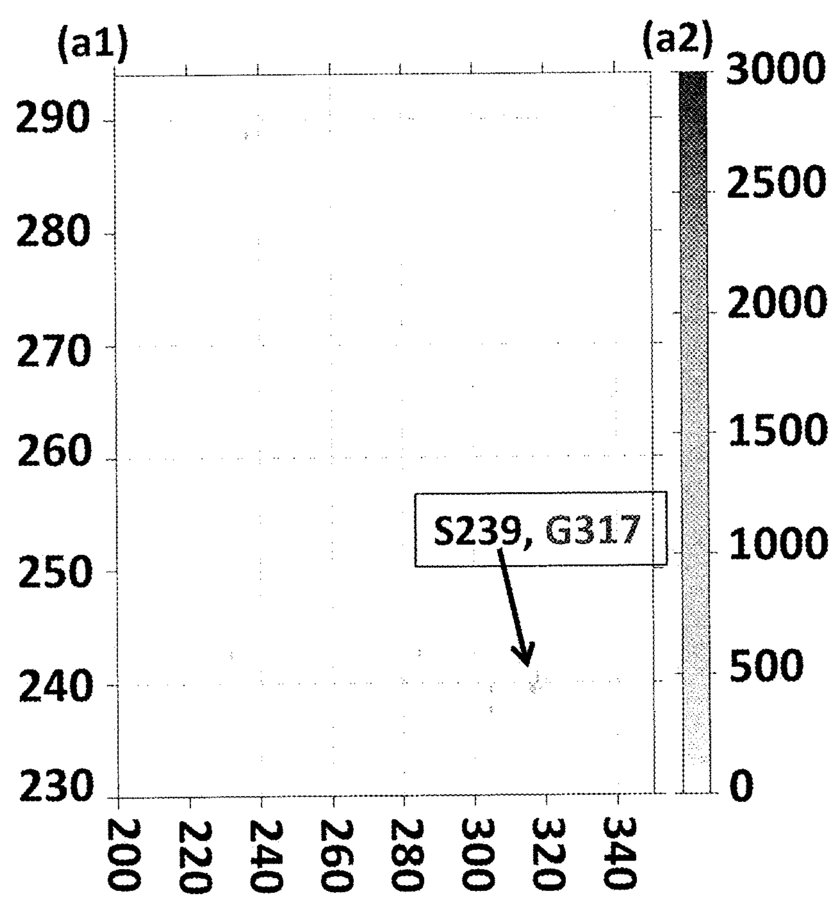

FIG. 25 shows a zoomed in region of a plot (y-axis label (a1)=pore amino acid residue number, y-axis label (a2)=number of pore/enzyme contacts, x-axis label=enzyme amino acid residue number) which shows which amino acids in the pore (αHL—(E111N/K147N)8) interact with particular amino acids in the enzyme (Phi29 DNA polymerase-(D12A/D66A)) from run 1. The black bands in the plot indicate an interaction between amino acids. The darkness of the grey band corresponds to the number of interactions between enzyme/pore, with dark grey=many interactions and light grey=fewer interactions. The first amino acid in each box corresponds to the interacting amino acid in the αHL—(E111N/K147N)8 and the second amino acid corresponds to the interacting amino acids in Phi29 DNA polymerase-(D12A/D66A).

Figure 26:
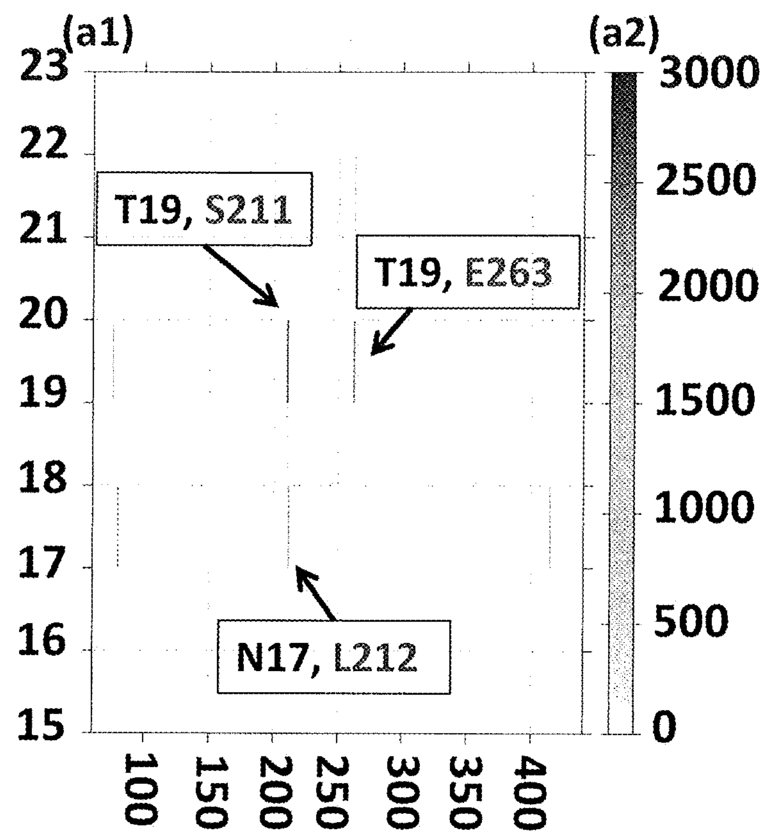
Figure 26:
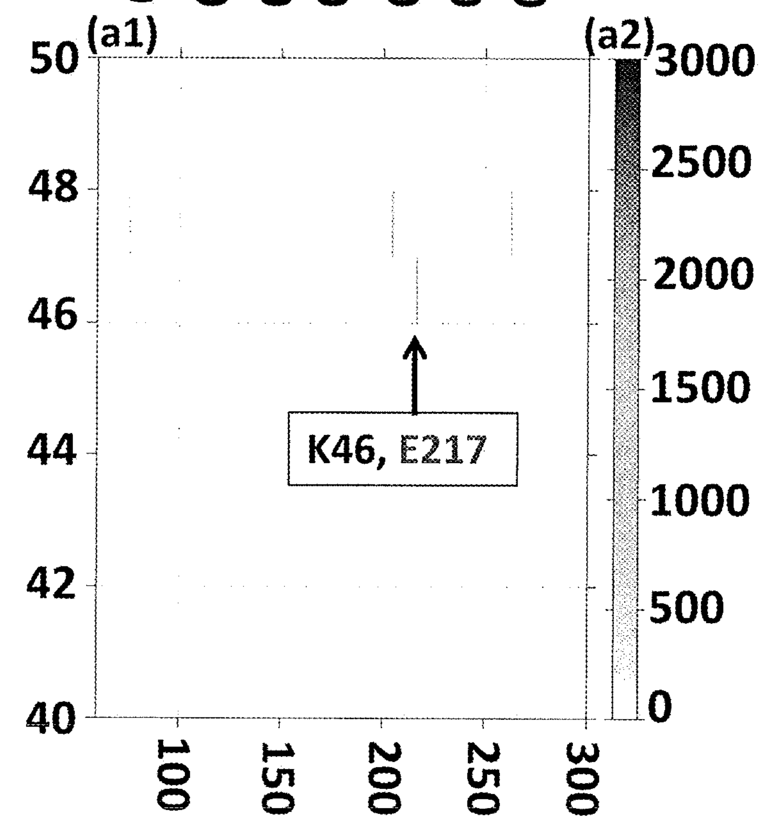

FIG. 26 shows two zoomed in regions of a plot (y-axis label (a1)=pore amino acid residue number, y-axis label (a2)=number of pore/enzyme contacts, x-axis label=enzyme amino acid residue number) which shows which amino acids in the pore (αHL—(E111N/K147N)8 interact with particular amino acids in the enzyme (Phi29 DNA polymerase-(D12A/D66A) from run 2. The grey bands in the plot indicate an interaction between amino acids. The darkness of the grey band corresponds to the number of interactions between enzyme/pore, with dark grey=many interactions and light grey=fewer interactions. The first amino acid in each box corresponds to the interacting amino acid in the αHL—(E111N/K147N)8 and the second amino acid corresponds to the interacting amino acids in Phi29 DNA polymerase-(D12A/D66A).

Figure 27:
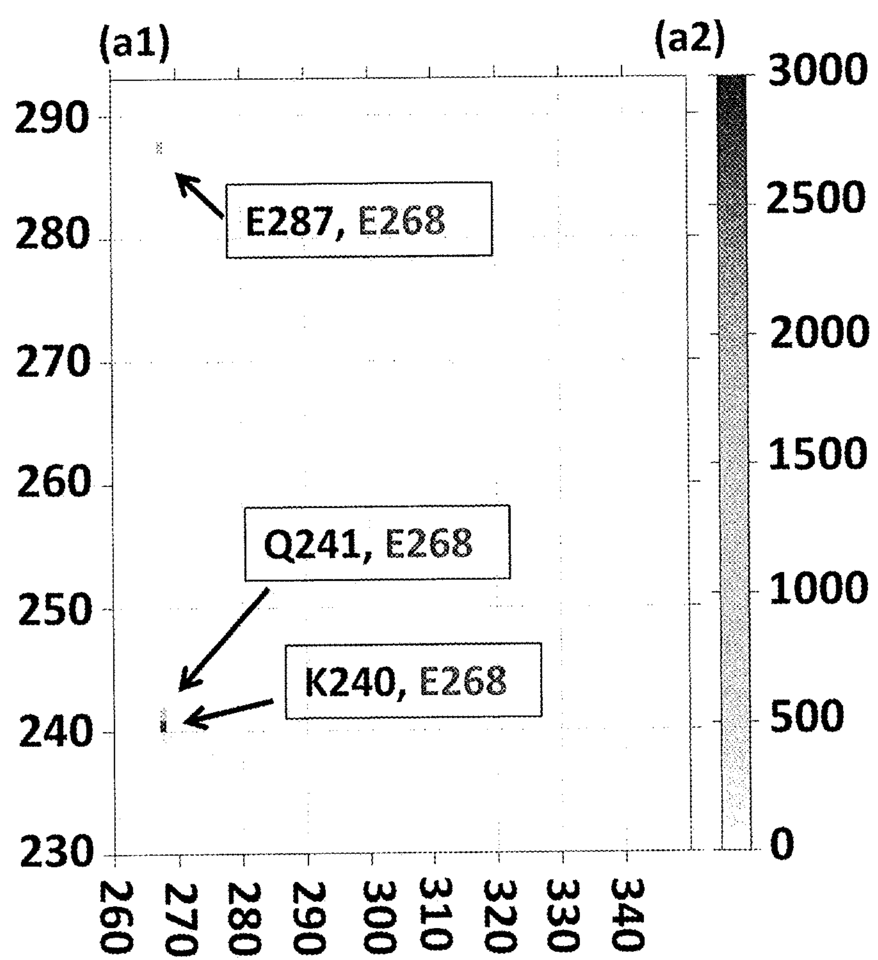

FIG. 27 shows a zoomed in region of a plot (y-axis label (a1)=pore amino acid residue number, y-axis label (a2)=number of pore/enzyme contacts, x-axis label=enzyme amino acid residue number) which shows which amino acids in the pore (αHL—(E111N/K147N)8 interact with particular amino acids in the enzyme (Phi29 DNA polymerase-(D12A/D66A)) from run 2. The grey bands in the plot indicate an interaction between amino acids. The darkness of the grey band corresponds to the number of interactions between enzyme/pore, with dark grey=many interactions and light grey=fewer interactions. The first amino acid in each box corresponds to the interacting amino acid in the αHL—(E111N/K147N)8 and the second amino acid corresponds to the interacting amino acids in Phi29 DNA polymerase-(D12A/D66A).

Figure 28:
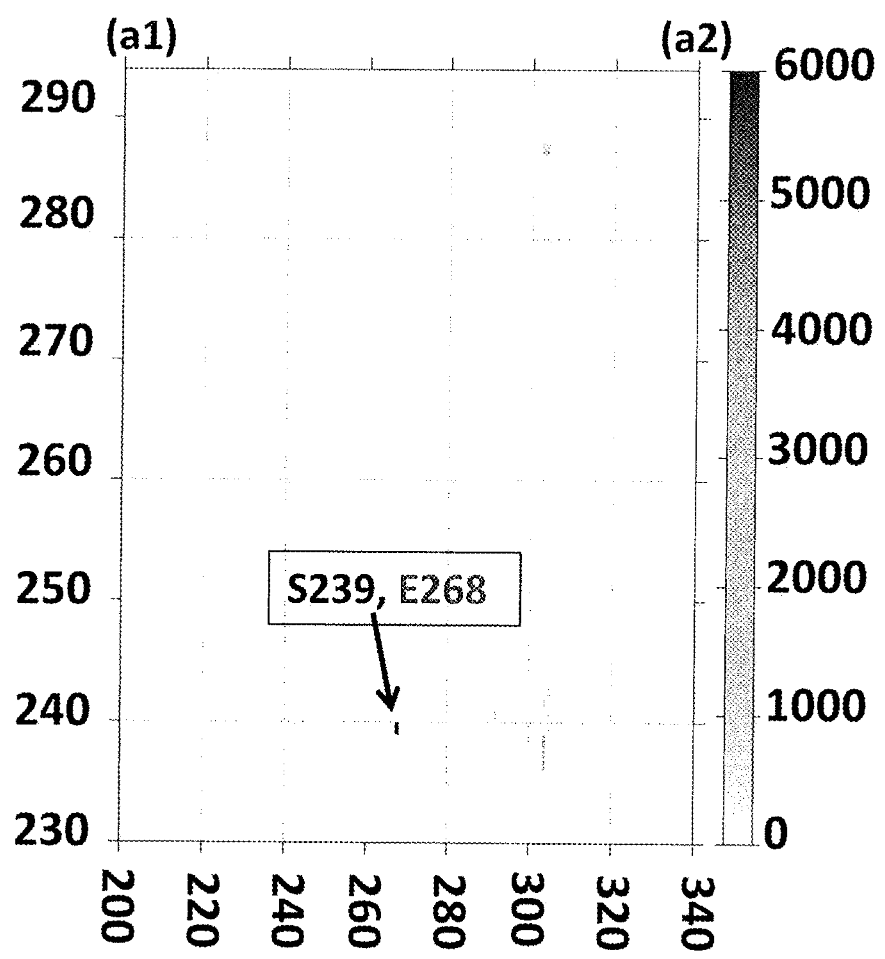

FIG. 28 shows a zoomed in region of a plot (y-axis label (a1)=pore amino acid residue number, y-axis label (a2) =number of pore/enzyme contacts, x-axis label=enzyme amino acid residue number) which shows which amino acids in the pore (αHL—(E111N/K147N)8 interact with particular amino acids in the enzyme (Phi29 DNA polymerase-(D12A/D66A) from run 3. The grey bands in the plot indicate an interaction between amino acids. The darkness of the grey band corresponds to the number of interactions between enzyme/pore, with dark grey=many interactions and light grey=fewer interactions. The first amino acid in each box corresponds to the interacting amino acid in the αHL—(E111N/K147N)8 and the second amino acid corresponds to the interacting amino acids in Phi29 DNA polymerase-(D12A/D66A).

Figure 29:
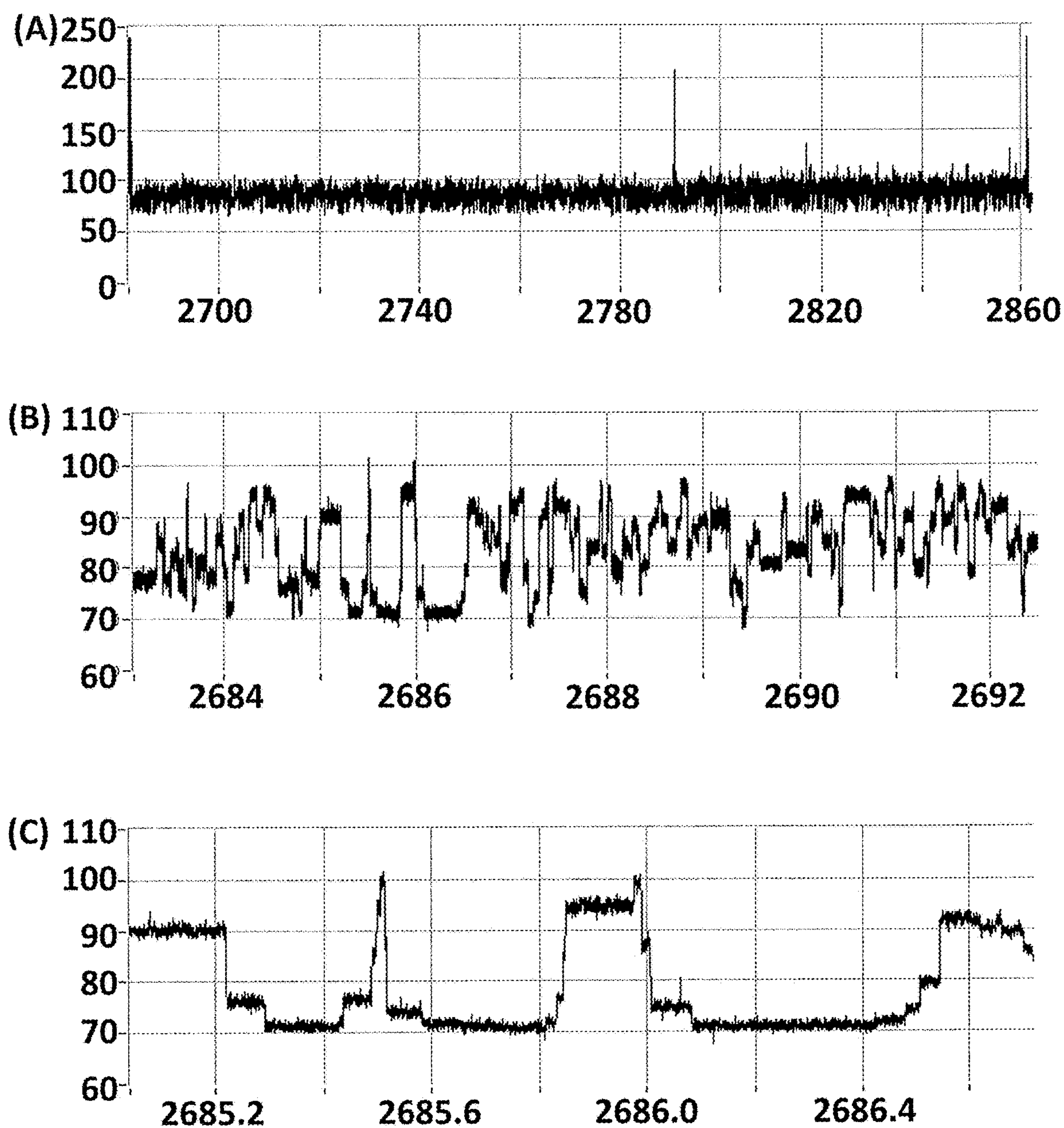

FIG. 29 shows example current traces (y-axis label=Current (pA), x-axis label=Time (s) for all three traces) of when a helicase (T4 Dda—E94C/C109A/C136A/A360C) controlled the translocation of the DNA construct X through the MspA nanopore MspA—((Del-L74/G75/D118/L119)D56N/E59R/L88N/D90N/D91N/Q126R/D134R/E139K)8 (SEQ ID NO: 2 with mutations D56N/E59R/L88N/D90N/D91N/Q126R/D134R/E139K and deletion of the amino acids L74/G75/D118/L119). Sections B and C show zoomed in regions of current trace A.

Figure 30:
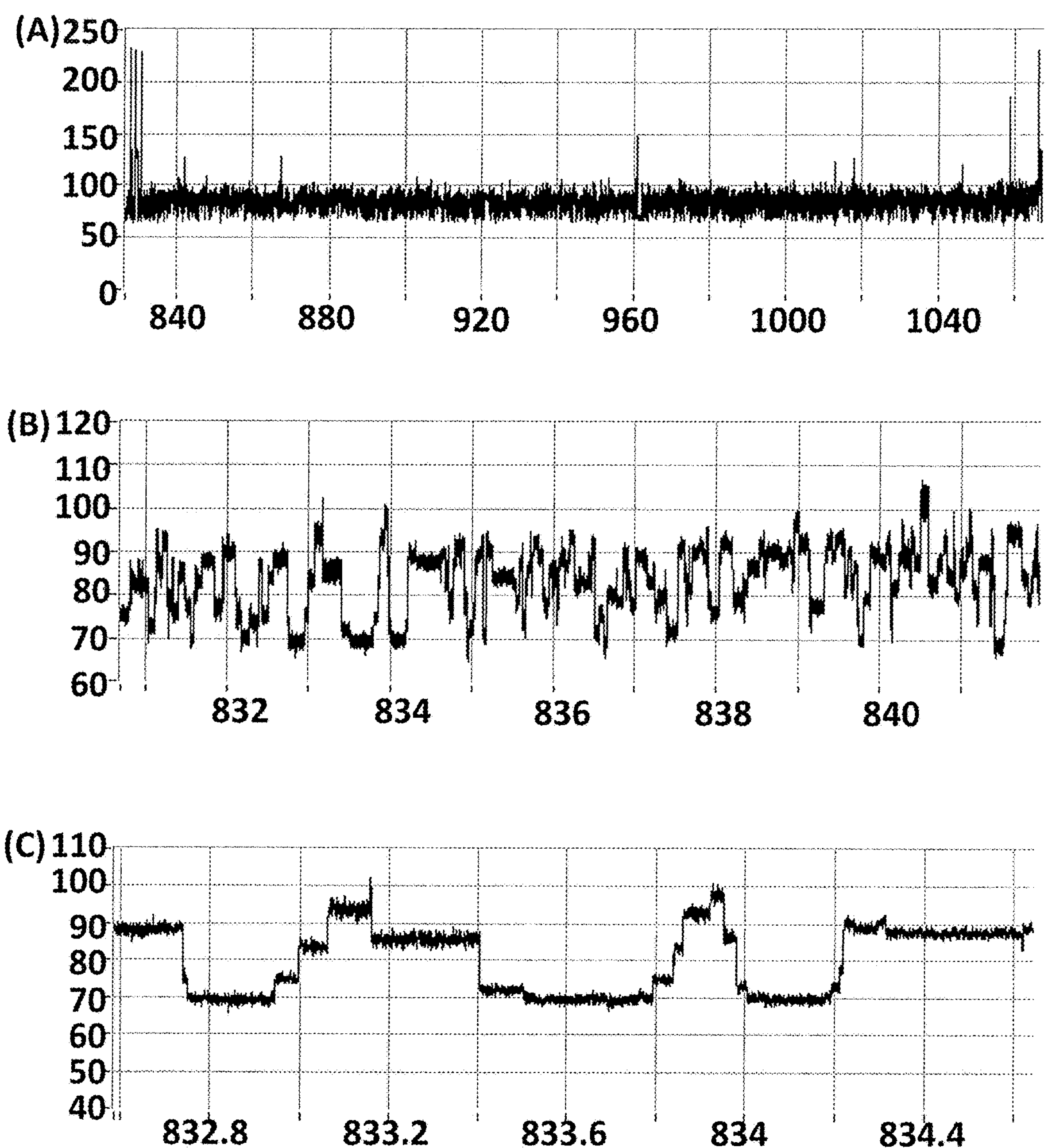

FIG. 30 shows example current traces (y-axis label=Current (pA), x-axis label=Time (s) for all three traces) of when a helicase (T4 Dda—E94C/C109A/C136A/A360C) controlled the translocation of the DNA construct X through the MspA nanopore MspA—((Del-L74/G75/D118/L119)D56F/E59R/L88N/D90N/D91N/Q126R/D134R/E139K)8 (SEQ ID NO: 2 with mutations D56F/E59R/L88N/D90N/D91N/Q126R/D134R/E139K and deletion of the amino acids L74/G75/D118/L119). Sections B and C show zoomed in regions of current trace A.

Figure 31:
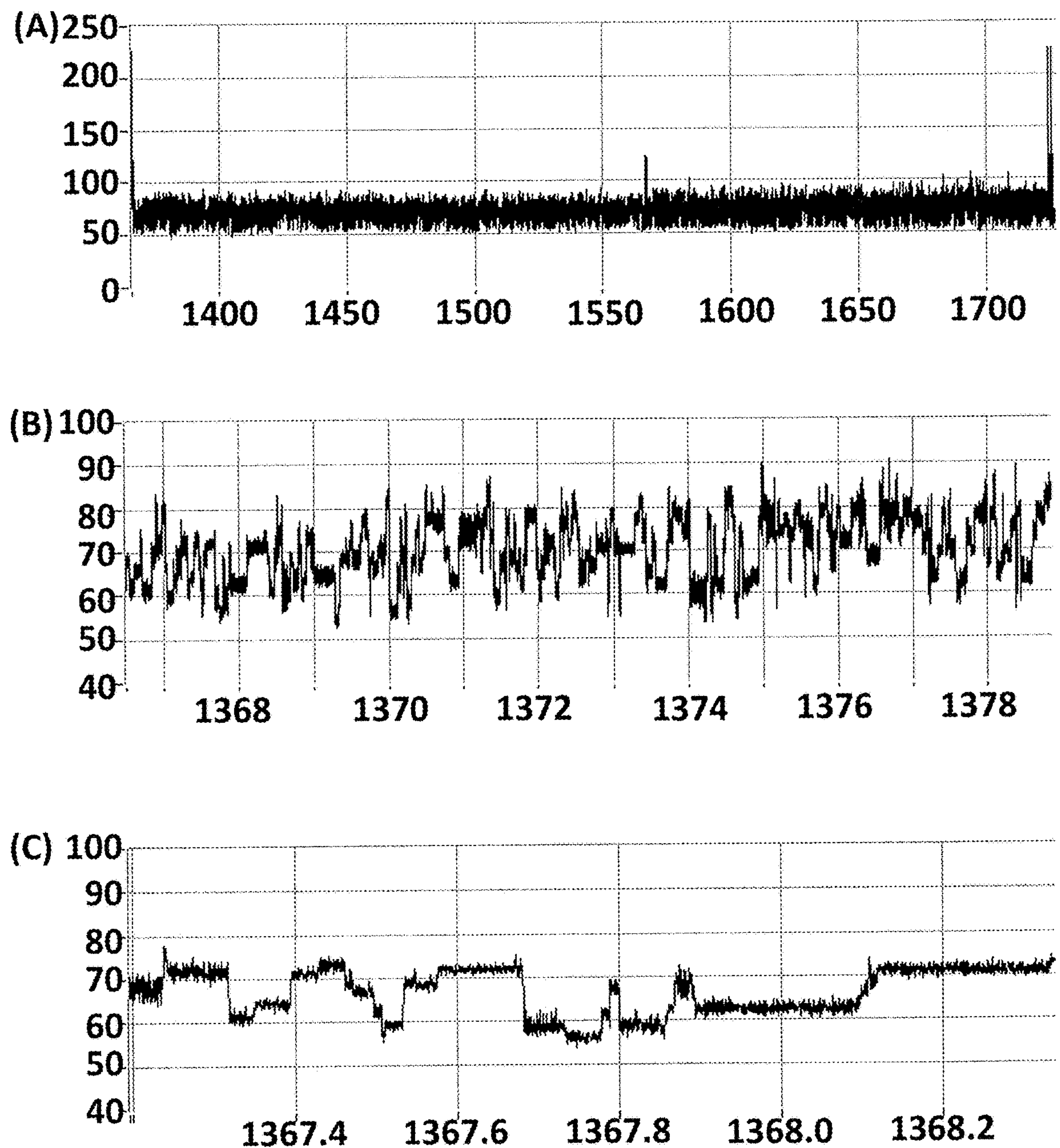

FIG. 31 shows example current traces (y-axis label=Current (pA), x-axis label=Time (s) for all three traces) of when a helicase (T4 Dda—E94C/C109A/C136A/K199L/A360C) controlled the translocation of the DNA construct X through the MspA nanopore MspA—((Del-L74/G75/D118/L119)D56F/E59R/L88N/D90N/D91N/Q126R/D134R/E139K)8 (SEQ ID NO: 2 with mutations D56F/E59R/L88N/D90N/D91N/Q126R/D134R/E139K and deletion of the amino acids L74/G75/D118/L119). Sections B and C show zoomed in regions of current trace A.

Figure 32:
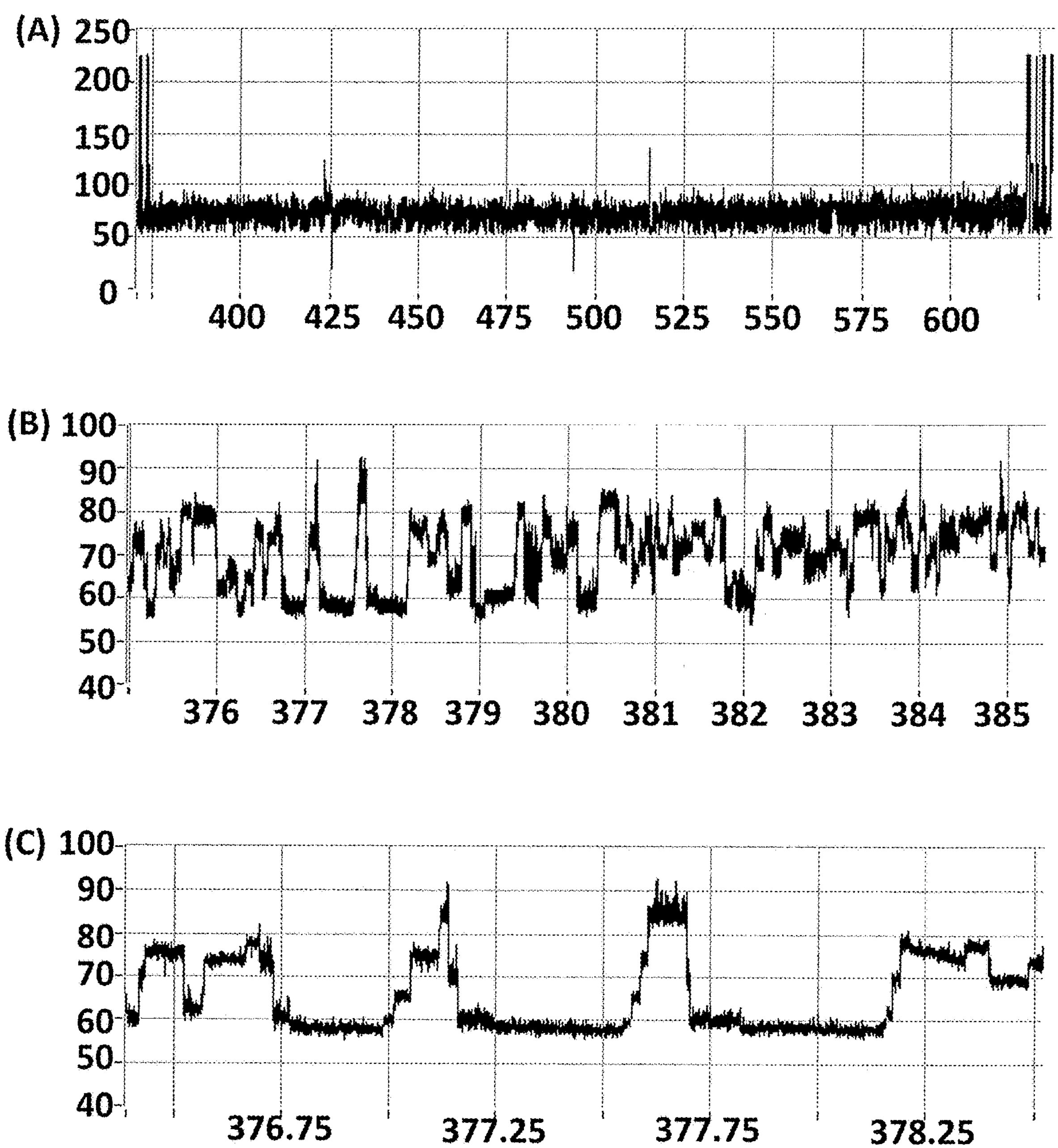

FIG. 32 shows example current traces (y-axis label=Current (pA), x-axis label=Time (s) for all three traces) of when a helicase (T4 Dda—E94C/C109A/C136A/A360C) controlled the translocation of the DNA construct X through the MspA nanopore MspA—((Del-L74/G75/D118/L119)D56L/E59L/L88N/D90N/D91N/Q126R/D134R/E139K)8 (SEQ ID NO: 2 with mutations D56L/E59L/L88N/D90N/D91N/Q126R/D134R/E139K and deletion of the amino acids L74/G75/D118/L119). Sections B and C show zoomed in regions of current trace A.

Figure 33:
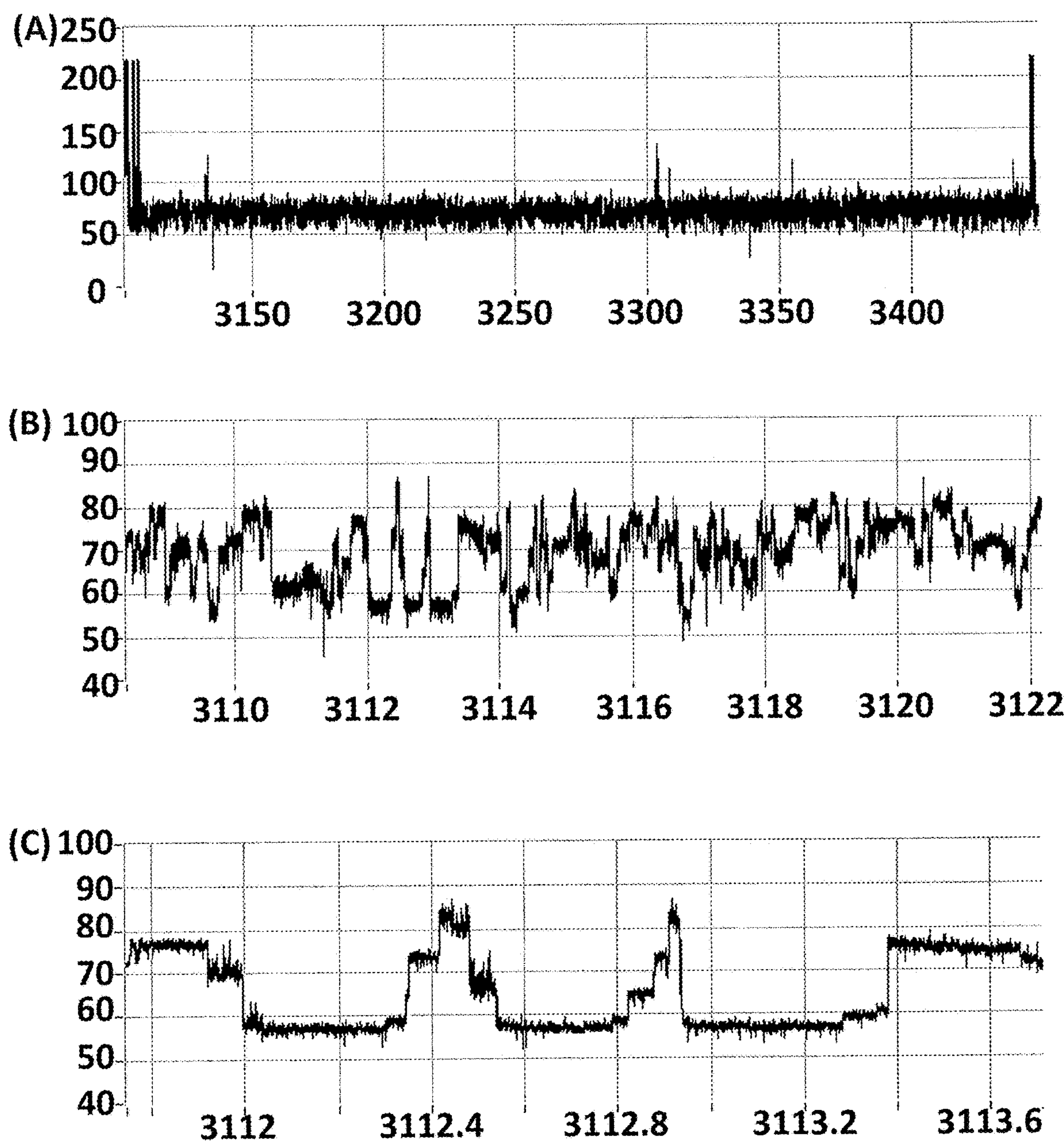

FIG. 33 shows example current traces (y-axis label=Current (pA), x-axis label=Time (s) for all three traces) of when a helicase (T4 Dda—E94C/C109A/C136A/A360C) controlled the translocation of the DNA construct X through the MspA nanopore MspA—((Del-L74/G75/D118/L119)G1A/D56N/E59F/L88N/D90N/D91N/Q126R/D134R/E139K)8 (SEQ ID NO: 2 with mutations G1A/D56N/E59F/L88N/D90N/D91N/Q126R/D134R/E139K and deletion of the amino acids L74/G75/D118/L119). Sections B and C show zoomed in regions of current trace A.

Figure 34:
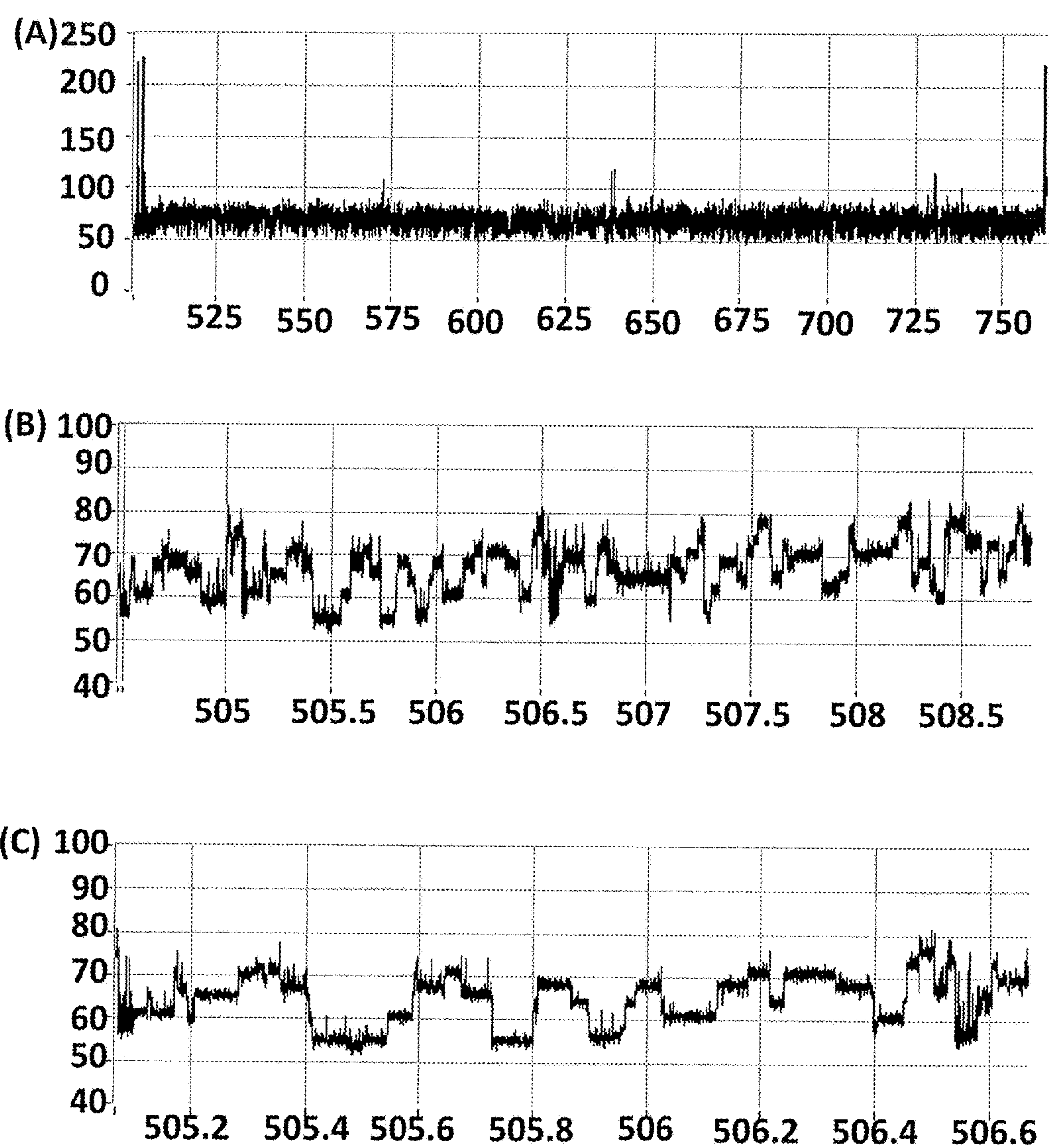

FIG. 34 shows example current traces (y-axis label=Current (pA), x-axis label=Time (s) for all three traces) of when a helicase (T4 Dda—E94C/C109A/C136A/K199L/A360C) controlled the translocation of the DNA construct X through the MspA nanopore MspA—((Del-L74/G75/D118/L119) G1A/D56N/E59F/L88N/D90N/D91N/Q126R/D134R/E139K)8 (SEQ ID NO: 2 with mutations G1A/D56N/E59F/L88N/D90N/D91N/Q126R/D134R/E139K and deletion of the amino acids L74/G75/D118/L119). Sections B and C show zoomed in regions of current trace A.

Figure 35:
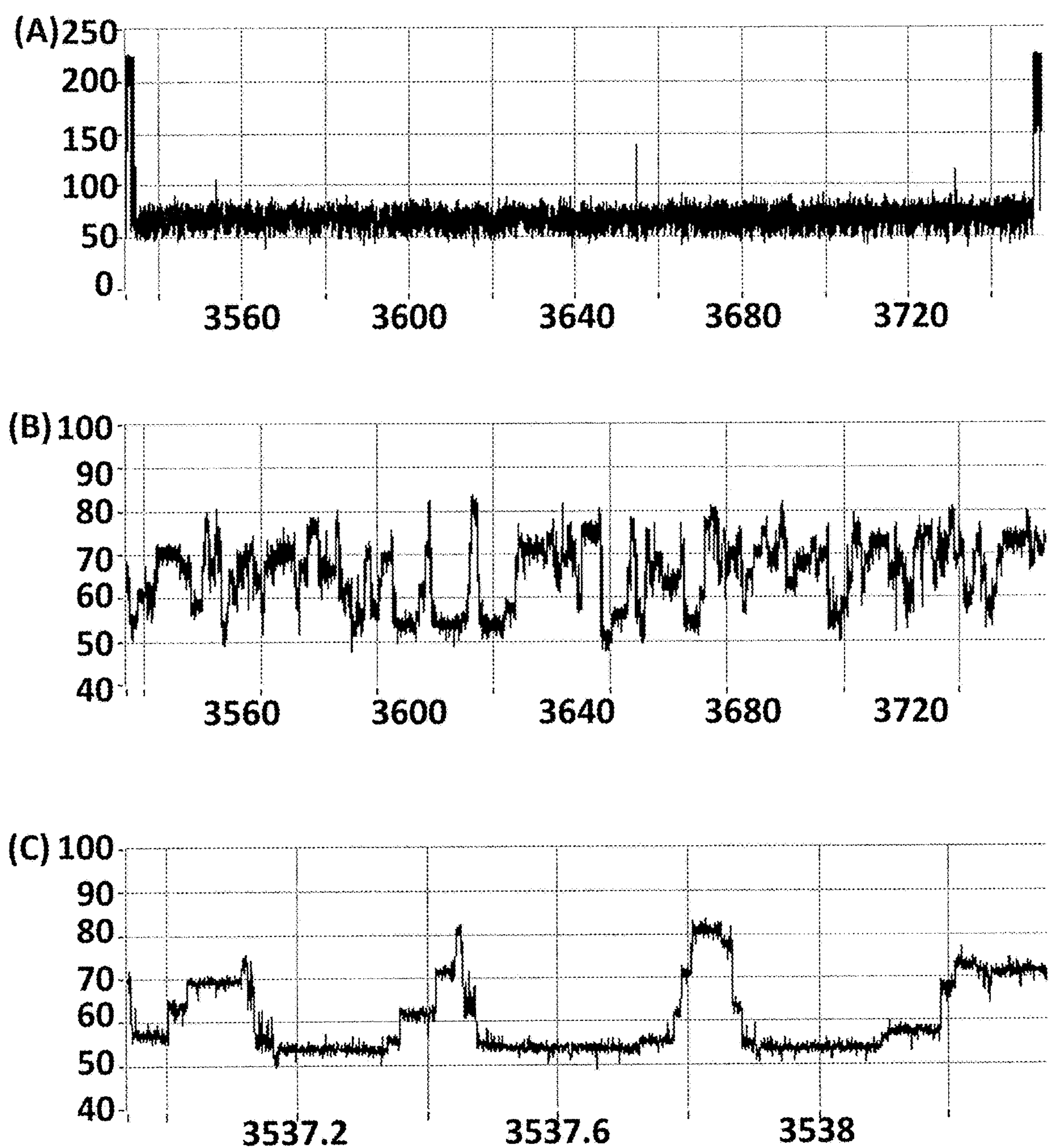

FIG. 35 shows example current traces (y-axis label=Current (pA), x-axis label=Time (s) for all three traces) of when a helicase (T4 Dda—E94C/C109A/C136A/A360C) controlled the translocation of the DNA construct X through the MspA nanopore MspA—((Del-L74/G75/D118/L119)D56N/E59Y/L88N/D90N/D91N/Q126R/D134R/E139K)8 (SEQ ID NO: 2 with mutations D56N/E59Y/L88N/D90N/D91N/Q126R/D134R/E139K and deletion of the amino acids L74/G75/D118/L119). Sections B and C show zoomed in regions of current trace A.

Figure 36:
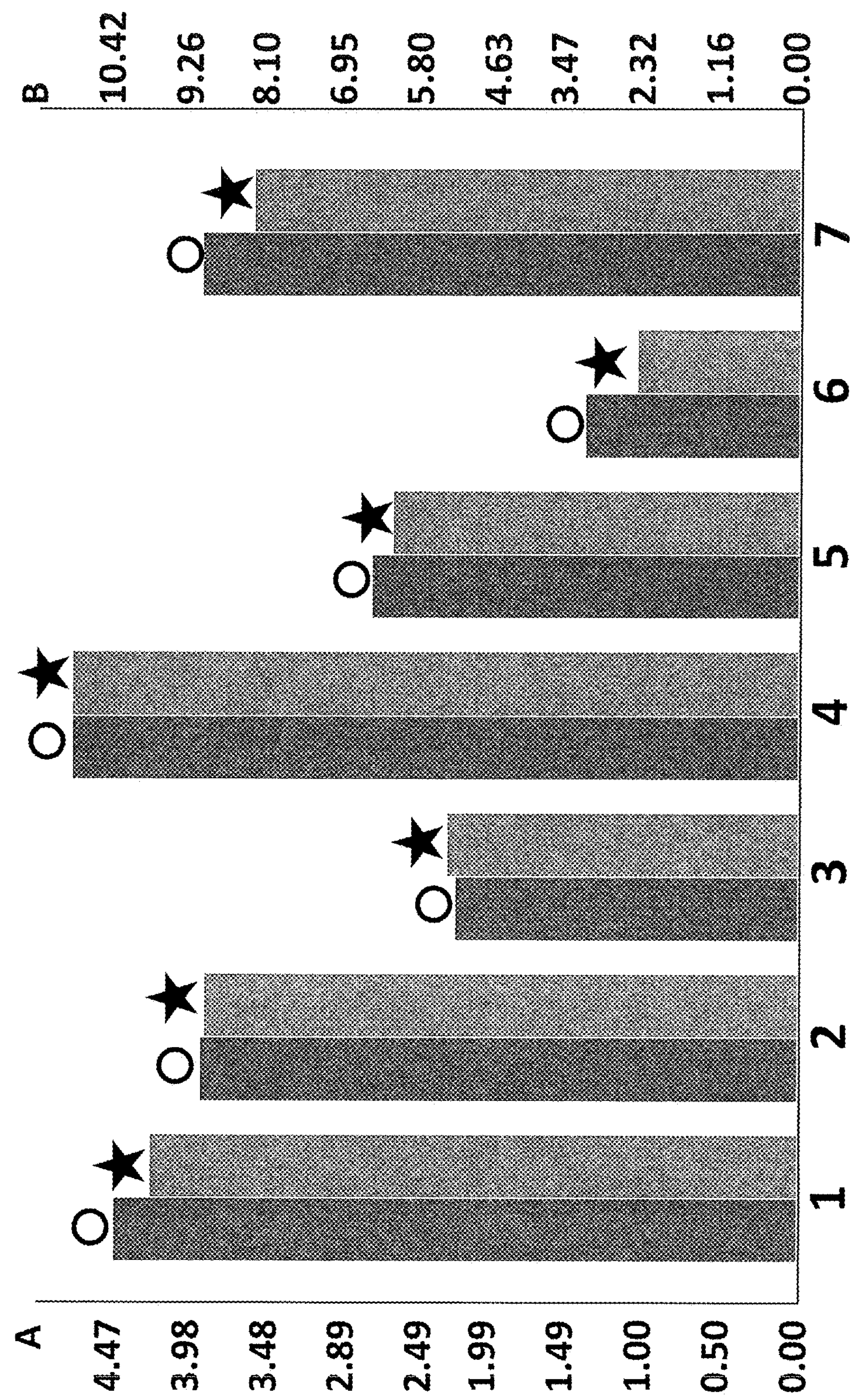

FIG. 36 shows a bar chart of various enzyme/pore combinations which were investigated in order to determine the number of slips forward per kilobase and the % bases missed when construct X was translocated through the nanopore under the control of the enzyme (x-axis label=pore and enzyme combinations 1-7 (see table 12) and y-axis label A=slips forward per kilobase and y-axis label B=% bases missed). The bar's labelled with a black star correspond to the % bases missed and those labelled with a circle correspond to the slips forward per kilobase.

Figure 37:
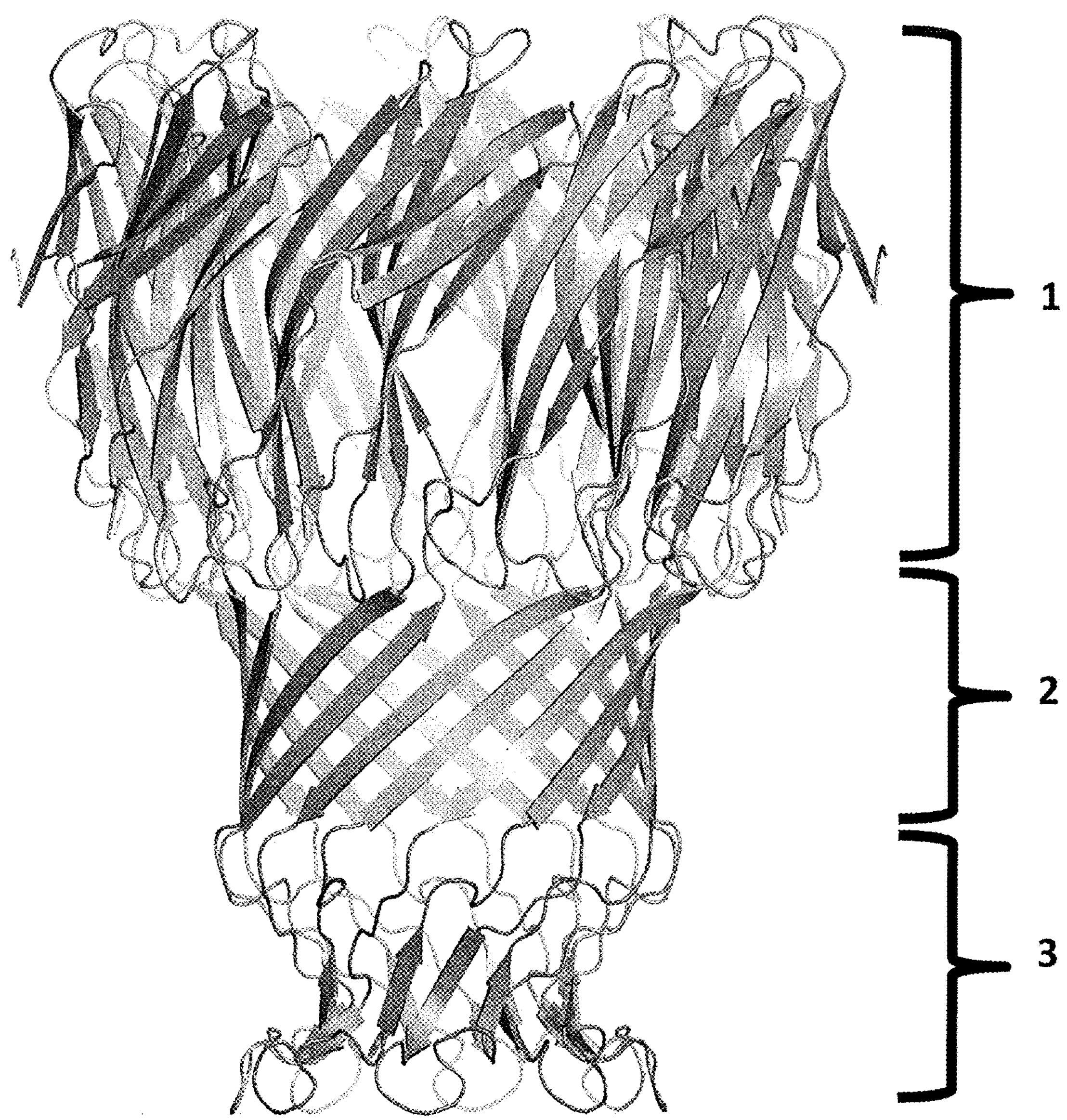

FIG. 37 shows a cartoon representation of the wild-type MspA nanopore. Region 1 corresponds to the cap forming region and includes residues 1-72 and 122-184. Region 2 corresponds to the barrel forming region and includes residues 73-82 and 112-121. Region 3 corresponds to the constriction and loops region and includes residues 83-111.

DESCRIPTION OF THE SEQUENCE LISTING

SEQ ID NO: 1 shows the codon optimised polynucleotide sequence encoding the wild-type MspA monomer. This mutant lacks the signal sequence.

SEQ ID NO: 2 shows the amino acid sequence of the mature form of the wild-type MspA monomer. This mutant lacks the signal sequence.

SEQ ID NO: 3 shows the polynucleotide sequence encoding one monomer of α-hemolysin—E111N/K147N (α-HL-NN; Stoddart et al., PNAS, 2009; 106(19): 7702-7707).

SEQ ID NO: 4 shows the amino acid sequence of one monomer of α-HL-NN.

SEQ ID NOs: 5 to 7 show the amino acid sequences of MspB, C and D.

SEQ ID NO: 8 shows the polynucleotide sequence encoding the Phi29 DNA polymerase.

SEQ ID NO: 9 shows the amino acid sequence of the Phi29 DNA polymerase.

SEQ ID NO: 10 shows the codon optimised polynucleotide sequence derived from the sbcB gene from *E. coli*. It encodes the exonuclease I enzyme (EcoExo I) from *E. coli.*

SEQ ID NO: 11 shows the amino acid sequence of exonuclease I enzyme (EcoExo I) from *E. coli.*

SEQ ID NO: 12 shows the codon optimised polynucleotide sequence derived from the xthA gene from *E. coli*. It encodes the exonuclease III enzyme from *E. coli.*

SEQ ID NO: 13 shows the amino acid sequence of the exonuclease III enzyme from *E. coli*. This enzyme performs distributive digestion of 5' monophosphate nucleosides from one strand of double stranded DNA (dsDNA) in a 3'-5' direction. Enzyme initiation on a strand requires a 5' overhang of approximately 4 nucleotides.

SEQ ID NO: 14 shows the codon optimised polynucleotide sequence derived from the recJ gene from *T. thermophilus*. It encodes the RecJ enzyme from *T. thermophilus* (TthRecJ-cd).

SEQ ID NO: 15 shows the amino acid sequence of the RecJ enzyme from *T. thermophilus* (TthRecJ-cd). This enzyme performs processive digestion of 5' monophosphate nucleosides from ssDNA in a 5'-3' direction. Enzyme initiation on a strand requires at least 4 nucleotides.

SEQ ID NO: 16 shows the codon optimised polynucleotide sequence derived from the bacteriophage lambda exo (redX) gene. It encodes the bacteriophage lambda exonuclease.

SEQ ID NO: 17 shows the amino acid sequence of the bacteriophage lambda exonuclease. The sequence is one of three identical subunits that assemble into a trimer. The enzyme performs highly processive digestion of nucleotides from one strand of dsDNA, in a 5'-3' direction (http://www.neb.com/nebecomm/products/productM0262.asp). Enzyme initiation on a strand preferentially requires a 5' overhang of approximately 4 nucleotides with a 5' phosphate.

SEQ ID NO: 18 shows the amino acid sequence of Hel308 Mbu.

SEQ ID NO: 19 shows the amino acid sequence of Hel308 Csy.

SEQ ID NO: 20 shows the amino acid sequence of Hel308 Tga.

SEQ ID NO: 21 shows the amino acid sequence of Hel308 Mhu.

SEQ ID NO: 22 shows the amino acid sequence of TraI Eco.

SEQ ID NO: 23 shows the amino acid sequence of XPD Mbu.

SEQ ID NO: 24 shows the amino acid sequence of Dda 1993.

SEQ ID NO: 25 shows the amino acid sequence of Trwc Cba.

SEQ ID NO: 26 shows positions 72 to 82 of SEQ ID NO: 2.

SEQ ID NO: 27 shows positions 111 to 121 of SEQ ID NO: 2.

SEQ ID NO: 28 shows a polynucleotide sequence used in Example 2.

SEQ ID NO: 29 shows a polynucleotide sequence used in Example 2.

SEQ ID NO: 30 shows a polynucleotide sequence used in Example 2.

SEQ ID NO: 31 shows a polynucleotide sequence used in Example 2.

SEQ ID NO: 32 shows a polynucleotide sequence used in Example 2.

SEQ ID NO: 33 shows a polynucleotide sequence used in Example 2.

SEQ ID NO: 34 shows a polynucleotide sequence used in Example 2.

SEQ ID NO: 35 shows the polynucleotide sequence encoding the lysenin monomer.

SEQ ID NO: 36 shows the amino acid sequence of the lysenin monomer.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms “a”, “an”, and “the” include plural referents unless the content clearly dictates otherwise. Thus, for example, reference to “a polynucleotide” includes two or more polynucleotides, reference to “a polynucleotide binding protein includes two or more such proteins, reference to “a helicase” includes two or more helicases, reference to “a monomer” refers to two or more monomers, reference to “a pore” includes two or more pores and the like.

All publications, patents and patent applications cited herein, whether supra or infra, are hereby incorporated by reference in their entirety.

Modification Methods

The present invention provides a method of improving the movement of a target polynucleotide with respect to a transmembrane pore when the movement is controlled by a polynucleotide binding protein. The method is preferably for improving the movement of a target polynucleotide through a transmembrane pore when the movement is controlled by a polynucleotide binding protein. Target polynucleotides are discussed in more detail below.

The method comprises modifying a part of the transmembrane pore which interacts with the polynucleotide binding protein or a part of the polynucleotide binding protein which interacts with the transmembrane pore. The method may comprise modifying both the transmembrane pore and the polynucleotide binding protein.

Methods of modifying pores and proteins, such as via amino acid introductions and/or substitutions, are known in the art and are discussed in more detail below.

Characterisation, such as sequencing, of a polynucleotide using a transmembrane pore typically involves analysing polymer units made up of k nucleotides where k is a positive integer (i.e. 'k-mers'). This is discussed in International Application No. PCT/GB2012/052343 (published as WO 2013/041878). As the target polynucleotide moves with respect to, or through the pore, different k-mers within the polynucleotide are analysed, typically by measuring the current flowing through the pore. The movement of the polynucleotide with respect to, such as through, the pore can be viewed as movement from one k-mer to another or from k-mer to k-mer.

The method of the invention preferably provides more consistent movement of the target polynucleotide with respect to, such as through, the transmembrane pore. The method preferably provides more consistent movement from one k-mer to another or from k-mer to k-mer as the target polynucleotide moves with respect to, such as through, the pore. The method preferably allows the target polynucleotide to move with respect to, such as through, the transmembrane pore more smoothly. The method preferably provides more regular or less irregular movement of the target polynucleotide with respect to, such as through, the transmembrane pore.

The method preferably reduces the amount of slipping forward associated with the movement of the target polynucleotide with respect to, such as through, the pore. Some helicases including the Dda helicase used in the Example move along the polynucleotide in a 5' to 3' direction. When the 5'end of the polynucleotide (the end away from which the helicase moves) is captured by the pore, the helicase works with the direction of the field resulting from the applied potential and moves the threaded polynucleotide into the pore and into the trans chamber. Slipping forward involves the DNA moving forwards relative to the the pore (i.e. towards its 3' and away from it 5' end) at least 4 consecutive nucleotides and typically more than 10 consecutive nucleotides. Slipping forward may involve movement forward of 100 consecutive nucleotides or more and this may happen more than once in each strand.

The method of the invention preferably reduces the noise associated with the movement of the target polynucleotide with respect to, such as through, the transmembrane pore. Unwanted movement of the target polynucleotide in any dimension as a k-mer is being analysed typically results in noise in the current signature or level for the k-mer. The method of the invention may reduce this noise by reducing unwanted movement associated with one or more k-mers, such as each k-mer, in the target polynucleotide. The method of the invention may reduce the noise associated with the current level or signature for one or more k-mers, such as each k-mer, in the target polynucleotide.

In a preferred embodiment, the target polynucleotide is double stranded and the method reduces the noise associated with the movement of the complement strand to a greater degree than it reduces the noise associated with the movement of the template strand and/or the method increases the consistency of the movement of the complement strand to a greater degree than it increases the consistency of the movement of the template strand. This is advantageous for strand sequencing of double stranded target polynucleotides. The two stands of the double stranded polynucleotide are preferably linked by a bridging moiety, such as a hairpin loop or hairpin loop adaptor. This is discussed in more detail below.

Transmembrane Pore

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well, gap, channel, trench or slit in the membrane along which or into which hydrated ions may flow.

Any transmembrane pore may be used in the invention. The pore may be biological or artificial. Suitable pores include, but are not limited to, protein pores, polynucleotide pores and solid state pores. The pore may be a polynucleotide origami pore, such as a DNA origami pore (Langecker et al., Science, 2012; 338: 932-936).

The transmembrane pore is preferably a transmembrane protein pore. A transmembrane protein pore is a polypeptide or a collection of polypeptides that permits hydrated ions, such as polynucleotides, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analytes such as nucleotides or polynucleotides to flow from one side of the membrane, such as a triblock copolymer membrane, to the other. The transmembrane protein pore typically allows a polynucleotide, such as DNA or RNA, to be moved through the pore.

The transmembrane protein pore may be a monomer or an oligomer. The pore is preferably made up of several repeating subunits, such as at least 6, at least 7, at least 8 or at least 9 subunits. The pore is preferably a hexameric, heptameric, octameric or nonameric pore. The pore may be a homo-oligomer or a hetero-oligomer.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β pore forming toxins, such as α-hemolysin, anthrax toxin and leukocidins, and outer membrane proteins/porins of bacteria, such as *Mycobacterium smegmatis* porin (Msp), for example MspA, MspB, MspC or MspD, outer membrane porin F (OmpF), outer membrane porin G (OmpG), outer membrane phospholipase A and *Neisseria* autotransporter lipoprotein (NalP), and other pores, such as lysenin. α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from lysenin. Suitable pores derived from lysenin are disclosed in International Application No. PCT/GB2013/050667 (published as WO 2013/153359). The transmembrane pore may be derived from Msp, such as MspA, or from α-hemolysin (α-HL).

The unmodified transmembrane pore used in the invention preferably comprises seven or more monomers comprising the sequence shown in SEQ ID NO: 2 or a variant thereof. The unmodified transmembrane pore more preferably comprises 8 or 9 monomers comprising the sequence shown in SEQ ID NO: 2 or a variant thereof. SEQ ID NO: 2 and variants thereof are discussed in more detail below. The pores modified in accordance with the invention may comprise any of the variants discussed below, especially the variants described with reference to the mutant Msp monomers of the invention.

In SEQ ID NO: 2 or a variant thereof, the part of the transmembrane pore which interacts with the polynucleotide binding protein typically comprises the amino acids at positions 12, 14, 48, 52, 53, 54, 55, 56, 57, 58, 59, 60, 134, 135, 136, 137, 138, 139, 169 and 170. These numbers correspond to the relevant positions in SEQ ID NO: 2 and may need to be altered in the case of variants where one or more amino acids have been inserted or deleted compared with SEQ ID NO: 2. A skilled person is capable of determining the corresponding position in a variant of SEQ ID NO: 2. For instance, position 4 in SEQ ID NO: 2 becomes position 6 in a variant having two amino acids added at the amino (N) terminus. If the variant is formed only by substitution of amino acids in SEQ ID NO: 2 (i.e. no amino acids are added to or deleted from SEQ ID NO: 2), the corresponding positions in the variant typically have the same numbering at the positions in SEQ ID NO: 2. The same is true for SEQ ID NOs: 4, 9, 24 and 36.

The part of the transmembrane pore which interacts with the polynucleotide binding protein preferably comprises the amino acids at positions:

(a) 12, 14, 52, 54, 56, 57, 59, 134, 136, 138, 139 and 169 in SEQ ID NO: 2 or at the corresponding positions in a variant thereof;

(b) 12, 14, 56, 57, 59, 134, 136, 139 and 169 in SEQ ID NO: 2 or at the corresponding positions in a variant thereof;

(c) 56, 57, 59, 134, 136, 139 and 169 in SEQ ID NO: 2 or at the corresponding positions in a variant thereof; or (d) 56, 57, 59, 134 and 139 in SEQ ID NO: 2 or at the corresponding positions in a variant thereof.

The part of the transmembrane pore which interacts with the polynucleotide binding protein preferably comprises the amino acid at position 56 in SEQ ID NO: 2 or at the corresponding position in the variant thereof. The amino acid at position 56 (aspartic acid; D) may be replaced with asparagine (N), arginine (R), phenylalanine (F), tyrosine (Y) or leucine (L).

The part of the transmembrane pore which interacts with the polynucleotide binding protein preferably comprises the amino acid at position 59 in SEQ ID NO: 2 or at the corresponding position in a variant thereof. The amino acid at position 59 (glutamic acid; E) may be replaced with asparagine (N), arginine (R), phenylalanine (F), tyrosine (Y) or leucine (L).

The transmembrane protein pore may also be derived from α-hemolysin (α-HL). The wild type α-HL pore is formed of seven identical monomers or subunits (i.e. it is heptameric). The sequence of one monomer or subunit of α-hemolysin-NN is shown in SEQ ID NO: 4. The transmembrane protein pore preferably comprises seven monomers each comprising the sequence shown in SEQ ID NO: 4 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 4 form loop regions. Residues 113 and 147 of SEQ ID NO: 4 form part of a constriction of the barrel or channel of α-HL.

In such embodiments, a pore comprising seven proteins or monomers each comprising the sequence shown in SEQ ID NO: 4 or a variant thereof are preferably used in the method of the invention. The seven proteins may be the same (homo-heptamer) or different (hetero-heptamer).

In SEQ ID NO: 4, the part of the transmembrane pore which interacts with the polynucleotide binding protein typically comprises the amino acids at positions 16, 17, 18, 19, 21, 46, 47, 93, 236, 237, 238, 239, 240, 241, 242, 281, 283, 285, 287, 288 and 293. These numbers correspond to the relevant positions in SEQ ID NO: 4 and may need to be altered in the case of variants where one or more amino acids have been inserted or deleted compared with SEQ ID NO: 4. A skilled person can determine the corresponding positions in a variant as discussed above.

The part of the transmembrane pore which interacts with the polynucleotide binding protein preferably comprises the amino acids at positions:

(a) 17, 18, 19, 46, 47, 93, 236, 237, 238, 239, 240, 241, 242, 287, 288 and 293 in SEQ ID NO: 4 or at the corresponding positions in the variant thereof;

(b) 17, 19, 46, 47, 93, 236, 237, 238, 239, 240, 241, 242 and 287 in SEQ ID NO: 4 or at the corresponding positions in the variant thereof; or (c) 17, 19, 46, 93, 236, 237, 239, 240, 287 and 288 in SEQ ID NO: 4 or at the corresponding positions in the variant thereof.

The amino acids at any of these positions may be replaced with phenylalanine (F), tryptophan (W), isoleucine (I), leucine (L), valine (V), alanine (A), arginine (R), lysine (K), aspartic acid (D), glutamic acid (E) or tyrosine (Y) in accordance with the invention.

A variant of SEQ ID NO: 4 is a protein that has an amino acid sequence which varies from that of SEQ ID NO: 4 and which retains its pore forming ability. The ability of a variant to form a pore can be assayed using any method known in the art. For instance, the variant may be inserted into an amphiphilic layer, such as a triblock copolymer membrane, along with other appropriate subunits and its ability to oligomerise to form a pore may be determined. Methods are known in the art for inserting subunits into amphiphilic layers, such as triblock copolymer membranes. Suitable methods are discussed above.

The variant may include modifications that facilitate covalent attachment to or interaction with the polynucleotide binding protein. The variant preferably comprises one or more reactive cysteine residues that facilitate attachment to the polynucleotide binding protein. For instance, the variant may include a cysteine at one or more of positions 8, 9, 17, 18, 19, 44, 45, 50, 51, 237, 239 and 287 and/or on the amino or carboxy terminus of SEQ ID NO: 4. Preferred variants comprise a substitution of the residue at position 8, 9, 17, 237, 239 and 287 of SEQ ID NO: 4 with cysteine (A8C, T9C, N17C, K237C, S239C or E287C). The variant is preferably any one of the variants described in International Application No. PCT/GB09/001690 (published as WO 2010/004273), PCT/GB09/001679 (published as WO 2010/004265) or PCT/GB10/000133 (published as WO 2010/086603).

The variant may also include modifications that facilitate any interaction with nucleotides.

The variant may be a naturally occurring variant which is expressed naturally by an organism, for instance by a *Staphylococcus* bacterium. Alternatively, the variant may be expressed in vitro or recombinantly by a bacterium such as *Escherichia coli*. Variants also include non-naturally occurring variants produced by recombinant technology. Over the entire length of the amino acid sequence of SEQ ID NO: 4, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed below.

Amino acid substitutions may be made to the amino acid sequence of SEQ ID NO: 4 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 4 may additionally be deleted from the polypeptides described above. Up to 1, 2, 3, 4, 5, 10, 20 or 30 residues may be deleted, or more.

Variants may be fragments of SEQ ID NO: 4. Such fragments retain pore-forming activity. Fragments may be at least 50, 100, 200 or 250 amino acids in length. A fragment preferably comprises the pore-forming domain of SEQ ID NO: 4. Fragments typically include residues 119, 121, 135. 113 and 139 of SEQ ID NO: 4.

One or more amino acids may be alternatively or additionally added to the polypeptides described above. An extension may be provided at the amino terminus or carboxy terminus of the amino acid sequence of SEQ ID NO: 4 or a variant or fragment thereof. The extension may be quite short, for example from 1 to 10 amino acids in length. Alternatively, the extension may be longer, for example up to 50 or 100 amino acids. A carrier protein may be fused to a pore or variant.

As discussed above, a variant of SEQ ID NO: 4 is a subunit that has an amino acid sequence which varies from that of SEQ ID NO: 4 and which retains its ability to form a pore. A variant typically contains the regions of SEQ ID NO: 4 that are responsible for pore formation. The pore forming ability of α-HL, which contains a β-barrel, is provided by β-strands in each subunit. A variant of SEQ ID NO: 4 typically comprises the regions in SEQ ID NO: 4 that form β-strands. The amino acids of SEQ ID NO: 4 that form β-strands are discussed above. One or more modifications can be made to the regions of SEQ ID NO: 4 that form β-strands as long as the resulting variant retains its ability to form a pore. Specific modifications that can be made to the β-strand regions of SEQ ID NO: 4 are discussed above.

A variant of SEQ ID NO: 4 preferably includes one or more modifications, such as substitutions, additions or deletions, within its α-helices and/or loop regions. Amino acids that form α-helices and loops are discussed above.

The variant of SEQ ID NO: 4 may be modified to assist its identification or purification as discussed below.

The transmembrane protein pore may also be derived from lysenin. The unmodified transmembrane pore used in the invention preferably comprises at least one monomer comprising the sequence shown in SEQ ID NO: 36 or a variant thereof.

In SEQ ID NO: 36 or a variant thereof, the part of the transmembrane pore which interacts with the polynucleotide binding protein typically comprises the amino acids at positions (i) 31 (serine; S), (ii) 33 (serine; S), (iii) 108 (proline; P), (iv) 109 (proline; P), (v) 110 (threonine) and (vi) 138 (proline; P). These numbers correspond to the relevant positions in SEQ ID NO: 36 and may need to be altered in the case of variants where one or more amino acids have been inserted or deleted compared with SEQ ID NO: 36. A skilled person can determine the corresponding positions in a variant as discussed above.

The part of the transmembrane pore which interacts with the polynucleotide binding protein preferably comprises any number and combination of these amino acids in SEQ ID NO: 36 or the variant thereof. The part of the transmembrane pore which interacts with the polynucleotide binding protein preferably comprises the amino acids at positions {i}, {ii}, {iii}, {iv}, {v}, {vi}, {i,ii}, {i,iii}, {i,iv}, {i,v}, {i,vi}, {ii,iii}, {ii,iv}, {ii,v}, {ii,vi}, {iii,iv}, {iii,v}, {iii,vi}, {iv,v}, {iv,vi}, {v,vi}, {i,ii,iii}, {i,ii,iv}, {i,ii,v}, {i,ii,vi}, {i,iii,iv}, {i,iii,v}, {i,iii,vi}, {i,iv,v}, {i,iv,vi}, {i,v,vi}, {ii,iii,iv}, {ii,iii,v}, {ii,iii,vi}, {ii,iv,v}, {ii,iv,vi}, {ii,v,vi}, {iii,iv,v}, {iii,iv,vi}, {iii,v,vi}, {iv,v,vi}, {i,ii,iii,iv}, {i,ii,iii,v}, {i,ii,iii,vi}, {i,ii,iv,v}, {i,ii,iv,vi}, {i,ii,v,vi}, {i,iii,iv,v}, {i,iii,iv,vi}, {i,iii,v,vi}, {i,iv,v,vi}, {ii,iii,iv,v}, {ii,iii,iv,vi}, {ii,iii,v,vi}, {ii,iv,v,vi}, {iii,iv,v,vi}, {i,ii,iii,iv,v}, {i,ii,iii,iv,vi}, {i,ii,iii,v,vi}, {i,ii,iv,v,vi}, {i,iii,iv,v,vi}, {ii,iii,iv,v,vi} or {i,ii,iii,iv,v,vi} in SEQ ID NO: 36 or at the corresponding positions in the variant thereof.

Any number and combination of (i) to (vi) as set out above may be replaced with phenylalanine (F), tryptophan (W), isoleucine (I), leucine (L), valine (V), alanine (A), arginine (R), lysine (K), aspartic acid (D), glutamic acid (E) or tyrosine (Y) in accordance with the invention.

A variant of SEQ ID NO: 36 is a protein that has an amino acid sequence which varies from that of SEQ ID NO: 36 and which retains its pore forming ability. The ability of a variant to form a pore can be assayed using any method known in the art as discussed above.

Over the entire length of the amino acid sequence of SEQ ID NO: 36, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 36 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed below.

Amino acid substitutions may be made to the amino acid sequence of SEQ ID NO: 36 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 36 may additionally be deleted from the variants described above. Up to 1, 2, 3, 4, 5, 10, 20 or 30 residues may be deleted, or more.

Variants may include fragments of SEQ ID NO: 36. Such fragments retain pore forming activity. This may be assayed as described above. Fragments may be at least 50, 100, 150, 200 or 250 amino acids in length. Such fragments may be used to produce the pores of the invention. Since the region of from about position 44 to about position 126 of SEQ ID NO: 36 can be modified by one or more deletions in accordance with the invention, a fragment does not have to contain the entire region. Hence, fragments shorter than the length of the unmodified region are envisaged by the invention. A fragment preferably comprises the pore forming domain of SEQ ID NO: 36. A fragment more preferably comprises the region from about position 44 to about position 126 of SEQ ID NO: 36.

One or more amino acids may be alternatively or additionally added to the variants described above. An extension may be provided at the amino terminal or carboxy terminal of the amino acid sequence of the variant of SEQ ID NO: 36, including a fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 36 and which retains its ability to form a pore. A variant typically contains the region of SEQ ID NO: 36 that is responsible for pore formation, namely from about position 44 to about position 126. It may contain a fragment of this region as discussed above.

The variant of SEQ ID NO: 36 may be any of those disclosed in International Application No. PCT/GB2013/050667 (published as WO 2013/153359).

In some embodiments, the transmembrane protein pore is chemically modified. The pore can be chemically modified in any way and at any site. Suitable modifications are discussed below with reference to the mutant Msp monomers. Such modifications can be applied to any of the pores used in the invention.

Polynucleotide Binding Protein

Suitable polynucleotide binding proteins are discussed below. The unmodified polynucleotide binding protein used in the invention preferably comprises the sequence shown in SEQ ID NO: 24 or a variant thereof. Suitable variants of SEQ ID NO: 24 are discussed below.

In SEQ ID NO: 24 or a variant thereof, the part of the polynucleotide binding protein which interacts with the transmembrane pore typically comprises the amino acids at positions 1, 2, 3, 4, 5, 6, 51, 176, 177, 178, 179, 180, 181, 185, 189, 191, 193, 194, 195, 197, 198, 199, 200, 201, 202, 203, 204, 207, 208, 209, 210, 211, 212, 213, 216, 219, 220, 221, 223, 224, 226, 227, 228, 229, 247, 254, 255, 256, 257, 258, 259, 260, 261, 298, 300, 304, 308, 318, 319, 321, 337, 347, 350, 351, 405, 415, 422, 434, 437, 438. These numbers correspond to the relevant positions in SEQ ID NO: 24 and may need to be altered in the case of variants where one or more amino acids have been inserted or deleted compared with SEQ ID NO: 24. A skilled person can determine the corresponding positions in a variant as discussed above. The part of the polynucleotide binding protein which interacts with the transmembrane pore preferably comprises the amino acids at (a) positions 1, 2, 4, 51, 177, 178, 179, 180, 185, 193, 195, 197, 198, 199, 200, 202, 203, 204, 207, 208, 209, 210, 211, 212, 216, 221, 223, 224, 226, 227, 228, 229, 254, 255, 256, 257, 258, 260, 304, 318, 321, 347, 350, 351, 405, 415, 422, 434, 437 and 438 in SEQ ID NO: 24 or at the corresponding positions in the variant thereof; or (b) positions 1, 2, 178, 179, 180, 185, 195, 197, 198, 199, 200, 202, 203, 207, 209, 210, 212, 216, 221, 223, 226, 227, 255, 258, 260, 304, 350 and 438 in SEQ ID NO: 24 or at the corresponding positions in the variant thereof.

The part of the polynucleotide binding protein which interacts with the transmembrane pore preferably comprises one or more of, such as 2, 3 or 4 of, the amino acids at positions 195, 198, 199 and 258 in SEQ ID NO: 24 or the variant thereof. The part of the polynucleotide binding protein which interacts with the transmembrane pore preferably comprises the amino acid at position 195, 198, 199 or 258 in SEQ ID NO: 24 or at the corresponding positions in the variant thereof. The modified polynucleotide binding protein of the invention preferably comprises a variant of SEQ ID NO: 24 which comprises one or more of the following modifications (a) W195A, (b) D198V, (c) K199L or (d) E258L. The variant may comprise {a}; {b}; {c}; {d}; {a,b}; {a,c}; {a,d}; {b,c}; {b,d}; {c,d}; {a,b,c}; {a,b,d}; {a,c,d}; {b,c,d}; or {a,b,c,d}. The variant of SEQ ID NO: 24 may further comprise any of the additional modifications discussed below. The modifications set out in this paragraph are preferred when the modified polynucleotide binding protein interacts with a pore derived from MspA, particularly any of the modified pores of the invention.

The part of the polynucleotide binding protein which interacts with the transmembrane pore preferably comprises the amino acid at position 199 of SEQ ID NO: 24 or at the corresponding position in the variant thereof. The modified polynucleotide binding protein of the invention preferably comprises a variant of SEQ ID NO: 24 which comprises K199A, K199V, K199F, K199D, K199S, K199W or K199L.

The unmodified polynucleotide binding protein used in the invention preferably comprises the sequence shown in SEQ ID NO: 9 or a variant thereof. A variant of SEQ ID NO: 9 is a protein that has an amino acid sequence which varies from that of SEQ ID NO: 9 and which retains its ability to bind a polynucleotide. The ability of a variant to bind a polynucleotide can be assayed using any method known in the art.

Over the entire length of the amino acid sequence of SEQ ID NO: 9, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 9 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed below.

The variant may be modified in any of the ways discussed above with reference to other variants. Preferred variants of SEQ ID NO: 9 lack amino acids 1 to 4.

In SEQ ID NO: 9 or variant thereof, the part of the polynucleotide binding protein which interacts with the transmembrane pore typically comprises the amino acids at positions 80, 81, 82, 84, 85, 205, 206, 209, 215, 216, 220, 221, 224, 236, 240, 241, 267, 270, 272, 278, 287, 289, 293, 296, 307, 308, 309, 310, 320, 321, 322, 323, 327, 349, 415, 418 and 419. These numbers correspond to the relevant positions in SEQ ID NO: 9 and may need to be altered in the case of variants where one or more amino acids have been inserted or deleted. A skilled person can determine the corresponding positions in a variant as discussed above.

The part of the polynucleotide binding protein which interacts with the transmembrane pore preferably comprises the amino acids at (a) positions 80, 84, 205, 209, 215, 216, 221, 224, 236, 241, 267, 272, 289, 296, 307, 308, 309, 320, 321, 322, and 419 in SEQ ID NO: 9 or at the corresponding positions in a variant thereof;

(b) positions 80, 84, 209, 215, 216, 221, 267, 272, 289, 307, 308, 309, 321 and 322 in SEQ ID NO: 9 or at the corresponding positions in a variant thereof; or (b) positions 215, 267, 272, 307, 308 and 322 in SEQ ID NO: 9 or at the corresponding positions in a variant thereof.

Any of these positions may be replaced with phenylalanine (F), tryptophan (W), isoleucine (I), leucine (L), valine (V), alanine (A), arginine (R), lysine (K), aspartic acid (D), glutamic acid (E) or tyrosine (Y) in accordance with the invention.

Parts which Interact

The part of the transmembrane pore which may be modified in accordance with the invention is typically the part of the transmembrane pore which interacts with or contacts the polynucleotide binding protein when the protein controls the movement of the target polynucleotide with respect to the pore. The part may comprise one or more amino acids which interact with or contact one or more amino acids in the polynucleotide binding protein when the protein controls the movement of the target polynucleotide with respect to the pore. Specific amino acids are discussed in more detail below.

The part of the polynucleotide binding protein which may be modified in accordance with the invention is typically the part of the protein which interacts with or contacts the transmembrane pore when the protein controls the movement of the target polynucleotide with respect to the pore. The part may comprise one or more amino acids which interact with or contact one or more amino acids in the transmembrane pore when the protein controls the movement of the target polynucleotide with respect to the pore. Specific amino acids are discussed in more detail below.

The part of the transmembrane pore which interacts with the polynucleotide binding protein and/or the part of the polynucleotide binding protein which interacts with the transmembrane pore can be identified using any method known in the art. The part(s) may be identified using protein modelling, x-ray diffraction measurement of the protein in a crystalline state (Rupp B (2009). Biomolecular Crystallography: Principles, Practice and Application to Structural Biology. New York: Garland Science.), nuclear magnetic resonance (NMR) spectroscopy of the protein in solution (Mark Rance; Cavanagh, John; Wayne J. Fairbrother; Arthur W. Hunt III; Skelton, Nicholas J. (2007). Protein NMR spectroscopy: principles and practice (2nd ed.). Boston: Academic Press.) or cryo-electron microscopy of the protein in a frozen-hydrated state (van Heel M, Gowen B, Matadeen R, Orlova E V, Finn R, Pape T, Cohen D, Stark H, Schmidt R, Schatz M, Patwardhan A (2000). "Single-particle electron cryo-microscopy: towards atomic resolution." Q Rev Biophys. 33: 307-69. Structural information of proteins determined by above mentioned methods are publicly available from the protein bank (PDB) database.

Protein modelling exploits the fact that protein structures are more conserved than protein sequences amongst homologues. Hence, producing atomic resolution models of proteins is dependent upon the identification of one or more protein structures that are likely to resemble the structure of the query sequence. In order to assess whether a suitable protein structure exists to use as a "template" to build a protein model, a search is performed on the protein data bank (PDB) database. A protein structure is considered a suitable template if it shares a reasonable level of sequence identity with the query sequence. If such a template exists, then the template sequence is "aligned" with the query sequence, i.e. residues in the query sequence are mapped onto the template residues. The sequence alignment and template structure are then used to produce a structural model of the query sequence. Hence, the quality of a protein model is dependent upon the quality of the sequence alignment and the template structure.

The part(s) may also be identified using molecular simulations or energy minimisations (Kalli A C, Campbell I D, Sansom M S P, (2013) "Conformational Changes in Talin on Binding to Anionic Phospholipid Membranes Facilitate Signaling by Integrin Transmembrane Helices" PLOS Computational Biology, 9, 10, e1003316 and Durrieu M, Lavery R, Baaden M, (2008) "Interactions between Neuronal Fusion Proteins Explored by Molecular Dynamics", Biophysical Journal, 94, 3436-3446).

Surface

The method preferably comprises making one or modifications to the surface of the transmembrane pore which interacts with the polynucleotide binding protein and/or to the surface of the polynucleotide binding protein which interacts with the transmembrane pore. Any number of modifications can be made, such as 2 or more, 3 or more, 5 or more, 10 or more, 15 or more, 20 or more, 25 or more, 30 or more, 50 or more or 100 or more modifications.

The surface of the transmembrane pore and/or the polynucleotide binding protein may be identified using any method in the art, including any of the methods disclosed above. For instance, the surface may be identified using protein modeling, molecular simulations or energy minimisations. Protein modelling is a general term to describe e.g. making models of proteins of unknown structure, simulating proteins to investigate dynamics, molecular docking.

Pore Entrance

The method comprises making one or modifications to the entrance of the transmembrane pore which interacts with the polynucleotide binding protein. Any number of modifications may be made as discussed above. The entrance of the pore may be identified as discussed above.

Modifications

Any modifications may be made in accordance with the invention. The method may involve making one or more modifications which (a) alter the charge, (b) alter the sterics, (c) alter the hydrogen bonding, (d) alter the π stacking or (e) alter the structure of the part of the transmembrane pore which interacts with the polynucleotide binding protein and/or the part of the polynucleotide binding protein which interacts with the transmembrane pore. Any number and combination of these may be altered. For instance, the method may involve making one or more modification which {a}; {b}; {c}; {d}; {e}; {a,b}; {a,c}; {a,d}; {a,e}; {b,c}; {b,d}; {b,e}; {c,d}; {c,e}; {d,e}; {a,b,c}; {a,b,d};

{a,b,e}; {a,c,d}; {a,c,e}; {a,d,e}; {b,c,d}; {b,c,e}; {b,d,e}; {c,d,e}; {a,b,c,d}; {a,b,c,e}; {a,b,d,e}; {a,c,d,e}; {b,c,d,e}; or {a,b,c,d,e}.

When modifying a protein, the one or more modifications typically involve introducing or replacing one or more amino acids. The invention typically involves making one or more amino acid substitutions.

Modifications which alter the charge may involve increasing the net negative charge or decreasing the net negative charge. The method preferably comprises making one or more modifications which decrease the net negative charge of the part of the transmembrane pore which interacts with the polynucleotide binding protein. Modifications which decrease net negative charge are discussed in more detail below with reference to mutant Msp monomers. Any of these modifications may be made in other transmembrane pores and/or polynucleotide binding proteins. In a preferred embodiment, the transmembrane pore comprises seven or more monomers, such as 8 or 9 monomers, comprising SEQ ID NO: 2 of a variant thereof and the method preferably comprises modifying one or more of the seven or more monomers, such as 2, 3, 4, 5, 6, 7, 8 or 9 of the monomers, so they do not comprise aspartic acid (D) or glutamic acid (E) at one or more of positions 56, 57, 59, 134 and 139 in SEQ ID NO: 2 or at one or more of the corresponding positions in the variant thereof. The method more preferably comprises modifying one or more of the monomers, such as 2, 3, 4, 5, 6, 7, 8 or 9 of the monomers, so they comprise one or more of (a) D56N, D56R, D56F, D56Y, D56L D56K, and/or (b) E57N, E57R, E57F, E57Y, E57L or E57K, and/or (c) E59N, E59R, E59F, E59Y, E59L, E59K, and/or (d) D134N, D134R, D134F, D134Y, D134L, D134K, and/or (e) E139N, E139R, E139F, E139Y, E139L or E139K. One or more of the monomers may comprise any number and combination of these modifications. For instance, one or more of the monomers may comprise {a}; {b}; {c}; {d}; {e}; {a,b}; {a,c}; {a,d}; {a,e}; {b,c}; {b,d}; {b,e}; {c,d}; {c,e}; {d,e}; {a,b,c}; {a,b,d}; {a,b,e}; {a,c,d}; {a,c,e}; {a,d,e}; {b,c,d}; {b,c,e}; {b,d,e}; {c,d,e}; {a,b,c,d}; {a,b,c,e}; {a,b,d,e}, {a,c,d,e}; {b,c,d,e}; or {a,b,c,d,e}. One or more of the monomers may comprise D56N and E59R, D56F and E59R, D56N and E59F, D56N and E59Y or D56L and E59L. One or more of the monomers may comprise D56N and E59R, D56F and E59R or D56N and E59F.

The modified transmembrane pore (i.e. the transmembrane pore resulting from the modification method of the invention) preferably does not comprise one or more monomers, such as 2, 3, 4, 5, 6, 7, 8 or 9 monomers, which are variants of SEQ ID NO: 2 comprising or consisting of E59R, D90N, D91N, D93N, D118R, D134R and E139K.

Modifications which alter the sterics may involve increasing or decreasing the size of amino acid residues, for instance by substitution. For instance, sterics can be increased by the introduction of one or more bulky amino acids, such as phenylalanine (F), tryptophan (W), tyrosine (Y) and histidine (H).

Modifications which alter the hydrogen bonding may involve the introduction or replacement of one or more amino acids which can hydrogen bond.

Modifications which alter the π stacking may involve the introduction or replacement of amino acids that interact through delocalised electron π systems. For instance, π stacking can be increased by the introduction of one or more aromatic amino acids, such as phenylalanine (F), tryptophan (W), tyrosine (Y) and histidine (H).

In a preferred embodiment, the transmembrane pore comprises one or more monomers comprising SEQ ID NO: 36 of a variant thereof and the method preferably comprises modifying one or more of the monomers so they comprise phenylalanine (F), tryptophan (W), isoleucine (I), leucine (L), valine (V), alanine (A), arginine (R), lysine (K), aspartic acid (D), glutamic acid (E) or tyrosine (Y) at one or more of positions (i) 31, (ii) 33, (iii) 108, (iv) 109, (v) 110 and (vi) 138 in SEQ ID NO: 36 or at one or more of the corresponding positions in the variant thereof, such as {i}, {ii}, {iii}, {iv}, {v}, {vi}, {i,ii}, {i,iii}, {i,iv}, {i,v}, {i,vi}, {ii,iii}, {ii,iv}, {ii,v}, {ii,vi}, {iii,iv}, {iii,v}, {iii,vi}, {iv,v}, {iv,vi}, {v,vi}, {i,ii,iii}, {i,ii,iv}, {i,ii,v}, {i,ii,vi}, {i,iii,iv}, {i,iii,v}, {i,iii,vi}, {i,iv,v}, {i,iv,vi}, {i,v,vi}, {ii,iii,iv}, {ii,iii,v}, {ii,iii,vi}, {ii,iv,v}, {ii,iv,vi}, {ii,v,vi}, {iii,iv,v}, {iii,iv,vi}, {iii,v,vi}, {iv,v,vi}, {i,ii,iii,iv}, {i,ii,iii,v}, {i,ii,iii,vi}, {i,ii,iv,v}, {i,ii,iv,vi}, {i,ii,v,vi}, {i,iii,iv,v}, {i,iii,iv,vi}, {i,iii,v,vi}, {i,iv,v,vi}, {ii,iii,iv,v}, {ii,iii,iv,vi}, {ii,iii,v,vi}, {ii,iv,v,vi}, {iii,iv,v,vi}, {i,ii,iii,iv,v}, {i,ii,iii,iv,vi}, {i,ii,iii,v,vi}, {i,ii,iv,v,vi}, {i,iii,iv,v,vi}, {ii,iii,iv,v,vi} or {i,ii,iii,iv,v,vi}.

In a preferred embodiment, the transmembrane pore comprises seven monomers comprising SEQ ID NO: 4 of a variant thereof and the method preferably comprises modifying one or more of the monomers, such as 1, 2, 3, 4, 5, 6 or 7 of the monomers, so they comprise phenylalanine (F), tryptophan (W), isoleucine (I), leucine (L), valine (V), alanine (A), arginine (R), lysine (K), aspartic acid (D), glutamic acid (E) or tyrosine (Y) at one or more of positions 16, 17, 18, 19, 21, 46, 47, 93, 236, 237, 238, 239, 240, 241, 242, 281, 283, 285, 287, 288 and 293 in SEQ ID NO: 4 or at one or more of the corresponding positions in the variant thereof.

In a more preferred embodiment, the transmembrane pore comprises seven monomers comprising SEQ ID NO: 4 of a variant thereof and the method preferably comprises modifying one or more of the monomers, such as 1, 2, 3, 4, 5, 6 or 7 of the monomers, so they comprise phenylalanine (F), tryptophan (W), isoleucine (I), leucine (L), valine (V), alanine (A), arginine (R), lysine (K), aspartic acid (D), glutamic acid (E) or tyrosine (Y) at one or more of positions (a) 17, 18, 19, 46, 47, 93, 236, 237, 238, 239, 240, 241, 242, 287, 288 and 293 in SEQ ID NO: 4 or at one or more of the corresponding positions in the variant thereof;

(b) 17, 19, 46, 47, 93, 236, 237, 238, 239, 240, 241, 242 and 287 in SEQ ID NO: 4 or at one or more of the corresponding positions in the variant thereof; or (c) 17, 19, 46, 93, 236, 237, 239, 240, 287 and 288 in SEQ ID NO: 4 or at one or more of the corresponding positions in the variant thereof.

Modified Pores

The method also provides a transmembrane pore modified in accordance with the invention. A part of the transmembrane pore which interacts with a polynucleotide binding protein has been modified. The part of the transmembrane pore which interacts with a polynucleotide binding protein when the polynucleotide binding protein is used to control the movement of a target polynucleotide with respect to, or through, the pore has been modified. Any of the modifications discussed above may be made in the pores of the invention.

The transmembrane pore preferably comprises seven or more monomers, such as 8 or 9 monomers, comprising the sequence shown in SEQ ID NO: 2 or a variant thereof. One or more of the seven or more monomers, such as 2, 3, 4, 5, 6, 7, 8 or 9 of the monomers, preferably comprises a variant of SEQ ID NO: 2 which comprises one or more of (a) D56N, D56R, D56F, D56Y or D56L, (b) E57N or E57R, (c) E59N, E59R, E59F, E59Y or E59L, (d) D134N or D134R and (e) E139N, E139R or E139K. Any number and combination of these modifications may be made in a single monomer as discussed above.

One or more of the seven or more monomers, such as 2, 3, 4, 5, 6, 7, 8 or 9 of the monomers, preferably comprises a variant of SEQ ID NO: 2 which comprises D56N, D56R, D56F, D56Y or D56L.

One or more of the seven or more monomers, such as 2, 3, 4, 5, 6, 7, 8 or 9 of the monomers, preferably comprises a variant of SEQ ID NO: 2 which comprises E59N, E59R, E59F, E59Y or E59L.

One or more of the seven or more monomers, such as 2, 3, 4, 5, 6, 7, 8 or 9 of the monomers, preferably comprises a variant of SEQ ID NO: 2 which comprises D56N and E59R, D56F and E59R, D56N and E59F, D56N and E59Y or D56L and E59L.

One or more of the seven or more monomers, such as 2, 3, 4, 5, 6, 7, 8 or 9 of the monomers, preferably comprises a variant of SEQ ID NO: 2 which comprises D56N and E59R, D56F and E59R or D56N and E59F.

One or more of the seven or more monomers, such as 2, 3, 4, 5, 6, 7, 8 or 9 of the monomers, are not variants of SEQ ID NO: 2 which comprise or consist of E59R, D90N, D91N, D93N, D118R, D134R and E139K.

The transmembrane pore preferably comprises one or more monomers comprising a variant of SEQ ID NO: 36 which comprises phenylalanine (F), tryptophan (W), isoleucine (I), leucine (L), valine (V), alanine (A), arginine (R), lysine (K), aspartic acid (D), glutamic acid (E) or tyrosine (Y) at one or more of positions (i) 31, (ii) 33, (iii) 108, (iv) 109, (v) 110 and (vi) 138 or at one or more the corresponding positions thereof, such as {i}, {ii}, {iii}, {iv}, {v}, {vi}, {i,ii}, {i,iii}, {i,iv}, {i,v}, {i,vi}, {ii,iii}, {ii,iv}, {ii,v}, {ii,vi}, {iii,iv}, {iii,v}, {iii,vi}, {iv,v}, {iv,vi}, {v,vi}, {i,ii,iii}, {i,ii,iv}, {i,ii,v}, {i,ii,vi}, {i,iii,iv}, {i,iii,v}, {i,iii,vi}, {i,iv,v}, {i,iv,vi}, {i,v,vi}, {ii,iii,iv}, {ii,iii,v}, {ii,iii,vi}, {ii,iv,v}, {ii,iv,vi}, {ii,v,vi}, {iii,iv,v}, {iii,iv,vi}, {iii,v,vi}, {iv,v,vi}, {i,ii,iii,iv}, {i,ii,iii,v}, {i,ii,iii,vi}, {i,ii,iv,v}, {i,ii,iv,vi}, {i,ii,v,vi}, {i,iii,iv,v}, {i,iii,iv,vi}, {i,iii,v,vi}, {i,iv,v,vi}, {ii,iii,iv,v}, {ii,iii,iv,vi}, {ii,iii,v,vi}, {ii,iv,v,vi}, {iii,iv,v,vi}, {i,ii,iii,iv,v}, {i,ii,iii,iv,vi}, {i,ii,iii,v,vi}, {i,ii,iv,v,vi}, {i,iii,iv,v,vi}, {ii,iii,iv,v,vi} or {i,ii,iii,iv,v,vi}.

The transmembrane pore preferably comprises seven monomers comprising SEQ ID NO: 4 or a variant thereof in which one or more of the monomers, such as 1, 2, 3, 4, 5, 6 or 7 of the monomers, is a variant of SEQ ID NO: 4 which comprises phenylalanine (F), tryptophan (W), isoleucine (I), leucine (L), valine (V), alanine (A), arginine (R), lysine (K), aspartic acid (D), glutamic acid (E) or tyrosine (Y) at one or more of positions 16, 17, 18, 19, 21, 46, 47, 93, 236, 237, 238, 239, 240, 241, 242, 281, 283, 285, 287, 288 and 293 or at one or more of the corresponding positions thereof, such as one or more of positions:

(a) 17, 18, 19, 46, 47, 93, 236, 237, 238, 239, 240, 241, 242, 287, 288 and 293 or at one or more of the corresponding positions thereof;
(b) 17, 19, 46, 47, 93, 236, 237, 238, 239, 240, 241, 242 and 287 in SEQ ID NO: 4 or at one or more of the corresponding positions thereof; or
(c) 17, 19, 46, 93, 236, 237, 239, 240, 287 and 288 in SEQ ID NO: 4 or at one or more of the corresponding positions thereof.

Mutant Msp Monomers

The present invention also provides mutant Msp monomers. The mutant Msp monomers may be used to form the pores of the invention. A mutant Msp monomer is a monomer whose sequence varies from that of a wild-type Msp monomer and which retains the ability to form a pore. Methods for confirming the ability of mutant monomers to form pores are well-known in the art and are discussed in more detail below.

The mutant monomers have improved polynucleotide reading properties i.e. display improved polynucleotide capture and nucleotide discrimination. In particular, pores constructed from the mutant monomers capture nucleotides and polynucleotides more easily than the wild type. In addition, pores constructed from the mutant monomers display an increased current range, which makes it easier to discriminate between different nucleotides, and a reduced variance of states, which increases the signal-to-noise ratio. In addition, the number of nucleotides contributing to the current as the polynucleotide moves with respect to, or through, pores constructed from the mutants is decreased. This makes it easier to identify a direct relationship between the observed current as the polynucleotide moves with respect to, or through, the pore and the polynucleotide sequence.

A mutant monomer of the invention comprises a variant of the sequence shown in SEQ ID NO: 2. SEQ ID NO: 2 is the wild-type MspA monomer. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a triblock copolymer membrane such that it diffuses to the membrane and is inserted by binding to the membrane and assembling into a functional state.

The mutant Msp monomer is modified in accordance with the invention. A part of the monomer which interacts with a polynucleotide binding protein has been modified. The part of the monomer which interacts with a polynucleotide binding protein when the polynucleotide binding protein is used to control the movement of a target polynucleotide with respect to, or through, a pore comprising the monomer has been modified. Any of the modifications discussed above may be made in the monomer of the invention.

The monomer preferably comprises a variant of SEQ ID NO: 2 which comprises one or more of (a) D56N, D56R, D56F, D56Y or D56L, (b) E57N or E57R, (c) E59N, E59R, E59F, E59Y or E59L, (d) D134N or D134R and (e) E139N, E139R or E139K. Any number and combination of these modifications may be made in the monomer as discussed above. The variant preferably comprises D56N and E59R, D56F and E59R, D56N and E59F, D56N and E59Y or D56L and E59L. The variant preferably comprises D56N and E59R, D56F and E59R or D56N and E59F. The monomer preferably does not comprise a variant of SEQ ID NO: 2 which comprises or consists of E59R, D90N, D91N, D93N, D118R, D134R and E139K.

Barrel Deletions

In the variant (of SEQ ID NO: 2), 2, 4, 6, 8 or 10 of the amino acids at positions 72 to 82 of SEQ ID NO: 2 may have been deleted. 2, 4, 6, 8 or 10 of the amino acids at positions 111 to 121 of SEQ ID NO: 2 may have also been deleted. In other words, 2, 4, 6, 8 or 10 amino acids may be deleted from the downward strand (positions 72 to 82) and the upward strand (positions 111 to 121) of the barrel region of SEQ ID NO: 2. These deletions and their advantages are discussed in more detail in UK Application No. 1417708.3 co-filed with this application.

The number of amino acids deleted from positions 72 to 82 may be different from the number of amino acids deleted from positions 111 to 121. The number of amino acids deleted from positions 72 to 82 is preferably the same as the number of amino acids deleted from positions 111 to 121.

Any combination of amino acids from positions 72 to 82 and amino acids from positions 111 to 121 may be deleted. The majority of the amino acids in the downward and upwards strands of the barrel in SEQ ID NO: 2 alternate between hydrophobic and hydrophilic. The hydrophobic amino acids are selected from tryptophan (W), leucine (L), valine (V), isoleucine (I), phenylalanine (F) and tyrosine (Y). The hydrophilic amino acids are selected from serine (S), glycine (G), asparagine (N), proline (P) and aspartic acid (D).

Positions 72 to 82 of SEQ ID NO: 2 correspond to W-S-L-G-V-G-I-N-F-S-Y (SEQ ID NO: 26 with the hydrophobic amino acids underlined). Positions 111 to 121 of SEQ ID NO: 2 correspond to P-G-V-S-I-S-A-D-L-G-N (SEQ ID NO: 27 with the hydrophobic amino acids underlined). This alternation between hydrophobic and hydrophilic amino acids results in the beta-sheet which forms part of the barrel of the pore.

The amino acids from positions 72 to 82 remaining after deletion (i.e. after 2, 4, 6, 8 or 10 amino acids have been deleted from positions 72 to 82) preferably comprise 3, 5, 7 or 9 consecutive amino acids which alternate between hydrophobic and hydrophilic.

The amino acids from positions 111 to 121 remaining after deletion (i.e. after 2, 4, 6, 8 or 10 amino acids have been deleted from positions 111 to 121) preferably comprise 3, 5, 7 or 9 consecutive amino acids which alternate between hydrophobic and hydrophilic.

The amino acids deleted from positions 72 to 82 may correspond to the amino acids deleted from positions 111 to 121 as shown in Table 1 below. For instance, if L74 and G75 are deleted from positions 72 to 82, D118 and L119 may be deleted from positions 111 to 121.

TABLE 1

Corresponding amino acids in the barrel of SEQ ID NO: 2

| Position in (a) | Corresponding position in (b) |
|---|---|
| W72 | N121 |
| S73 | G120 |
| L74 | L119 |
| G75 | D118 |
| V76 | A117 |
| G77 | S116 |
| I78 | I115 |
| N79 | S114 |
| F80 | V113 |
| S81 | G112 |
| Y82 | P111 |

One or more positions of the amino acids that have been deleted from positions 72 to 82 may not correspond to the one or more positions of the amino acids that have been deleted from positions 111 to 121 as shown in Table 1. For instance, if L74 and G75 are deleted from positions 72 to 82, A117 and D118 may be deleted from positions 111 to 121.

The positions of (all of) the amino acids that have been deleted from positions 72 to 82 may not correspond to the positions of (all of) the amino acids that have been deleted from positions 111 to 121 as shown in Table 1. For instance, if L74 and G75 are deleted from positions 72 to 82, I115 and S116 may be deleted from positions 111 to 121.

The amino acids deleted from positions 72 to 82 are preferably consecutive. The amino acids deleted from positions 111 to 121 are preferably consecutive. The amino acids deleted from positions 72 to 82 and the amino acids deleted from positions 111 to 121 are preferably consecutive.

The invention preferably provides mutant monomers comprising a variant of the sequence shown in SEQ ID NO: 2, wherein in the variant (i) L74, G75, D118 and L119 have been deleted, (ii) G75, V76, A117 and D118 have been deleted, (iii) V76, G77, S116 and A117 have been deleted, (iv) G77, I78, I115 and S116 have been deleted, (v) I78, N79, S114 and I115 have been deleted, (vi) N79, F80, V113 and S114 have been deleted or (vii) F80, S81, G112 and V113 have been deleted. The invention preferably comprises a variant of the sequence shown in SEQ ID NO: 2, wherein in the variant L74, G75, V76, G77, S116, A117, D118 and L119 have been deleted. The invention preferably comprises a variant of the sequence shown in SEQ ID NO: 2, wherein in the variant L74, G75, N79, F80, V113, S114, D118 and L119 or L74, G75, F80, S81, G112, V113, D118 and L119.

The skilled person can identify other combinations of amino acids that may be deleted in accordance with the invention. The following discussion using the numbering of residues in SEQ ID NO: 2 (i.e. before any amino acids have been deleted as defined above).

Positions 90 and 91

In wild-type MspA, amino acids 90 and 91 are both aspartic acid (D). These amino acids in each monomer form part of an inner constriction of the pore. The variant preferably does not comprise aspartic acid (D) at position 90. The variant preferably does not comprise aspartic acid (D) or glutamic acid (E) at position 90. The variant preferably does not have a negatively charged amino acid at position 90.

The variant preferably does not comprise aspartic acid (D) at position 91. The variant preferably does not comprise aspartic acid (D) or glutamic acid (E) at position 91. The variant preferably does not have a negatively charged amino acid at position 91.

The variant preferably comprises serine (S), glutamine (Q), leucine (L), methionine (M), isoleucine (I), alanine (A), valine (V), glycine (G), phenylalanine (F), tryptophan (W), tyrosine (Y), histidine (H), threonine (T), arginine (R), lysine (K), asparagine (N) or cysteine (C) at position 90 and/or position 91. Any combinations of these amino acids at positions 90 and 91 are envisaged by the invention. The variant preferably comprises asparagine (N) at position 90 and/or position 91. The variant more preferably comprises asparagine (N) at position 90 and position 91. These amino acids are preferably inserted at position 90 and/or 91 by substitution.

Position 93

In wild-type MspA, amino acid 93 is aspartic acid (D). This amino acid in each monomer also forms part of an inner constriction of the pore.

The variant preferably comprises aspartic acid (D) or glutamic acid (E) at position 93. The variant preferably has a negative charge at position 93. The glutamic acid (E) is preferably introduced by substitution.

Cap Forming Region

In wild-type MspA, amino acids 1 to 72 and 122 to 184 form the cap of the pore. Of these amino acids, V9, Q12, D13, R14, T15, W40, I49, P53, G54, D56, E57, E59, T61, E63, Y66, Q67, I68, F70, P123, I125, Q126, E127, V128, A129, T130, F131, S132, V133, D134, S136, G137, E139, V144, H148, T150, V151, T152, F163, R165, I167, S169, T170 and S173 face inwards into the channel of the pore.

Barrel Forming Region

In wild-type MspA, amino acids 72 to 82 and 112 to 121 form the barrel of the pore. Of these amino acids, S73, G75, G77, N79, S81, G112, S114, S116, D118 and G120 face inwards into the channel of the pore. S73, G75, G77, N79, S81 face inwards in the downwards strand and G112, S114, S116, D118 and G120 face inwards in the upwards strand.

Decreased Net Negative Charge

The variant preferably comprises one or more modifications which decrease the net negative charge of the inward facing amino acids in the cap forming region and/or the barrel forming region of the monomer. The variant preferably comprises two or more modifications which decrease the net negative charge of the inward facing amino acids in the cap forming region and the barrel forming region of the monomer. Any such modifications to the barrel forming region are in addition to the deletions of the invention discussed above.

The variant may comprise any number of modifications, such as 1 or more, 2 or more, 3 or more, 4 or more, 5 or more, 6 or more, 7 or more, 8 or more, 9 or more, 10 or more, 15 or more, 20 or more, 30 or more, or 40 or more modifications.

The net negative charge may be decreased by any means known in the art. The net negative charge is decreased in a manner that does not interfere with the ability of the mutant monomer to form a pore. This can be measured as discussed above.

The net negative charge of the inward facing amino acids in the cap forming region and/or the barrel forming region may be decreased. This means that the inward facing amino acids in the cap forming region and/or the barrel forming region comprise fewer negatively charged amino acids than in SEQ ID NO: 2 and/or comprises more positively charged amino acids than in SEQ ID NO: 2. The one or more modifications may lead to a net positive charge in the inward facing amino acids in the cap forming region and/or the barrel forming region.

The net charge can be measured using methods known in the art. For instance, the isoelectric point may be used to define the net charge of the inward facing amino acids in the cap forming region and/or the barrel forming region.

The one or more modifications are preferably one or more deletions of negatively charged amino acids. Removal of one or more negatively charged amino acids reduces the net negative charge of the inward facing amino acids in the cap forming region and/or barrel forming region. A negatively charged amino acid is an amino acid with a net negative charge. Negatively charged amino acids include, but are not limited to, aspartic acid (D) and glutamic acid (E). Methods for deleting amino acids from proteins, such as MspA monomers, are well known in the art.

The one or more modifications are preferably one or more substitutions of negatively charged amino acids with one or more positively charged, uncharged, non-polar and/or aromatic amino acids. A positively charged amino acid is an amino acid with a net positive charge. The positively charged amino acid(s) can be naturally-occurring or non-naturally-occurring. The positively charged amino acid(s) may be synthetic or modified. For instance, modified amino acids with a net positive charge may be specifically designed for use in the invention. A number of different types of modification to amino acids are well known in the art.

Preferred naturally-occurring positively charged amino acids include, but are not limited to, histidine (H), lysine (K) and arginine (R). Any number and combination of H, K and/or R may be substituted for the inward facing amino acids in the cap forming region and/or barrel forming region.

The uncharged amino acids, non-polar amino acids and/or aromatic amino acids can be naturally occurring or non-naturally-occurring. They may be synthetic or modified. Uncharged amino acids have no net charge. Suitable uncharged amino acids include, but are not limited to, cysteine (C), serine (S), threonine (T), methionine (M), asparagines (N) and glutamine (Q). Non-polar amino acids have non-polar side chains. Suitable non-polar amino acids include, but are not limited to, glycine (G), alanine (A), proline (P), isoleucine (I), leucine (L) and valine (V). Aromatic amino acids have an aromatic side chain. Suitable aromatic amino acids include, but are not limited to, histidine (H), phenylalanine (F), tryptophan (W) and tyrosine (Y). Any number and combination of these amino acids may be substituted into the inward facing amino acids in the cap forming region and/or the barrel forming region.

The one or more negatively charged amino acids are preferably substituted with alanine (A), valine (V), asparagine (N) or glycine (G). Preferred substitutions include, but are not limited to, substitution of D with A, substitution of D with V, substitution of D with N and substitution of D with G.

The one or more modifications are preferably one or more introductions of positively charged amino acids. The introduction of positive charge decreases the net negative charge. The one or more positively charged amino acids may be introduced by addition or substitution. Any amino acid may be substituted with a positively charged amino acid. One or more uncharged amino acids, non-polar amino acids and/or aromatic amino acids may be substituted with one or more positively charged amino acids. Any number of positively charged amino acids may be introduced.

Wild-type MspA comprises a polar glutamine (Q) at position 126. The one or more modifications preferably reduce the net negative charge at position 126. The one or more modifications preferably increase the net positive charge at positions 126. This can be achieved by replacing the polar amino acid at position 126 or an adjacent or a nearby inward facing amino acid with a positively charged amino acid. The variant preferably comprises a positively charged amino acid at position 126. The variant preferably comprises a positively charged amino acid at one or more of positions 123, 125, 127 and 128. The variant may comprise any number and combination of positively charged amino acids at positions 123, 125, 127 and 128. The positively charged amino acid(s) may be introduced by addition or substitution.

The one or more modifications are preferably one or more introductions of positively charged amino acids which neutralise one or more negatively charged amino acids. The neutralisation of negative charge decreases the net negative charge. The one or more positively charged amino acids may be introduced by addition or substitution. Any amino acid may be substituted with a positively charged amino acid. One or more uncharged amino acids, non-polar amino acids and/or aromatic amino acids may be substituted with one or more positively charged amino acids. Any number of positively charged amino acids may be introduced. The number is typically the same as the number of negatively charged amino acids being neutralised.

The one or more positively charged amino acids may be introduced at any position in the cap forming region and/or the barrel forming region as long as they neutralise the negative charge of the one or more inward facing negatively charged amino acids. To effectively neutralise the negative charge in the cap forming region, there is typically 5 or fewer amino acids in the variant between each positively charged amino acid that is introduced and the negatively charged amino acid it is neutralising. There are preferably 4 or fewer, 3 or fewer or 2 or fewer amino acids in the cap forming region of the variant between each positively charged amino acid that is introduced and the negatively charged amino acid it is neutralising. There is more preferably two amino acids in the cap forming region of the variant between each positively charged amino acid that is introduced and the negatively charged amino acid it is neutralising. Each positively charged amino acid is most preferably introduced adjacent in the cap forming region of the variant to the negatively charged amino acid it is neutralising.

To effectively neutralise the negative charge in the barrel forming region, there is typically 5 or fewer inward facing amino acids between each positively charged amino acid that is introduced and the negatively charged amino acid it is neutralising. There is preferably 4 or fewer, 3 or fewer or 2 or fewer inward facing amino acids in the barrel forming region of the variant between each positively charged amino acid that is introduced and the negatively charged amino acid it is neutralising. There is more preferably one inward facing amino acid in the barrel forming region of the variant between each positively charged amino acid that is introduced and the negatively charged amino acid it is neutralising. Each positively charged amino acid is most preferably introduced at the inward facing position adjacent in the barrel forming region of the variant to the negatively charged amino acid it is neutralising.

Wild-type MspA comprises aspartic acid (D) at positions 118 and 134 and glutamic acid (E) at position 139. Amino acid 118 in each monomer is present within the barrel of the pore (FIG. 37). The variant preferably comprises a positively charged amino acid at one or more of positions 114, 116, 120, 123, 70, 73, 75, 77 and 79. Positive charges at one or more of these positions neutralise the negative charge at position 118. Positively charged amino acids may present at any number and combination of positions 114, 116, 120, 123, 70, 73, 75, 77 and 79. The amino acids may be introduced by addition or substitution.

Amino acids 134 and 139 in each monomer are part of the cap. The variant comprises a positively charged amino acid at one or more of positions 129, 132, 136, 137, 59, 61 and 63. Positive charges at one or more of these positions neutralise the negative charge at position 134. Positively charged amino acids may be present at any number and combination of positions 129, 132, 136, 137, 59, 61 and 63. The amino acids may be introduced by addition or substitution.

The variant preferably comprises a positively charged amino acid at one or more of positions 137, 138, 141, 143, 45, 47, 49 and 51. Positive charges at one or more of these positions neutralise the negative charge at position 139. Positively charged amino acids may be present at any number and combination of positions 137, 138, 141, 143, 45, 47, 49 and 51. The amino acids may be introduced by addition or substitution.

Positions 118, 126, 134 and 139

The one or more modifications preferably reduce the net negative charge at one or more of positions 118, 126, 134 and 139. The one or more modifications preferably reduce the net negative charge at 118; 126; 134; 139; 118 and 126; 118 and 134; 118 and 139; 126 and 134; 126 and 139; 134 and 139; 118, 126 and 134; 118, 126 and 139; 118, 134 and 139; 126, 134 and 139; or 118, 126, 134 and 139.

The variant preferably does not comprise aspartic acid (D) or glutamic acid (E) at one or more of positions 118, 126, 134 and 139. The variant preferably does not comprise aspartic acid (D) or glutamic acid (E) at any of the combination of positions 118, 126, 134 and 139 disclosed above. The variant more preferably comprises arginine (R), glycine (G) or asparagine (N) at one or more of positions 118, 126, 134 and 139, such as any of the combinations of positions 118, 126, 134 and 139 disclosed above. The variant most preferably comprises D118R, Q126R, D134R and E139K.

Methods for introducing or substituting naturally-occurring amino acids are well known in the art. For instance, methionine (M) may be substituted with arginine (R) by replacing the codon for methionine (ATG) with a codon for arginine (CGT) at the relevant position in a polynucleotide encoding the mutant monomer. The polynucleotide can then be expressed as discussed below.

Methods for introducing or substituting non-naturally-occurring amino acids are also well known in the art. For instance, non-naturally-occurring amino acids may be introduced by including synthetic aminoacyl-tRNAs in the IVTT system used to express the mutant monomer. Alternatively, they may be introduced by expressing the mutant monomer in *E. coli* that are auxotrophic for specific amino acids in the presence of synthetic (i.e. non-naturally-occurring) analogues of those specific amino acids. They may also be produced by naked ligation if the mutant monomer is produced using partial peptide synthesis.

The one or more modifications are preferably one or more chemical modifications of one or more negatively charged amino acids which neutralise their negative charge. For instance, the one or more negatively charged amino acids may be reacted with a carbodiimide.

Other Modifications

The variant preferably comprises one or more of:

(a) serine (S) at position 75;

(b) serine (S) at position 77; and (c) asparagine (N) or lysine (K) at position 88.

The variant may comprise any number and combination of (a) to (c), including (a), (b), (c), (a) and (b), (b) and (c), (a) and (c) and (a), (b) and (c). The variant preferably comprises G75S, G77S and L88N.

The variant most preferably comprises (a) D90N, D91N, D93N, D118R, D134R and E139K, (b) L88N, D90N, D91N, D93N, D118R, D134R and E139K, (c) G75S, G77S, L88N, D90N, D91N, D93N, D118R, Q126R, D134R and E139K or (d) G75S, G77S, L88N, D90N, D91N, D118R, Q126R, D134R and E139K.

The variant preferably further comprises one or more of:

(e) phenylalanine (F) at position 89;

(f) glutamic acid (E) at position 95 and lysine (K) at position 98;

(g) aspartic acid (D) at position 96;

(h) glycine (G) at position 102;

(i) alanine (A) at position 103; and (j) alanine (A), serine (S) or proline (P) at position 108.

The may comprise any number and combination of (e) to (j).

Variants

In addition to the specific mutations discussed above, the variant of SEQ ID NO: 2 may include other mutations. Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http.//www.ncbi.nlm.nih.gov/).

SEQ ID NO: 2 is the mature form of the wild-type MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 2 below. Where amino acids have similar polarity, this can also be determined by reference to the hydropathy scale for amino acid side chains in Table 3.

TABLE 2

| Chemical properties of amino acids | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

TABLE 3

| Hydropathy scale | |
|---|---|
| Side Chain | Hydropathy |
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its α-helices and/or loop regions.

The monomers derived from Msp may be modified to assist their identification or purification, for example by the addition of a streptavidin tag or by the addition of a signal sequence to promote their secretion from a cell where the monomer does not naturally contain such a sequence. Other suitable tags are discussed in more detail below. The monomer may be labelled with a revealing label. The revealing label may be any suitable label which allows the monomer to be detected. Suitable labels are described below.

The monomer derived from Msp may also be produced using D-amino acids. For instance, the monomer derived from Msp may comprise a mixture of L-amino acids and D-amino acids. This is conventional in the art for producing such proteins or peptides.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with $NaBH_4$, amidination with methylacetimidate or acylation with acetic anhydride.

The monomer derived from Msp can be produced using standard methods known in the art. The monomer derived from Msp may be made synthetically or by recombinant means. For example, the monomer may be synthesized by in vitro transcription and translation (IVTT). Alternatively the monomer may be synthesized by recombinant protein expression in *E. coli*. Suitable methods for producing pores and monomers are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

In some embodiments, the mutant monomer is chemically modified. The mutant monomer can be chemically modified in any way and at any site. The mutant monomer is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The mutant monomer may be chemically modified by the attachment of any molecule. For instance, the mutant monomer may be chemically modified by attachment of a dye or a fluorophore.

In some embodiments, the mutant monomer is chemically modified with a molecular adaptor that facilitates the interaction between a pore comprising the monomer and a target nucleotide or target polynucleotide sequence. The presence of the adaptor improves the host-guest chemistry of the pore and the nucleotide or polynucleotide sequence and thereby improves the sequencing ability of pores formed from the mutant monomer. The principles of host-guest chemistry are well-known in the art. The adaptor has an effect on the physical or chemical properties of the pore that improves its interaction with the nucleotide or polynucleotide sequence. The adaptor may alter the charge of the barrel or channel of the pore or specifically interact with or bind to the nucleotide or polynucleotide sequence thereby facilitating its interaction with the pore.

The molecular adaptor is preferably a cyclic molecule, a cyclodextrin, a species that is capable of hybridization, a DNA binder or interchelator, a peptide or peptide analogue, a synthetic polymer, an aromatic planar molecule, a small positively-charged molecule or a small molecule capable of hydrogen-bonding.

The adaptor may be cyclic. A cyclic adaptor preferably has the same symmetry as the pore. The adaptor preferably has eight-fold symmetry since Msp typically has eight subunits around a central axis. This is discussed in more detail below.

The adaptor typically interacts with the nucleotide or polynucleotide sequence via host-guest chemistry. The adaptor is typically capable of interacting with the nucleotide or polynucleotide sequence. The adaptor comprises one or more chemical groups that are capable of interacting with the nucleotide or polynucleotide sequence. The one or more chemical groups preferably interact with the nucleotide or polynucleotide sequence by non-covalent interactions, such as hydrophobic interactions, hydrogen bonding, Van der Waal's forces, π-cation interactions and/or electrostatic forces. The one or more chemical groups that are capable of interacting with the nucleotide or polynucleotide sequence are preferably positively charged. The one or more chemical groups that are capable of interacting with the nucleotide or polynucleotide sequence more preferably comprise amino groups. The amino groups can be attached to primary, secondary or tertiary carbon atoms. The adaptor even more preferably comprises a ring of amino groups, such as a ring of 6, 7 or 8 amino groups. The adaptor most preferably comprises a ring of eight amino groups. A ring of protonated amino groups may interact with negatively charged phosphate groups in the nucleotide or polynucleotide sequence.

The correct positioning of the adaptor within the pore can be facilitated by host-guest chemistry between the adaptor and the pore comprising the mutant monomer. The adaptor preferably comprises one or more chemical groups that are capable of interacting with one or more amino acids in the pore. The adaptor more preferably comprises one or more chemical groups that are capable of interacting with one or more amino acids in the pore via non-covalent interactions, such as hydrophobic interactions, hydrogen bonding, Van der Waal's forces, π-cation interactions and/or electrostatic forces. The chemical groups that are capable of interacting with one or more amino acids in the pore are typically hydroxyls or amines. The hydroxyl groups can be attached to primary, secondary or tertiary carbon atoms. The hydroxyl groups may form hydrogen bonds with uncharged amino acids in the pore. Any adaptor that facilitates the interaction between the pore and the nucleotide or polynucleotide sequence can be used.

Suitable adaptors include, but are not limited to, cyclodextrins, cyclic peptides and cucurbiturils. The adaptor is preferably a cyclodextrin or a derivative thereof. The cyclodextrin or derivative thereof may be any of those disclosed in Eliseev, A. V., and Schneider, H-J. (1994) *J. Am. Chem. Soc.* 116, 6081-6088. The adaptor is more preferably heptakis-6-amino-β-cyclodextrin ($am_7$-βCD), 6-monodeoxy-6-monoamino-β-cyclodextrin ($am_1$-βCD) or heptakis-(6-deoxy-6-guanidino)-cyclodextrin ($gu_7$-βCD). The guanidino group in $gu_7$-βCD has a much higher pKa than the primary amines in $am_7$-βCD and so is more positively charged. This $gu_7$-βCD adaptor may be used to increase the dwell time of the nucleotide in the pore, to increase the accuracy of the residual current measured, as well as to increase the base detection rate at high temperatures or low data acquisition rates.

If a succinimidyl 3-(2-pyridyldithio)propionate (SPDP) crosslinker is used as discussed in more detail below, the adaptor is preferably heptakis(6-deoxy-6-amino)-6-N-mono (2-pyridyl)dithiopropanoyl-β-cyclodextrin ($am_6amPDP_1$-βCD).

More suitable adaptors include γ-cyclodextrins, which comprise 8 sugar units (and therefore have eight-fold symmetry). The γ-cyclodextrin may contain a linker molecule or may be modified to comprise all or more of the modified sugar units used in the β-cyclodextrin examples discussed above.

The molecular adaptor is preferably covalently attached to the mutant monomer. The adaptor can be covalently attached to the pore using any method known in the art. The adaptor is typically attached via chemical linkage. If the molecular adaptor is attached via cysteine linkage, the one or more cysteines have preferably been introduced to the mutant by substitution. The mutant monomers of the invention can of course comprise a cysteine residue at one or more of positions 88, 90, 91, 103 and 105. The mutant monomer may be chemically modified by attachment of a molecular adaptor to one or more, such as 2, 3, 4 or 5, of these cysteines. Alternatively, the mutant monomer may be chemically modified by attachment of a molecule to one or more cysteines introduced at other positions. The molecular adaptor is preferably attached to one or more of positions 90, 91 and 103 of SEQ ID NO: 2.

The reactivity of cysteine residues may be enhanced by modification of the adjacent residues. For instance, the basic groups of flanking arginine, histidine or lysine residues will change the pKa of the cysteines thiol group to that of the more reactive $S^-$ group. The reactivity of cysteine residues may be protected by thiol protective groups such as dTNB. These may be reacted with one or more cysteine residues of the mutant monomer before a linker is attached. The molecule may be attached directly to the mutant monomer. The molecule is preferably attached to the mutant monomer using a linker, such as a chemical crosslinker or a peptide linker.

Suitable chemical crosslinkers are well-known in the art. Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate and 2,5-dioxopyrrolidin-1-yl 8-(pyridin-2-yldisulfanyl)octananoate. The most preferred crosslinker is succinimidyl 3-(2-pyridyldithio)propionate (SPDP). Typically, the molecule is covalently attached to the bifunctional crosslinker before the molecule/crosslinker complex is covalently attached to the mutant monomer but it is also possible to covalently attach the bifunctional crosslinker to the monomer before the bifunctional crosslinker/monomer complex is attached to the molecule.

The linker is preferably resistant to dithiothreitol (DTT). Suitable linkers include, but are not limited to, iodoacetamide-based and Maleimide-based linkers.

In other embodiment, the monomer may be attached to a polynucleotide binding protein. This forms a modular sequencing system that may be used in the methods of sequencing of the invention. Polynucleotide binding proteins are discussed below.

The polynucleotide binding protein is preferably covalently attached to the mutant monomer. The protein can be covalently attached to the monomer using any method known in the art. The monomer and protein may be chemically fused or genetically fused. The monomer and protein are genetically fused if the whole construct is expressed from a single polynucleotide sequence. Genetic fusion of a monomer to a polynucleotide binding protein is discussed in International Application No. PCT/GB09/001679 (published as WO 2010/004265).

If the polynucleotide binding protein is attached via cysteine linkage, the one or more cysteines have preferably been introduced to the mutant by substitution. The mutant monomers of the invention can of course comprise cysteine residues at one or more of positions 10 to 15, 51 to 60, 136 to 139 and 168 to 172. These positions are present in loop regions which have low conservation amongst homologues indicating that mutations or insertions may be tolerated. They are therefore suitable for attaching a polynucleotide binding protein. The reactivity of cysteine residues may be enhanced by modification as described above.

The polynucleotide binding protein may be attached directly to the mutant monomer or via one or more linkers. The molecule may be attached to the mutant monomer using the hybridization linkers described in International Application No. PCT/GB10/000132 (published as WO 2010/086602). Alternatively, peptide linkers may be used. Peptide linkers are amino acid sequences. The length, flexibility and hydrophilicity of the peptide linker are typically designed such that it does not to disturb the functions of the monomer and molecule. Preferred flexible peptide linkers are stretches of 2 to 20, such as 4, 6, 8, 10 or 16, serine and/or glycine amino acids. More preferred flexible linkers include $(SG)_1$, $(SG)_2$, $(SG)_3$, $(SG)_4$, $(SG)_5$ and $(SG)_8$ wherein S is serine and G is glycine. Preferred rigid linkers are stretches of 2 to 30, such as 4, 6, 8, 16 or 24, proline amino acids. More preferred rigid linkers include $(P)_{12}$ wherein P is proline.

The mutant monomer may be chemically modified with a molecular adaptor and a polynucleotide binding protein.

The reactivity of cysteine residues may be enhanced by modification of the adjacent residues. For instance, the basic groups of flanking arginine, histidine or lysine residues will change the pKa of the cysteines thiol group to that of the more reactive $S^-$ group. The reactivity of cysteine residues may be protected by thiol protective groups such as dTNB. These may be reacted with one or more cysteine residues of the monomer before a linker is attached.

The molecule (with which the monomer is chemically modified) may be attached directly to the monomer or attached via a linker as disclosed in International Application Nos. PCT/GB09/001690 (published as WO 2010/004273), PCT/GB09/001679 (published as WO 2010/004265) or PCT/GB10/000133 (published as WO 2010/086603).

Any of the proteins described herein, such as the mutant monomers and pores of the invention, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the protein. An example of this would be to react a gel-shift reagent to a cysteine engineered on the outside of the protein. This has been demonstrated as a method for separating hemolysin hetero-oligomers (Chem Biol. 1997 July; 4(7):497-505).

Any of the proteins described herein, such as the mutant monomers and pores of the invention, may be labelled with a revealing label. The revealing label may be any suitable label which allows the protein to be detected. Suitable labels include, but are not limited to, fluorescent molecules, radioisotopes, e.g. $^{125}I$, $^{35}S$, enzymes, antibodies, antigens, polynucleotides and ligands such as biotin.

Any of the proteins described herein, such as the monomers or pores of the invention, may be made synthetically or by recombinant means. For example, the protein may be synthesized by in vitro translation and transcription (IVTT). The amino acid sequence of the protein may be modified to include non-naturally occurring amino acids or to increase the stability of the protein. When a protein is produced by synthetic means, such amino acids may be introduced during production. The protein may also be altered following either synthetic or recombinant production.

Proteins may also be produced using D-amino acids. For instance, the protein may comprise a mixture of L-amino acids and D-amino acids. This is conventional in the art for producing such proteins or peptides.

The protein may also contain other non-specific modifications as long as they do not interfere with the function of the protein. A number of non-specific side chain modifications are known in the art and may be made to the side chains of the protein(s). Such modifications include, for example, reductive alkylation of amino acids by reaction with an aldehyde followed by reduction with $NaBH_4$, amidination with methylacetimidate or acylation with acetic anhydride.

Any of the proteins described herein, including the monomers and pores of the invention, can be produced using standard methods known in the art. Polynucleotide sequences encoding a protein may be derived and replicated using standard methods in the art. Polynucleotide sequences encoding a protein may be expressed in a bacterial host cell using standard techniques in the art. The protein may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

Proteins may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

Constructs

The invention also provides a construct comprising two or more covalently attached MspA monomers, wherein at least one of the monomers is a mutant monomer of the invention. The construct of the invention retains its ability to form a pore. This may be determined as discussed above. One or more constructs of the invention may be used to form pores for characterising, such as sequencing, polynucleotides. The construct may comprise at least 2, at least 3, at least 4, at least 5, at least 6, at least 7, at least 8, at least 9 or at least 10 monomers. The construct preferably comprises two monomers. The two or more monomers may be the same or different.

At least one monomer in the construct is a mutant monomer of the invention. 2 or more, 3 or more, 4 or more, 5 or more, 6 or more, 7 or more, 8 or more, 9 or more or 10 or more monomers in the construct may be mutant monomers of the invention. All of the monomers in the construct are preferably mutant monomers of the invention. The mutant monomers may be the same or different. In a preferred embodiment, the construct comprises two mutant monomers of the invention.

The mutant monomers of the invention in the construct are preferably approximately the same length or are the same length. The barrels of the mutant monomers of the invention in the construct are preferably approximately the same length or are the same length. Length may be measured in number of amino acids and/or units of length.

The construct may comprise one or more monomers which are not mutant monomers of the invention. MspA mutant monomers which are non mutant monomers of the invention include monomers comprising SEQ ID NO: 2 or a comparative variant of SEQ ID NO: 2. At least one monomer in the construct may comprise SEQ ID NO: 2 or a comparative variant of the sequence shown in SEQ ID NO: 2 which comprises one or more of, preferably all of, D90N, D91N, D93N, D118R, D134R and E139K. At least one monomer in the construct may be any of the monomers disclosed in International Application No. PCT/GB2012/050301 (published as WO/2012/107778), including those comprising a comparative variant of the sequence shown in SEQ ID NO: 2 which comprises G75S, G77S, L88N, D90N, D91N, D93N, D118R, Q126R, D134R and E139K. A comparative variant of SEQ ID NO: 2 is at least 50% homologous to SEQ ID NO: 2 over its entire sequence based on amino acid identity. More preferably, the comparative variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence.

The monomers in the construct are preferably genetically fused. Monomers are genetically fused if the whole construct is expressed from a single polynucleotide sequence. The coding sequences of the monomers may be combined in any way to form a single polynucleotide sequence encoding the construct.

The monomers may be genetically fused in any configuration. The monomers may be fused via their terminal amino acids. For instance, the amino terminus of the one monomer may be fused to the carboxy terminus of another monomer. The second and subsequent monomers in the construct (in the amino to carboxy direction) may comprise a methionine at their amino terminal ends (each of which is fused to the carboxy terminus of the previous monomer). For instance, if M is a monomer (without an amino terminal methionine) and mM is a monomer with an amino terminal methionine, the construct may comprise the sequence M-mM, M-mM-mM or M-mM-mM-mM. The presences of these methionines typically results from the expression of the start codons (i.e. ATGs) at the 5' end of the polynucleotides encoding the second or subsequent monomers within the polynucleotide encoding entire construct. The first monomer in the construct (in the amino to carboxy direction) may also comprise a methionine (e.g. mM-mM, mM-mM-mM or mM-mM-mM-mM).

The two or more monomers may be genetically fused directly together. The monomers are preferably genetically fused using a linker. The linker may be designed to constrain the mobility of the monomers. Preferred linkers are amino acid sequences (i.e. peptide linkers). Any of the peptide linkers discussed above may be used.

In another preferred embodiment, the monomers are chemically fused. Two monomers are chemically fused if the two parts are chemically attached, for instance via a chemical crosslinker. Any of the chemical crosslinkers discussed above may be used. The linker may be attached to one or more cysteine residues introduced into a mutant monomer of the invention. Alternatively, the linker may be attached to a terminus of one of the monomers in the construct.

If a construct contains different monomers, crosslinkage of monomers to themselves may be prevented by keeping the concentration of linker in a vast excess of the monomers. Alternatively, a "lock and key" arrangement may be used in which two linkers are used. Only one end of each linker may react together to form a longer linker and the other ends of the linker each react with a different monomers. Such linkers are described in International Application No. PCT/GB10/000132 (published as WO 2010/086602).

Mutant αHL and Lysenin Monomers

The present invention also provides mutant αHL monomers. The mutant Msp monomers may be used to form the pores of the invention. A mutant αHL monomer is a monomer whose sequence varies from that of a wild-type αHL monomer and which retains the ability to form a pore. Methods for confirming the ability of mutant monomers to form pores are well-known in the art and are discussed in more detail below.

A mutant monomer of the invention comprises a variant of the sequence shown in SEQ ID NO: 4. Variants are discussed above. The mutant αHL monomer is modified in accordance with the invention. A part of the monomer which interacts with a polynucleotide binding protein has been modified. The part of the monomer which interacts with a polynucleotide binding protein when the polynucleotide binding protein is used to control the movement of a target polynucleotide with respect to, or through, a pore comprising the monomer has been modified. Any of the modifications discussed above may be made in the monomer of the invention.

The monomer preferably comprises a variant of SEQ ID NO: 4 which comprises phenylalanine (F), tryptophan (W), isoleucine (I), leucine (L), valine (V), alanine (A), arginine (R), lysine (K), aspartic acid (D), glutamic acid (E) or tyrosine (Y) at one or more of positions:

(a) 16, 17, 18, 19, 21, 46, 47, 93, 236, 237, 238, 239, 240, 241, 242, 281, 283, 285, 287, 288 and 293 or at one or more of the corresponding positions thereof;

(b) 17, 18, 19, 46, 47, 93, 236, 237, 238, 239, 240, 241, 242, 287, 288 and 293 or the corresponding positions thereof;

(c) 17, 19, 46, 47, 93, 236, 237, 238, 239, 240, 241, 242 and 287 or the corresponding positions thereof; or (d) 17, 19, 46, 93, 236, 237, 239, 240, 287 and 288 or the corresponding positions thereof.

The present invention also provides mutant lysenin monomers. The mutant lysenin monomers may be used to form the pores of the invention. A mutant lysenin monomer is a monomer whose sequence varies from that of a wild-type lysenin monomer and which retains the ability to form a pore. Methods for confirming the ability of mutant monomers to form pores are well-known in the art and are discussed in more detail below.

A mutant monomer of the invention comprises a variant of the sequence shown in SEQ ID NO: 36. Variants are discussed above. The mutant lysenin monomer is modified in accordance with the invention. A part of the monomer which interacts with a polynucleotide binding protein has been modified. The part of the monomer which interacts with a polynucleotide binding protein when the polynucleotide binding protein is used to control the movement of a target polynucleotide with respect to, or through, a pore comprising the monomer has been modified. Any of the modifications discussed above may be made in the monomer of the invention.

The monomer preferably comprises a variant of SEQ ID NO: 36 which comprises phenylalanine (F), tryptophan (W), isoleucine (I), leucine (L), valine (V), alanine (A), arginine (R), lysine (K), aspartic acid (D), glutamic acid (E) or tyrosine (Y) at one or more of positions 31, 33, 108, 109, 110 and 138 or the corresponding positions thereof.

The mutant αHL monomers and mutant lysenin monomers of the invention may be used to form constructs, homo-oligomeric pores and hetero-oligomeric pores in the same way as mutant Msp monomers discussed above. Such pores typically comprise seven mutant αHL monomers.

Modified Polynucleotide Binding Proteins

The method also provides a polynucleotide binding protein modified in accordance with the invention. A part of the polynucleotide binding protein which interacts with a transmembrane pore has been modified. The part of the polynucleotide binding protein which interacts with a transmembrane pore when the polynucleotide binding protein is used to control the movement of a target polynucleotide with respect to, or through, the pore has been modified. Any of the modifications discussed above may be made in the proteins of the invention.

The polynucleotide binding protein preferably comprises a variant of the sequence shown in SEQ ID NO: 24. Preferred variants are discussed above. The part of the variant of SEQ ID NO: 24 that may be modified in accordance with the invention is discussed above. The modified polynucleotide binding protein of the invention preferably comprises a variant of SEQ ID NO: 24 which comprises K199A, K199V, K199F, K199D, K199S, K199W or K199L. The variant of SEQ ID NO: 24 preferably further comprises any of the modifications discussed below.

The polynucleotide binding protein preferably comprises a variant of the sequence shown in SEQ ID NO: 9. Preferred variants are discussed above. The part of the variant of SEQ ID NO: 9 that may be modified in accordance with the invention is discussed above. The modified polynucleotide binding protein of the invention preferably comprises a variant of SEQ ID NO: 9 which comprises phenylalanine (F), tryptophan (W), isoleucine (I), leucine (L), valine (V), alanine (A), arginine (R), lysine (K), aspartic acid (D), glutamic acid (E) or tyrosine (Y) at one or more of positions 80, 81, 82, 84, 85, 205, 206, 209, 215, 216, 220, 221, 224, 236, 240, 241, 267, 270, 272, 278, 287, 289, 293, 296, 307, 308, 309, 310, 320, 321, 322, 323, 327, 349, 415, 418 and 419 or the corresponding positions thereof, such as at one or more of:

(a) positions 80, 84, 205, 209, 215, 216, 221, 224, 236, 241, 267, 272, 289, 296, 307, 308, 309, 320, 321, 322, and 419 or the corresponding positions thereof;

(b) positions 80, 84, 209, 215, 216, 221, 267, 272, 289, 307, 308, 309, 321 and 322 or the corresponding positions thereof; or (b) positions 215, 267, 272, 307, 308 and 322 or the corresponding positions thereof.

Polynucleotides

The present invention provides polynucleotide sequences which encode a modified transmembrane pore of the invention. The modified pore may be any of those discussed above or below.

The present invention also provides polynucleotide sequences which encode a mutant monomer of the invention. The mutant monomer may be any of those discussed above. The polynucleotide sequence preferably comprises a sequence at least 50%, 60%, 70%, 80%, 90% or 95% homologous based on nucleotide identity to the sequence of SEQ ID NO: 1 over the entire sequence. There may be at least 80%, for example at least 85%, 90% or 95% nucleotide identity over a stretch of 300 or more, for example 375, 450, 525 or 600 or more, contiguous nucleotides ("hard homology"). Homology may be calculated as described above. The polynucleotide sequence may comprise a sequence that differs from SEQ ID NO: 1 on the basis of the degeneracy of the genetic code.

The present invention also provides polynucleotide sequences which encode any of the genetically fused constructs of the invention. The polynucleotide preferably comprises two or more variants of the sequence shown in SEQ ID NO: 1. The polynucleotide sequence preferably comprises two or more sequences having at least 50%, 60%, 70%, 80%, 90% or 95% homology to SEQ ID NO: 1 based on nucleotide identity over the entire sequence. There may be at least 80%, for example at least 85%, 90% or 95% nucleotide identity over a stretch of 600 or more, for example 750, 900, 1050 or 1200 or more, contiguous nucleotides ("hard homology"). Homology may be calculated as described above.

The present invention also provides polynucleotide sequences which encode any of the modified polynucleotide binding proteins of the invention. The polynucleotide sequence preferably comprises a sequence at least 50%, 60%, 70%, 80%, 90% or 95% homologous based on nucleotide identity to the sequence of SEQ ID NO: 9, 11, 13, 15, 17, 18, 19, 20, 21, 22, 23, 24 or 25 over the entire sequence. There may be at least 80%, for example at least 85%, 90% or 95% nucleotide identity over a stretch of 300 or more, for example 375, 450, 525 or 600 or more, contiguous nucleotides ("hard homology"). Homology may be calculated as described above. The polynucleotide sequence may comprise a sequence that differs from SEQ ID NO: 9, 11, 13, 15, 17, 18, 19, 20, 21, 22, 23, 24 or 25 on the basis of the degeneracy of the genetic code.

Polynucleotide sequences may be derived and replicated using standard methods in the art. Chromosomal DNA encoding wild-type Msp may be extracted from a pore producing organism, such as *Mycobacterium smegmatis*. The gene encoding the pore subunit may be amplified using PCR involving specific primers. The amplified sequence may then undergo site-directed mutagenesis. Suitable methods of site-directed mutagenesis are known in the art and include, for example, combine chain reaction. Polynucleotides encoding a construct of the invention can be made using well-known techniques, such as those described in Sambrook, J. and Russell, D. (2001). Molecular Cloning: A Laboratory Manual, 3rd Edition. Cold Spring Harbor Laboratory Press, Cold Spring Harbor, N.Y.

The resulting polynucleotide sequence may then be incorporated into a recombinant replicable vector such as a cloning vector. The vector may be used to replicate the polynucleotide in a compatible host cell. Thus polynucleotide sequences may be made by introducing a polynucleotide into a replicable vector, introducing the vector into a compatible host cell, and growing the host cell under conditions which bring about replication of the vector. The vector may be recovered from the host cell. Suitable host cells for cloning of polynucleotides are known in the art and described in more detail below.

The polynucleotide sequence may be cloned into suitable expression vector. In an expression vector, the polynucleotide sequence is typically operably linked to a control sequence which is capable of providing for the expression of the coding sequence by the host cell. Such expression vectors can be used to express a pore subunit.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different polynucleotide sequences may be introduced into the vector.

The expression vector may then be introduced into a suitable host cell. Thus, a mutant monomer or construct of the invention can be produced by inserting a polynucleotide sequence into an expression vector, introducing the vector into a compatible bacterial host cell, and growing the host cell under conditions which bring about expression of the polynucleotide sequence. The recombinantly-expressed monomer or construct may self-assemble into a pore in the host cell membrane. Alternatively, the recombinant pore produced in this manner may be removed from the host cell and inserted into another membrane. When producing pores comprising at least two different monomers or constructs, the different monomers or constructs may be expressed separately in different host cells as described above, removed from the host cells and assembled into a pore in a separate membrane, such as a rabbit cell membrane.

The vectors may be for example, plasmid, virus or phage vectors provided with an origin of replication, optionally a promoter for the expression of the said polynucleotide sequence and optionally a regulator of the promoter. The vectors may contain one or more selectable marker genes, for example a tetracycline resistance gene. Promoters and other expression regulation signals may be selected to be compatible with the host cell for which the expression vector is designed. A T7, trc, lac, ara or $\lambda_L$ promoter is typically used.

The host cell typically expresses the monomer or construct at a high level. Host cells transformed with a polynucleotide sequence will be chosen to be compatible with the expression vector used to transform the cell. The host cell is typically bacterial and preferably *Escherichia coli*. Any cell with a λ DE3 lysogen, for example C41 (DE3), BL21 (DE3), JM109 (DE3), B834 (DE3), TUNER, Origami and Origami B, can express a vector comprising the T7 promoter. In addition to the conditions listed above any of the methods cited in Proc Natl Acad Sci USA. 2008 Dec. 30; 105(52):20647-52 may be used to express the Msp proteins.

The invention also comprises a method of producing a mutant monomer of the invention or a construct of the invention. The method comprises expressing a polynucleotide of the invention in a suitable host cell. The polynucleotide is preferably part of a vector and is preferably operably linked to a promoter.

Pores

The invention also provides various pores. The movement of target polynucleotides with respect to, such as through, the pores of the invention is typically more consistent. The pores preferably allow more consistent movement from k-mer to k-mer as the target polynucleotide moves with respect to, such as through, the pore. The pores preferably allow the target polynucleotide to move with respect to, such as through, the pore more smoothly. The pore preferably reduces the amount of stuttering associated with the movement of the target polynucleotide with respect to, such as through, the pore. The pores preferably provide more regular or less irregular movement of the target polynucleotide with respect to, such as through, the pore.

The noise associated with the movement of a target polynucleotide with respect to, such as through, the pore of the invention is typically reduced. The pores of the invention may reduce this noise by reducing unwanted movement associated with one or more k-mers, such as each k-mer, in the target polynucleotide. The pores of the invention may reduce the noise associated with the current level or signature for one or more k-mers, such as each k-mer, in the target polynucleotide.

If the target polynucleotide is double stranded, the noise associated with movement of the complement strand relative to the template strand is reduced and/or the movement of the complement strand relative to the template strand is more consistent using the pores of the invention. This is advantageous for strand sequencing of double stranded target polynucleotides.

The pores of the invention are ideal for characterising, such as sequencing, polynucleotide sequences because they can discriminate between different nucleotides with a high degree of sensitivity. The pores can surprisingly distinguish between the four nucleotides in DNA and RNA. The pores of the invention can even distinguish between methylated and unmethylated nucleotides. The base resolution of pores of the invention is surprisingly high. The pores show almost complete separation of all four DNA nucleotides. The pores further discriminate between deoxycytidine monophosphate (dCMP) and methyl-dCMP based on the dwell time in the pore and the current flowing through the pore.

The pores of the invention can also discriminate between different nucleotides under a range of conditions. In particular, the pores will discriminate between nucleotides under conditions that are favourable to the characterising, such as sequencing, of nucleic acids. The extent to which the pores of the invention can discriminate between different nucleotides can be controlled by altering the applied potential, the salt concentration, the buffer, the temperature and the presence of additives, such as urea, betaine and DTT. This allows the function of the pores to be fine-tuned, particularly when sequencing. This is discussed in more detail below. The pores of the invention may also be used to identify polynucleotide polymers from the interaction with one or more monomers rather than on a nucleotide by nucleotide basis.

A pore of the invention may be isolated, substantially isolated, purified or substantially purified. A pore of the invention is isolated or purified if it is completely free of any other components, such as lipids or other pores. A pore is substantially isolated if it is mixed with carriers or diluents which will not interfere with its intended use. For instance, a pore is substantially isolated or substantially purified if it is present in a form that comprises less than 10%, less than 5%, less than 2% or less than 1% of other components, such as triblock copolymers, lipids or other pores. Alternatively, a pore of the invention may be present in a membrane. Suitable membranes are discussed below.

A pore of the invention may be present as an individual or single pore. Alternatively, a pore of the invention may be present in a homologous or heterologous population of two or more pores.

Modified Pores

The invention provides a transmembrane pore in which a part of the transmembrane pore which interacts with a polynucleotide binding protein has been modified. The pore may be any of those discussed above. Where the pore comprises one or more variants of SEQ ID NO: 2, the one or more variants preferably do not comprise or consist of E59R, D90N, D91N, D93N, D118R, D134R and E139K.

Homo-Oligomeric Pores

The invention also provides a homo-oligomeric pore derived from Msp comprising identical mutant monomers of the invention. The homo-oligomeric pore may comprise any of the mutants of the invention. The homo-oligomeric pore of the invention is ideal for characterising, such as sequencing, polynucleotides. The homo-oligomeric pore of the invention may have any of the advantages discussed above.

The homo-oligomeric pore may contain any number of mutant monomers. The pore typically comprises at least 7, at least 8, at least 9 or at least 10 identical mutant monomers, such as 7, 8, 9 or 10 mutant monomers. The pore preferably comprises eight or nine identical mutant monomers. One or more, such as 2, 3, 4, 5, 6, 7, 8, 9 or 10, of the mutant monomers is preferably chemically modified as discussed above.

A preferred homo-oligomeric pore comprises eight or nine subunits each comprising a variant of SEQ ID NO: 2 in which L74, G75, D118 and L119 have been deleted and which comprises D56N, E59R, L88N, D90N, D91N, Q126R, D134R and E139K.

Methods for making pores are discussed in more detail below.

Hetero-Oligomeric Pores

The invention also provides a hetero-oligomeric pore derived from Msp comprising at least one mutant monomer of the invention. The hetero-oligomeric pore of the invention is ideal for characterising, such as sequencing, polynucleotides. Hetero-oligomeric pores can be made using methods known in the art (e.g. Protein Sci. 2002 July; 11(7):1813-24).

The hetero-oligomeric pore contains sufficient monomers to form the pore. The monomers may be of any type. The pore typically comprises at least 7, at least 8, at least 9 or at least 10 monomers, such as 7, 8, 9 or 10 monomers. The pore preferably comprises eight or nine monomers.

In a preferred embodiment, all of the monomers (such as 10, 9, 8 or 7 of the monomers) are mutant monomers of the invention and at least one of them differs from the others. In a more preferred embodiment, the pore comprises eight or nine mutant monomers of the invention and at least one of them differs from the others. They may all differ from one another.

The mutant monomers of the invention in the pore are preferably approximately the same length or are the same length. The barrels of the mutant monomers of the invention in the pore are preferably approximately the same length or are the same length. Length may be measured in number of amino acids and/or units of length. The mutant monomers of the invention in the pore preferably have the same number of amino acids deleted from positions 72 to 82 and/or positions 111 to 121.

In another preferred embodiment, at least one of the mutant monomers is not a mutant monomer of the invention. In this embodiment, the remaining monomers are preferably mutant monomers of the invention. Hence, the pore may comprise 9, 8, 7, 6, 5, 4, 3, 2 or 1 mutant monomers of the invention. Any number of the monomers in the pore may not be a mutant monomer of the invention. The pore preferably comprises seven or eight mutant monomers of the invention and a monomer which is not a monomer of the invention. The mutant monomers of the invention may be the same or different.

The mutant monomers of the invention in the construct are preferably approximately the same length or are the same length. The barrels of the mutant monomers of the invention in the construct are preferably approximately the same length or are the same length. Length may be measured in number of amino acids and/or units of length.

The pore may comprise one or more monomers which are not mutant monomers of the invention. MspA mutant monomers which are non mutant monomers of the invention include monomers comprising SEQ ID NO: 2 or a comparative variant of SEQ ID NO: 2. At least one monomer in the pore may comprise SEQ ID NO: 2 or a comparative variant of the sequence shown in SEQ ID NO: 2 which comprises one or more of, preferably all of, D90N, D91N, D93N, D118R, D134R and E139K. At least one monomer in the pore may be any of the monomers disclosed in International Application No. PCT/GB2012/050301 (published as WO/2012/107778), including those comprising a comparative variant of the sequence shown in SEQ ID NO: 2 which comprises G75S, G77S, L88N, D90N, D91N, D93N, D118R, Q126R, D134R and E139K. A comparative variant of SEQ ID NO: 2 is at least 50% homologous to SEQ ID NO: 2 over its entire sequence based on amino acid identity. More preferably, the comparative variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence.

In all the embodiments discussed above, one or more, such as 2, 3, 4, 5, 6, 7, 8, 9 or 10, of the mutant monomers is preferably chemically modified as discussed above.

Methods for making pores are discussed in more detail below.

Construct-Containing Pores

The invention also provides a pore comprising at least one construct of the invention. A construct of the invention comprises two or more covalently attached monomers derived from Msp wherein at least one of the monomers is a mutant monomer of the invention. In other words, a construct must contain more than one monomer. The pore contains sufficient constructs and, if necessary, monomers to form the pore. For instance, an octameric pore may comprise (a) four constructs each comprising two constructs, (b) two constructs each comprising four monomers or (b) one construct comprising two monomers and six monomers that do not form part of a construct. For instance, an nonameric pore may comprise (a) four constructs each comprising two constructs and one monomer that does not form part of a construct, (b) two constructs each comprising four monomers and a monomer that does not form part of a construct or (b) one construct comprising two monomers and seven monomers that do not form part of a construct. Other combinations of constructs and monomers can be envisaged by the skilled person.

At least two of the monomers in the pore are in the form of a construct of the invention. The construct, and hence the pore, comprises at least one mutant monomer of the invention. The pore typically comprises at least 7, at least 8, at least 9 or at least 10 monomers, such as 7, 8, 9 or 10 monomers, in total (at least two of which must be in a construct). The pore preferably comprises eight or nine monomers (at least two of which must be in a construct).

The construct containing pore may be a homo-oligomer (i.e. include identical constructs) or be a hetero-oligomer (i.e. where at least one construct differs from the others).

A pore typically contains (a) one construct comprising two monomers and (b) 5, 6, 7 or 8 monomers. The construct may be any of those discussed above. The monomers may be any of those discussed above, including mutant monomers of the invention, monomers comprising SEQ ID NO: 2 and mutant monomers comprising a comparative variant of SEQ ID NO: 2 as discussed above.

Another typical pore comprises more than one construct of the invention, such as two, three or four constructs of the invention. If necessary, such pores further comprise sufficient additional monomers or constructs to form the pore. The additional monomer(s) may be any of those discussed above, including mutant monomers of the invention, monomers comprising SEQ ID NO: 2 and mutant monomers comprising a comparative variant of SEQ ID NO: 2 as discussed above. The additional construct(s) may be any of those discussed above or may be a construct comprising two or more covalently attached MspA monomers each comprising a monomer comprising SEQ ID NO: 2 or a comparative variant of SEQ ID NO: 2 as discussed above.

A further pore of the invention comprises only constructs comprising 2 monomers, for example a pore may comprise 4, 5, 6, 7 or 8 constructs comprising 2 monomers. At least one construct is a construct of the invention, i.e. at least one monomer in the at least one construct, and preferably each monomer in the at least one construct, is a mutant monomer of the invention. All of the constructs comprising 2 monomers may be constructs of the invention.

A specific pore according to the invention comprises four constructs of the invention each comprising two monomers, wherein at least one monomer in each construct, and preferably each monomer in each construct, is a mutant monomer of the invention. The constructs may oligomerise into a pore with a structure such that only one monomer of each construct contributes to the channel of the pore. Typically the other monomers of the construct will be on the outside of the channel of the pore. For example, pores of the invention may comprise 5, 6, 7 or 8 constructs comprising 2 monomers where the channel comprises 8 monomers.

Mutations can be introduced into the construct as described above. The mutations may be alternating, i.e. the mutations are different for each monomer within a two monomer construct and the constructs are assembled as a homo-oligomer resulting in alternating modifications. In other words, monomers comprising MutA and MutB are fused and assembled to form an A-B:A-B:A-B:A-B pore. Alternatively, the mutations may be neighbouring, i.e. identical mutations are introduced into two monomers in a construct and this is then oligomerised with different mutant monomers or constructs. In other words, monomers comprising MutA are fused followed by oligomerisation with MutB-containing monomers to form A-A:B:B:B:B:B:B.

One or more of the monomers of the invention in a construct-containing pore may be chemically-modified as discussed above.

Combinations

The invention also provides a combination of a transmembrane pore and a polynucleotide binding protein in which a part of the transmembrane pore which interacts with the polynucleotide binding protein and/or a part of the polynucleotide binding protein which interacts with the transmembrane pore has been modified. The pore may be any of those discussed above. The polynucleotide binding protein may be any of those discussed above.

The pore in the combination preferably comprises seven or more monomers, such as 8 or 9 monomers, comprising the sequence shown in SEQ ID NO: 2 or a variant thereof, wherein one or more of the seven or more monomers, such as 2, 3, 4, 5, 6, 7, 8 or 9 of the monomers, comprises a variant of SEQ ID NO: 2 which comprises (a) D56N, D56R, D56F, D56Y or D56L and/or (b) E59N, E59R, E59F, E59Y or E59L (preferably D56N and E59R, D56F and E59R, D56N and E59F, D56N and E59Y or D56L and E59L or more preferably D56N and E59R, D56F and E59R or D56N and E59F) and the modified polynucleotide binding protein in the combination preferably comprises a variant of SEQ ID NO: 24 which comprises K199A, K199V, K199F, K199D, K199S, K199W or K199L. The variant of SEQ ID NO: 24 preferably further comprises any of the modifications discussed below:

Preferred combinations of variants are shown in each row below.

| SEQ ID NO: 2 comprising | SEQ ID NO: 24 comprising |
|---|---|
| D56N and E59R | K199L |
| D56F and E59R | K199L |
| D56N and E59F | K199L |

Polynucleotide Characterisation

The invention provides a method of characterising a target polynucleotide. The method involves measuring one or more characteristics of the target polynucleotide. The target polynucleotide may also be called the template polynucleotide or the polynucleotide of interest.

Polynucleotide

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the polynucleotide can be oxidized or methylated.

The polynucleotide may be single stranded or double stranded. At least a portion of the polynucleotide is preferably double stranded.

The polynucleotide can be a nucleic acid, such as deoxyribonucleic acid (DNA) or ribonucleic acid (RNA). The polynucleotide can comprise one strand of RNA hybridised to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The PNA backbone is composed of repeating N-(2-aminoethyl)-glycine units linked by peptide bonds. The GNA backbone is composed of repeating glycol units linked by phosphodiester bonds. The TNA backbone is composed of repeating threose sugars linked together by phosphodiester bonds. LNA is formed from ribonucleotides as discussed above having an extra bridge connecting the 2' oxygen and 4' carbon in the ribose moiety.

The polynucleotide is most preferably ribonucleic nucleic acid (RNA) or deoxyribonucleic acid (DNA).

The polynucleotide can be any length. For example, the polynucleotide can be at least 10, at least 50, at least 100, at least 150, at least 200, at least 250, at least 300, at least 400 or at least 500 nucleotides or nucleotide pairs in length. The polynucleotide can be 1000 or more nucleotides or nucleotide pairs, 5000 or more nucleotides or nucleotide pairs in length or 100000 or more nucleotides or nucleotide pairs in length.

Any number of polynucleotides can be investigated. For instance, the method of the invention may concern characterising 2, 3, 4, 5, 6, 7, 8, 9, 10, 20, 30, 50, 100 or more polynucleotides. If two or more polynucleotides are characterized, they may be different polynucleotides or two instances of the same polynucleotide.

The polynucleotide can be naturally occurring or artificial. For instance, the method may be used to verify the sequence of a manufactured oligonucleotide. The method is typically carried out in vitro.

Sample

Each analyte is typically present in any suitable sample. The invention is typically carried out on two or more samples that are known to contain or suspected to contain the analytes. Alternatively, the invention may be carried out on two or more samples to confirm the identity of two or more analytes whose presence in the samples is known or expected.

The first sample and/or second sample may be a biological sample. The invention may be carried out in vitro using at least one sample obtained from or extracted from any organism or microorganism. The first sample and/or second sample may be a non-biological sample. The non-biological sample is preferably a fluid sample. Examples of non-biological samples include surgical fluids, water such as drinking water, sea water or river water, and reagents for laboratory tests.

The first sample and/or second sample is typically processed prior to being used in the invention, for example by centrifugation or by passage through a membrane that filters out unwanted molecules or cells, such as red blood cells. The first sample and/or second sample may be measured immediately upon being taken. The first sample and/or second sample may also be typically stored prior to assay, preferably below −70° C.

Characterisation

The method may involve measuring two, three, four or five or more characteristics of the polynucleotide. The one or more characteristics are preferably selected from (i) the length of the polynucleotide, (ii) the identity of the polynucleotide, (iii) the sequence of the polynucleotide, (iv) the secondary structure of the polynucleotide and (v) whether or not the polynucleotide is modified. Any combination of (i) to (v) may be measured in accordance with the invention, such as {i}, {ii}, {iii}, {iv}, {v}, {i,ii}, {i,iii}, {i,iv}, {i,v}, {ii,iii}, {ii,iv}, {ii,v}, {iii,iv}, {iii,v}, {iv,v}, {i,ii,iii}, {i,ii,iv}, {i,ii,v}, {i,iii,iv}, {i,iii,v}, {i,iv,v}, {ii,iii,iv}, {ii,iii,v}, {ii,iv,v}, {iii,iv,v}, {i,ii,iii,iv}, {i,ii,iii,v}, {i,ii,iv,v}, {i,iii,iv,v}, {ii,iii,iv,v} or {i,ii,iii,iv,v}. Different combinations of (i) to (v) may be measured for the first polynucleotide compared with the second polynucleotide, including any of those combinations listed above.

For (i), the length of the polynucleotide may be measured for example by determining the number of interactions between the polynucleotide and the pore or the duration of interaction between the polynucleotide and the pore.

For (ii), the identity of the polynucleotide may be measured in a number of ways. The identity of the polynucleotide may be measured in conjunction with measurement of the sequence of the polynucleotide or without measurement of the sequence of the polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the polynucleotide is modified by methylation, by oxidation, by damage, with one or more proteins or with one or more labels, tags or spacers. Specific modifications will result in specific interactions with the pore which can be measured using the methods described below. For instance, methylcytosine may be distinguished from cytosine on the basis of the current flowing through the pore during its interaction with each nucleotide.

The target polynucleotide is contacted with a pore of the invention. The pore is typically present in a membrane. Suitable membranes are discussed below. The method may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The method may be carried out using the apparatus described in International Application No. PCT/GB08/000562 (WO 2008/102120).

A variety of different types of measurements may be made. This includes without limitation: electrical measurements and optical measurements. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO 2000/28312. Alternatively, electrical measurements may be made using a multi-channel system, for example as described in International Application WO 2009/077734 and International Application WO 2011/067559.

The method is preferably carried out with a potential applied across the membrane. The applied potential may be a voltage potential. Alternatively, the applied potential may be a chemical potential. An example of this is using a salt gradient across a membrane, such as an amphiphilic layer. A salt gradient is disclosed in Holden et al., J Am Chem Soc. 2007 Jul. 11; 129(27):8650-5. In some instances, the current passing through the pore as a polynucleotide moves with respect to the pore is used to estimate or determine the sequence of the polynucleotide. This is strand sequencing.

The method may involve measuring the current passing through the pore as the polynucleotide moves with respect to, such as through, the pore. Therefore the apparatus used in the method may also comprise an electrical circuit capable of applying a potential and measuring an electrical signal across the membrane and pore. The methods may be carried out using a patch clamp or a voltage clamp. The methods preferably involve the use of a voltage clamp.

The method of the invention may involve the measuring of a current passing through the pore as the polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from +5 V to −5 V, such as from +4 V to −4 V, +3 V to −3 V or +2 V to −2 V. The voltage used is typically from −600 mV to +600 mV or −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The method is typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), cesium chloride (CsCl) or a mixture of potassium ferrocyanide and potassium ferricyanide is typically used. KCl, NaCl and a mixture of potassium ferrocyanide and potassium ferricyanide are preferred. The charge carriers may be asymmetric across the membrane. For instance, the type and/or concentration of the charge carriers may be different on each side of the membrane.

The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The method is typically carried out in the presence of a buffer. In the exemplary apparatus discussed above, the buffer is present in the aqueous solution in the chamber. Any buffer may be used in the method of the invention. Typically, the buffer is phosphate buffer. Other suitable buffers are HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The method may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

Polynucleotide Binding Protein

Step (a) preferably comprises contacting the polynucleotide with a polynucleotide binding protein such that the protein controls the movement of the polynucleotide with respect to, such as through, the pore.

More preferably, the method comprises (a) contacting the polynucleotide with the pore of the invention and a polynucleotide binding protein such that the protein controls the movement of the polynucleotide through the pore and (b) taking one or more measurements as the polynucleotide moves with respect to the pore, wherein the measurements are indicative of one or more characteristics of the polynucleotide, and thereby characterising the polynucleotide.

More preferably, the method comprises (a) contacting the polynucleotide with the pore of the invention and a polynucleotide binding protein such that the protein controls the movement of the polynucleotide through the pore and (b) measuring the current through the pore as the polynucleotide moves with respect to the pore, wherein the current is indicative of one or more characteristics of the polynucleotide, and thereby characterising the polynucleotide.

The polynucleotide binding protein may be any protein that is capable of binding to the polynucleotide and controlling its movement with respect to, or through, the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The protein may modify the polynucleotide by orienting it or moving it to a specific position, i.e. controlling its movement. The polynucleotide binding protein is preferably a modified polynucleotide binding protein of the invention.

The polynucleotide binding protein is preferably derived from a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the polynucleotide and controlling its movement with respect to, or through, the pore. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases and topoisomerases, such as gyrases. Suitable enzymes include, but are not limited to, exonuclease I from *E. coli* (SEQ ID NO: 11), exonuclease III enzyme from *E. coli* (SEQ ID NO: 13), RecJ from *T. thermophilus* (SEQ ID NO: 15) and bacteriophage lambda exonuclease (SEQ ID NO: 17), TatD exonuclease and variants thereof. Three subunits comprising the sequence shown in SEQ ID NO: 15 or a variant thereof interact to form a trimer exonuclease. The polymerase may be PyroPhage® 3173 DNA Polymerase (which is commercially available from Lucigen® Corporation), SD Polymerase (commercially available from Bioron®) or variants thereof. The enzyme is preferably Phi29 DNA polymerase (SEQ ID NO: 9) or a variant thereof. The topoisomerase is preferably a member of any of the Moiety Classification (EC) groups 5.99.1.2 and 5.99.1.3. The enzyme is most preferably derived from a helicase, such as Hel308 Mbu (SEQ ID NO: 18), Hel308 Csy (SEQ ID NO: 19), Hel308 Mhu (SEQ ID NO: 21), TraI Eco (SEQ ID NO: 22), XPD Mbu (SEQ ID NO: 23) or a variant thereof. Any helicase may be used in the invention. The helicase may be or be derived from a Hel308 helicase, a RecD helicase, such as TraI helicase or a TrwC helicase, a XPD helicase or a Dda helicase. The helicase may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013098561); PCT/GB2013/051925 (published as WO 2014/013260); PCT/GB2013/051924 (published as WO 2014/013259); PCT/GB2013/051928 (published as WO 2014/013262) and PCT/GB2014/052736 (published as WO/2015/055981).

The helicase preferably comprises the sequence shown in SEQ ID NO: 25 (Trwc Cba) or a variant thereof, the sequence shown in SEQ ID NO: 18 (Hel308 Mbu) or a variant thereof or the sequence shown in SEQ ID NO: 24 (Dda) or a variant thereof. Variants may differ from the native sequences in any of the ways discussed below for transmembrane pores. A preferred variant of SEQ ID NO: 24 comprises (a) E94C and A360C or (b) E94C, A360C, C109A and C136A and then optionally (ΔM1)G1G2 (i.e. deletion of M1 and then addition G1 and G2).

Any number of helicases may be used in accordance with the invention. For instance, 1, 2, 3, 4, 5, 6, 7, 8, 9, 10 or more helicases may be used. In some embodiments, different numbers of helicases may be used.

The method of the invention preferably comprises contacting the polynucleotide with two or more helicases. The two or more helicases are typically the same helicase. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. Preferred helicase constructs for use in the invention are described in International Application Nos. PCT/GB2013/051925 (published as WO 2014/013260); PCT/GB2013/051924 (published as WO 2014/013259); PCT/GB2013/051928 (published as WO 2014/013262) and PCT/GB2014/052736 (published as WO/2015/055981).

A variant of SEQ ID NOs: 9, 11, 13, 15, 17, 18, 19, 20, 21, 22, 23, 24 or 25 is an enzyme that has an amino acid sequence which varies from that of SEQ ID NO: 9, 11, 13, 15, 17, 18, 19, 20, 21, 22, 23, 24 or 25 and which retains polynucleotide binding ability. This can be measured using any method known in the art. For instance, the variant can be contacted with a polynucleotide and its ability to bind to and move along the polynucleotide can be measured. The variant may include modifications that facilitate binding of the polynucleotide and/or facilitate its activity at high salt concentrations and/or room temperature. Variants may be modified such that they bind polynucleotides (i.e. retain polynucleotide binding ability) but do not function as a helicase (i.e. do not move along polynucleotides when provided with all the necessary components to facilitate movement, e.g. ATP and $Mg^{2+}$). Such modifications are known in the art. For instance, modification of the $Mg^{2+}$ binding domain in helicases typically results in variants which do not function as helicases. These types of variants may act as molecular brakes (see below).

Over the entire length of the amino acid sequence of SEQ ID NO: 9, 11, 13, 15, 17, 18, 19, 20, 21, 22, 23, 24 or 25, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 9, 11, 13, 15, 17, 18, 19, 20, 21, 22, 23, 24 or 25 over the entire sequence. There may be at least 80%, for example at least 85%, 90% or 95%, amino acid identity over a stretch of 200 or more, for example 230, 250, 270, 280, 300, 400, 500, 600, 700, 800, 900 or 1000 or more, contiguous amino acids ("hard homology"). Homology is determined as described above. The variant may differ from the wild-type sequence in any of the ways discussed above with reference to SEQ ID NO: 2 and 4 above. The enzyme may be covalently attached to the pore. Any method may be used to covalently attach the enzyme to the pore.

A preferred molecular brake is TrwC Cba-Q594A (SEQ ID NO: 25 with the mutation Q594A). This variant does not function as a helicase (i.e. binds polynucleotides but does not move along them when provided with all the necessary components to facilitate movement, e.g. ATP and $Mg^{2-}$).

In strand sequencing, the polynucleotide is translocated through the pore either with or against an applied potential. Exonucleases that act progressively or processively on double stranded polynucleotides can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

Any helicase may be used in the method. Helicases may work in two modes with respect to the pore. First, the method is preferably carried out using a helicase such that it moves the polynucleotide through the pore with the field resulting from the applied voltage. In this mode the 5' end of the polynucleotide is first captured in the pore, and the helicase moves the polynucleotide into the pore such that it is passed through the pore with the field until it finally translocates through to the trans side of the membrane. Alternatively, the method is preferably carried out such that a helicase moves the polynucleotide through the pore against the field resulting from the applied voltage. In this mode the 3' end of the polynucleotide is first captured in the pore, and the helicase moves the polynucleotide through the pore such that it is pulled out of the pore against the applied field until finally ejected back to the cis side of the membrane.

The method may also be carried out in the opposite direction. The 3' end of the polynucleotide may be first captured in the pore and the helicase may move the polynucleotide into the pore such that it is passed through the pore with the field until it finally translocates through to the trans side of the membrane.

When the helicase is not provided with the necessary components to facilitate movement or is modified to hinder or prevent its movement, it can bind to the polynucleotide and act as a brake slowing the movement of the polynucleotide when it is pulled into the pore by the applied field. In the inactive mode, it does not matter whether the polynucleotide is captured either 3' or 5' down, it is the applied field which pulls the polynucleotide into the pore towards the trans side with the enzyme acting as a brake. When in the inactive mode, the movement control of the polynucleotide by the helicase can be described in a number of ways including ratcheting, sliding and braking. Helicase variants which lack helicase activity can also be used in this way.

The polynucleotide may be contacted with the polynucleotide binding protein and the pore in any order. It is preferred that, when the polynucleotide is contacted with the polynucleotide binding protein, such as a helicase, and the pore, the polynucleotide firstly forms a complex with the protein. When the voltage is applied across the pore, the polynucleotide/protein complex then forms a complex with the pore and controls the movement of the polynucleotide with respect to, such as through, the pore.

Any steps in the method using a polynucleotide binding protein are typically carried out in the presence of free nucleotides or free nucleotide analogues and an enzyme cofactor that facilitates the action of the polynucleotide binding protein. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the construct to function. The enzyme cofactor is preferably a divalent metal cation. The divalent metal cation is preferably $Mg^{2+}$, $Mn^{2-}$, $Ca^{2+}$ or $Co^{2+}$. The enzyme cofactor is most preferably $Mg^{2+}$.

Helicase(s) and Molecular Brake(s)

In a preferred embodiment, the method comprises:

(a) providing the polynucleotide with one or more helicases and one or more molecular brakes attached to the polynucleotide;

(b) contacting the polynucleotide with a pore of the invention and applying a potential across the pore such that the one or more helicases and the one or more molecular brakes are brought together and both control the movement of the polynucleotide through the pore;

(c) taking one or more measurements as the polynucleotide moves with respect to the pore wherein the measurements are indicative of one or more characteristics of the polynucleotide and thereby characterising the polynucleotide.

This type of method is discussed in detail in the International application No PCT/GB2014/052737.

The one or more helicases may be any of those discussed above. The one or more molecular brakes may be any compound or molecule which binds to the polynucleotide and slows the movement of the polynucleotide through the pore. The one or more molecular brakes preferably comprise one or more compounds which bind to the polynucleotide. The one or more compounds are preferably one or more macrocycles. Suitable macrocycles include, but are not limited to, cyclodextrins, calixarenes, cyclic peptides, crown ethers, cucurbiturils, pillararenes, derivatives thereof or a combination thereof. The cyclodextrin or derivative thereof may be any of those disclosed in Eliseev, A. V., and Schneider, H-J. (1994) *J. Am. Chem. Soc.* 116, 6081-6088. The agent is more preferably heptakis-6-amino-β-cyclodextrin ($am_7$-βCD), 6-monodeoxy-6-monoamino-β-cyclodextrin ($am_1$-βCD) or heptakis-(6-deoxy-6-guanidino)-cyclodextrin ($gu_7$-βCD).

The one or more molecular brakes are preferably not one or more single stranded binding proteins (SSB). The one or more molecular brakes are more preferably not a single-stranded binding protein (SSB) comprising a carboxy-terminal (C-terminal) region which does not have a net negative charge or (ii) a modified SSB comprising one or more modifications in its C-terminal region which decreases the net negative charge of the C-terminal region. The one or more molecular brakes are most preferably not any of the SSBs disclosed in International Application No. PCT/GB2013/051924 (published as WO 2014/013259).

The one or more molecular brakes are preferably one or more polynucleotide binding proteins. The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

The polynucleotide binding protein is preferably derived from a polynucleotide handling enzyme. The one or more molecular brakes may be derived from any of the polynucleotide handling enzymes discussed above. Modified versions of Phi29 polymerase (SEQ ID NO: 8) which act as molecular brakes are disclosed in U.S. Pat. No. 5,576,204. The one or more molecular brakes are preferably derived from a helicase.

Any number of molecular brakes derived from a helicase may be used. For instance, 1, 2, 3, 4, 5, 6, 7, 8, 9, 10 or more helicases may be used as molecular brakes. If two or more helicases are be used as molecular brakes, the two or more helicases are typically the same helicase. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. The one or more molecular brakes derived from helicases are preferably modified to reduce the size of an opening in the polynucleotide binding domain through which in at least one conformational state the polynucleotide can unbind from the helicase. This is disclosed in WO 2014/013260.

Preferred helicase constructs for use in the invention are described in International Application Nos. PCT/GB2013/051925 (published as WO 2014/013260); PCT/GB2013/051924 (published as WO 2014/013259); PCT/GB2013/051928 (published as WO 2014/013262) and PCT/GB2014/052736.

Spacers

The one or more helicases may be stalled at one or more spacers as discussed in International Application No. PCT/GB2014/050175. Any configuration of one or more helicases and one or more spacers disclosed in the International Application may be used in this invention.

Membrane

The pore of the invention may be present in a membrane. In the method of the invention, the polynucleotide is typically contacted with the pore of the invention in a membrane. Any membrane may be used in accordance with the invention. Suitable membranes are well-known in the art. The membrane is preferably an amphiphilic layer. An amphiphilic layer is a layer formed from amphiphilic molecules, such as phospholipids, which have both hydrophilic and lipophilic properties. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave asamphiphiles. The copolymer may be a triblock, tetrablock or pentablock copolymer. The membrane is preferably a triblock copolymer membrane.

Archaebacterial bipolar tetraether lipids are naturally occurring lipids that are constructed such that the lipid forms a monolayer membrane. These lipids are generally found in extremophiles that survive in harsh biological environments, thermophiles, halophiles and acidophiles. Their stability is believed to derive from the fused nature of the final bilayer. It is straightforward to construct block copolymer materials that mimic these biological entities by creating a triblock polymer that has the general motif hydrophilic-hydrophobic-hydrophilic. This material may form monomeric membranes that behave similarly to lipid bilayers and encompass a range of phase behaviours from vesicles through to laminar membranes. Membranes formed from these triblock copolymers hold several advantages over biological lipid membranes. Because the triblock copolymer is synthesized, the exact construction can be carefully controlled to provide the correct chain lengths and properties required to form membranes and to interact with pores and other proteins.

Block copolymers may also be constructed from sub-units that are not classed as lipid sub-materials; for example a hydrophobic polymer may be made from siloxane or other non-hydrocarbon based monomers. The hydrophilic sub-section of block copolymer can also possess low protein binding properties, which allows the creation of a membrane that is highly resistant when exposed to raw biological samples. This head group unit may also be derived from non-classical lipid head-groups.

Triblock copolymer membranes also have increased mechanical and environmental stability compared with biological lipid membranes, for example a much higher operational temperature or pH range. The synthetic nature of the block copolymers provides a platform to customize polymer based membranes for a wide range of applications.

The membrane is most preferably one of the membranes disclosed in International Application No. PCT/GB2013/052766 (published as WO/2014/06443) or PCT/GB2013/052767 (published as WO/2014/064444).

The amphiphilic molecules may be chemically-modified or functionalised to facilitate coupling of the polynucleotide.

The amphiphilic layer may be a monolayer or a bilayer. The amphiphilic layer is typically planar. The amphiphilic layer may be curved. The amphiphilic layer may be supported.

Amphiphilic membranes are typically naturally mobile, essentially acting as two dimensional fluids with lipid diffusion rates of approximately $10^{-8}$ cm s−1. This means that the pore and coupled polynucleotide can typically move within an amphiphilic membrane.

The membrane may be a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Coupling

The polynucleotide is preferably coupled to the membrane comprising the pore of the invention. The method may comprise coupling the polynucleotide to the membrane comprising the pore of the invention. The polynucleotide is preferably coupled to the membrane using one or more anchors. The polynucleotide may be coupled to the membrane using any known method.

Each anchor comprises a group which couples (or binds) to the polynucleotide and a group which couples (or binds) to the membrane. Each anchor may covalently couple (or bind) to the polynucleotide and/or the membrane. If a Y adaptor and/or a hairpin loop adaptors are used, the polynucleotide is preferably coupled to the membrane using the adaptor(s).

The polynucleotide may be coupled to the membrane using any number of anchors, such as 2, 3, 4 or more anchors. For instance, a polynucleotide may be coupled to the membrane using two anchors each of which separately couples (or binds) to both the polynucleotide and membrane.

The one or more anchors may comprise the one or more helicases and/or the one or more molecular brakes.

If the membrane is an amphiphilic layer, such as a copolymer membrane or a lipid bilayer, the one or more anchors preferably comprise a polypeptide anchor present in the membrane and/or a hydrophobic anchor present in the membrane. The hydrophobic anchor is preferably a lipid, fatty acid, sterol, carbon nanotube, polypeptide, protein or amino acid, for example cholesterol, palmitate or tocopherol. In preferred embodiments, the one or more anchors are not the pore.

The components of the membrane, such as the amphiphilic molecules, copolymer or lipids, may be chemically-modified or functionalised to form the one or more anchors. Examples of suitable chemical modifications and suitable ways of functionalising the components of the membrane are discussed in more detail below. Any proportion of the membrane components may be functionalized, for example at least 0.01%, at least 0.1%, at least 1%, at least 10%, at least 25%, at least 50% or 100%.

The polynucleotide may be coupled directly to the membrane. The one or more anchors used to couple the polynucleotide to the membrane preferably comprise a linker. The one or more anchors may comprise one or more, such as 2, 3, 4 or more, linkers. One linker may be used to couple more than one, such as 2, 3, 4 or more, polynucleotides to the membrane.

Preferred linkers include, but are not limited to, polymers, such as polynucleotides, polyethylene glycols (PEGs), polysaccharides and polypeptides. These linkers may be linear, branched or circular. For instance, the linker may be a circular polynucleotide. The polynucleotide may hybridise to a complementary sequence on the circular polynucleotide linker.

The coupling may be permanent or stable. In other words, the coupling may be such that the polynucleotide remains coupled to the membrane when interacting with the pore.

The coupling may be transient. In other words, the coupling may be such that the polynucleotide may decouple from the membrane when interacting with the pore.

Coupling of polynucleotides to a linker or to a functionalised membrane can also be achieved by a number of other means provided that a complementary reactive group or an anchoring group can be added to the polynucleotide. The addition of reactive groups to either end of a polynucleotide has been reported previously. The one or more anchors preferably couple the polynucleotide to the membrane via hybridisation. Hybridisation in the one or more anchors allows coupling in a transient manner as discussed above. The one or more anchors may comprise a single stranded or double stranded polynucleotide. One part of the anchor may be ligated to a single stranded or double stranded polynucleotide. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." Proc Natl Acad Sci USA 89(20): 9823-5). Alternatively, either a single stranded or double stranded polynucleotide can be ligated to a double stranded polynucleotide and then the two strands separated by thermal or chemical denaturation. If the polynucleotide is a synthetic strand, the one or more anchors can be incorporated during the chemical synthesis of the polynucleotide. For instance, the polynucleotide can be synthesised using a primer having a reactive group attached to it.

Ideally, the polynucleotide is coupled to the membrane without having to functionalise the polynucleotide. This can be achieved by coupling the one or more anchors, such as a polynucleotide binding protein or a chemical group, to the membrane and allowing the one or more anchors to interact with the polynucleotide or by functionalizing the membrane. The one or more anchors may be coupled to the membrane by any of the methods described herein. In particular, the one or more anchors may comprise one or more linkers, such as maleimide functionalised linkers.

In this embodiment, the polynucleotide is typically RNA, DNA, PNA, TNA or LNA and may be double or single stranded. This embodiment is particularly suited to genomic DNA polynucleotides.

Where the one or more anchors comprise a protein, they may be able to anchor directly into the membrane without further functonalisation, for example if it already has an external hydrophobic region which is compatible with the membrane. Examples of such proteins include, but are not limited to, transmembrane proteins, intramembrane proteins and membrane proteins.

According to a preferred embodiment, the one or more anchors may be used to couple a polynucleotide to the membrane when the polynucleotide is attached to a leader sequence which preferentially threads into the pore. Leader sequences are discussed in more detail below. Preferably, the polynucleotide is attached (such as ligated) to a leader sequence which preferentially threads into the pore. Such a leader sequence may comprise a homopolymeric polynucleotide or an abasic region. The leader sequence is typically designed to hybridise to the one or more anchors either directly or via one or more intermediate polynucleotides (or splints). In such instances, the one or more anchors typically comprise a polynucleotide sequence which is complementary to a sequence in the leader sequence or a sequence in the one or more intermediate polynucleotides (or splints). In such instances, the one or more splints typically comprise a polynucleotide sequence which is complementary to a sequence in the leader sequence.

Double Stranded Polynucleotide

The polynucleotide may be double stranded. If the polynucleotide is double stranded, the method preferably further comprises before the contacting step ligating a bridging moiety, such as a hairpin loop, to one end of the polynucleotide. The two strands of the polynucleotide may then be separated as or before the polynucleotide is contacted with the pore in accordance with the invention. The two strands may be separated as the polynucleotide movement through the pore is controlled by a polynucleotide binding protein, such as a helicase, or molecular brake. This is described in International Application No. PCT/GB2012/051786 (published as WO 2013/014451).

Linking and interrogating both strands on a double stranded construct in this way increases the efficiency and accuracy of characterization.

Round the Corner Sequencing

In a preferred embodiment, a target double stranded polynucleotide is provided with a bridging moiety, such as a hairpin loop, at one end and the method comprises contacting the polynucleotide with the pore of the invention such that both strands of the polynucleotide move through the pore and taking one or more measurements as the both strands of the polynucleotide move with respect to the pore wherein the measurements are indicative of one or more characteristics of the strands of the polynucleotide and thereby characterising the target double stranded polynucleotide. Any of the embodiments discussed above equally apply to this embodiment.

Leader Sequence

Before the contacting step, the method preferably comprises attaching to the polynucleotide a leader sequence which preferentially threads into the pore. The leader sequence facilitates the method of the invention. The leader sequence is designed to preferentially thread into the pore of the invention and thereby facilitate the movement of polynucleotide through the pore. The leader sequence can also be used to link the polynucleotide to the one or more anchors as discussed above.

Double Coupling

The method of the invention may involve double coupling of a double stranded polynucleotide. In a preferred embodiment, the method of the invention comprises:

(a) providing the double stranded polynucleotide with a Y adaptor at one end and a bridging moiety adaptor, such as a hairpin loop adaptor, at the other end, wherein the Y adaptor comprises one or more first anchors for coupling the polynucleotide to the membrane, wherein the bridging moiety adaptor comprises one or more second anchors for coupling the polynucleotide to the membrane and wherein the strength of coupling of the bridging moiety adaptor to the membrane is greater than the strength of coupling of the Y adaptor to the membrane;
(b) contacting the polynucleotide provided in step (a) with the pore the invention such that the polynucleotide moves through the pore; and
(c) taking one or more measurements as the polynucleotide moves with respect to the pore, wherein the measurements are indicative of one or more characteristics of the polynucleotide, and thereby characterising the target polynucleotide.

This type of method is discussed in detail in International Application No. PCT/GB2015/050991.

Adding Hairpin Loops and Leader Sequences

Before provision, a double stranded polynucleotide may be contacted with a MuA transposase and a population of double stranded MuA substrates, wherein a proportion of the substrates in the population are Y adaptors comprising the leader sequence and wherein a proportion of the substrates in the population are hairpin loop adaptors. The transposase fragments the double stranded polynucleotide analyte and ligates MuA substrates to one or both ends of the fragments. This produces a plurality of modified double stranded polynucleotides comprising the leader sequence at one end and the hairpin loop at the other. The modified double stranded polynucleotides may then be investigated using the method of the invention.

These MuA based methods are disclosed in International Application No. PCT/GB2014/052505 (published as WO/2015/022544). They are also discussed in detail in International Application No. PCT/GB2015/050991.

One or more helicases may be attached to the MuA substrate Y adaptors before they are contacted with the double stranded polynucleotide and MuA transposase. Alternatively, one or more helicases may be attached to the MuA substrate Y adaptors before they are contacted with the double stranded polynucleotide and MuA transposase.

One or more molecular brakes may be attached to the MuA substrate hairpin loop adaptors before they are contacted with the double stranded polynucleotide and MuA transposase. Alternatively, one or more molecular brakes may be attached to the MuA substrate hairpin loop adaptors before they are contacted with the double stranded polynucleotide and MuA transposase.

Uncoupling

The method of the invention may involve characterising multiple target polynucleotides and uncoupling of the at least the first target polynucleotide.

In a preferred embodiment, the invention involves characterising two or more target polynucleotides. The method comprises:

(a) providing a first polynucleotide in a first sample;
(b) providing a second polynucleotide in a second sample;
(c) coupling the first polynucleotide in the first sample to a membrane using one or more anchors;
(d) contacting the first polynucleotide with the pore of the invention such that the polynucleotide moves through the pore;
(e) taking one or more measurements as the first polynucleotide moves with respect to the pore wherein the measurements are indicative of one or more characteristics of the first polynucleotide and thereby characterising the first polynucleotide;
(f) uncoupling the first polynucleotide from the membrane;
(g) coupling the second polynucleotide in the second sample to the membrane using one or more anchors;
(h) contacting the second polynucleotide with the pore of the invention such that the second polynucleotide moves through the pore; and
(i) taking one or more measurements as the second polynucleotide moves with respect to the pore wherein the measurements are indicative of one or more characteristics of the second polynucleotide and thereby characterising the second polynucleotide.

This type of method is discussed in detail in International Application No. PCT/GB2015/050992. If one or more anchors comprise a hydrophobic anchor, such as cholesterol, the agent is preferably a cyclodextrin or a derivative thereof or a lipid. The cyclodextrin or derivative thereof may be any of those disclosed in Eliseev, A. V., and Schneider, H-J. (1994) *J. Am. Chem. Soc.* 116, 6081-6088. The agent is more preferably heptakis-6-amino-β-cyclodextrin ($am_7$-βCD), 6-monodeoxy-6-monoamino-β-cyclodextrin ($am_1$-βCD) or heptakis-(6-deoxy-6-guanidino)-cyclodextrin ($gu_7$-βCD). Any of the lipids disclosed herein may be used.

Modified Polynucleotides

Before characterisation, a target polynucleotide may be modified by contacting the polynucleotide with a polymerase and a population of free nucleotides under conditions in which the polymerase forms a modified polynucleotide using the target polynucleotide as a template, wherein the polymerase replaces one or more of the nucleotide species in the target polynucleotide with a different nucleotide species when forming the modified polynucleotide. The modified polynucleotide may then be provided with one or more helicases attached to the polynucleotide and one or more molecular brakes attached to the polynucleotide. This type of modification is described in International Application No. PCT/GB2015/050483. Any of the polymerases discussed above may be used. The polymerase is preferably Klenow or 9o North.

The template polynucleotide is contacted with the polymerase under conditions in which the polymerase forms a modified polynucleotide using the template polynucleotide as a template. Such conditions are known in the art. For instance, the polynucleotide is typically contacted with the polymerase in commercially available polymerase buffer, such as buffer from New England Biolabs®. The temperature is preferably from 20 to 37° C. for Klenow or from 60 to 75° C. for 9o North. A primer or a 3' hairpin is typically used as the nucleation point for polymerase extension.

Characterisation, such as sequencing, of a polynucleotide using a transmembrane pore typically involves analyzing polymer units made up of k nucleotides where k is a positive integer (i.e. 'k-mers'). This is discussed in International Application No. PCT/GB2012/052343 (published as WO 2013/041878). While it is desirable to have clear separation between current measurements for different k-mers, it is common for some of these measurements to overlap. Especially with high numbers of polymer units in the k-mer, i.e. high values of k, it can become difficult to resolve the measurements produced by different k-mers, to the detriment of deriving information about the polynucleotide, for example an estimate of the underlying sequence of the polynucleotide.

By replacing one or more nucleotide species in the target polynucleotide with different nucleotide species in the modified polynucleotide, the modified polynucleotide contains k-mers which differ from those in the target polynucleotide. The different k-mers in the modified polynucleotide are capable of producing different current measurements from the k-mers in the target polynucleotide and so the modified polynucleotide provides different information from the target polynucleotide. The additional information from the modified polynucleotide can make it easier to characterise the target polynucleotide. In some instances, the modified polynucleotide itself may be easier to characterise. For instance, the modified polynucleotide may be designed to include k-mers with an increased separation or a clear separation between their current measurements or k-mers which have a decreased noise.

The polymerase preferably replaces two or more of the nucleotide species in the target polynucleotide with different nucleotide species when forming the modified polynucleotide. The polymerase may replace each of the two or more nucleotide species in the target polynucleotide with a distinct nucleotide species. The polymerase may replace each of the two or more nucleotide species in the target polynucleotide with the same nucleotide species.

If the target polynucleotide is DNA, the different nucleotide species in the modified typically comprises a nucleobase which differs from adenine, guanine, thymine, cytosine or methylcytosine and/or comprises a nucleoside which differs from deoxyadenosine, deoxyguanosine, thymidine, deoxycytidine or deoxymethylcytidine. If the target polynucleotide is RNA, the different nucleotide species in the modified polynucleotide typically comprises a nucleobase which differs from adenine, guanine, uracil, cytosine or methylcytosine and/or comprises a nucleoside which differs from adenosine, guanosine, uridine, cytidine or methylcytidine. The different nucleotide species may be any of the universal nucleotides discussed above.

The polymerase may replace the one or more nucleotide species with a different nucleotide species which comprises a chemical group or atom absent from the one or more nucleotide species. The chemical group may be a propynyl group, a thio group, an oxo group, a methyl group, a hydroxymethyl group, a formyl group, a carboxy group, a carbonyl group, a benzyl group, a propargyl group or a propargylamine group.

The polymerase may replace the one or more nucleotide species with a different nucleotide species which lacks a chemical group or atom present in the one or more nucleotide species. The polymerase may replace the one or more of the nucleotide species with a different nucleotide species having an altered electronegativity. The different nucleotide species having an altered electronegativity preferably comprises a halogen atom.

The method preferably further comprises selectively removing the nucleobases from the one or more different nucleotides species in the modified polynucleotide.

Other Characterisation Methods

In another embodiment, a polynucleotide is characterised by detecting labelled species that are released as a polymerase incorporates nucleotides into the polynucleotide. The polymerase uses the polynucleotide as a template. Each labelled species is specific for each nucleotide. The polynucleotide is contacted with a pore of the invention, a polymerase and labelled nucleotides such that phosphate labelled species are sequentially released when nucleotides are added to the polynucleotide(s) by the polymerase, wherein the phosphate species contain a label specific for each nucleotide. The polymerase may be any of those discussed above. The phosphate labelled species are detected using the pore and thereby characterising the polynucleotide. This type of method is disclosed in European Application No. 13187149.3 (published as EP 2682460). Any of the embodiments discussed above equally apply to this method.

In another embodiment, the invention also provides a method of characterising a target polynucleotide, comprising a) contacting the target polynucleotide with a transmembrane pore and a polynucleotide binding protein selected from TatD exonuclease, PyroPhage® 3173 DNA Polymerase, SD Polymerase and variants thereof such that the protein controls the movement of the polynucleotide with respect to the transmembrane pore; and c) taking one or more measurements as the polynucleotide moves with respect to the transmembrane pore, wherein the measurements are indicative of one or more characteristics of the polynucleotide, and thereby characterising the target polynucleotide. In this embodiment, the transmembrane pore and/or the polynucleotide binding protein are preferably not modified in accordance with the invention. Any of the embodiments discussed above with reference to characterisation of polynucleotides equally applies to this embodiment. The transmembrane pore may be any of those discussed above.

Kits

The present invention also provides a kit for characterising a target polynucleotide. In one embodiment, the kit comprises a pore of the invention and the components of a membrane. The membrane is preferably formed from the components. The pore is preferably present in the membrane. The kit may comprise components of any of the membranes disclosed above, such as an amphiphilic layer or a triblock copolymer membrane. The kit may further comprise a polynucleotide binding protein, preferably a modified polynucleotide binding protein of the invention.

In another embodiment, the kit comprises a modified polynucleotide binding protein of the invention and a polynucleotide adaptor. The polynucleotide binding protein is preferably bound to the adaptor. The adaptor may be any of those discussed above.

The kit may further comprise one or more anchors for coupling the polynucleotide to the membrane.

The kit is preferably for characterising a double stranded polynucleotide and preferably comprises a Y adaptor and a hairpin loop adaptor. The Y adaptor preferably has one or more helicases attached and the hairpin loop adaptor preferably has one or more molecular brakes attached. The one or more helicases and/or the one or more molecular brakes may be modified in accordance with the invention. The Y adaptor preferably comprises one or more first anchors for coupling the polynucleotide to the membrane, the hairpin loop adaptor preferably comprises one or more second anchors for coupling the polynucleotide to the membrane and the strength of coupling of the hairpin loop adaptor to the membrane is preferably greater than the strength of coupling of the Y adaptor to the membrane.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides or voltage or patch clamp apparatus. Reagents may be present in the kit in a dry state such that a fluid sample resuspends the reagents. The kit may also, optionally, comprise instructions to enable the kit to be used in the method of the invention or details regarding for which organism the method may be used.

Apparatus

The invention also provides an apparatus for characterising a target polynucleotide. The apparatus comprises a plurality of pores of the invention or a plurality of combinations of the invention. The apparatus also comprises a plurality of membranes. The plurality of pores are preferably present in the plurality of membranes. The number of pores and membranes is preferably equal. Preferably, a single pore is present in each membrane.

The apparatus preferably further comprises instructions for carrying out the method of the invention. The apparatus may be any conventional apparatus for polynucleotide analysis, such as an array or a chip. Any of the embodiments discussed above with reference to the methods of the invention are equally applicable to the apparatus of the invention. The apparatus may further comprise any of the features present in the kit of the invention.

The apparatus is preferably set up to carry out the method of the invention.

The apparatus preferably comprises:

a sensor device that is capable of supporting the plurality of pores and membranes and being operable to perform polynucleotide characterisation using the pores and membranes; and at least one port for delivery of the material for performing the characterisation.

Alternatively, the apparatus preferably comprises:

a sensor device that is capable of supporting the plurality of pores and membranes being operable to perform polynucleotide characterisation using the pores and membranes; and at least one reservoir for holding material for performing the characterisation.

The apparatus more preferably comprises:

a sensor device that is capable of supporting the membrane and plurality of pores and membranes and being operable to perform polynucleotide characterising using the pores and membranes;

at least one reservoir for holding material for performing the characterising;

a fluidics system configured to controllably supply material from the at least one reservoir to the sensor device; and one or more containers for receiving respective samples, the fluidics system being configured to supply the samples selectively from one or more containers to the sensor device.

The apparatus may be any of those described in International Application No. No. PCT/GB08/004127 (published as WO 2009/077734), PCT/GB10/000789 (published as WO 2010/122293), International Application No. PCT/GB10/002206 (published as WO 2011/067559) or International Application No. PCT/US99/25679 (published as WO 00/28312).

The following Example illustrates the invention.

Example 1

This example describes the simulations which were run to investigate the interaction between MspA—(G75S/G77S/L88N/D90N/D91N/D118R/Q126R/D134R/E139K)8 (SEQ ID NO: 2 with mutations G75S/G77S/L88N/D90N/D91N/D118R/Q126R/D134R/E139K=MspA mutant 1) or MspA—((Del-L74/G75/D118/L119)D56N/E59R/L88N/D90N/D91N/Q126R/D134R/E139K)8 (SEQ ID NO: 2 with mutations D56N/E59R/L88N/D90N/D91N/Q126R/D134R/E139K and deletion of the amino acids L74/G75/D118/L119=MspA mutant 2) with T4 Dda—E94C/A360C/C109A/C136A (SEQ ID NO: 24 with mutations E94C/A360C/C114A/C171A/C421D and then (ΔM1)G1G2)).

Simulations were performed using the GROMACS package version 4.0.5, with the GROMOS 53a6 forcefield and the SPC water model.

The MspA mutant 1 and MspA mutant 2 models were based on the crystal structure of MspA found in the protein data bank, accession code 1UUN. The relevant mutations were made using PyMOL, and in the case of MspA mutant 2 the residues L74/G75/D118/L119 were deleted from the barrel. The resultant pore models were then energy minimised using the steepest descents algorithm. The T4 Dda—E94C/A360C/C109A/C136A model was based on the Dda1993 structure found in the protein data bank, accession code 3UPU. Again, relevant mutations were made using PyMOL, and the model was energy minimised using the steepest descents algorithm.

Figure 1:
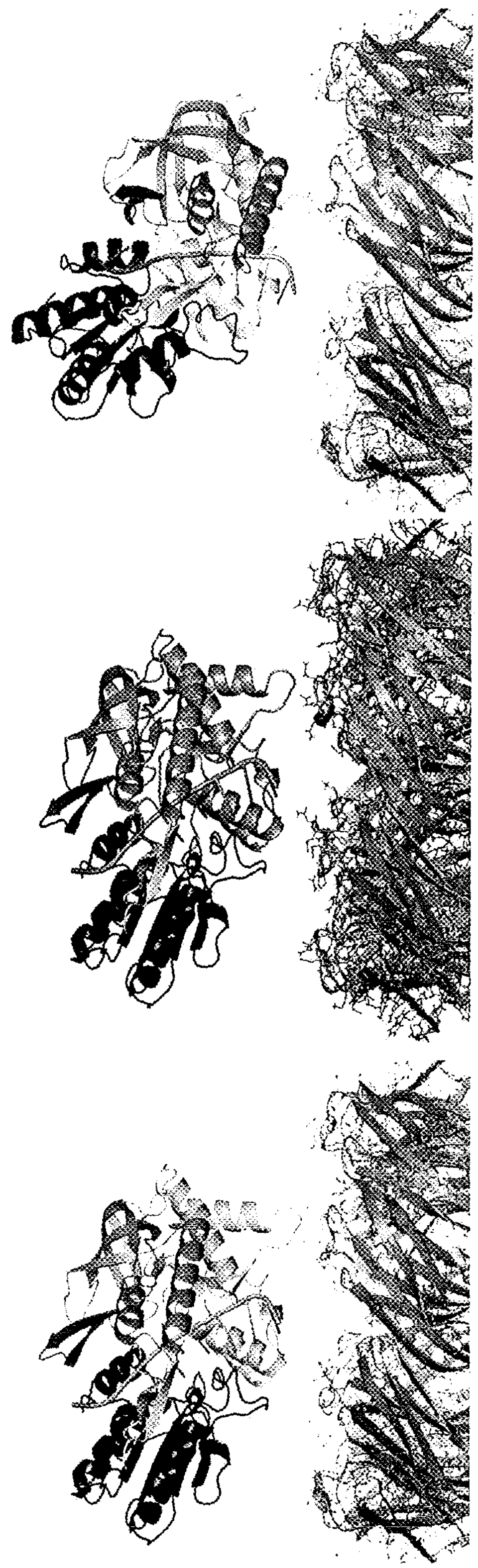
FIG. 1 shows the three different initial simulation orientations of T4 Dda—E94C/A360C/C109A/C136A (SEQ ID NO: 24 with mutations E94C/A360C/C109A/C136A and then (ΔM1)G1G2) with respect to either MspA—(G75S/G77S/L88N/D90N/D91N/D118R/Q126R/D134R/E139K)8 (SEQ ID NO: 2 with mutations G75S/G77S/L88N/D90N/D91N/D118R/Q126R/D134R/E139K=MspA mutant 1) or MspA—((Del-L74/G75/D118/L119)D56N/E59R/L88N/D90N/D91N/Q126R/D134R/E139K)8 (SEQ ID NO: 2 with mutations D56N/E59R/L88N/D90N/D91N/Q126R/D134R/E139K and deletion of the amino acids L74/G75/D118/L119=MspA mutant 2). The difference between run 1 and run 2 was that both the enzyme and pore had different side chain conformations despite the pore and enzyme being in the same position. In run three the enzyme has been tilted slightly with respect to the nanopore.
Figure 2:
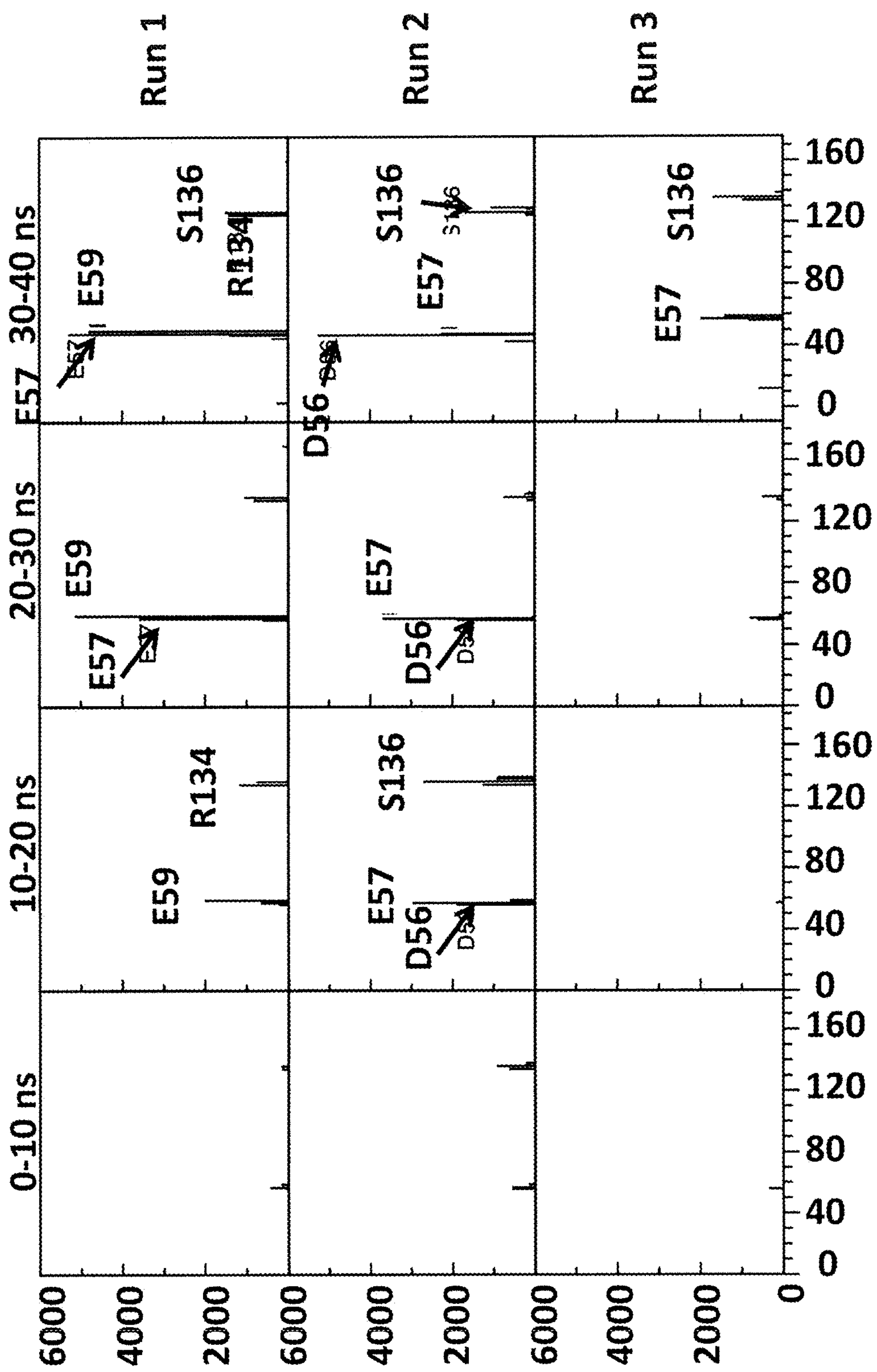
FIG. 2 shows a plot (y-axis label=number of pore/enzyme contacts, x-axis label=pore amino acid residue number) of the interaction points of the nanopore MspA mutant 1 with T4 Dda—E94C/A360C/C109A/C136A. Each row of the plot shows the interaction points for the different enzyme/nanopore orientations e.g. runs 1-3.
Figure 3:
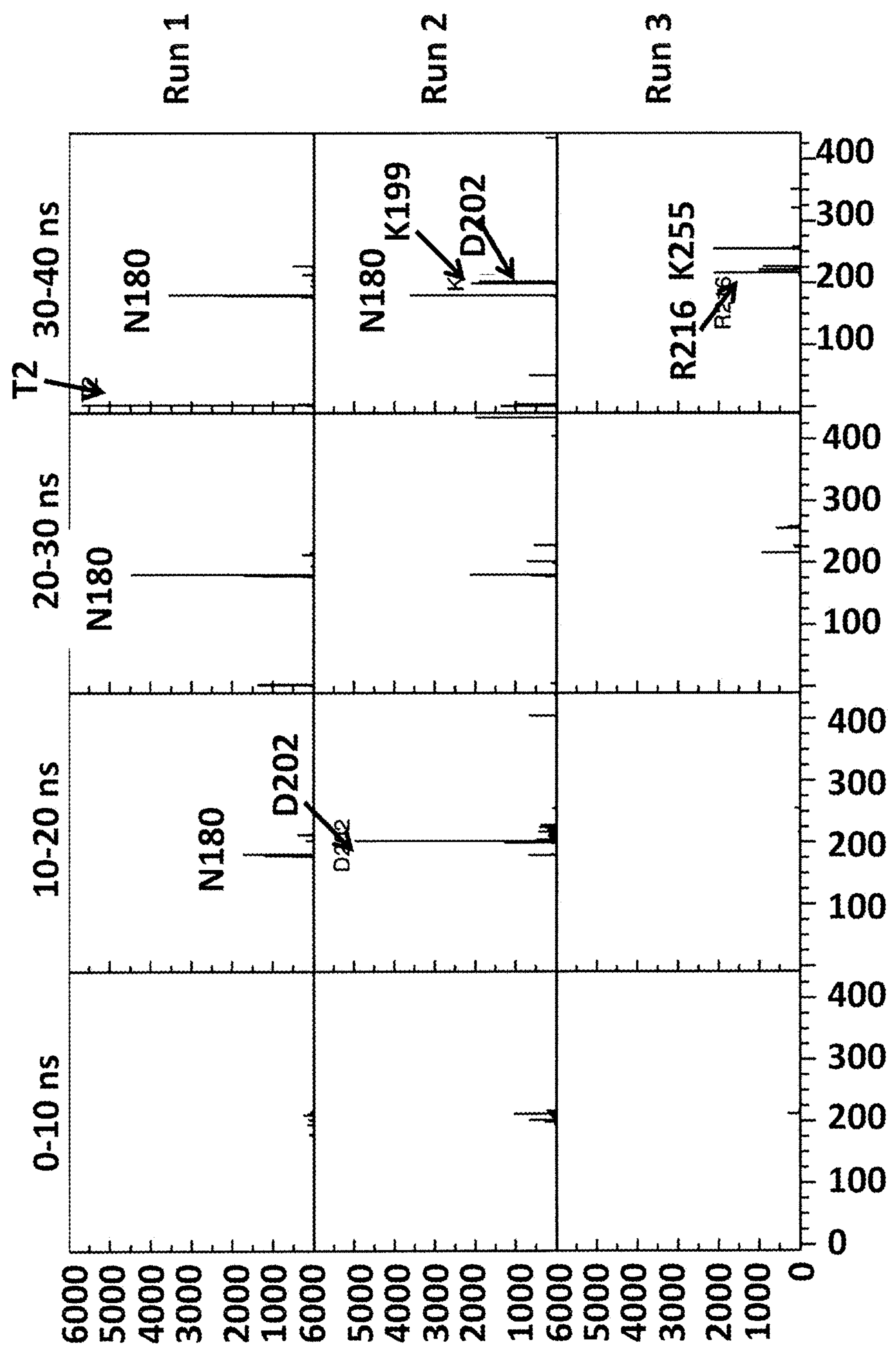
FIG. 3 shows a plot (y-axis label=number of pore/enzyme contacts, x-axis label=enzyme amino acid residue number) of the interaction points of the enzyme T4 Dda—E94C/A360C/C109A/C136A with MspA mutant 1. Each row of the plot shows the interaction points for the different enzyme/nanopore orientations e.g. runs 1-3.
Figure 4:
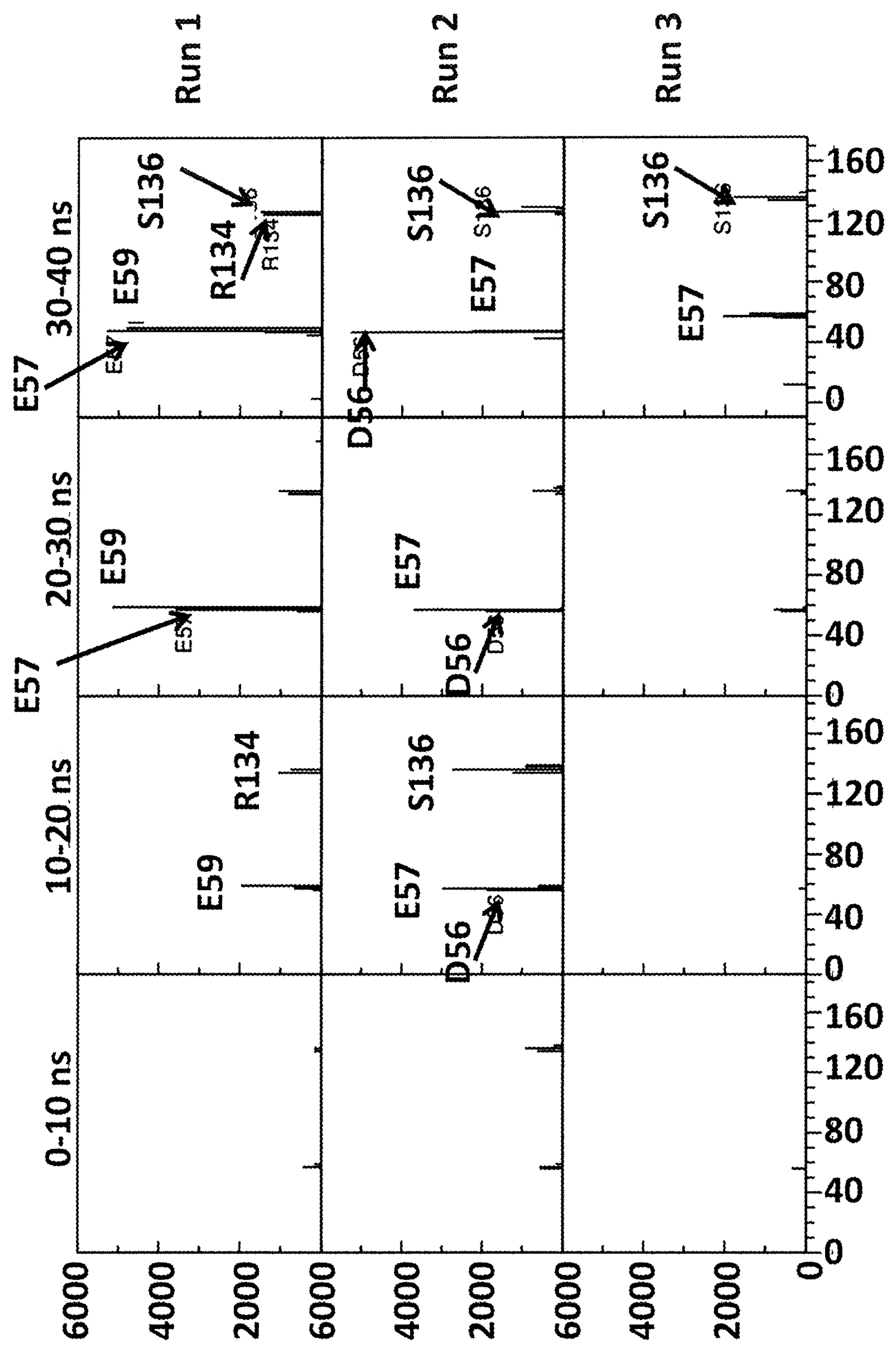
FIG. 4 shows a plot (y-axis label=number of pore/enzyme contacts, x-axis label=pore amino acid residue number) of the interaction points of the nanopore MspA mutant 2 with T4 Dda—E94C/A360C/C109A/C136A. Each row of the plots shows the interaction points for the different enzyme/nanopore orientations e.g. runs 1-3.
Figure 5:
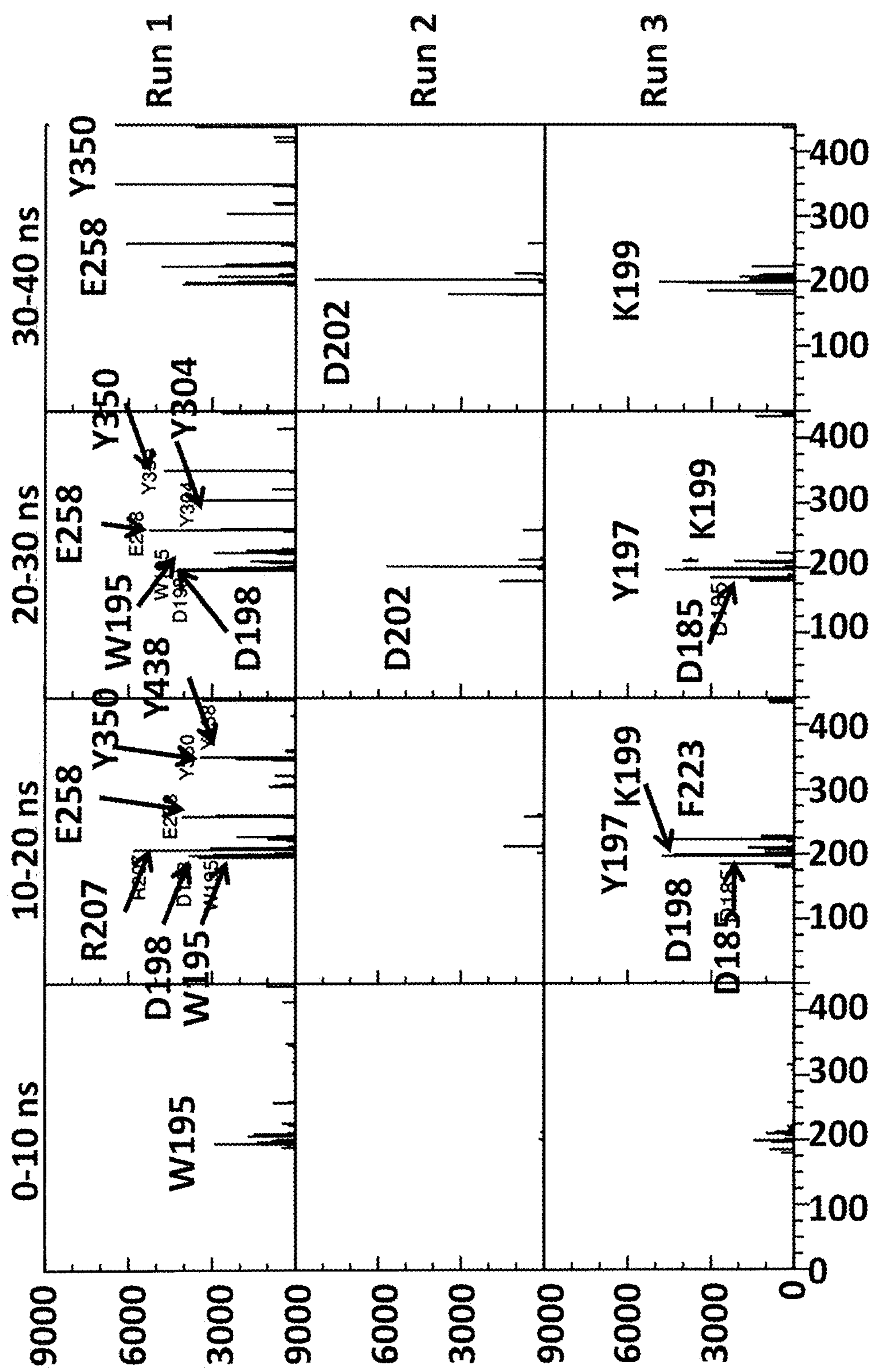
FIG. 5 shows a plot (y-axis label=number of pore/enzyme contacts, x-axis label=enzyme amino acid residue number) of the interaction points of the enzyme T4 Dda—E94C/A360C/C109A/C136A with MspA mutant 2. Each row of the plot shows the interaction points for the different enzyme/nanopore orientations e.g. runs 1-3.

The T4 Dda—E94C/A360C/C109A/C136A model was then placed above MspA mutant 1 and MspA mutant 2. Three simulations were performed for the T4 Dda—E94C/A360C/C109A/C136A/MspA mutant 1 and T4 Dda—E94C/A360C/C109A/C136A/MspA mutant 2 systems, with the orientation of T4 Dda—E94C/A360C/C109A/C136A differing in each simulation (See FIG. 1 for cartoon representations of the three different simulation orientations). The pore was placed into a lipid membrane comprising DPPC molecules and the simulation box was solvated. Throughout the simulation, restraints were applied to the backbone of the pore. However, the enzyme was unrestrained. The system was simulated in the NPT ensemble for 40 ns, using the Berendsen thermostat and Berendsen barostat to 300 K.

Figure 6:
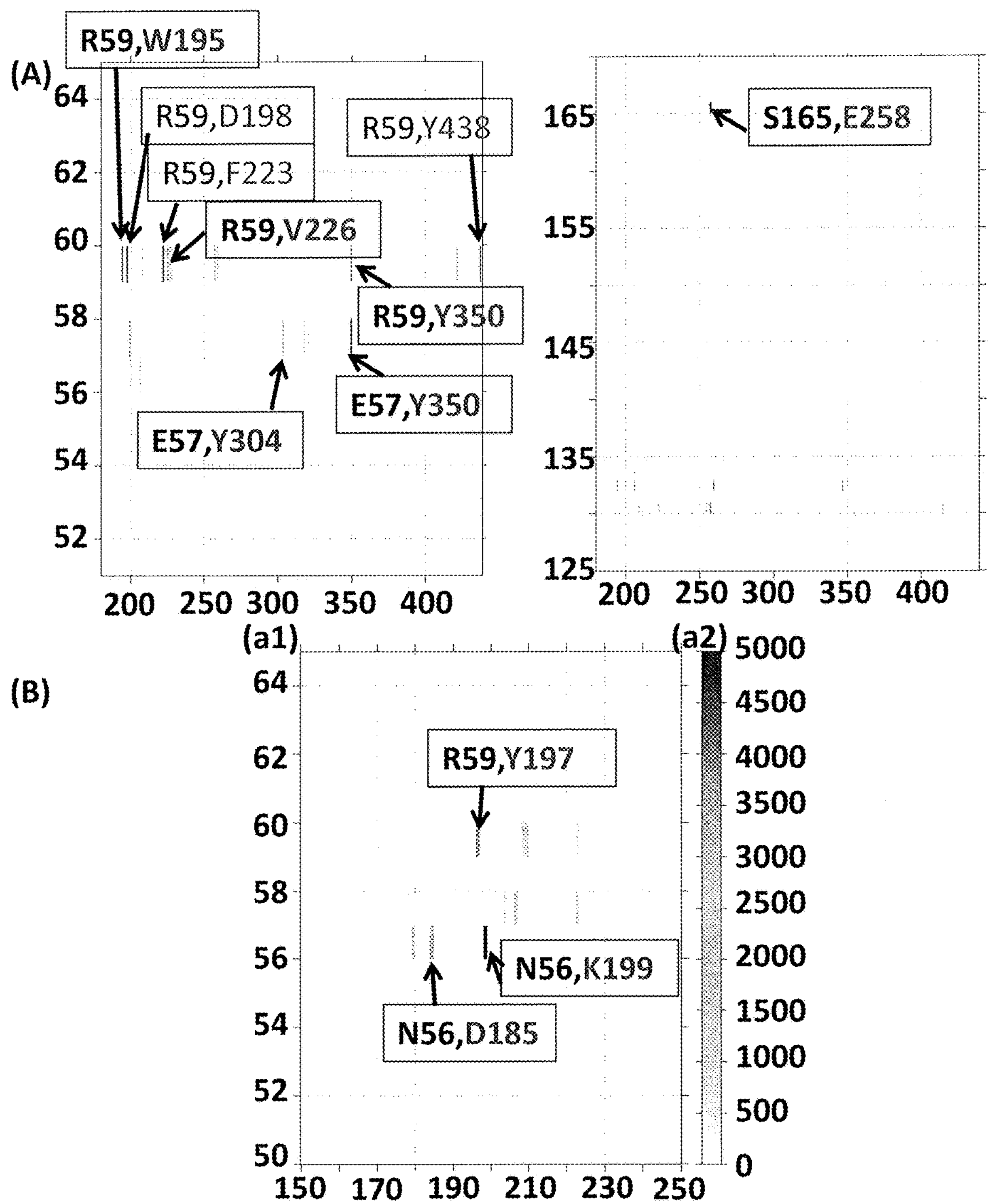
FIG. 6(A) shows two regions of a plot (y-axis label=pore amino acid residue number, x-axis label=enzyme amino acid residue number) which shows which amino acids in the pore (MspA mutant 2) interact with particular amino acids in the enzyme (T4 Dda—E94C/A360C/C109A/C136A) from run 1.
FIG. 6(B) shows a region of a plot (y-axis label (a1)=pore amino acid residue number, y-axis label (a2)=number of pore/enzyme contacts, x-axis label=enzyme amino acid residue number) which shows which amino acids in the pore (MspA mutant 2) interact with particular amino acids in the enzyme (T4 Dda—E94C/A360C/C109A/C136A) from run 3. The grey bands in the plots indicate an interaction between amino acids. The darkness of the grey band corresponds to the number of interactions between enzyme/pore, with dark grey=many interactions and light grey=fewer interactions. The first amino acid in each box corresponds to the interacting amino acid in the MspA mutant 2 and the second amino acid corresponds to the interacting amino acids in T4 Dda—E94C/A360C/C109A/C136A.

The contacts between the enzyme and pore were analysed using both GROMACS analysis software and also locally written code. FIGS. 2 to 5 showed the amino acid residues which interacted in MspA mutant 1 (FIGS. 2 and 3) and MspA mutant 2 (FIGS. 4 and 5) with the enzyme T4 Dda—E94C/A360C/C109A/C136A. The tables below show the number of contacts observed for both pore and enzyme amino acids (Table 4 shows the MspA mutant 1 amino acid contact points observed when the interactions were measured between MspA mutant 1 and T4 Dda—E94C/A360C/C109A/C136A, Table 5 shows the T4 Dda—E94C/A360C/C109A/C136A amino acid contact points observed when the interactions were measured between MspA mutant 1 and T4 Dda—E94C/A360C/C109A/C136A, Table 6 shows the MspA mutant 2 amino acid contact points observed when the interactions were measured between MspA mutant 2 and T4 Dda—E94C/A360C/C109A/C136A, Table 7 shows the T4 Dda—E94C/A360C/C109A/C136A amino acid contact points observed when the interactions were measured between MspA mutant 2 and T4 Dda—E94C/A360C/C109A/C136A). FIG. 6 shows which amino acids in the pore (MspA mutant 2) interacted with particular amino acids in the enzyme (T4 Dda—E94C/A360C/C109A/C136A). The data obtained from the simulations showed that a greater number of interaction points were detected between MspA mutant 2 and T4 Dda—E94C/A360C/C109A/C136A than were detected between MspA mutant 1 and T4 Dda—E94C/A360C/C109A/C136A.

TABLE 4

| Run 1 | | Run 2 | | Run 3 | |
|---|---|---|---|---|---|
| Pore Amino Acid Residue | Number of Contacts | Pore Amino Acid Residue | Number of Contacts | Pore Amino Acid Residue | Number of Contacts |
| 57 | 5304 | 56 | 5271 | 57 | 2068 |
| 59 | 4806 | 57 | 2262 | 136 | 1800 |
| 136 | 1515 | 136 | 1697 | 59 | 1419 |
| 134 | 1443 | 139 | 1053 | 134 | 975 |
| 56 | 1402 | 52 | 720 | 56 | 817 |
| 54 | 382 | 134 | 215 | 12 | 581 |
| 12 | 263 | 138 | 196 | 139 | 180 |
| 169 | 49 | 55 | 5 | 58 | 87 |
| 14 | 17 | 59 | 1 | 137 | 32 |
| 58 | 8 | | | 14 | 8 |
| 55 | 4 | | | 48 | 5 |
| 52 | 4 | | | 169 | 3 |
| 138 | 2 | | | | |
| 139 | 1 | | | | |
| 137 | 1 | | | | |

TABLE 5

| Run 1 | | Run 2 | | Run 3 | |
|---|---|---|---|---|---|
| Enzyme Amino Acid Residue | Number of Contacts | Enzyme Amino Acid Residue | Number of Contacts | Enzyme Amino Acid Residue | Number of Contacts |
| 2 | 5702 | 180 | 3619 | 255 | 2365 |
| 180 | 3644 | 199 | 2104 | 216 | 2126 |
| 179 | 2205 | 202 | 1909 | 221 | 1027 |
| 178 | 1550 | 1 | 1378 | 227 | 929 |
| 227 | 513 | 4 | 981 | 351 | 239 |
| 4 | 390 | 51 | 678 | 321 | 223 |
| 177 | 297 | 434 | 282 | 254 | 199 |
| 212 | 275 | 179 | 153 | 258 | 198 |
| 1 | 169 | 178 | 101 | 224 | 177 |
| 194 | 75 | 177 | 84 | 257 | 137 |
| 204 | 58 | 197 | 71 | 256 | 115 |
| 176 | 56 | 5 | 19 | 223 | 109 |
| 213 | 46 | 201 | 19 | 212 | 54 |
| 3 | 37 | 181 | 19 | 308 | 25 |
| 216 | 33 | 200 | 2 | 207 | 21 |
| 211 | 28 | 6 | 1 | 350 | 11 |
| 202 | 28 | | | 228 | 5 |
| 224 | 26 | | | 210 | 4 |
| 223 | 26 | | | 319 | 3 |
| 191 | 17 | | | 304 | 2 |
| 199 | 12 | | | 209 | 2 |
| 201 | 8 | | | 347 | 1 |
| 434 | 4 | | | 261 | 1 |
| 405 | 1 | | | 260 | 1 |
| 255 | 1 | | | 247 | 1 |

TABLE 6

| Run 1 | | Run 2 | | Run 3 | |
|---|---|---|---|---|---|
| Pore Amino Acid Residue | Number of Contacts | Pore Amino Acid Residue | Number of Contacts | Pore Amino Acid Residue | Number of Contacts |
| 59 | 26063 | 59 | 7271 | 56 | 9681 |
| 57 | 10231 | 57 | 4828 | 59 | 7422 |
| 134 | 6034 | 169 | 3039 | 57 | 3640 |
| 136 | 5757 | 134 | 499 | 136 | 3160 |
| 169 | 3357 | 136 | 28 | 12 | 2083 |
| 56 | 1689 | 56 | 17 | 14 | 1132 |
| 137 | 374 | 54 | 1 | 134 | 432 |
| 58 | 134 | 14 | 1 | 54 | 44 |
| 14 | 10 | 12 | 1 | 169 | 8 |
| 135 | 9 | | | 53 | 2 |
| 60 | 6 | | | | |
| 170 | 5 | | | | |

TABLE 7

| Run 1 | | Run 2 | | Run 3 | |
|---|---|---|---|---|---|
| Enzyme Amino Acid Residue | Number of Contacts | Enzyme Amino Acid Residue | Number of Contacts | Enzyme Amino Acid Residue | Number of Contacts |
| 350 | 7013 | 202 | 8318 | 199 | 4908 |
| 258 | 6277 | 180 | 3505 | 197 | 3828 |
| 223 | 4829 | 179 | 1297 | 185 | 3158 |
| 195 | 4081 | 212 | 1089 | 198 | 2873 |
| 198 | 3990 | 258 | 617 | 207 | 1998 |
| 438 | 3642 | 211 | 324 | 202 | 1645 |
| 260 | 3113 | 198 | 236 | 223 | 1559 |
| 207 | 2781 | 265 | 57 | 180 | 1427 |
| 226 | 2563 | 260 | 55 | 209 | 1309 |
| 304 | 2489 | 259 | 37 | 210 | 1152 |
| 200 | 2116 | 255 | 24 | 203 | 1150 |

TABLE 7-continued

| Run 1 | | Run 2 | | Run 3 | |
|---|---|---|---|---|---|
| Enzyme Amino Acid Residue | Number of Contacts | Enzyme Amino Acid Residue | Number of Contacts | Enzyme Amino Acid Residue | Number of Contacts |
| 227 | 1307 | 1 | 22 | 204 | 646 |
| 347 | 845 | 200 | 19 | 437 | 466 |
| 321 | 831 | 300 | 18 | 200 | 431 |
| 422 | 818 | 203 | 14 | 211 | 347 |
| 318 | 740 | 261 | 12 | 405 | 176 |
| 415 | 733 | 216 | 10 | 227 | 97 |
| 210 | 639 | 177 | 10 | 258 | 94 |
| 229 | 555 | 213 | 9 | 212 | 72 |
| 255 | 552 | 207 | 6 | 256 | 68 |
| 224 | 492 | 337 | 2 | 216 | 55 |
| 228 | 461 | 204 | 2 | 189 | 42 |
| 208 | 395 | 434 | 1 | 228 | 22 |
| 193 | 307 | 298 | 1 | 220 | 18 |
| 256 | 256 | | | 219 | 17 |

Example 2

Figure 7:
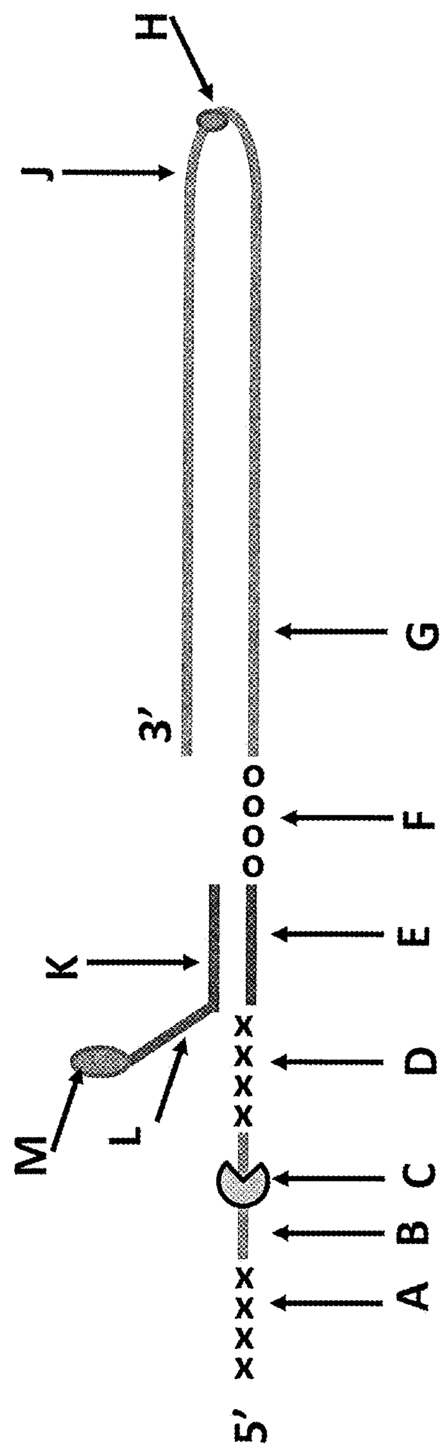
FIG. 7 shows DNA construct X used in Example 2. Section A corresponded to thirty iSpC3 spacers. Section B corresponded to SEQ ID NO: 28. Label C corresponded to the enzyme T4 Dda—E94C/C109A/C136A/A360C (SEQ ID NO: 24 with mutations E94C/C109A/C136A/A360C). Section D corresponded to four iSp18 spacers. Section E corresponded to SEQ ID NO: 29. Section F corresponded to four i5NitInd groups (IDT). Section G corresponded to SEQ ID NO: 30. Section H corresponded to four iSpC3 spacers. Section J corresponded to SEQ ID NO: 31. Section K corresponded to SEQ ID NO: 32. Section L corresponded to six iSp18 spacers and two thymine residues. Section M corresponded to a 3' cholesterol tether.
Figure 8:
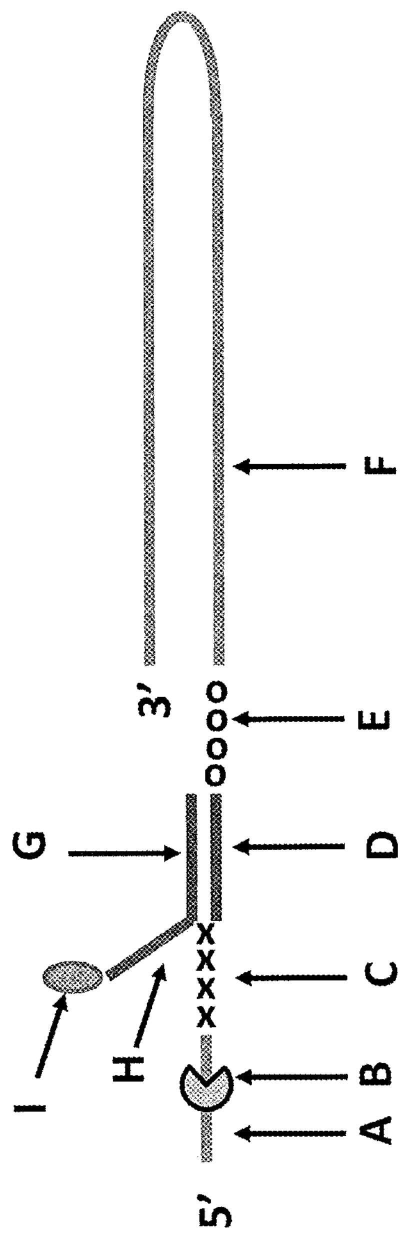
FIG. 8 shows DNA construct Y used in Example 2. Section A corresponded to SEQ ID NO: 33. Label B corresponded to the enzyme T4 Dda—E94C/C109A/C136A/A360C (SEQ ID NO: 24 with mutations E94C/C109A/C136A/A360C). Section C corresponded to four iSpC3 spacers. Section D corresponded to SEQ ID NO: 27. Section E corresponded to four i5NitInd groups (IDT). Section F corresponded to SEQ ID NO: 34. Section G corresponded to SEQ ID NO: 32. Section H corresponded to six iSp18 spacers and two thymine residues. Section I corresponded to a 3' cholesterol tether.

This example describes how a helicase—T4 Dda—E94C/C109A/C136A/A360C (SEQ ID NO: 24 with mutations E94C/C109A/C136A/A360C) was used to control the movement of DNA construct X or Y (shown in FIGS. 7 and 8) through a number of different MspA nanopores. All of the nanopores tested exhibited changes in current as the DNA translocated through the nanopore. The mutant nanopores tested exhibited either more consistent movement of the target polynucleotide or reduced noise associated with the movement of the target polynucleotide as it translocated through the nanopore or both.

Materials and Methods

Prior to setting up the experiment, DNA construct X or Y (final concentration 0.1 nM) was pre-incubated at room temperature for five minutes with T4 Dda—E94C/C109A/C136A/A360C (final concentration added to the nanopore system 10 nM, which was provided in buffer (253 mM KCl, 50 mM potassium phosphate, pH 8.0, 2 mM EDTA)). After five minutes, TMAD (100 μM final concentration added to the nanopore system) was added to the pre-mix and the mixture incubated for a further 5 minutes. Finally, MgCl2 (2 mM final concentration added to the nanopore system), ATP (2 mM final concentration added to the nanopore system) and KCl (500 mM final concentration added to the nanopore system) were added to the pre-mix.

Electrical measurements were acquired from single MspA nanopores inserted in block co-polymer in buffer (25 mM K Phosphate buffer, 150 mM Potassium Ferrocyanide (II), 150 mM Potassium Ferricyanide (III), pH 8.0). After achieving a single pore inserted in the block co-polymer, then buffer (2 mL, 25 mM K Phosphate buffer, 150 mM Potassium Ferrocyanide (II), 150 mM Potassium Ferricyanide (III), pH 8.0) was flowed through the system to remove any excess MspA nanopores. 150 uL of 500 mM KCl, 25 mM K Phosphate, pH 8.0 was then flowed through the system. After 10 minutes a further 150 uL of 500 mM KCl, 25 mM K Phosphate, pH 8.0 was flowed through the system and then the enzyme (T4 Dda—E94C/C109A/C136A/A360C, 10 nM final concentration), DNA construct X or Y (0.1 nM final concentration), fuel (MgCl2 2 mM final concentration, ATP 2 mM final concentration) pre-mix (150 μL total) was then flowed into the single nanopore experimental system. The experiment was run at −120 mV and helicase-controlled DNA movement monitored.

Results

A number of different nanopores were investigated in order to determine the effect of mutations to regions of the transmembrane pore which were thought to interact with the helicase T4 Dda—E94C/C109A/C136A/A360C. The mutant pores which were investigated are listed below with the baseline nanopore with which they were compared. A number of different parameters were investigated in order to identify improved nanopores 1) the average noise of the signal (where noise is equal to the standard deviation of all events in a strand, calculated over all strands) which in an improved nanopore would be lower than the baseline, 2) the average current range which was a measure of the spread of current levels within a signal and which in an improved nanopore would be higher than the baseline, 3) the average signal to noise quoted in the table is the signal to noise (average current range divided by average noise of the signal) over all strands and in an improved nanopore would be higher than the baseline and 4) the percentage of complement slipping forwards which in an improved nanopore would be lower than the baseline.

The measurement of complement slipping forwards was calculated using the following procedure 1) the helicase controlled DNA movements were mapped to a model, 2) the helicase-controlled DNA movements were then subjected to filtering, 3) the mapped helicase controlled DNA movements were checked to ensure accurate mapping, 4) the transitions that were classified as a slipping forward movement of at least four consecutive nucleotides were then added together and a percentage based on the total number of transitions was calculated.

In table 8 below, MspA mutant 3 (which contained the additional mutations D56N/E59R) was compared to MspA mutant 1 (baseline). MspA mutant 3 exhibited a lower mean noise of the signal, a higher mean current range and a higher average signal to noise than MspA mutant 1. Therefore, the D56N/E59R mutations which were made to improve the interaction between the nanopore and the enzyme resulted in reduced noise associated with the movement of the target polynucleotide through the nanopore.

In table 8 below, a number of MspA mutants 4-7 and 24 were compared to MspA mutant 1 (baseline). MspA mutants 4-7 and 24 all differed from MspA mutant 1 in that residues had been deleted and that mutations had been made in order to effect how the enzyme and the nanopore interacted (the mutations which the nanopores had in common were L88N/D90N/D91N/Q126R/D134R/E139K). MspA mutants 4-7 and 24 exhibited an improvement in at least one of the measured parameters (mean noise of the signal, median noise of the signal, mean current range, average signal to noise and percentage of complement slipping forwards) when compared to MspA mutant 1. However, the measured improvements were attributed to the combination of changes made to the nanopores (MspA mutants 4-7 and 24) e.g. deletions and the mutations which were made in order to effect how the enzyme and the nanopore interacted.

Pore ID's

MspA mutant 1=MspA—(G75S/G77S/L88N/D90N/D91N/D118R/Q126R/D134R/E139K)8 (SEQ ID NO: 2 with mutations G75S/G77S/L88N/D90N/D91N/D118R/Q126R/D134R/E139K).

MspA Mutant 3=MspA—(D56N/E59R/G75S/G77S/L88N/D90N/D91N/D118R/Q126R/D134R/E139K)8 (SEQ ID NO: 2 with mutations D56N/E59R/G75S/G77S/L88N/D90N/D91N/D118R/Q126R/D134R/E139K).

MspA mutant 4=MspA—((Del-L74/G75/D118/L119)E57R/E59N/L88N/D90N/D91N/Q126R/D134R/E139K)8 (SEQ ID NO: 2 with mutations E57R/E59N/L88N/D90N/D91N/Q126R/D134R/E139K and deletion of the amino acids L74/G75/D118/L119)

Figure 9:
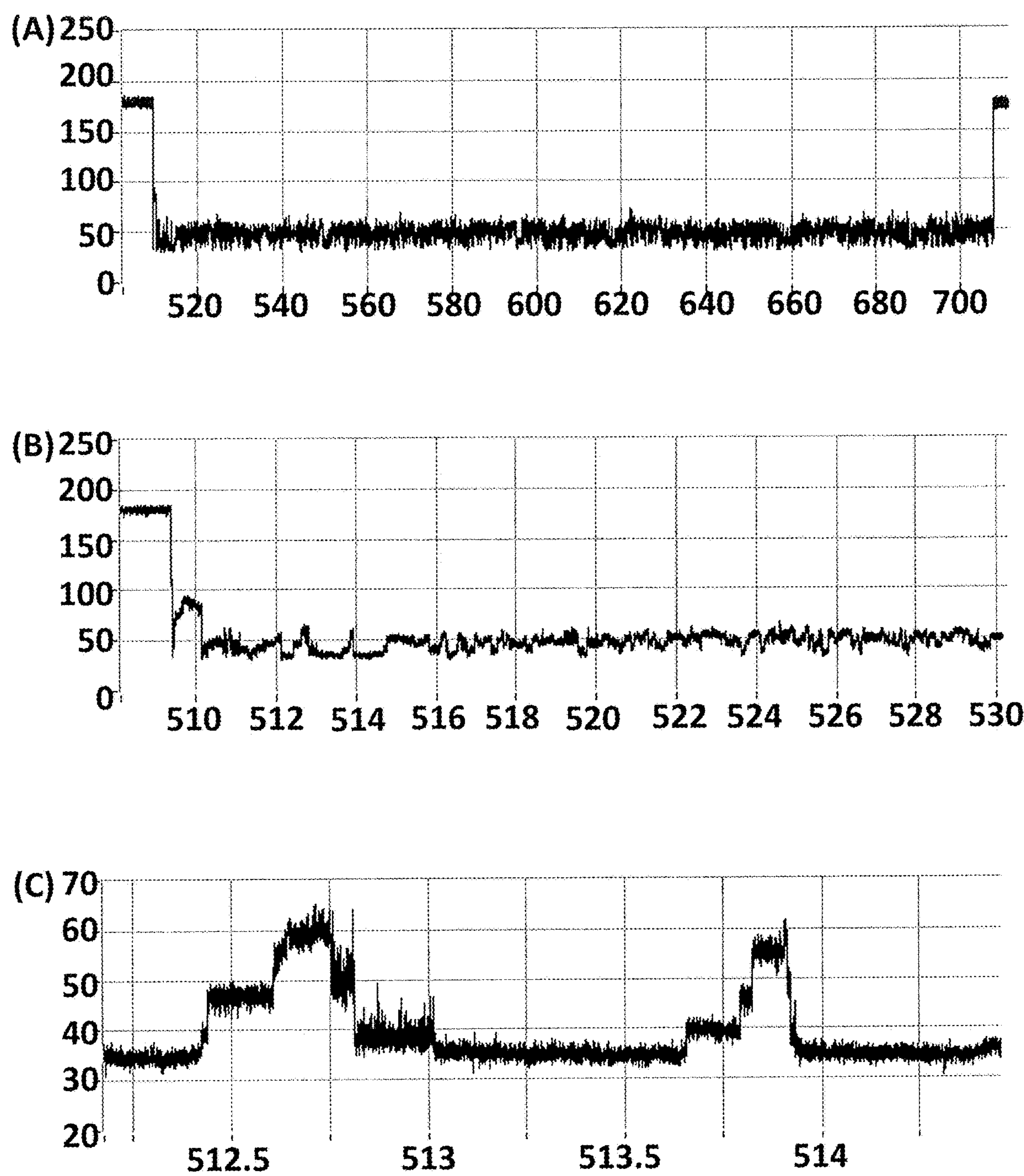
FIG. 9 shows example current traces (y-axis label=Current (pA), x-axis label=Time (s) for all three traces) of when a helicase (T4 Dda—E94C/C109A/C136A/A360C) controlled the translocation of the DNA construct X through the MspA nanopore MspA—((Del-L74/G75/D118/L119)D56W/E59R/L88N/D90N/D91N/Q126R/D134R/E139K)8 (SEQ ID NO: 2 with mutations D56W/E59R/L88N/D90N/D91N/Q126R/D134R/E139K and deletion of the amino acids L74/G75/D118/L119). Sections B and C show zoomed in regions of current trace A.

MspA mutant 5=MspA—((Del-L74/G75/D118/L119)D56W/E59R/L88N/D90N/D91N/Q126R/D134R/E139K)8 (SEQ ID NO: 2 with mutations D56W/E59R/L88N/D90N/D91N/Q126R/D134R/E139K and deletion of the amino acids L74/G75/D118/L119). Example helicase controlled DNA movement shown in FIG. 9.

Figure 10:
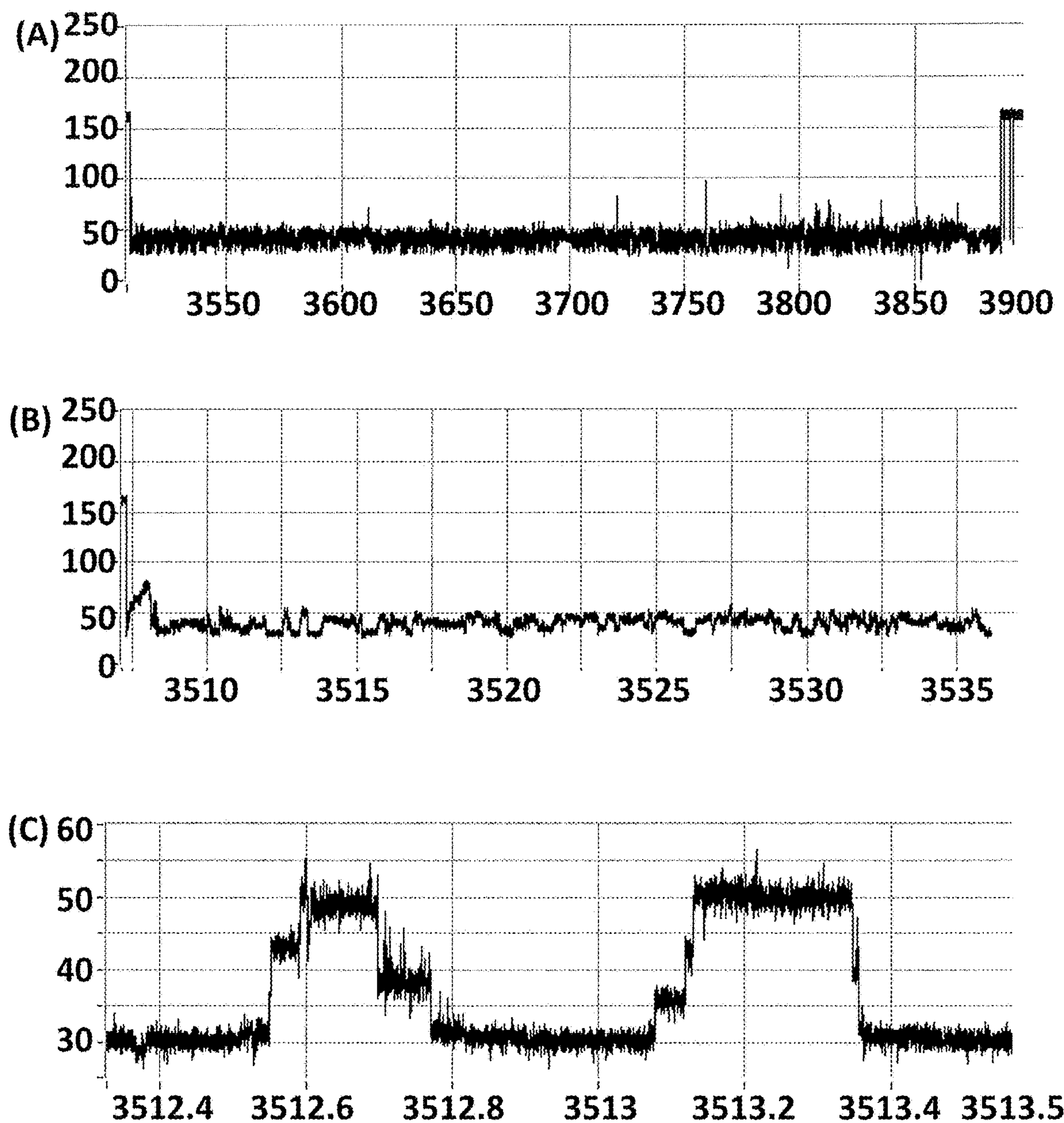
FIG. 10 shows example current traces (y-axis label=Current (pA), x-axis label=Time (s) for all three traces) of when a helicase (T4 Dda—E94C/C109A/C136A/A360C) controlled the translocation of the DNA construct X through the MspA nanopore MspA—((Del-L74/G75/D118/L119)E59Y/L88N/D90N/D91N/Q126R/D134R/E139K)8 (SEQ ID NO: 2 with mutations E59Y/L88N/D90N/D91N/Q126R/D134R/E139K and deletion of the amino acids L74/G75/D118/L119). Sections B and C show zoomed in regions of current trace A.

MspA mutant 6=MspA—((Del-L74/G75/D118/L119)E59Y/L88N/D90N/D91N/Q126R/D134R/E139K)8 (SEQ ID NO: 2 with mutations E59Y/L88N/D90N/D91N/Q126R/D134R/E139K and deletion of the amino acids L74/G75/D118/L119). Example helicase controlled DNA movement shown in FIG. 10.

MspA mutant 7=MspA—((Del-L74/G75/D118/L119)D56N/E59S/L88N/D90N/D91N/Q126R/D134R/E139K)8 (SEQ ID NO: 2 with mutations D56N/E59S/L88N/D90N/D91N/Q126R/D134R/E139K and deletion of the amino acids L74/G75/D118/L119)

MspA mutant 24=MspA—((Del-L74/G75/D118/L119)D56N/E59W/L88N/D90N/D91N/Q126R/D134R/E139K)8 (SEQ ID NO: 2 with mutations D56N/E59W/L88N/D90N/D91N/Q126R/D134R/E139K and deletion of the amino acids L74/G75/D118/L119). Example helicase controlled DNA movement shown in FIG. 20.

TABLE 8

| Pore ID | Mean Noise of thee Signal | Median Noise of the Signal | Standard Deviation of the Noise of the Signal | Mean Current Range (pA) | Median Current Range (pA) | Standard Deviation of the Current Range | Average Signal to Noise (S2N) | Median S2N | Standard Deviation of S2N | Percentage of complement slipping forwards |
|---|---|---|---|---|---|---|---|---|---|---|
| 1 | 1.35 | 1.35 | 0.14 | 15.48 | 15.78 | 2.23 | 11.44 | | | |
| 3 | 1.31 | 1.24 | 0.26 | 15.64 | 15.60 | 1.76 | 11.94 | | | |
| 4 | 1.40 | 1.22 | 0.45 | 14.74 | 14.64 | 1.88 | 10.56 | | | |
| 5 | 1.35 | 1.28 | 0.26 | 14.38 | 14.26 | 1.79 | 10.69 | 11.95 | 0.33 | 0.25 |
| 6 | 1.36 | 1.32 | 0.23 | 14.96 | 14.89 | 1.72 | 11.00 | 11.89 | 1.17 | 0.27 |
| 7 | 1.31 | 1.27 | 0.23 | 14.96 | 14.91 | 1.73 | 11.39 | 11.26 | 0.29 | 0.43 |
| 24 | 1.38 | 1.32 | 0.26 | 15.16 | 15.09 | 1.85 | 10.97 | | | |

In table 9 below, a number of MspA mutants 8-19 and 23 were compared to MspA mutant 2 (baseline). MspA mutants 8-19 and 23 all had the same residues deleted (L74/G75/D118/L119) and the following mutations (D90N/D91N/Q126R/D134R/E134K) as MspA mutant 2 but they differed from MspA mutant 2 in the fact that they had been mutated at a range of positions which effected how the enzyme and the nanopore interacted. Of the various parameters which were investigated and measured—mean noise of the signal, mean current range, average signal to noise and percentage of complement slipping forwards MspA mutants 8-19 and 23 exhibited an improvement in at least one of these parameters when compared to the baseline nanopore MspA mutant 2. Therefore, the mutations which were made to improve the interaction between the nanopore and the enzyme resulted either in reduced noise associated with the movement of the target polynucleotide through the pore or more consistent movement of the target through the pore.

In table 9 below, a number of MspA mutants 20-22 were compared to MspA mutant 2 (baseline). MspA mutants 20-22 all differed from MspA mutant 2 in the residues which had been deleted and the mutations which were made in order to effect how the enzyme and the nanopore interacted (the mutations which the nanopores had in common were L88N/D90N/D91N/Q126R/D134R/E139K). MspA mutants 20-22 exhibited an improvement in at least one of the measured parameters (mean noise of the signal, mean current range, average signal to noise and percentage of complement slipping forwards) when compared to MspA mutant 2. However, the measured improvements in noise and movement consistency were attributed to the combination of changes made to the nanopores (MspA mutants 20-22) e.g. deletions and the mutations which were made in order to effect how the enzyme and the nanopore interacted.

Pore ID's

Figure 11:
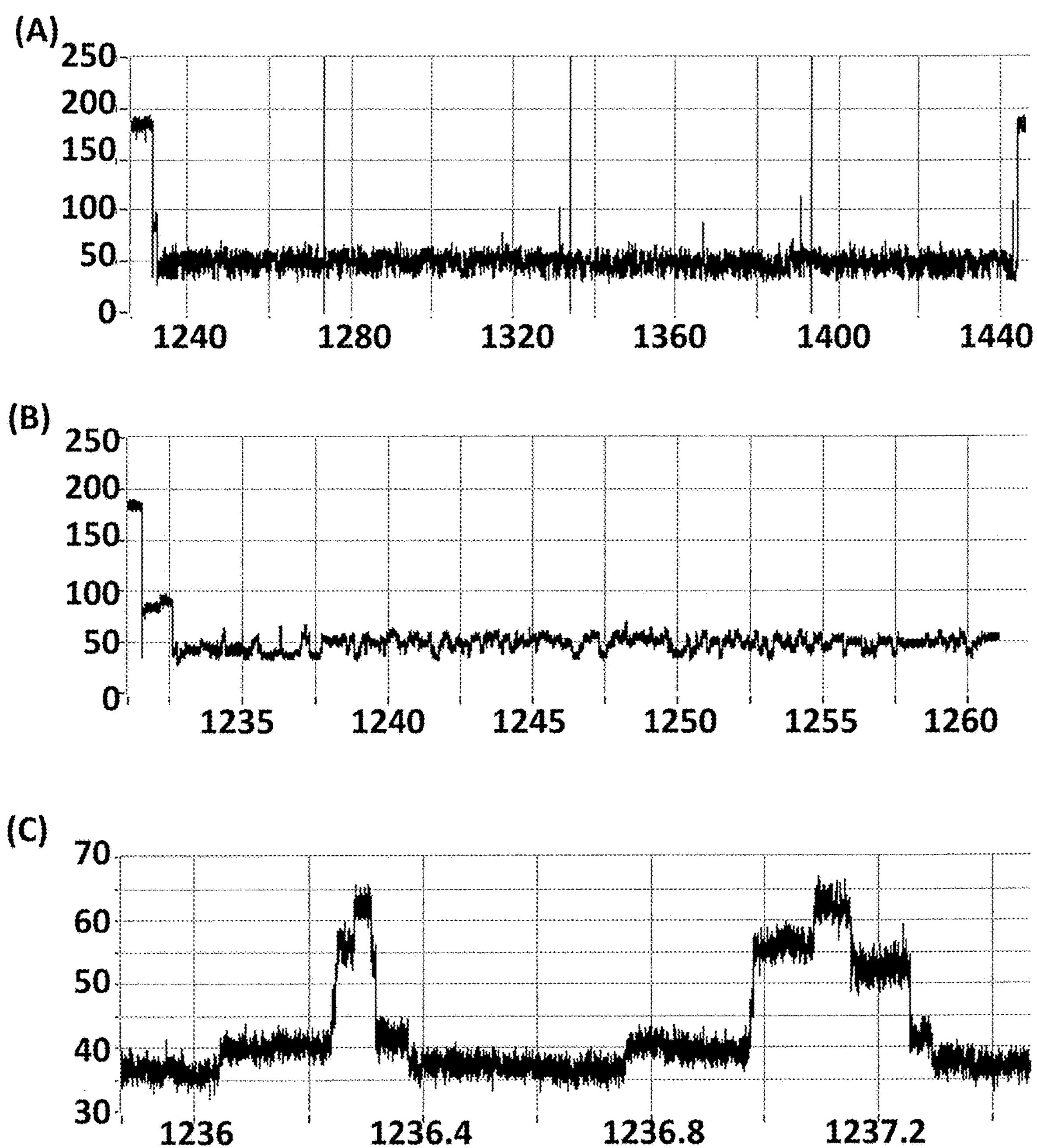
FIG. 11 shows example current traces (y-axis label=Current (pA), x-axis label=Time (s) for all three traces) of when a helicase (T4 Dda—E94C/C109A/C136A/A360C) controlled the translocation of the DNA construct X through the MspA nanopore MspA—((Del-L74/G75/D118/L119)D56N/E59R/L88N/D90N/D91N/Q126R/D134R/

MspA mutant 2=MspA—((Del-L74/G75/D118/L119) D56N/E59R/L88N/D90N/D91N/Q126R/D134R/E139K)8 (SEQ ID NO: 2 with mutations D56N/E59R/L88N/D90N/D91N/Q126R/D134R/E139K and deletion of the amino acids L74/G75/D118/L119). Example helicase controlled DNA movement shown in FIG. 11.

MspA mutant 8=MspA—((Del-L74/G75/D118/L119) D56N/L88N/D90N/D91N/Q126R/D134R/E139K)8 (SEQ ID NO: 2 with mutations D56N/L88N/D90N/D91N/Q126R/D134R/E139K and deletion of the amino acids L74/G75/D118/L119)

MspA mutant 9=MspA—((Del-L74/G75/D118/L119)E59N/L88N/D90N/D91N/Q126R/D134R/E139K)8 (SEQ ID NO: 2 with mutations E59N/L88N/D90N/D91N/Q126R/D134R/E139K and deletion of the amino acids L74/G75/D118/L119)

MspA mutant 10=MspA—((Del-L74/G75/D118/L119) D56N/E57N/E59N/L88N/D90N/D91N/Q126R/D134R/E139K)8 (SEQ ID NO: 2 with mutations D56N/E57N/E59N/L88N/D90N/D91N/Q126R/D134R/E139K and deletion of the amino acids L74/G75/D118/L119)

MspA mutant 11=MspA—((Del-L74/G75/D118/L119) E59R/L88N/D90N/D91N/Q126R/D134R/E139K)8 (SEQ ID NO: 2 with mutations E59R/L88N/D90N/D91N/Q126R/D134R/E139K and deletion of the amino acids L74/G75/D118/L119)

MspA mutant 12=MspA—((Del-L74/G75/D118/L119) D56Y/E59R/L88N/D90N/D91N/Q126R/D134R/E139K)8 (SEQ ID NO: 2 with mutations)D56Y/E59R/L88N/D90N/D91N/Q126R/D134R/E139K and deletion of the amino acids L74/G75/D118/L119). Example helicase controlled DNA movement shown in FIG. 12.

MspA mutant 13=MspA—((Del-L74/G75/D118/L119) D56N/E57D/E59R/L88N/D90N/D91N/Q126R/D134R/E139K)8 (SEQ ID NO: 2 with mutations D56N/E57D/E59R/L88N/D90N/D91N/Q126R/D134R/E139K and deletion of the amino acids L74/G75/D118/L119). Example helicase controlled DNA movement shown in FIG. 13.

MspA mutant 14=MspA—((Del-L74/G75/D118/L119) D56N/E59T/L88N/D90N/D91N/Q126R/D134R/E139K)8 (SEQ ID NO: 2 with mutations D56N/E59T/L88N/D90N/D91N/Q126R/D134R/E139K and deletion of the amino acids L74/G75/D118/L119). Example helicase controlled DNA movement shown in FIG. 14.

MspA mutant 15=MspA—((Del-L74/G75/D118/L119) D56N/E59Q/L88N/D90N/D91N/Q126R/D134R/E139K)8 (SEQ ID NO: 2 with mutations D56N/E59Q/L88N/D90N/D91N/Q126R/D134R/E139K and deletion of the amino acids L74/G75/D118/L119). Example helicase controlled DNA movement shown in FIG. 15.

MspA mutant 16=MspA—((Del-L74/G75/D118/L119) E59F/L88N/D90N/D91N/Q126R/D134R/E139K)8 (SEQ ID NO: 2 with mutations E59F/L88N/D90N/D91N/Q126R/D134R/E139K and deletion of the amino acids L74/G75/D118/L119). Example helicase controlled DNA movement shown in FIG. 16.

MspA mutant 17=MspA—((Del-L74/G75/D118/L119) D56N/E59R/L88N/D90N/D91N/Q126R/D134N/E139K)8 (SEQ ID NO: 2 with mutations D56N/E59R/L88N/D90N/D91N/Q126R/D134N/E139K and deletion of the amino acids L74/G75/D118/L119). Example helicase controlled DNA movement shown in FIG. 19.

MspA mutant 18=MspA—((Del-L74/G75/D118/L119) D56N/E59F/L88N/D90N/D91N/Q126R/D134R/E139K)8 (SEQ ID NO: 2 with mutations D56N/E59F/L88N/D90N/D91N/Q126R/D134R/E139K and deletion of the amino acids L74/G75/D118/L119). Example helicase controlled DNA movement shown in FIG. 17.

MspA mutant 19=MspA—((Del-L74/G75/D118/L119) D56F/E59R/L88N/D90N/D91N/Q126R/D134R/E139K)8 (SEQ ID NO: 2 with mutations D56F/E59R/L88N/D90N/D91N/Q126R/D134R/E139K and deletion of the amino acids L74/G75/D118/L119). Example helicase controlled DNA movement shown in FIG. 18.

MspA mutant 20=MspA—((Del-F80/S81/G112/V113) D56N/E59R/G75 S/G77S/L88N/D90N/D91N/D118R/Q126R/D134R/E139K)8 (SEQ ID NO: 2 with mutations D56N/E59R/G75S/G77S/L88N/D90N/D91N/D118R/Q126R/D134R/E139K and deletion of the amino acids F80/S81/G112/V113)

MspA mutant 21=MspA—((Del-G75/V76/A117/D118) D56N/E59R/G77S/L88N/D90N/D91N/Q126R/D134R/E139K)8 (SEQ ID NO: 2 with mutations D56N/E59R/G77S/L88N/D90N/D91N/Q126R/D134R/E139K and deletion of the amino acids G75/V76/A117/D118)

MspA mutant 22=MspA—((Del-N79/F80/V113N114) D56N/E59R/G75 S/G77S/L88N/D90N/D91N/D118R/Q126R/D134R/E139K)8 (SEQ ID NO: 2 with mutations D56N/E59R/G75S/G77S/L88N/D90N/D91N/D118R/Q126R/D134R/E139K and deletion of the amino acids N79/F80/V113/V114)

MspA mutant 23=MspA—((Del-L74/G75/D118/L119) D56N/E59Y/L88N/D90N/D91N/Q126R/D134R/E139K)8 (SEQ ID NO: 2 with mutations D56N/E59Y/L88N/D90N/D91N/Q126R/D134R/E139K and deletion of the amino acids L74/G75/D118/L119).

TABLE 9

| Pore ID | Mean Noise of the Signal | Median Noise of the Signal | Standard Deviation of the Noise of the Signal | Mean Current Range (pA) | Median Current Range (pA) | Standard Deviation of the Current Range (pA) | Average Signal to Noise (S2N) | Median S2N | Standard Deviation of S2N | Percentage of complement slipping forwards |
|---|---|---|---|---|---|---|---|---|---|---|
| 2 | 1.22 | 1.17 | 0.20 | 15.31 | 15.32 | 1.66 | 12.50 | | | 0.49 |
| 8 | 1.20 | 1.17 | 0.15 | 14.74 | 14.62 | 1.66 | 12.28 | | | |
| 9 | 1.11 | 1.08 | 0.19 | 14.74 | 14.71 | 2.36 | 13.28 | | | |
| 10 | 1.46 | 1.35 | 0.36 | 19.02 | 19.16 | 2.07 | 13.03 | | | |
| 11 | 1.26 | 1.22 | 0.24 | 16.08 | 16.16 | 1.84 | 12.76 | | | |
| 12 | 1.24 | 1.19 | 0.22 | 15.93 | 15.92 | 1.83 | 12.88 | 13.34 | 1.12 | 0.60 |
| 13 | 1.19 | 1.16 | 0.19 | 15.45 | 15.36 | 1.77 | 12.95 | 11.95 | 0.33 | 0.70 |
| 14 | 1.31 | 1.26 | 0.24 | 16.04 | 16.09 | 1.87 | 12.29 | 12.61 | 0.87 | 0.80 |
| 15 | 1.22 | 1.16 | 0.25 | 15.55 | 15.53 | 1.72 | 12.76 | 13.33 | 0.86 | 0.55 |
| 16 | 1.37 | 1.33 | 0.22 | 15.68 | 15.68 | 1.81 | 11.44 | 11.79 | 0.64 | 0.30 |
| 17 | 1.31 | 1.27 | 0.21 | 16.04 | 16.05 | 1.93 | 12.25 | 12.03 | 0.57 | 0.65 |
| 18 | 1.24 | 1.17 | 0.27 | 15.77 | 15.66 | 1.86 | 12.76 | 12.76 | 0.12 | 0.25 |
| 19 | 1.33 | 1.28 | 0.24 | 15.61 | 15.60 | 1.92 | 11.74 | 12.29 | 0.59 | 0.38 |
| 20 | 1.32 | 1.22 | 0.32 | 17.11 | 17.15 | 2.11 | 12.96 | | | |
| 21 | 1.27 | 1.21 | 0.24 | 15.81 | 15.84 | 1.69 | 12.48 | | | |
| 22 | 1.21 | 1.13 | 0.28 | 15.82 | 15.82 | 1.90 | 13.13 | | | |
| 23 | 1.48 | 1.43 | 0.24 | 15.90 | 15.93 | 1.92 | 10.72 | 10.37 | 0.66 | 0.30 |

Example 3

This example describes the simulations which were run to investigate the interaction between α-hemolysin—(E111N/K147N)8 (SEQ ID NO: 4) with Phi29 DNA polymerase-(D12A/D66A) (SEQ ID NO: 9 with mutations D12A/D66A).

Simulations were performed using the GROMACS package version 4.0.5, with the GROMOS 53a6 forcefield and the SPC water model.

The αHL—(E111N/K147N)8 model was based on the crystal structure of αHL wild-type found in the protein data bank, accession code 7AHL. The relevant mutations were made using PyMOL and the resultant pore model was then energy minimised using the steepest descents algorithm. The Phi29 DNA polymerase-(D12A/D66A) (SEQ ID NO: 9 with mutations D12A/D66A) model was based on the crystal structure of Phi29 DNA polymerase-(D12A/D66A) found in the protein data bank, accession code 2PYL.

The Phi29 DNA polymerase-(D12A/D66A) model was then placed above αHL—(E111N/K147N)8. Three simulations were performed for the Phi29 DNA polymerase-(D12A/D66A)/αHL—(E111N/K147N)8 system, with the orientation of Phi29 DNA polymerase-(D12A/D66A) differing in each simulation (See FIG. 21 for cartoon representations of the three different simulation orientations). The pore was placed into a lipid membrane comprising DPPC molecules and the simulation box was solvated. Throughout the simulation, restraints were applied to the backbone of the pore. However, the enzyme was unrestrained. The system was simulated in the NPT ensemble for 40 ns, using the Berendsen thermostat and Berendsen barostat to 300 K.

The contacts between the enzyme and pore were analysed using both GROMACS analysis software and also locally written code. FIGS. 22 and 23 show the amino acid residues which interacted in αHL—(E111N/K147N)8 with Phi29 DNA polymerase-(D12A/D66A). The tables below show the number of contacts observed for both pore and enzyme amino acids (Table 10 shows the αHL—(E111N/K147N)8 amino acid contact points observed when the interactions were measured between αHL—(E111N/K147N)8 and Phi29 DNA polymerase-(D12A/D66A), Table 11 shows the Phi29 DNA polymerase-(D12A/D66A) amino acid contact points observed when the interactions were measured between αHL—(E111N/K147N)8 and Phi29 DNA polymerase-(D12A/D66A). Table 10 shows all the amino acids residues in αHL—E111N/K147N)8 that made more than 100 contacts with Phi29 DNA polymerase-(D12A/D66A) and Table 11 shows all the amino acid residues in Phi29 DNA polymerase-(D12A/D66A) that made more than 100 contacts with αHL—(E111N/K147N)8. FIGS. 24-28 show which amino acids in the pore (αHL—(E111N/K147N)8) interacted with particular amino acids in the enzyme (Phi29 DNA polymerase-(D12A/D66A) in runs 1-3.

TABLE 10

| Run 1 | | Run 2 | | Run 3 | |
|---|---|---|---|---|---|
| Pore Amino Acid Residue | Number of Contacts | Pore Amino Acid Residue | Number of Contacts | Pore Amino Acid Residue | Number of Contacts |
| S239 | 3802 | T19 | 5932 | S239 | 6420 |
| N93 | 2785 | N17 | 5125 | E287 | 4255 |
| K240 | 1217 | K240 | 2679 | K237 | 2618 |
| Q242 | 1159 | K46 | 2481 | R236 | 2568 |
| K237 | 958 | E287 | 2243 | A238 | 1796 |
| K288 | 706 | Q241 | 1802 | K240 | 1791 |
| E287 | 337 | N47 | 1496 | Q242 | 1032 |
| D285 | 107 | T18 | 535 | N293 | 967 |
| | | S239 | 442 | K288 | 775 |
| | | K21 | 398 | Q241 | 609 |
| | | K288 | 361 | R281 | 256 |
| | | S16 | 163 | K283 | 118 |
| | | K237 | 136 | N17 | 112 |

TABLE 11

| Run 1 | | Run 2 | | Run 3 | |
|---|---|---|---|---|---|
| Enzyme Amino Acid Residue | Number of Contacts | Enzyme Amino Acid Residue | Number of Contacts | Enzyme Acid Residue | Number of Contacts |
| E322 | 4107 | E272 | 6820 | R308 | 9172 |
| F309 | 1675 | E267 | 3135 | E272 | 5732 |
| G321 | 1642 | S215 | 2941 | S307 | 2304 |
| R289 | 798 | E221 | 1778 | F309 | 1409 |

TABLE 11-continued

| Run 1 | | Run 2 | | | |
|---|---|---|---|---|---|
| Enzyme | | Enzyme | | Run 3 | |
| Amino Acid Residue | Number of Contacts | Amino Acid Residue | Number of Contacts | Enzyme Acid Residue | Number of Contacts |
| G320 | 764 | D84 | 1738 | R289 | 1064 |
| E241 | 697 | L216 | 1346 | E221 | 699 |
| R236 | 528 | K209 | 1126 | E296 | 643 |
| K240 | 420 | K80 | 1048 | Y224 | 511 |
| G323 | 359 | E419 | 788 | E322 | 363 |
| R308 | 180 | K205 | 633 | E293 | 308 |
| | | E418 | 463 | H287 | 275 |
| | | V270 | 383 | W327 | 166 |
| | | G85 | 213 | K220 | 148 |
| | | R415 | 177 | S349 | 129 |
| | | W81 | 167 | E418 | 113 |
| | | D278 | 147 | Y310 | 108 |
| | | S82 | 122 | | |
| | | K206 | 107 | | |

Example 4

This example describes how a number of different helicases were used to control the movement of DNA construct X (see FIG. 7) through a number of different MspA nanopores. All of the nanopores tested exhibited changes in current as the DNA translocated through the nanopore. This example investigates the number of slips forward per kilobase and the % bases missed in construct X for a number of pore/enzyme combinations. The helicases investigated in the example moved along the polynucleotide in a 5' to 3' direction. When the 5'end of the polynucleotide (the end away from which the helicase moves) was captured by the pore, the helicase worked with the direction of the field resulting from the applied potential and moved the threaded polynucleotide into the pore and into the trans chamber. In this Example, slipping forward involved the DNA moving forwards relative to the the pore (i.e. towards its 3' and away from it 5' end) at least 4 consecutive nucleotides.

Materials and Methods

Prior to setting up the experiment, DNA construct X (final concentration 0.1 nM) was pre-incubated at room temperature for five minutes with the appropriate enzyme (either T4 Dda—E94C/C109A/C136A/A360C or T4 Dda—E94C/C109A/C136A/K199L/A360C (final concentration added to the nanopore system 10 nM, which was provided in buffer (253 mM KCl, 50 mM potassium phosphate, pH 8.0, 2 mM EDTA)). After five minutes, TMAD (100 μM final concentration added to the nanopore system) was added to the pre-mix and the mixture incubated for a further 5 minutes. Finally, MgCl2 (2 mM final concentration added to the nanopore system), ATP (2 mM final concentration added to the nanopore system) and KCl (500 mM final concentration added to the nanopore system) were added to the pre-mix.

Electrical measurements were acquired from single MspA nanopores inserted in block co-polymer in buffer (25 mM K Phosphate buffer, 150 mM Potassium Ferrocyanide (II), 150 mM Potassium Ferricyanide (III), pH 8.0) as described in Example 2. The appropriate MspA nanopore was selected from the list below (MspA mutants 2, 19, 25, 26 or 27).

Results

A number of different nanopores/enzyme combinations were investigated in order to determine the affect of mutations to regions of the transmembrane pore and enzyme which were thought to interact with each other. These mutation positions were identified in the molecular modeling experiment described in Example 1. Two different parameters were investigated in order to identify pore and enzyme combinations which exhibited improved helicase controlled DNA translocation 1) the number of slips forward per kilobase and 2) the % bases missed in construct X.

The measurement of slips forward per kilobase was calculated using the following procedure 1) the helicase controlled DNA movements were mapped to a model, 2) the helicase-controlled DNA movements were then subjected to filtering, 3) the mapped helicase controlled DNA movements were checked to ensure accurate mapping, 4) the transitions that were classified as a slipping forward movement of at least four consecutive nucleotides were determined per kilobase. The % bases missed in construct X is a measure of the number of bases in construct X which are missed as a result of slips forward along DNA construct X expressed as a percentage.

Table 12 below shows the different pore and enzyme combinations tested, the corresponding figure number which shows a number of example current traces when the helicase controlled the movement of construct X through the nanopore and the appropriate column reference for FIG. 36 which shows the data relating to 1) the number of slips forward per kilobase and 2) the % bases missed in construct X. All of the pore/enzyme combinations show less than 5 slips forward per kilobase and less than 12% bases missed in construct X. However, the combination of MspA mutant 26 with T4 Dda—E94C/C109A/C136A/K199L/A360C produced the lowest slips forward per kilobase and the lowest % bases missed in construct X. Therefore, this was a particularly preferred combination which was predicted from the modeling experiment in Example 1 to produce a pore and enzyme with a particularly favourable interaction and more consistent movement.

Pore ID's

MspA mutant 25=MspA—((Del-L74/G75/D118/L119)D56L/E59L/L88N/D90N/D91N/Q126R/D134R/E139K)8 (SEQ ID NO: 2 with mutations D56L/E59L/L88N/D90N/D91N/Q126R/D134R/E139K and deletion of the amino acids L74/G75/D118/L119)

MspA mutant 26=MspA—((Del-L74/G75/D118/L119)G1A/D56N/E59F/L88N/D90N/D91N/Q126R/D134R/E139K)8 (SEQ ID NO: 2 with mutations G1A/D56N/E59F/L88N/D90N/D91N/Q126R/D134R/E139K and deletion of the amino acids L74/G75/D118/L119).

MspA mutant 27=MspA—((Del-L74/G75/D118/L119)D56N/E59Y/L88N/D90N/D91N/Q126R/D134R/E139K)8 (SEQ ID NO: 2 with mutations D56N/E59Y/L88N/D90N/D91N/Q126R/D134R/E139K and deletion of the amino acids L74/G75/D118/L119).

TABLE 12

| Nanopore | Enzyme | FIG. Showing Example Current Trace | Column in FIG. 36 Corresponding to this Combination |
|---|---|---|---|
| MspA Mutant 2 | T4 Dda - E94C/C109A/C136A/A360C | 29 | 1 |

TABLE 12-continued

| Nanopore | Enzyme | FIG. Showing Example Current Trace | Column in FIG. 36 Corresponding to this Combination |
|---|---|---|---|
| MspA Mutant 19 | T4 Dda - E94C/C109A/C136A/A360C | 30 | 2 |
| MspA Mutant 19 | T4 Dda - E94C/C109A/C136A/K199L/A360C | 31 | 3 |
| MspA Mutant 25 | T4 Dda - E94C/C109A/C136A/A360C | 32 | 4 |
| MspA Mutant 26 | T4 Dda - E94C/C109A/C136A/A360C | 33 | 5 |
| MspA Mutant 26 | T4 Dda - E94C/C109A/C136A/K199L/A360C | 34 | 6 |
| MspA Mutant 27 | T4 Dda - E94C/C109A/C136A/A360C | 35 | 7 |

The invention claimed is:

1. A method of characterizing a target polynucleotide, comprising:

a) providing a transmembrane MspA pore and a polynucleotide binding protein in which a part of the transmembrane MspA pore which interacts with the polynucleotide binding protein and a part of the polynucleotide binding protein which interacts with the transmembrane MspA pore has been modified, wherein the modification of the transmembrane MspA pore comprises an amino acid substitution, insertion, or deletion relative to an unmodified transmembrane MspA pore, and wherein the modification of the polynucleotide binding protein comprises an amino acid substitution, insertion, or deletion relative to an unmodified polynucleotide binding protein;

b) contacting the transmembrane MspA pore and polynucleotide binding protein provided in (a) with the target polynucleotide such that the polynucleotide binding protein controls the movement of the target polynucleotide with respect to the transmembrane MspA pore; and c) taking one or more electrical or optical measurements as the target polynucleotide moves with respect to the transmembrane MspA pore.

2. The method according to claim 1, wherein the surface of the polynucleotide binding protein which interacts with the transmembrane MspA pore has been modified.

3. The method according to claim 1, wherein the polynucleotide binding protein is a helicase.

4. The method according to claim 1, wherein the polynucleotide binding protein is a Hel308 helicase, a RecD helicase, a TraI helicase, a TrwC helicase, a XPD helicase, or a Dda helicase.

5. The method according to claim 1, wherein the polynucleotide binding protein is a Dda helicase.

6. The method according to claim 1, wherein the modification(s) alter the charge, sterics, hydrogen bonding, π stacking or structure of the part of the transmembrane MspA pore which interacts with the polynucleotide binding protein and/or the part of the polynucleotide binding protein which interacts with the transmembrane MspA pore.

7. The method of claim 1, wherein the transmembrane MspA pore is comprised of seven or more modified MspA monomers.

8. The method according to claim 7, wherein the part of the MspA monomer which interacts with the polynucleotide binding protein comprises modified amino acids at positions:

(a) 12, 14, 48, 52, 53, 54, 55, 56, 57, 58, 59, 60, 134, 135, 136, 137, 138, 139, 169 and 170 in SEQ ID NO: 2;

(b) 12, 14, 52, 54, 56, 57, 59, 134, 136, 138, 139 and 169 in SEQ ID NO: 2;

(c) 12, 14, 56, 57, 59, 134, 136, 139 and 169 in SEQ ID NO: 2;

(d) 56, 57, 59, 134, 136, 139 and 169 in SEQ ID NO: 2; or (e) 56, 57, 59, 134 and 139 in SEQ ID NO: 2.

9. The method according to claim 8, wherein the one or more of the seven or more monomers are modified such that they do not comprise aspartic acid (D) or glutamic acid (E) at one or more of positions 56, 57, 59, 134 and 139 of SEQ ID NO: 2.

10. The method according to claim 9, wherein the one or more of the seven or more monomers are modified such that they comprise one or more of (a) D56N or D56R, (b) E57N or E57R, (c) E59N or E59R, (d) D134N or D134R and (e) E139N, E139R or E139K.

11. The method according to claim 8, wherein the MspA monomer further comprises amino acid substitutions selected from the group consisting of:

(a) D90N, D91N, D118R, D134R and E139K and optionally D93N;

(b) L88N, D90N, D91N, D93N, D118R, D134R, and E139K;

(c) G75S, G77S, L88N, D90N, D91N, D93N, D118R, Q126R, D134R, and E139K; or (d) G75S, G77S, L88N, D90N, D91N, D118R, 0126R, D134R, and E139K.

12. The method according to claim 8, wherein the MspA monomer further comprises amino acid deletions relative to SEQ ID NO: 2 selected from the group consisting of:

(a) 2, 4, 6, 8 or 10 of the amino acids at positions 72 to 82 of SEQ ID NO: 2 and (b) 2, 4, 6, 8 or 10 of the amino acids at positions 111 to 121 of SEQ ID NO: 2.

13. The method according to claim 1, wherein the transmembrane MspA pore is comprised of seven or more modified MspA monomers and the polynucleotide binding protein is a modified Dda helicase.

14. The method according to claim 13, wherein the part of the Dda helicase which interacts with the MspA pore comprises modified amino acids at positions:

(a) positions 1, 2, 3, 4, 5, 6, 51, 176, 177, 178, 179, 180, 181, 185, 189, 191, 193, 194, 195, 197, 198, 199, 200, 201, 202, 203, 204, 207, 208, 209, 210, 211, 212, 213, 216, 219, 220, 221, 223, 224, 226, 227, 228, 229, 247, 254, 255, 256, 257, 258, 259, 260, 261, 298, 300, 304, 308, 318, 319, 321, 337, 347, 350, 351, 405, 415, 422, 434, 437, and 438 in SEQ ID NO: 24;

(b) positions 1, 2, 4, 51, 177, 178, 179, 180, 185, 193, 195, 197, 198, 199, 200, 202, 203, 204, 207, 208, 209, 210, 211, 212, 216, 221, 223, 224, 226, 227, 228, 229, 254, 255, 256, 257, 258, 260, 304, 318, 321, 347, 350, 351, 405, 415, 422, 434, 437, and 438 in SEQ ID NO: 24; or (c) positions 1, 2, 178, 179, 180, 185, 195, 197, 198, 199, 200, 202, 203, 207, 209, 210, 212, 216, 221, 223, 226, 227, 255, 258, 260, 304, 350 and 438 in SEQ ID NO: 24.

15. The method according to claim 14, wherein the modified Dda helicase further comprises an amino acid substitutions relative to SEQ ID NO: 24 at:

(a) E94C and A360C or (b) E94C, A360C, C109A and C136A.

* * * * *

SEQUENCE LISTING

```
<160> NUMBER OF SEQ ID NOS: 36

<210> SEQ ID NO 1
<211> LENGTH: 558
<212> TYPE: DNA
<213> ORGANISM: Mycobacterium smegmatis

<400> SEQUENCE: 1

atgggcctgg ataacgaact tagcctggtg gacggccaag atcgcacgct gacggtgcaa     60

caatgggata ccttcctgaa tggtgtgttt ccgctggatc gtaaccgcct gacccgtgaa    120

tggtttcatt ccggtcgcgc aaaatatatc gtcgcaggcc cgggtgctga cgaattcgaa    180

ggcacgctgg aactgggtta tcagattggc tttccgtggt cactgggcgt tggtatcaac    240

ttctcgtaca ccacgccgaa tattctgatc gatgacggtg atattaccgc accgccgttt    300

ggcctgaaca gcgtgattac gccgaacctg tttccgggtg ttagcatctc tgccgatctg    360

ggcaacggtc cgggcattca agaagtggca acctttagtg tggacgtttc cggcgctgaa    420

ggcggtgtcg cggtgtctaa tgcccacggt accgttacgg gcgcggccgg cggtgtcctg    480

ctgcgtccgt tcgcgcgcct gattgcgagc accggcgact ctgttacgac ctatggcgaa    540

ccgtggaata tgaactaa                                                  558


<210> SEQ ID NO 2
<211> LENGTH: 184
<212> TYPE: PRT
<213> ORGANISM: Mycobacterium smegmatis

<400> SEQUENCE: 2

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95
```

```
Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Ala Glu Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180


<210> SEQ ID NO 3
<211> LENGTH: 885
<212> TYPE: DNA
<213> ORGANISM: Artificial Sequence
<220> FEATURE:
<223> OTHER INFORMATION: Polynucleotide sequence encoding one monomer of
      alpha-hemolysin-E111N/K147N (alpha-HL-NN)

<400> SEQUENCE: 3

atggcagatt ctgatattaa tattaaaacc ggtactacag atattggaag caatactaca     60

gtaaaaacag gtgatttagt cacttatgat aaagaaaatg gcatgcacaa aaaagtattt    120

tatagtttta tcgatgataa aaatcacaat aaaaaactgc tagttattag aacaaaaggt    180

accattgctg gtcaatatag agtttatagc gaagaaggtg ctaacaaaag tggtttagcc    240

tggccttcag cctttaaggt acagttgcaa ctacctgata atgaagtagc tcaaatatct    300

gattactatc caagaaattc gattgataca aaaaactata tgagtacttt aacttatgga    360

ttcaacggta atgttactgg tgatgataca ggaaaaattg gcggccttat tggtgcaaat    420

gtttcgattg gtcatacact gaactatgtt caacctgatt tcaaaacaat tttagagagc    480

ccaactgata aaaaagtagg ctggaaagtg atatttaaca atatggtgaa tcaaaattgg    540

ggaccatacg atcgagattc ttggaacccg gtatatggca atcaactttt catgaaaact    600

agaaatggtt ctatgaaagc agcagataac ttccttgatc ctaacaaagc aagttctcta    660

ttatcttcag ggttttcacc agacttcgct acagttatta ctatggatag aaaagcatcc    720

aaacaacaaa caaatataga tgtaatatac gaacgagttc gtgatgatta ccaattgcat    780

tggacttcaa caaattggaa aggtaccaat actaaagata aatggacaga tcgttcttca    840

gaaagatata aaatcgattg ggaaaaagaa gaaatgacaa attaa                    885


<210> SEQ ID NO 4
<211> LENGTH: 293
<212> TYPE: PRT
<213> ORGANISM: Artificial Sequence
<220> FEATURE:
<223> OTHER INFORMATION: Amino acid sequence of one monomer of  -HL-NN

<400> SEQUENCE: 4

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
```

```
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290


<210> SEQ ID NO 5
<211> LENGTH: 184
<212> TYPE: PRT
<213> ORGANISM: Mycobacterium smegmatis

<400> SEQUENCE: 5

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125
```

```
Ala Thr Phe Ser Val Asp Val Ser Gly Pro Ala Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180


<210> SEQ ID NO 6
<211> LENGTH: 184
<212> TYPE: PRT
<213> ORGANISM: Mycobacterium smegmatis

<400> SEQUENCE: 6

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
                85                  90                  95

Pro Pro Phe Gly Leu Glu Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180


<210> SEQ ID NO 7
<211> LENGTH: 183
<212> TYPE: PRT
<213> ORGANISM: Mycobacterium smegmatis

<400> SEQUENCE: 7

Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
            20                  25                  30

Asn Arg Leu Thr Arg Glu Trp Phe His Ser Gly Arg Ala Thr Tyr His
        35                  40                  45

Val Ala Gly Pro Gly Ala Asp Glu Phe Glu Gly Thr Leu Glu Leu Gly
    50                  55                  60

Tyr Gln Val Gly Phe Pro Trp Ser Leu Gly Val Gly Ile Asn Phe Ser
65                  70                  75                  80
```

```
Tyr Thr Thr Pro Asn Ile Leu Ile Asp Gly Gly Asp Ile Thr Gln Pro
                85                  90                  95

Pro Phe Gly Leu Asp Thr Ile Ile Thr Pro Asn Leu Phe Pro Gly Val
            100                 105                 110

Ser Ile Ser Ala Asp Leu Gly Asn Gly Pro Gly Ile Gln Glu Val Ala
        115                 120                 125

Thr Phe Ser Val Asp Val Lys Gly Ala Lys Gly Ala Val Ala Val Ser
    130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
            180
```

```
<210> SEQ ID NO 8
<211> LENGTH: 1830
<212> TYPE: DNA
<213> ORGANISM: Bacteriophage phi-29

<400> SEQUENCE: 8

atgaaacaca tgccgcgtaa aatgtatagc tgcgcgtttg aaaccacgac caaagtggaa      60

gattgtcgcg tttgggccta tggctacatg aacatcgaag atcattctga atacaaaatc     120

ggtaacagtc tggatgaatt tatggcatgg gtgctgaaag ttcaggcgga tctgtacttc     180

cacaacctga aatttgatgg cgcattcatt atcaactggc tggaacgtaa tggctttaaa     240

tggagcgcgg atggtctgcc gaacacgtat aataccatta tctctcgtat gggccagtgg     300

tatatgattg atatctgcct gggctacaaa ggtaaacgca aaattcatac cgtgatctat     360

gatagcctga aaaaactgcc gtttccggtg aagaaaattg cgaaagattt caaactgacg     420

gttctgaaag gcgatattga ttatcacaaa gaacgtccgg ttggttacaa aatcaccccg     480

gaagaatacg catacatcaa aaacgatatc cagatcatcg cagaagcgct gctgattcag     540

tttaaacagg gcctggatcg catgaccgcg ggcagtgata gcctgaaagg tttcaaagat     600

atcatcacga ccaaaaaatt caaaaaagtg ttcccgacgc tgagcctggg tctggataaa     660

gaagttcgtt atgcctaccg cggcggtttt acctggctga acgatcgttt caaagaaaaa     720

gaaattggcg agggtatggt gtttgatgtt aatagtctgt atccggcaca gatgtacagc     780

cgcctgctgc cgtatggcga accgatcgtg ttcgagggta aatatgtttg ggatgaagat     840

tacccgctgc atattcagca catccgttgt gaatttgaac tgaaagaagg ctatattccg     900

accattcaga tcaaacgtag tcgcttctat aagggtaacg aatacctgaa aagctctggc     960

ggtgaaatcg cggatctgtg gctgagtaac gtggatctgg aactgatgaa agaacactac    1020

gatctgtaca acgttgaata catcagcggc ctgaaattta aagccacgac cggtctgttc    1080

aaagatttca tcgataaatg gacctacatc aaaacgacct ctgaaggcgc gattaaacag    1140

ctggccaaac tgatgctgaa cagcctgtat ggcaaattcg cctctaatcc ggatgtgacc    1200

ggtaaagttc cgtacctgaa agaaaatggc gcactgggtt ttcgcctggg cgaagaagaa    1260

acgaaagatc cggtgtatac cccgatgggt gttttcatta cggcctgggc acgttacacg    1320

accatcaccg cggcccaggc atgctatgat cgcattatct actgtgatac cgattctatt    1380

catctgacgg gcaccgaaat cccggatgtg attaaagata tcgttgatcc gaaaaaactg    1440

ggttattggg cccacgaaag tacgtttaaa cgtgcaaaat acctgcgcca gaaaacctac    1500
```

```
atccaggata tctacatgaa agaagtggat ggcaaactgg ttgaaggttc tccggatgat   1560

tacaccgata tcaaattcag tgtgaaatgc gccggcatga cggataaaat caaaaaagaa   1620

gtgaccttcg aaaacttcaa agttggtttc agccgcaaaa tgaaaccgaa accggtgcag   1680

gttccgggcg gtgtggttct ggtggatgat acgtttacca ttaaatctgg cggtagtgcg   1740

tggagccatc cgcagttcga aaaaggcggt ggctctggtg gcggttctgg cggtagtgcc   1800

tggagccacc cgcagtttga aaaataataa                                    1830
```

<210> SEQ ID NO 9
<211> LENGTH: 608
<212> TYPE: PRT
<213> ORGANISM: Bacteriophage phi-29

<400> SEQUENCE: 9

```
Met Lys His Met Pro Arg Lys Met Tyr Ser Cys Ala Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320
```

```
Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Ser
                565                 570                 575

Gly Gly Ser Ala Trp Ser His Pro Gln Phe Glu Lys Gly Gly Gly Ser
            580                 585                 590

Gly Gly Gly Ser Gly Gly Ser Ala Trp Ser His Pro Gln Phe Glu Lys
        595                 600                 605
```

<210> SEQ ID NO 10
<211> LENGTH: 1390
<212> TYPE: DNA
<213> ORGANISM: Escherichia coli

<400> SEQUENCE: 10

```
atgatgaacg atggcaaaca gcagagcacc ttcctgtttc atgattatga aaccttcggt      60

acccatccgg ccctggatcg tccggcgcag tttgcggcca ttcgcaccga tagcgaattc     120

aatgtgattg gcgaaccgga agtgttttat tgcaaaccgg ccgatgatta tctgccgcag     180

ccgggtgcgg tgctgattac cggtattacc ccgcaggaag cgcgcgcgaa aggtgaaaac     240

gaagcggcgt ttgccgcgcg cattcatagc ctgtttaccg tgccgaaaac ctgcattctg     300

ggctataaca atgtgcgctt cgatgatgaa gttacccgta atatctttta tcgtaacttt     360

tatgatccgt atgcgtggag ctggcagcat gataacagcc gttgggatct gctggatgtg     420

atgcgcgcgt gctatgcgct gcgcccggaa ggcattaatt ggccggaaaa cgatgatggc     480
```

```
ctgccgagct ttcgtctgga acatctgacc aaagccaacg gcattgaaca tagcaatgcc    540

catgatgcga tggccgatgt ttatgcgacc attgcgatgg cgaaactggt taaaacccgt    600

cagccgcgcc tgtttgatta tctgtttacc caccgtaaca aacacaaact gatggcgctg    660

attgatgttc cgcagatgaa accgctggtg catgtgagcg gcatgtttgg cgcctggcgc    720

ggcaacacca gctgggtggc cccgctggcc tggcacccgg aaaatcgtaa cgccgtgatt    780

atggttgatc tggccggtga tattagcccg ctgctggaac tggatagcga taccctgcgt    840

gaacgcctgt ataccgccaa aaccgatctg ggcgataatg ccgccgtgcc ggtgaaactg    900

gttcacatta acaaatgccc ggtgctggcc caggcgaaca ccctgcgccc ggaagatgcg    960

gatcgtctgg gtattaatcg ccagcattgt ctggataatc tgaaaatcct gcgtgaaaac   1020

ccgcaggtgc gtgaaaaagt ggtggcgatc ttcgcggaag cggaaccgtt caccccgagc   1080

gataacgtgg atgcgcagct gtataacggc ttctttagcg atgccgatcg cgcggcgatg   1140

aaaatcgttc tggaaaccga accgcgcaat ctgccggcgc tggatattac ctttgttgat   1200

aaacgtattg aaaaactgct gtttaattat cgtgcgcgca attttccggg taccctggat   1260

tatgccgaac agcagcgttg gctggaacat cgtcgtcagg ttttcacccc ggaatttctg   1320

cagggttatg cggatgaact gcagatgctg gttcagcagt atgccgatga taaagaaaaa   1380

gtggcgctgc                                                          1390
```

<210> SEQ ID NO 11
<211> LENGTH: 485
<212> TYPE: PRT
<213> ORGANISM: Escherichia coli

<400> SEQUENCE: 11

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Cys Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Cys Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Cys
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205
```

```
Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
    290                 295                 300

Lys Cys Pro Val Leu Ala Gln Ala Asn Thr Leu Arg Pro Glu Asp Ala
305                 310                 315                 320

Asp Arg Leu Gly Ile Asn Arg Gln His Cys Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
        435                 440                 445

Met Leu Val Gln Gln Tyr Ala Asp Asp Lys Glu Lys Val Ala Leu Leu
    450                 455                 460

Lys Ala Leu Trp Gln Tyr Ala Glu Glu Ile Val Ser Gly Ser Gly His
465                 470                 475                 480

His His His His His
                485
```

<210> SEQ ID NO 12
<211> LENGTH: 804
<212> TYPE: DNA
<213> ORGANISM: Escherichia coli

<400> SEQUENCE: 12

```
atgaaatttg tctcttttaa tatcaacggc ctgcgcgcca gacctcacca gcttgaagcc     60

atcgtcgaaa agcaccaacc ggatgtgatt ggcctgcagg agacaaaagt tcatgacgat    120

atgtttccgc tcgaagaggt ggcgaagctc ggctacaacg tgttttatca cgggcagaaa    180

ggccattatg gcgtggcgct gctgaccaaa gagacgccga ttgccgtgcg tcgcggcttt    240

cccggtgacg acgaagaggc gcagcggcgg attattatgg cggaaatccc ctcactgctg    300

ggtaatgtca ccgtgatcaa cggttacttc ccgcagggtg aaagccgcga ccatccgata    360

aaattcccgg caaaagcgca gttttatcag aatctgcaaa actacctgga aaccgaactc    420

aaacgtgata atccggtact gattatgggc gatatgaata tcagccctac agatctggat    480

atcggcattg gcgaagaaaa ccgtaagcgc tggctgcgta ccggtaaatg ctctttcctg    540
```

```
ccggaagagc gcgaatggat ggacaggctg atgagctggg ggttggtcga taccttccgc    600

catgcgaatc cgcaaacagc agatcgtttc tcatggtttg attaccgctc aaaaggtttt    660

gacgataacc gtggtctgcg catcgacctg ctgctcgcca gccaaccgct ggcagaatgt    720

tgcgtagaaa ccggcatcga ctatgaaatc cgcagcatgg aaaaaccgtc cgatcacgcc    780

cccgtctggg cgaccttccg ccgc                                           804


<210> SEQ ID NO 13
<211> LENGTH: 268
<212> TYPE: PRT
<213> ORGANISM: Escherichia coli

<400> SEQUENCE: 13

Met Lys Phe Val Ser Phe Asn Ile Asn Gly Leu Arg Ala Arg Pro His
1               5                   10                  15

Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45

Lys Leu Gly Tyr Asn Val Phe Tyr His Gly Gln Lys Gly His Tyr Gly
    50                  55                  60

Val Ala Leu Leu Thr Lys Glu Thr Pro Ile Ala Val Arg Arg Gly Phe
65                  70                  75                  80

Pro Gly Asp Asp Glu Glu Ala Gln Arg Arg Ile Ile Met Ala Glu Ile
                85                  90                  95

Pro Ser Leu Leu Gly Asn Val Thr Val Ile Asn Gly Tyr Phe Pro Gln
            100                 105                 110

Gly Glu Ser Arg Asp His Pro Ile Lys Phe Pro Ala Lys Ala Gln Phe
        115                 120                 125

Tyr Gln Asn Leu Gln Asn Tyr Leu Glu Thr Glu Leu Lys Arg Asp Asn
    130                 135                 140

Pro Val Leu Ile Met Gly Asp Met Asn Ile Ser Pro Thr Asp Leu Asp
145                 150                 155                 160

Ile Gly Ile Gly Glu Glu Asn Arg Lys Arg Trp Leu Arg Thr Gly Lys
                165                 170                 175

Cys Ser Phe Leu Pro Glu Glu Arg Glu Trp Met Asp Arg Leu Met Ser
            180                 185                 190

Trp Gly Leu Val Asp Thr Phe Arg His Ala Asn Pro Gln Thr Ala Asp
        195                 200                 205

Arg Phe Ser Trp Phe Asp Tyr Arg Ser Lys Gly Phe Asp Asp Asn Arg
    210                 215                 220

Gly Leu Arg Ile Asp Leu Leu Leu Ala Ser Gln Pro Leu Ala Glu Cys
225                 230                 235                 240

Cys Val Glu Thr Gly Ile Asp Tyr Glu Ile Arg Ser Met Glu Lys Pro
                245                 250                 255

Ser Asp His Ala Pro Val Trp Ala Thr Phe Arg Arg
            260                 265


<210> SEQ ID NO 14
<211> LENGTH: 1275
<212> TYPE: DNA
<213> ORGANISM: Thermus thermophilus

<400> SEQUENCE: 14

atgtttcgtc gtaaagaaga tctggatccg ccgctggcac tgctgccgct gaaaggcctg     60
```

```
cgcgaagccg ccgcactgct ggaagaagcg ctgcgtcaag gtaaacgcat tcgtgttcac    120

ggcgactatg atgcggatgg cctgaccggc accgcgatcc tggttcgtgg tctggccgcc    180

ctgggtgcgg atgttcatcc gtttatcccg caccgcctgg aagaaggcta tggtgtcctg    240

atggaacgcg tcccggaaca tctggaagcc tcggacctgt ttctgaccgt tgactgcggc    300

attaccaacc atgcggaact gcgcgaactg ctggaaaatg gcgtggaagt cattgttacc    360

gatcatcata cgccgggcaa aacgccgccg ccgggtctgg tcgtgcatcc ggcgctgacg    420

ccggatctga aagaaaaacc gaccggcgca ggcgtggcgt ttctgctgct gtgggcactg    480

catgaacgcc tgggcctgcc gccgccgctg gaatacgcgg acctggcagc cgttggcacc    540

attgccgacg ttgccccgct gtggggttgg aatcgtgcac tggtgaaaga aggtctggca    600

cgcatcccgg cttcatcttg ggtgggcctg cgtctgctgg ctgaagccgt gggctatacc    660

ggcaaagcgg tcgaagtcgc tttccgcatc gcgccgcgca tcaatgcggc ttcccgcctg    720

ggcgaagcgg aaaaagccct gcgcctgctg ctgacggatg atgcggcaga agctcaggcg    780

ctggtcggcg aactgcaccg tctgaacgcc cgtcgtcaga ccctggaaga agcgatgctg    840

cgcaaactgc tgccgcaggc cgacccggaa gcgaaagcca tcgttctgct ggacccggaa    900

ggccatccgg gtgttatggg tattgtggcc tctcgcatcc tggaagcgac cctgcgcccg    960

gtctttctgg tggcccaggg caaaggcacc gtgcgttcgc tggctccgat ttccgccgtc   1020

gaagcactgc gcagcgcgga agatctgctg ctgcgttatg gtggtcataa agaagcggcg   1080

ggtttcgcaa tggatgaagc gctgtttccg gcgttcaaag cacgcgttga agcgtatgcc   1140

gcacgtttcc cggatccggt tcgtgaagtg gcactgctgg atctgctgcc ggaaccgggc   1200

ctgctgccgc aggtgttccg tgaactggca ctgctggaac cgtatggtga aggtaacccg   1260

gaaccgctgt tcctg                                                    1275
```

```
<210> SEQ ID NO 15
<211> LENGTH: 425
<212> TYPE: PRT
<213> ORGANISM: Thermus thermophilus

<400> SEQUENCE: 15

Met Phe Arg Arg Lys Glu Asp Leu Asp Pro Pro Leu Ala Leu Leu Pro
1               5                   10                  15

Leu Lys Gly Leu Arg Glu Ala Ala Ala Leu Leu Glu Glu Ala Leu Arg
            20                  25                  30

Gln Gly Lys Arg Ile Arg Val His Gly Asp Tyr Asp Ala Asp Gly Leu
        35                  40                  45

Thr Gly Thr Ala Ile Leu Val Arg Gly Leu Ala Ala Leu Gly Ala Asp
    50                  55                  60

Val His Pro Phe Ile Pro His Arg Leu Glu Glu Gly Tyr Gly Val Leu
65                  70                  75                  80

Met Glu Arg Val Pro Glu His Leu Glu Ala Ser Asp Leu Phe Leu Thr
                85                  90                  95

Val Asp Cys Gly Ile Thr Asn His Ala Glu Leu Arg Glu Leu Leu Glu
            100                 105                 110

Asn Gly Val Glu Val Ile Val Thr Asp His His Thr Pro Gly Lys Thr
        115                 120                 125

Pro Pro Pro Gly Leu Val Val His Pro Ala Leu Thr Pro Asp Leu Lys
    130                 135                 140

Glu Lys Pro Thr Gly Ala Gly Val Ala Phe Leu Leu Leu Trp Ala Leu
```

```
145                 150                 155                 160

His Glu Arg Leu Gly Leu Pro Pro Pro Leu Glu Tyr Ala Asp Leu Ala
                165                 170                 175

Ala Val Gly Thr Ile Ala Asp Val Ala Pro Leu Trp Gly Trp Asn Arg
            180                 185                 190

Ala Leu Val Lys Glu Gly Leu Ala Arg Ile Pro Ala Ser Ser Trp Val
        195                 200                 205

Gly Leu Arg Leu Leu Ala Glu Ala Val Gly Tyr Thr Gly Lys Ala Val
    210                 215                 220

Glu Val Ala Phe Arg Ile Ala Pro Arg Ile Asn Ala Ala Ser Arg Leu
225                 230                 235                 240

Gly Glu Ala Glu Lys Ala Leu Arg Leu Leu Leu Thr Asp Asp Ala Ala
                245                 250                 255

Glu Ala Gln Ala Leu Val Gly Glu Leu His Arg Leu Asn Ala Arg Arg
            260                 265                 270

Gln Thr Leu Glu Glu Ala Met Leu Arg Lys Leu Leu Pro Gln Ala Asp
        275                 280                 285

Pro Glu Ala Lys Ala Ile Val Leu Leu Asp Pro Glu Gly His Pro Gly
    290                 295                 300

Val Met Gly Ile Val Ala Ser Arg Ile Leu Glu Ala Thr Leu Arg Pro
305                 310                 315                 320

Val Phe Leu Val Ala Gln Gly Lys Gly Thr Val Arg Ser Leu Ala Pro
                325                 330                 335

Ile Ser Ala Val Glu Ala Leu Arg Ser Ala Glu Asp Leu Leu Leu Arg
            340                 345                 350

Tyr Gly Gly His Lys Glu Ala Ala Gly Phe Ala Met Asp Glu Ala Leu
        355                 360                 365

Phe Pro Ala Phe Lys Ala Arg Val Glu Ala Tyr Ala Ala Arg Phe Pro
    370                 375                 380

Asp Pro Val Arg Glu Val Ala Leu Leu Asp Leu Leu Pro Glu Pro Gly
385                 390                 395                 400

Leu Leu Pro Gln Val Phe Arg Glu Leu Ala Leu Leu Glu Pro Tyr Gly
                405                 410                 415

Glu Gly Asn Pro Glu Pro Leu Phe Leu
            420                 425
```

<210> SEQ ID NO 16
<211> LENGTH: 738
<212> TYPE: DNA
<213> ORGANISM: Bacteriophage lambda

<400> SEQUENCE: 16

```
tccggaagcg gctctggtag tggttctggc atgacaccgg acattatcct gcagcgtacc      60

gggatcgatg tgagagctgt cgaacagggg gatgatgcgt ggcacaaatt acggctcggc     120

gtcatcaccg cttcagaagt tcacaacgtg atagcaaaac cccgctccgg aaagaagtgg     180

cctgacatga aaatgtccta cttccacacc ctgcttgctg aggtttgcac cggtgtggct     240

ccggaagtta acgctaaagc actggcctgg ggaaaacagt acgagaacga cgccagaacc     300

ctgtttgaat tcacttccgg cgtgaatgtt actgaatccc cgatcatcta tcgcgacgaa     360

agtatgcgta ccgcctgctc tcccgatggt ttatgcagtg acggcaacgg ccttgaactg     420

aaatgcccgt ttacctcccg ggatttcatg aagttccggc tcggtggttt cgaggccata     480

aagtcagctt acatggccca ggtgcagtac agcatgtggg tgacgcgaaa aaatgcctgg     540
```

```
tactttgcca actatgaccc gcgtatgaag cgtgaaggcc tgcattatgt cgtgattgag    600

cgggatgaaa agtacatggc gagttttgac gagatcgtgc cggagttcat cgaaaaaatg    660

gacgaggcac tggctgaaat tggttttgta tttggggagc aatggcgatc tggctctggt    720

tccggcagcg gttccgga                                                  738


<210> SEQ ID NO 17
<211> LENGTH: 226
<212> TYPE: PRT
<213> ORGANISM: Bacteriophage lambda

<400> SEQUENCE: 17

Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
            20                  25                  30

Thr Ala Ser Glu Val His Asn Val Ile Ala Lys Pro Arg Ser Gly Lys
        35                  40                  45

Lys Trp Pro Asp Met Lys Met Ser Tyr Phe His Thr Leu Leu Ala Glu
    50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
        115                 120                 125

Glu Leu Lys Cys Pro Phe Thr Ser Arg Asp Phe Met Lys Phe Arg Leu
    130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
    210                 215                 220

Trp Arg
225


<210> SEQ ID NO 18
<211> LENGTH: 760
<212> TYPE: PRT
<213> ORGANISM: Methanococcoides burtonii

<400> SEQUENCE: 18

Met Met Ile Arg Glu Leu Asp Ile Pro Arg Asp Ile Ile Gly Phe Tyr
1               5                   10                  15

Glu Asp Ser Gly Ile Lys Glu Leu Tyr Pro Pro Gln Ala Glu Ala Ile
            20                  25                  30

Glu Met Gly Leu Leu Glu Lys Lys Asn Leu Leu Ala Ala Ile Pro Thr
        35                  40                  45

Ala Ser Gly Lys Thr Leu Leu Ala Glu Leu Ala Met Ile Lys Ala Ile
```

```
    50                  55                  60

Arg Glu Gly Gly Lys Ala Leu Tyr Ile Val Pro Leu Arg Ala Leu Ala
65                  70                  75                  80

Ser Glu Lys Phe Glu Arg Phe Lys Glu Leu Ala Pro Phe Gly Ile Lys
                85                  90                  95

Val Gly Ile Ser Thr Gly Asp Leu Asp Ser Arg Ala Asp Trp Leu Gly
            100                 105                 110

Val Asn Asp Ile Ile Val Ala Thr Ser Glu Lys Thr Asp Ser Leu Leu
        115                 120                 125

Arg Asn Gly Thr Ser Trp Met Asp Glu Ile Thr Thr Val Val Val Asp
    130                 135                 140

Glu Ile His Leu Leu Asp Ser Lys Asn Arg Gly Pro Thr Leu Glu Val
145                 150                 155                 160

Thr Ile Thr Lys Leu Met Arg Leu Asn Pro Asp Val Gln Val Val Ala
                165                 170                 175

Leu Ser Ala Thr Val Gly Asn Ala Arg Glu Met Ala Asp Trp Leu Gly
            180                 185                 190

Ala Ala Leu Val Leu Ser Glu Trp Arg Pro Thr Asp Leu His Glu Gly
        195                 200                 205

Val Leu Phe Gly Asp Ala Ile Asn Phe Pro Gly Ser Gln Lys Lys Ile
    210                 215                 220

Asp Arg Leu Glu Lys Asp Asp Ala Val Asn Leu Val Leu Asp Thr Ile
225                 230                 235                 240

Lys Ala Glu Gly Gln Cys Leu Val Phe Glu Ser Ser Arg Arg Asn Cys
                245                 250                 255

Ala Gly Phe Ala Lys Thr Ala Ser Ser Lys Val Ala Lys Ile Leu Asp
            260                 265                 270

Asn Asp Ile Met Ile Lys Leu Ala Gly Ile Ala Glu Glu Val Glu Ser
        275                 280                 285

Thr Gly Glu Thr Asp Thr Ala Ile Val Leu Ala Asn Cys Ile Arg Lys
    290                 295                 300

Gly Val Ala Phe His His Ala Gly Leu Asn Ser Asn His Arg Lys Leu
305                 310                 315                 320

Val Glu Asn Gly Phe Arg Gln Asn Leu Ile Lys Val Ile Ser Ser Thr
                325                 330                 335

Pro Thr Leu Ala Ala Gly Leu Asn Leu Pro Ala Arg Arg Val Ile Ile
            340                 345                 350

Arg Ser Tyr Arg Arg Phe Asp Ser Asn Phe Gly Met Gln Pro Ile Pro
        355                 360                 365

Val Leu Glu Tyr Lys Gln Met Ala Gly Arg Ala Gly Arg Pro His Leu
    370                 375                 380

Asp Pro Tyr Gly Glu Ser Val Leu Leu Ala Lys Thr Tyr Asp Glu Phe
385                 390                 395                 400

Ala Gln Leu Met Glu Asn Tyr Val Glu Ala Asp Ala Glu Asp Ile Trp
                405                 410                 415

Ser Lys Leu Gly Thr Glu Asn Ala Leu Arg Thr His Val Leu Ser Thr
            420                 425                 430

Ile Val Asn Gly Phe Ala Ser Thr Arg Gln Glu Leu Phe Asp Phe Phe
        435                 440                 445

Gly Ala Thr Phe Phe Ala Tyr Gln Gln Asp Lys Trp Met Leu Glu Glu
    450                 455                 460

Val Ile Asn Asp Cys Leu Glu Phe Leu Ile Asp Lys Ala Met Val Ser
465                 470                 475                 480
```

```
Glu Thr Glu Asp Ile Glu Asp Ala Ser Lys Leu Phe Leu Arg Gly Thr
                485                 490                 495

Arg Leu Gly Ser Leu Val Ser Met Leu Tyr Ile Asp Pro Leu Ser Gly
            500                 505                 510

Ser Lys Ile Val Asp Gly Phe Lys Asp Ile Gly Lys Ser Thr Gly Gly
        515                 520                 525

Asn Met Gly Ser Leu Glu Asp Asp Lys Gly Asp Asp Ile Thr Val Thr
    530                 535                 540

Asp Met Thr Leu Leu His Leu Val Cys Ser Thr Pro Asp Met Arg Gln
545                 550                 555                 560

Leu Tyr Leu Arg Asn Thr Asp Tyr Thr Ile Val Asn Glu Tyr Ile Val
                565                 570                 575

Ala His Ser Asp Glu Phe His Glu Ile Pro Asp Lys Leu Lys Glu Thr
            580                 585                 590

Asp Tyr Glu Trp Phe Met Gly Glu Val Lys Thr Ala Met Leu Leu Glu
        595                 600                 605

Glu Trp Val Thr Glu Val Ser Ala Glu Asp Ile Thr Arg His Phe Asn
    610                 615                 620

Val Gly Glu Gly Asp Ile His Ala Leu Ala Asp Thr Ser Glu Trp Leu
625                 630                 635                 640

Met His Ala Ala Ala Lys Leu Ala Glu Leu Leu Gly Val Glu Tyr Ser
                645                 650                 655

Ser His Ala Tyr Ser Leu Glu Lys Arg Ile Arg Tyr Gly Ser Gly Leu
            660                 665                 670

Asp Leu Met Glu Leu Val Gly Ile Arg Gly Val Gly Arg Val Arg Ala
        675                 680                 685

Arg Lys Leu Tyr Asn Ala Gly Phe Val Ser Val Ala Lys Leu Lys Gly
    690                 695                 700

Ala Asp Ile Ser Val Leu Ser Lys Leu Val Gly Pro Lys Val Ala Tyr
705                 710                 715                 720

Asn Ile Leu Ser Gly Ile Gly Val Arg Val Asn Asp Lys His Phe Asn
                725                 730                 735

Ser Ala Pro Ile Ser Ser Asn Thr Leu Asp Thr Leu Leu Asp Lys Asn
            740                 745                 750

Gln Lys Thr Phe Asn Asp Phe Gln
        755                 760


<210> SEQ ID NO 19
<211> LENGTH: 707
<212> TYPE: PRT
<213> ORGANISM: Cenarchaeum symbiosum

<400> SEQUENCE: 19

Met Arg Ile Ser Glu Leu Asp Ile Pro Arg Pro Ala Ile Glu Phe Leu
1               5                   10                  15

Glu Gly Glu Gly Tyr Lys Lys Leu Tyr Pro Pro Gln Ala Ala Ala Ala
            20                  25                  30

Lys Ala Gly Leu Thr Asp Gly Lys Ser Val Leu Val Ser Ala Pro Thr
        35                  40                  45

Ala Ser Gly Lys Thr Leu Ile Ala Ala Ile Ala Met Ile Ser His Leu
    50                  55                  60

Ser Arg Asn Arg Gly Lys Ala Val Tyr Leu Ser Pro Leu Arg Ala Leu
65                  70                  75                  80

Ala Ala Glu Lys Phe Ala Glu Phe Gly Lys Ile Gly Gly Ile Pro Leu
```

```
                85                  90                  95

Gly Arg Pro Val Arg Val Gly Val Ser Thr Gly Asp Phe Glu Lys Ala
            100                 105                 110

Gly Arg Ser Leu Gly Asn Asn Asp Ile Leu Val Leu Thr Asn Glu Arg
        115                 120                 125

Met Asp Ser Leu Ile Arg Arg Arg Pro Asp Trp Met Asp Glu Val Gly
    130                 135                 140

Leu Val Ile Ala Asp Glu Ile His Leu Ile Gly Asp Arg Ser Arg Gly
145                 150                 155                 160

Pro Thr Leu Glu Met Val Leu Thr Lys Leu Arg Gly Leu Arg Ser Ser
                165                 170                 175

Pro Gln Val Val Ala Leu Ser Ala Thr Ile Ser Asn Ala Asp Glu Ile
            180                 185                 190

Ala Gly Trp Leu Asp Cys Thr Leu Val His Ser Thr Trp Arg Pro Val
        195                 200                 205

Pro Leu Ser Glu Gly Val Tyr Gln Asp Gly Glu Val Ala Met Gly Asp
    210                 215                 220

Gly Ser Arg His Glu Val Ala Ala Thr Gly Gly Gly Pro Ala Val Asp
225                 230                 235                 240

Leu Ala Ala Glu Ser Val Ala Glu Gly Gly Gln Ser Leu Ile Phe Ala
                245                 250                 255

Asp Thr Arg Ala Arg Ser Ala Ser Leu Ala Ala Lys Ala Ser Ala Val
            260                 265                 270

Ile Pro Glu Ala Lys Gly Ala Asp Ala Ala Lys Leu Ala Ala Ala Ala
        275                 280                 285

Lys Lys Ile Ile Ser Ser Gly Gly Glu Thr Lys Leu Ala Lys Thr Leu
    290                 295                 300

Ala Glu Leu Val Glu Lys Gly Ala Ala Phe His His Ala Gly Leu Asn
305                 310                 315                 320

Gln Asp Cys Arg Ser Val Val Glu Glu Glu Phe Arg Ser Gly Arg Ile
                325                 330                 335

Arg Leu Leu Ala Ser Thr Pro Thr Leu Ala Ala Gly Val Asn Leu Pro
            340                 345                 350

Ala Arg Arg Val Val Ile Ser Ser Val Met Arg Tyr Asn Ser Ser Ser
        355                 360                 365

Gly Met Ser Glu Pro Ile Ser Ile Leu Glu Tyr Lys Gln Leu Cys Gly
    370                 375                 380

Arg Ala Gly Arg Pro Gln Tyr Asp Lys Ser Gly Glu Ala Ile Val Val
385                 390                 395                 400

Gly Gly Val Asn Ala Asp Glu Ile Phe Asp Arg Tyr Ile Gly Gly Glu
                405                 410                 415

Pro Glu Pro Ile Arg Ser Ala Met Val Asp Asp Arg Ala Leu Arg Ile
            420                 425                 430

His Val Leu Ser Leu Val Thr Thr Ser Pro Gly Ile Lys Glu Asp Asp
        435                 440                 445

Val Thr Glu Phe Phe Leu Gly Thr Leu Gly Gly Gln Gln Ser Gly Glu
    450                 455                 460

Ser Thr Val Lys Phe Ser Val Ala Val Ala Leu Arg Phe Leu Gln Glu
465                 470                 475                 480

Glu Gly Met Leu Gly Arg Arg Gly Gly Arg Leu Ala Ala Thr Lys Met
                485                 490                 495

Gly Arg Leu Val Ser Arg Leu Tyr Met Asp Pro Met Thr Ala Val Thr
            500                 505                 510
```

```
Leu Arg Asp Ala Val Gly Glu Ala Ser Pro Gly Arg Met His Thr Leu
        515                 520                 525

Gly Phe Leu His Leu Val Ser Glu Cys Ser Glu Phe Met Pro Arg Phe
    530                 535                 540

Ala Leu Arg Gln Lys Asp His Glu Val Ala Glu Met Met Leu Glu Ala
545                 550                 555                 560

Gly Arg Gly Glu Leu Leu Arg Pro Val Tyr Ser Tyr Glu Cys Gly Arg
                565                 570                 575

Gly Leu Leu Ala Leu His Arg Trp Ile Gly Glu Ser Pro Glu Ala Lys
            580                 585                 590

Leu Ala Glu Asp Leu Lys Phe Glu Ser Gly Asp Val His Arg Met Val
        595                 600                 605

Glu Ser Ser Gly Trp Leu Leu Arg Cys Ile Trp Glu Ile Ser Lys His
    610                 615                 620

Gln Glu Arg Pro Asp Leu Leu Gly Glu Leu Asp Val Leu Arg Ser Arg
625                 630                 635                 640

Val Ala Tyr Gly Ile Lys Ala Glu Leu Val Pro Leu Val Ser Ile Lys
                645                 650                 655

Gly Ile Gly Arg Val Arg Ser Arg Arg Leu Phe Arg Gly Gly Ile Lys
            660                 665                 670

Gly Pro Gly Asp Leu Ala Ala Val Pro Val Glu Arg Leu Ser Arg Val
        675                 680                 685

Glu Gly Ile Gly Ala Thr Leu Ala Asn Asn Ile Lys Ser Gln Leu Arg
    690                 695                 700

Lys Gly Gly
705


<210> SEQ ID NO 20
<211> LENGTH: 720
<212> TYPE: PRT
<213> ORGANISM: Thermococcus gammatolerans

<400> SEQUENCE: 20

Met Lys Val Asp Glu Leu Pro Val Asp Glu Arg Leu Lys Ala Val Leu
1               5                   10                  15

Lys Glu Arg Gly Ile Glu Glu Leu Tyr Pro Pro Gln Ala Glu Ala Leu
            20                  25                  30

Lys Ser Gly Ala Leu Glu Gly Arg Asn Leu Val Leu Ala Ile Pro Thr
        35                  40                  45

Ala Ser Gly Lys Thr Leu Val Ser Glu Ile Val Met Val Asn Lys Leu
    50                  55                  60

Ile Gln Glu Gly Gly Lys Ala Val Tyr Leu Val Pro Leu Lys Ala Leu
65                  70                  75                  80

Ala Glu Glu Lys Tyr Arg Glu Phe Lys Glu Trp Glu Lys Leu Gly Leu
                85                  90                  95

Lys Val Ala Ala Thr Thr Gly Asp Tyr Asp Ser Thr Asp Asp Trp Leu
            100                 105                 110

Gly Arg Tyr Asp Ile Ile Val Ala Thr Ala Glu Lys Phe Asp Ser Leu
        115                 120                 125

Leu Arg His Gly Ala Arg Trp Ile Asn Asp Val Lys Leu Val Val Ala
    130                 135                 140

Asp Glu Val His Leu Ile Gly Ser Tyr Asp Arg Gly Ala Thr Leu Glu
145                 150                 155                 160

Met Ile Leu Thr His Met Leu Gly Arg Ala Gln Ile Leu Ala Leu Ser
```

```
                165                 170                 175

Ala Thr Val Gly Asn Ala Glu Glu Leu Ala Glu Trp Leu Asp Ala Ser
            180                 185                 190

Leu Val Val Ser Asp Trp Arg Pro Val Gln Leu Arg Arg Gly Val Phe
        195                 200                 205

His Leu Gly Thr Leu Ile Trp Glu Asp Gly Lys Val Glu Ser Tyr Pro
    210                 215                 220

Glu Asn Trp Tyr Ser Leu Val Val Asp Ala Val Lys Arg Gly Lys Gly
225                 230                 235                 240

Ala Leu Val Phe Val Asn Thr Arg Arg Ser Ala Glu Lys Glu Ala Leu
                245                 250                 255

Ala Leu Ser Lys Leu Val Ser Ser His Leu Thr Lys Pro Glu Lys Arg
            260                 265                 270

Ala Leu Glu Ser Leu Ala Ser Gln Leu Glu Asp Asn Pro Thr Ser Glu
        275                 280                 285

Lys Leu Lys Arg Ala Leu Arg Gly Gly Val Ala Phe His His Ala Gly
    290                 295                 300

Leu Ser Arg Val Glu Arg Thr Leu Ile Glu Asp Ala Phe Arg Glu Gly
305                 310                 315                 320

Leu Ile Lys Val Ile Thr Ala Thr Pro Thr Leu Ser Ala Gly Val Asn
                325                 330                 335

Leu Pro Ser Phe Arg Val Ile Ile Arg Asp Thr Lys Arg Tyr Ala Gly
            340                 345                 350

Phe Gly Trp Thr Asp Ile Pro Val Leu Glu Ile Gln Gln Met Met Gly
        355                 360                 365

Arg Ala Gly Arg Pro Arg Tyr Asp Lys Tyr Gly Glu Ala Ile Ile Val
    370                 375                 380

Ala Arg Thr Asp Glu Pro Gly Lys Leu Met Glu Arg Tyr Ile Arg Gly
385                 390                 395                 400

Lys Pro Glu Lys Leu Phe Ser Met Leu Ala Asn Glu Gln Ala Phe Arg
                405                 410                 415

Ser Gln Val Leu Ala Leu Ile Thr Asn Phe Gly Ile Arg Ser Phe Pro
            420                 425                 430

Glu Leu Val Arg Phe Leu Glu Arg Thr Phe Tyr Ala His Gln Arg Lys
        435                 440                 445

Asp Leu Ser Ser Leu Glu Tyr Lys Ala Lys Glu Val Val Tyr Phe Leu
    450                 455                 460

Ile Glu Asn Glu Phe Ile Asp Leu Asp Leu Glu Asp Arg Phe Ile Pro
465                 470                 475                 480

Leu Pro Phe Gly Lys Arg Thr Ser Gln Leu Tyr Ile Asp Pro Leu Thr
                485                 490                 495

Ala Lys Lys Phe Lys Asp Ala Phe Pro Ala Ile Glu Arg Asn Pro Asn
            500                 505                 510

Pro Phe Gly Ile Phe Gln Leu Ile Ala Ser Thr Pro Asp Met Ala Thr
        515                 520                 525

Leu Thr Ala Arg Arg Arg Glu Met Glu Asp Tyr Leu Asp Leu Ala Tyr
    530                 535                 540

Glu Leu Glu Asp Lys Leu Tyr Ala Ser Ile Pro Tyr Tyr Glu Asp Ser
545                 550                 555                 560

Arg Phe Gln Gly Phe Leu Gly Gln Val Lys Thr Ala Lys Val Leu Leu
                565                 570                 575

Asp Trp Ile Asn Glu Val Pro Glu Ala Arg Ile Tyr Glu Thr Tyr Ser
            580                 585                 590
```

```
Ile Asp Pro Gly Asp Leu Tyr Arg Leu Leu Glu Leu Ala Asp Trp Leu
        595                 600                 605

Met Tyr Ser Leu Ile Glu Leu Tyr Lys Leu Phe Glu Pro Lys Glu Glu
    610                 615                 620

Ile Leu Asn Tyr Leu Arg Asp Leu His Leu Arg Leu Arg His Gly Val
625                 630                 635                 640

Arg Glu Glu Leu Leu Glu Leu Val Arg Leu Pro Asn Ile Gly Arg Lys
                645                 650                 655

Arg Ala Arg Ala Leu Tyr Asn Ala Gly Phe Arg Ser Val Glu Ala Ile
            660                 665                 670

Ala Asn Ala Lys Pro Ala Glu Leu Leu Ala Val Glu Gly Ile Gly Ala
        675                 680                 685

Lys Ile Leu Asp Gly Ile Tyr Arg His Leu Gly Ile Glu Lys Arg Val
    690                 695                 700

Thr Glu Glu Lys Pro Lys Arg Lys Gly Thr Leu Glu Asp Phe Leu Arg
705                 710                 715                 720


<210> SEQ ID NO 21
<211> LENGTH: 799
<212> TYPE: PRT
<213> ORGANISM: Methanospirillum hungatei

<400> SEQUENCE: 21

Met Glu Ile Ala Ser Leu Pro Leu Pro Asp Ser Phe Ile Arg Ala Cys
1               5                   10                  15

His Ala Lys Gly Ile Arg Ser Leu Tyr Pro Pro Gln Ala Glu Cys Ile
            20                  25                  30

Glu Lys Gly Leu Leu Glu Gly Lys Asn Leu Leu Ile Ser Ile Pro Thr
        35                  40                  45

Ala Ser Gly Lys Thr Leu Leu Ala Glu Met Ala Met Trp Ser Arg Ile
    50                  55                  60

Ala Ala Gly Gly Lys Cys Leu Tyr Ile Val Pro Leu Arg Ala Leu Ala
65                  70                  75                  80

Ser Glu Lys Tyr Asp Glu Phe Ser Lys Lys Gly Val Ile Arg Val Gly
                85                  90                  95

Ile Ala Thr Gly Asp Leu Asp Arg Thr Asp Ala Tyr Leu Gly Glu Asn
            100                 105                 110

Asp Ile Ile Val Ala Thr Ser Glu Lys Thr Asp Ser Leu Leu Arg Asn
        115                 120                 125

Arg Thr Pro Trp Leu Ser Gln Ile Thr Cys Ile Val Leu Asp Glu Val
    130                 135                 140

His Leu Ile Gly Ser Glu Asn Arg Gly Ala Thr Leu Glu Met Val Ile
145                 150                 155                 160

Thr Lys Leu Arg Tyr Thr Asn Pro Val Met Gln Ile Ile Gly Leu Ser
                165                 170                 175

Ala Thr Ile Gly Asn Pro Ala Gln Leu Ala Glu Trp Leu Asp Ala Thr
            180                 185                 190

Leu Ile Thr Ser Thr Trp Arg Pro Val Asp Leu Arg Gln Gly Val Tyr
        195                 200                 205

Tyr Asn Gly Lys Ile Arg Phe Ser Asp Ser Glu Arg Pro Ile Gln Gly
    210                 215                 220

Lys Thr Lys His Asp Asp Leu Asn Leu Cys Leu Asp Thr Ile Glu Glu
225                 230                 235                 240

Gly Gly Gln Cys Leu Val Phe Val Ser Ser Arg Arg Asn Ala Glu Gly
```

```
                245                 250                 255

Phe Ala Lys Lys Ala Ala Gly Ala Leu Lys Ala Gly Ser Pro Asp Ser
            260                 265                 270

Lys Ala Leu Ala Gln Glu Leu Arg Arg Leu Arg Asp Arg Asp Glu Gly
        275                 280                 285

Asn Val Leu Ala Asp Cys Val Glu Arg Gly Ala Ala Phe His His Ala
    290                 295                 300

Gly Leu Ile Arg Gln Glu Arg Thr Ile Ile Glu Glu Gly Phe Arg Asn
305                 310                 315                 320

Gly Tyr Ile Glu Val Ile Ala Ala Thr Pro Thr Leu Ala Ala Gly Leu
                325                 330                 335

Asn Leu Pro Ala Arg Arg Val Ile Ile Arg Asp Tyr Asn Arg Phe Ala
            340                 345                 350

Ser Gly Leu Gly Met Val Pro Ile Pro Val Gly Glu Tyr His Gln Met
        355                 360                 365

Ala Gly Arg Ala Gly Arg Pro His Leu Asp Pro Tyr Gly Glu Ala Val
    370                 375                 380

Leu Leu Ala Lys Asp Ala Pro Ser Val Glu Arg Leu Phe Glu Thr Phe
385                 390                 395                 400

Ile Asp Ala Glu Ala Glu Arg Val Asp Ser Gln Cys Val Asp Asp Ala
                405                 410                 415

Ser Leu Cys Ala His Ile Leu Ser Leu Ile Ala Thr Gly Phe Ala His
            420                 425                 430

Asp Gln Glu Ala Leu Ser Ser Phe Met Glu Arg Thr Phe Tyr Phe Phe
        435                 440                 445

Gln His Pro Lys Thr Arg Ser Leu Pro Arg Leu Val Ala Asp Ala Ile
    450                 455                 460

Arg Phe Leu Thr Thr Ala Gly Met Val Glu Glu Arg Glu Asn Thr Leu
465                 470                 475                 480

Ser Ala Thr Arg Leu Gly Ser Leu Val Ser Arg Leu Tyr Leu Asn Pro
                485                 490                 495

Cys Thr Ala Arg Leu Ile Leu Asp Ser Leu Lys Ser Cys Lys Thr Pro
            500                 505                 510

Thr Leu Ile Gly Leu Leu His Val Ile Cys Val Ser Pro Asp Met Gln
        515                 520                 525

Arg Leu Tyr Leu Lys Ala Ala Asp Thr Gln Leu Leu Arg Thr Phe Leu
    530                 535                 540

Phe Lys His Lys Asp Asp Leu Ile Leu Pro Leu Pro Phe Glu Gln Glu
545                 550                 555                 560

Glu Glu Glu Leu Trp Leu Ser Gly Leu Lys Thr Ala Leu Val Leu Thr
                565                 570                 575

Asp Trp Ala Asp Glu Phe Ser Glu Gly Met Ile Glu Glu Arg Tyr Gly
            580                 585                 590

Ile Gly Ala Gly Asp Leu Tyr Asn Ile Val Asp Ser Gly Lys Trp Leu
        595                 600                 605

Leu His Gly Thr Glu Arg Leu Val Ser Val Glu Met Pro Glu Met Ser
    610                 615                 620

Gln Val Val Lys Thr Leu Ser Val Arg Val His His Gly Val Lys Ser
625                 630                 635                 640

Glu Leu Leu Pro Leu Val Ala Leu Arg Asn Ile Gly Arg Val Arg Ala
                645                 650                 655

Arg Thr Leu Tyr Asn Ala Gly Tyr Pro Asp Pro Glu Ala Val Ala Arg
            660                 665                 670
```

```
Ala Gly Leu Ser Thr Ile Ala Arg Ile Ile Gly Glu Gly Ile Ala Arg
        675                 680                 685

Gln Val Ile Asp Glu Ile Thr Gly Val Lys Arg Ser Gly Ile His Ser
    690                 695                 700

Ser Asp Asp Asp Tyr Gln Gln Lys Thr Pro Glu Leu Leu Thr Asp Ile
705                 710                 715                 720

Pro Gly Ile Gly Lys Lys Met Ala Glu Lys Leu Gln Asn Ala Gly Ile
                725                 730                 735

Ile Thr Val Ser Asp Leu Leu Thr Ala Asp Glu Val Leu Leu Ser Asp
            740                 745                 750

Val Leu Gly Ala Ala Arg Ala Arg Lys Val Leu Ala Phe Leu Ser Asn
        755                 760                 765

Ser Glu Lys Glu Asn Ser Ser Ser Asp Lys Thr Glu Glu Ile Pro Asp
    770                 775                 780

Thr Gln Lys Ile Arg Gly Gln Ser Ser Trp Glu Asp Phe Gly Cys
785                 790                 795


<210> SEQ ID NO 22
<211> LENGTH: 1756
<212> TYPE: PRT
<213> ORGANISM: Escherichia coli

<400> SEQUENCE: 22

Met Met Ser Ile Ala Gln Val Arg Ser Ala Gly Ser Ala Gly Asn Tyr
1               5                   10                  15

Tyr Thr Asp Lys Asp Asn Tyr Tyr Val Leu Gly Ser Met Gly Glu Arg
            20                  25                  30

Trp Ala Gly Lys Gly Ala Glu Gln Leu Gly Leu Gln Gly Ser Val Asp
        35                  40                  45

Lys Asp Val Phe Thr Arg Leu Leu Glu Gly Arg Leu Pro Asp Gly Ala
    50                  55                  60

Asp Leu Ser Arg Met Gln Asp Gly Ser Asn Lys His Arg Pro Gly Tyr
65                  70                  75                  80

Asp Leu Thr Phe Ser Ala Pro Lys Ser Val Ser Met Met Ala Met Leu
                85                  90                  95

Gly Gly Asp Lys Arg Leu Ile Asp Ala His Asn Gln Ala Val Asp Phe
            100                 105                 110

Ala Val Arg Gln Val Glu Ala Leu Ala Ser Thr Arg Val Met Thr Asp
        115                 120                 125

Gly Gln Ser Glu Thr Val Leu Thr Gly Asn Leu Val Met Ala Leu Phe
    130                 135                 140

Asn His Asp Thr Ser Arg Asp Gln Glu Pro Gln Leu His Thr His Ala
145                 150                 155                 160

Val Val Ala Asn Val Thr Gln His Asn Gly Glu Trp Lys Thr Leu Ser
                165                 170                 175

Ser Asp Lys Val Gly Lys Thr Gly Phe Ile Glu Asn Val Tyr Ala Asn
            180                 185                 190

Gln Ile Ala Phe Gly Arg Leu Tyr Arg Glu Lys Leu Lys Glu Gln Val
        195                 200                 205

Glu Ala Leu Gly Tyr Glu Thr Glu Val Val Gly Lys His Gly Met Trp
    210                 215                 220

Glu Met Pro Gly Val Pro Val Glu Ala Phe Ser Gly Arg Ser Gln Ala
225                 230                 235                 240

Ile Arg Glu Ala Val Gly Glu Asp Ala Ser Leu Lys Ser Arg Asp Val
```

```
                245                 250                 255

Ala Ala Leu Asp Thr Arg Lys Ser Lys Gln His Val Asp Pro Glu Ile
            260                 265                 270

Arg Met Ala Glu Trp Met Gln Thr Leu Lys Glu Thr Gly Phe Asp Ile
        275                 280                 285

Arg Ala Tyr Arg Asp Ala Ala Asp Gln Arg Thr Glu Ile Arg Thr Gln
    290                 295                 300

Ala Pro Gly Pro Ala Ser Gln Asp Gly Pro Asp Val Gln Gln Ala Val
305                 310                 315                 320

Thr Gln Ala Ile Ala Gly Leu Ser Glu Arg Lys Val Gln Phe Thr Tyr
                325                 330                 335

Thr Asp Val Leu Ala Arg Thr Val Gly Ile Leu Pro Pro Glu Asn Gly
            340                 345                 350

Val Ile Glu Arg Ala Arg Ala Gly Ile Asp Glu Ala Ile Ser Arg Glu
        355                 360                 365

Gln Leu Ile Pro Leu Asp Arg Glu Lys Gly Leu Phe Thr Ser Gly Ile
    370                 375                 380

His Val Leu Asp Glu Leu Ser Val Arg Ala Leu Ser Arg Asp Ile Met
385                 390                 395                 400

Lys Gln Asn Arg Val Thr Val His Pro Glu Lys Ser Val Pro Arg Thr
                405                 410                 415

Ala Gly Tyr Ser Asp Ala Val Ser Val Leu Ala Gln Asp Arg Pro Ser
            420                 425                 430

Leu Ala Ile Val Ser Gly Gln Gly Gly Ala Ala Gly Gln Arg Glu Arg
        435                 440                 445

Val Ala Glu Leu Val Met Met Ala Arg Glu Gln Gly Arg Glu Val Gln
    450                 455                 460

Ile Ile Ala Ala Asp Arg Arg Ser Gln Met Asn Leu Lys Gln Asp Glu
465                 470                 475                 480

Arg Leu Ser Gly Glu Leu Ile Thr Gly Arg Arg Gln Leu Leu Glu Gly
                485                 490                 495

Met Ala Phe Thr Pro Gly Ser Thr Val Ile Val Asp Gln Gly Glu Lys
            500                 505                 510

Leu Ser Leu Lys Glu Thr Leu Thr Leu Leu Asp Gly Ala Ala Arg His
        515                 520                 525

Asn Val Gln Val Leu Ile Thr Asp Ser Gly Gln Arg Thr Gly Thr Gly
    530                 535                 540

Ser Ala Leu Met Ala Met Lys Asp Ala Gly Val Asn Thr Tyr Arg Trp
545                 550                 555                 560

Gln Gly Gly Glu Gln Arg Pro Ala Thr Ile Ile Ser Glu Pro Asp Arg
                565                 570                 575

Asn Val Arg Tyr Ala Arg Leu Ala Gly Asp Phe Ala Ala Ser Val Lys
            580                 585                 590

Ala Gly Glu Glu Ser Val Ala Gln Val Ser Gly Val Arg Glu Gln Ala
        595                 600                 605

Ile Leu Thr Gln Ala Ile Arg Ser Glu Leu Lys Thr Gln Gly Val Leu
    610                 615                 620

Gly His Pro Glu Val Thr Met Thr Ala Leu Ser Pro Val Trp Leu Asp
625                 630                 635                 640

Ser Arg Ser Arg Tyr Leu Arg Asp Met Tyr Arg Pro Gly Met Val Met
                645                 650                 655

Glu Gln Trp Asn Pro Glu Thr Arg Ser His Asp Arg Tyr Val Ile Asp
            660                 665                 670
```

```
Arg Val Thr Ala Gln Ser His Ser Leu Thr Leu Arg Asp Ala Gln Gly
        675                 680                 685

Glu Thr Gln Val Val Arg Ile Ser Ser Leu Asp Ser Ser Trp Ser Leu
    690                 695                 700

Phe Arg Pro Glu Lys Met Pro Val Ala Asp Gly Glu Arg Leu Arg Val
705                 710                 715                 720

Thr Gly Lys Ile Pro Gly Leu Arg Val Ser Gly Gly Asp Arg Leu Gln
                725                 730                 735

Val Ala Ser Val Ser Glu Asp Ala Met Thr Val Val Val Pro Gly Arg
            740                 745                 750

Ala Glu Pro Ala Ser Leu Pro Val Ser Asp Ser Pro Phe Thr Ala Leu
        755                 760                 765

Lys Leu Glu Asn Gly Trp Val Glu Thr Pro Gly His Ser Val Ser Asp
    770                 775                 780

Ser Ala Thr Val Phe Ala Ser Val Thr Gln Met Ala Met Asp Asn Ala
785                 790                 795                 800

Thr Leu Asn Gly Leu Ala Arg Ser Gly Arg Asp Val Arg Leu Tyr Ser
                805                 810                 815

Ser Leu Asp Glu Thr Arg Thr Ala Glu Lys Leu Ala Arg His Pro Ser
            820                 825                 830

Phe Thr Val Val Ser Glu Gln Ile Lys Ala Arg Ala Gly Glu Thr Leu
        835                 840                 845

Leu Glu Thr Ala Ile Ser Leu Gln Lys Ala Gly Leu His Thr Pro Ala
    850                 855                 860

Gln Gln Ala Ile His Leu Ala Leu Pro Val Leu Glu Ser Lys Asn Leu
865                 870                 875                 880

Ala Phe Ser Met Val Asp Leu Leu Thr Glu Ala Lys Ser Phe Ala Ala
                885                 890                 895

Glu Gly Thr Gly Phe Thr Glu Leu Gly Gly Glu Ile Asn Ala Gln Ile
            900                 905                 910

Lys Arg Gly Asp Leu Leu Tyr Val Asp Val Ala Lys Gly Tyr Gly Thr
        915                 920                 925

Gly Leu Leu Val Ser Arg Ala Ser Tyr Glu Ala Glu Lys Ser Ile Leu
    930                 935                 940

Arg His Ile Leu Glu Gly Lys Glu Ala Val Thr Pro Leu Met Glu Arg
945                 950                 955                 960

Val Pro Gly Glu Leu Met Glu Thr Leu Thr Ser Gly Gln Arg Ala Ala
                965                 970                 975

Thr Arg Met Ile Leu Glu Thr Ser Asp Arg Phe Thr Val Val Gln Gly
            980                 985                 990

Tyr Ala Gly Val Gly Lys Thr Thr  Gln Phe Arg Ala Val  Met Ser Ala
        995                 1000                1005

Val Asn  Met Leu Pro Ala Ser  Glu Arg Pro Arg Val  Val Gly Leu
    1010                1015                1020

Gly Pro  Thr His Arg Ala Val  Gly Glu Met Arg Ser  Ala Gly Val
    1025                1030                1035

Asp Ala  Gln Thr Leu Ala Ser  Phe Leu His Asp Thr  Gln Leu Gln
    1040                1045                1050

Gln Arg  Ser Gly Glu Thr Pro  Asp Phe Ser Asn Thr  Leu Phe Leu
    1055                1060                1065

Leu Asp  Glu Ser Ser Met Val  Gly Asn Thr Glu Met  Ala Arg Ala
    1070                1075                1080
```

```
Tyr Ala  Leu Ile Ala Ala Gly  Gly Gly Arg Ala Val  Ala Ser Gly
    1085                 1090                 1095

Asp Thr  Asp Gln Leu Gln Ala  Ile Ala Pro Gly Gln  Ser Phe Arg
    1100                 1105                 1110

Leu Gln  Gln Thr Arg Ser Ala  Ala Asp Val Val Ile  Met Lys Glu
    1115                 1120                 1125

Ile Val  Arg Gln Thr Pro Glu  Leu Arg Glu Ala Val  Tyr Ser Leu
    1130                 1135                 1140

Ile Asn  Arg Asp Val Glu Arg  Ala Leu Ser Gly Leu  Glu Ser Val
    1145                 1150                 1155

Lys Pro  Ser Gln Val Pro Arg  Leu Glu Gly Ala Trp  Ala Pro Glu
    1160                 1165                 1170

His Ser  Val Thr Glu Phe Ser  His Ser Gln Glu Ala  Lys Leu Ala
    1175                 1180                 1185

Glu Ala  Gln Gln Lys Ala Met  Leu Lys Gly Glu Ala  Phe Pro Asp
    1190                 1195                 1200

Ile Pro  Met Thr Leu Tyr Glu  Ala Ile Val Arg Asp  Tyr Thr Gly
    1205                 1210                 1215

Arg Thr  Pro Glu Ala Arg Glu  Gln Thr Leu Ile Val  Thr His Leu
    1220                 1225                 1230

Asn Glu  Asp Arg Arg Val Leu  Asn Ser Met Ile His  Asp Ala Arg
    1235                 1240                 1245

Glu Lys  Ala Gly Glu Leu Gly  Lys Glu Gln Val Met  Val Pro Val
    1250                 1255                 1260

Leu Asn  Thr Ala Asn Ile Arg  Asp Gly Glu Leu Arg  Arg Leu Ser
    1265                 1270                 1275

Thr Trp  Glu Lys Asn Pro Asp  Ala Leu Ala Leu Val  Asp Asn Val
    1280                 1285                 1290

Tyr His  Arg Ile Ala Gly Ile  Ser Lys Asp Asp Gly  Leu Ile Thr
    1295                 1300                 1305

Leu Gln  Asp Ala Glu Gly Asn  Thr Arg Leu Ile Ser  Pro Arg Glu
    1310                 1315                 1320

Ala Val  Ala Glu Gly Val Thr  Leu Tyr Thr Pro Asp  Lys Ile Arg
    1325                 1330                 1335

Val Gly  Thr Gly Asp Arg Met  Arg Phe Thr Lys Ser  Asp Arg Glu
    1340                 1345                 1350

Arg Gly  Tyr Val Ala Asn Ser  Val Trp Thr Val Thr  Ala Val Ser
    1355                 1360                 1365

Gly Asp  Ser Val Thr Leu Ser  Asp Gly Gln Gln Thr  Arg Val Ile
    1370                 1375                 1380

Arg Pro  Gly Gln Glu Arg Ala  Glu Gln His Ile Asp  Leu Ala Tyr
    1385                 1390                 1395

Ala Ile  Thr Ala His Gly Ala  Gln Gly Ala Ser Glu  Thr Phe Ala
    1400                 1405                 1410

Ile Ala  Leu Glu Gly Thr Glu  Gly Asn Arg Lys Leu  Met Ala Gly
    1415                 1420                 1425

Phe Glu  Ser Ala Tyr Val Ala  Leu Ser Arg Met Lys  Gln His Val
    1430                 1435                 1440

Gln Val  Tyr Thr Asp Asn Arg  Gln Gly Trp Thr Asp  Ala Ile Asn
    1445                 1450                 1455

Asn Ala  Val Gln Lys Gly Thr  Ala His Asp Val Leu  Glu Pro Lys
    1460                 1465                 1470

Pro Asp  Arg Glu Val Met Asn  Ala Gln Arg Leu Phe  Ser Thr Ala
```

```
    1475                1480                1485

Arg Glu  Leu Arg Asp Val Ala  Ala Gly Arg Ala Val  Leu Arg Gln
    1490                1495                1500

Ala Gly  Leu Ala Gly Gly Asp  Ser Pro Ala Arg Phe  Ile Ala Pro
    1505                1510                1515

Gly Arg  Lys Tyr Pro Gln Pro  Tyr Val Ala Leu Pro  Ala Phe Asp
    1520                1525                1530

Arg Asn  Gly Lys Ser Ala Gly  Ile Trp Leu Asn Pro  Leu Thr Thr
    1535                1540                1545

Asp Asp  Gly Asn Gly Leu Arg  Gly Phe Ser Gly Glu  Gly Arg Val
    1550                1555                1560

Lys Gly  Ser Gly Asp Ala Gln  Phe Val Ala Leu Gln  Gly Ser Arg
    1565                1570                1575

Asn Gly  Glu Ser Leu Leu Ala  Asp Asn Met Gln Asp  Gly Val Arg
    1580                1585                1590

Ile Ala  Arg Asp Asn Pro Asp  Ser Gly Val Val Val  Arg Ile Ala
    1595                1600                1605

Gly Glu  Gly Arg Pro Trp Asn  Pro Gly Ala Ile Thr  Gly Gly Arg
    1610                1615                1620

Val Trp  Gly Asp Ile Pro Asp  Asn Ser Val Gln Pro  Gly Ala Gly
    1625                1630                1635

Asn Gly  Glu Pro Val Thr Ala  Glu Val Leu Ala Gln  Arg Gln Ala
    1640                1645                1650

Glu Glu  Ala Ile Arg Arg Glu  Thr Glu Arg Arg Ala  Asp Glu Ile
    1655                1660                1665

Val Arg  Lys Met Ala Glu Asn  Lys Pro Asp Leu Pro  Asp Gly Lys
    1670                1675                1680

Thr Glu  Leu Ala Val Arg Asp  Ile Ala Gly Gln Glu  Arg Asp Arg
    1685                1690                1695

Ser Ala  Ile Ser Glu Arg Glu  Thr Ala Leu Pro Glu  Ser Val Leu
    1700                1705                1710

Arg Glu  Ser Gln Arg Glu Arg  Glu Ala Val Arg Glu  Val Ala Arg
    1715                1720                1725

Glu Asn  Leu Leu Gln Glu Arg  Leu Gln Gln Met Glu  Arg Asp Met
    1730                1735                1740

Val Arg  Asp Leu Gln Lys Glu  Lys Thr Leu Gly Gly  Asp
    1745                1750                1755


<210> SEQ ID NO 23
<211> LENGTH: 726
<212> TYPE: PRT
<213> ORGANISM: Methanococcoides burtonii

<400> SEQUENCE: 23

Met Ser Asp Lys Pro Ala Phe Met Lys Tyr Phe Thr Gln Ser Ser Cys
1               5                   10                  15

Tyr Pro Asn Gln Gln Glu Ala Met Asp Arg Ile His Ser Ala Leu Met
            20                  25                  30

Gln Gln Gln Leu Val Leu Phe Glu Gly Ala Cys Gly Thr Gly Lys Thr
        35                  40                  45

Leu Ser Ala Leu Val Pro Ala Leu His Val Gly Lys Met Leu Gly Lys
    50                  55                  60

Thr Val Ile Ile Ala Thr Asn Val His Gln Gln Met Val Gln Phe Ile
65                  70                  75                  80
```

```
Asn Glu Ala Arg Asp Ile Lys Lys Val Gln Asp Val Lys Val Ala Val
                85                  90                  95

Ile Lys Gly Lys Thr Ala Met Cys Pro Gln Glu Ala Asp Tyr Glu Glu
            100                 105                 110

Cys Ser Val Lys Arg Glu Asn Thr Phe Glu Leu Met Glu Thr Glu Arg
        115                 120                 125

Glu Ile Tyr Leu Lys Arg Gln Glu Leu Asn Ser Ala Arg Asp Ser Tyr
    130                 135                 140

Lys Lys Ser His Asp Pro Ala Phe Val Thr Leu Arg Asp Glu Leu Ser
145                 150                 155                 160

Lys Glu Ile Asp Ala Val Glu Glu Lys Ala Arg Gly Leu Arg Asp Arg
                165                 170                 175

Ala Cys Asn Asp Leu Tyr Glu Val Leu Arg Ser Asp Ser Glu Lys Phe
            180                 185                 190

Arg Glu Trp Leu Tyr Lys Glu Val Arg Ser Pro Glu Glu Ile Asn Asp
        195                 200                 205

His Ala Ile Lys Asp Gly Met Cys Gly Tyr Glu Leu Val Lys Arg Glu
    210                 215                 220

Leu Lys His Ala Asp Leu Leu Ile Cys Asn Tyr His His Val Leu Asn
225                 230                 235                 240

Pro Asp Ile Phe Ser Thr Val Leu Gly Trp Ile Glu Lys Glu Pro Gln
                245                 250                 255

Glu Thr Ile Val Ile Phe Asp Glu Ala His Asn Leu Glu Ser Ala Ala
            260                 265                 270

Arg Ser His Ser Ser Leu Ser Leu Thr Glu His Ser Ile Glu Lys Ala
        275                 280                 285

Ile Thr Glu Leu Glu Ala Asn Leu Asp Leu Leu Ala Asp Asp Asn Ile
    290                 295                 300

His Asn Leu Phe Asn Ile Phe Leu Glu Val Ile Ser Asp Thr Tyr Asn
305                 310                 315                 320

Ser Arg Phe Lys Phe Gly Glu Arg Glu Arg Val Arg Lys Asn Trp Tyr
                325                 330                 335

Asp Ile Arg Ile Ser Asp Pro Tyr Glu Arg Asn Asp Ile Val Arg Gly
            340                 345                 350

Lys Phe Leu Arg Gln Ala Lys Gly Asp Phe Gly Glu Lys Asp Asp Ile
        355                 360                 365

Gln Ile Leu Leu Ser Glu Ala Ser Glu Leu Gly Ala Lys Leu Asp Glu
    370                 375                 380

Thr Tyr Arg Asp Gln Tyr Lys Lys Gly Leu Ser Ser Val Met Lys Arg
385                 390                 395                 400

Ser His Ile Arg Tyr Val Ala Asp Phe Met Ser Ala Tyr Ile Glu Leu
                405                 410                 415

Ser His Asn Leu Asn Tyr Tyr Pro Ile Leu Asn Val Arg Arg Asp Met
            420                 425                 430

Asn Asp Glu Ile Tyr Gly Arg Val Glu Leu Phe Thr Cys Ile Pro Lys
        435                 440                 445

Asn Val Thr Glu Pro Leu Phe Asn Ser Leu Phe Ser Val Ile Leu Met
    450                 455                 460

Ser Ala Thr Leu His Pro Phe Glu Met Val Lys Lys Thr Leu Gly Ile
465                 470                 475                 480

Thr Arg Asp Thr Cys Glu Met Ser Tyr Gly Thr Ser Phe Pro Glu Glu
                485                 490                 495

Lys Arg Leu Ser Ile Ala Val Ser Ile Pro Pro Leu Phe Ala Lys Asn
```

```
            500                 505                 510

Arg Asp Asp Arg His Val Thr Glu Leu Leu Glu Gln Val Leu Leu Asp
        515                 520                 525

Ser Ile Glu Asn Ser Lys Gly Asn Val Ile Leu Phe Phe Gln Ser Ala
    530                 535                 540

Phe Glu Ala Lys Arg Tyr Tyr Ser Lys Ile Glu Pro Leu Val Asn Val
545                 550                 555                 560

Pro Val Phe Leu Asp Glu Val Gly Ile Ser Ser Gln Asp Val Arg Glu
                565                 570                 575

Glu Phe Phe Ser Ile Gly Glu Glu Asn Gly Lys Ala Val Leu Leu Ser
            580                 585                 590

Tyr Leu Trp Gly Thr Leu Ser Glu Gly Ile Asp Tyr Arg Asp Gly Arg
        595                 600                 605

Gly Arg Thr Val Ile Ile Ile Gly Val Gly Tyr Pro Ala Leu Asn Asp
    610                 615                 620

Arg Met Asn Ala Val Glu Ser Ala Tyr Asp His Val Phe Gly Tyr Gly
625                 630                 635                 640

Ala Gly Trp Glu Phe Ala Ile Gln Val Pro Thr Ile Arg Lys Ile Arg
                645                 650                 655

Gln Ala Met Gly Arg Val Val Arg Ser Pro Thr Asp Tyr Gly Ala Arg
            660                 665                 670

Ile Leu Leu Asp Gly Arg Phe Leu Thr Asp Ser Lys Lys Arg Phe Gly
        675                 680                 685

Lys Phe Ser Val Phe Glu Val Phe Pro Pro Ala Glu Arg Ser Glu Phe
    690                 695                 700

Val Asp Val Asp Pro Glu Lys Val Lys Tyr Ser Leu Met Asn Phe Phe
705                 710                 715                 720

Met Asp Asn Asp Glu Gln
                725


<210> SEQ ID NO 24
<211> LENGTH: 439
<212> TYPE: PRT
<213> ORGANISM: Dickeya dadantii

<400> SEQUENCE: 24

Met Thr Phe Asp Asp Leu Thr Glu Gly Gln Lys Asn Ala Phe Asn Ile
1               5                   10                  15

Val Met Lys Ala Ile Lys Glu Lys Lys His His Val Thr Ile Asn Gly
            20                  25                  30

Pro Ala Gly Thr Gly Lys Thr Thr Leu Thr Lys Phe Ile Ile Glu Ala
        35                  40                  45

Leu Ile Ser Thr Gly Glu Thr Gly Ile Ile Leu Ala Ala Pro Thr His
    50                  55                  60

Ala Ala Lys Lys Ile Leu Ser Lys Leu Ser Gly Lys Glu Ala Ser Thr
65                  70                  75                  80

Ile His Ser Ile Leu Lys Ile Asn Pro Val Thr Tyr Glu Glu Asn Val
                85                  90                  95

Leu Phe Glu Gln Lys Glu Val Pro Asp Leu Ala Lys Cys Arg Val Leu
            100                 105                 110

Ile Cys Asp Glu Val Ser Met Tyr Asp Arg Lys Leu Phe Lys Ile Leu
        115                 120                 125

Leu Ser Thr Ile Pro Pro Trp Cys Thr Ile Ile Gly Ile Gly Asp Asn
    130                 135                 140
```

```
Lys Gln Ile Arg Pro Val Asp Pro Gly Glu Asn Thr Ala Tyr Ile Ser
145                 150                 155                 160

Pro Phe Phe Thr His Lys Asp Phe Tyr Gln Cys Glu Leu Thr Glu Val
                165                 170                 175

Lys Arg Ser Asn Ala Pro Ile Ile Asp Val Ala Thr Asp Val Arg Asn
            180                 185                 190

Gly Lys Trp Ile Tyr Asp Lys Val Val Asp Gly His Gly Val Arg Gly
        195                 200                 205

Phe Thr Gly Asp Thr Ala Leu Arg Asp Phe Met Val Asn Tyr Phe Ser
    210                 215                 220

Ile Val Lys Ser Leu Asp Asp Leu Phe Glu Asn Arg Val Met Ala Phe
225                 230                 235                 240

Thr Asn Lys Ser Val Asp Lys Leu Asn Ser Ile Ile Arg Lys Lys Ile
                245                 250                 255

Phe Glu Thr Asp Lys Asp Phe Ile Val Gly Glu Ile Ile Val Met Gln
            260                 265                 270

Glu Pro Leu Phe Lys Thr Tyr Lys Ile Asp Gly Lys Pro Val Ser Glu
        275                 280                 285

Ile Ile Phe Asn Asn Gly Gln Leu Val Arg Ile Ile Glu Ala Glu Tyr
    290                 295                 300

Thr Ser Thr Phe Val Lys Ala Arg Gly Val Pro Gly Glu Tyr Leu Ile
305                 310                 315                 320

Arg His Trp Asp Leu Thr Val Glu Thr Tyr Gly Asp Asp Glu Tyr Tyr
                325                 330                 335

Arg Glu Lys Ile Lys Ile Ile Ser Ser Asp Glu Glu Leu Tyr Lys Phe
            340                 345                 350

Asn Leu Phe Leu Gly Lys Thr Ala Glu Thr Tyr Lys Asn Trp Asn Lys
        355                 360                 365

Gly Gly Lys Ala Pro Trp Ser Asp Phe Trp Asp Ala Lys Ser Gln Phe
    370                 375                 380

Ser Lys Val Lys Ala Leu Pro Ala Ser Thr Phe His Lys Ala Gln Gly
385                 390                 395                 400

Met Ser Val Asp Arg Ala Phe Ile Tyr Thr Pro Cys Ile His Tyr Ala
                405                 410                 415

Asp Val Glu Leu Ala Gln Gln Leu Leu Tyr Val Gly Val Thr Arg Gly
            420                 425                 430

Arg Tyr Asp Val Phe Tyr Val
        435


<210> SEQ ID NO 25
<211> LENGTH: 970
<212> TYPE: PRT
<213> ORGANISM: Clostridium botulinum

<400> SEQUENCE: 25

Met Leu Ser Val Ala Asn Val Arg Ser Pro Ser Ala Ala Ala Ser Tyr
1               5                   10                  15

Phe Ala Ser Asp Asn Tyr Tyr Ala Ser Ala Asp Ala Asp Arg Ser Gly
            20                  25                  30

Gln Trp Ile Gly Asp Gly Ala Lys Arg Leu Gly Leu Glu Gly Lys Val
        35                  40                  45

Glu Ala Arg Ala Phe Asp Ala Leu Leu Arg Gly Glu Leu Pro Asp Gly
    50                  55                  60

Ser Ser Val Gly Asn Pro Gly Gln Ala His Arg Pro Gly Thr Asp Leu
65                  70                  75                  80
```

```
Thr Phe Ser Val Pro Lys Ser Trp Ser Leu Leu Ala Leu Val Gly Lys
                85                  90                  95

Asp Glu Arg Ile Ile Ala Ala Tyr Arg Glu Ala Val Val Glu Ala Leu
            100                 105                 110

His Trp Ala Glu Lys Asn Ala Ala Glu Thr Arg Val Val Glu Lys Gly
        115                 120                 125

Met Val Val Thr Gln Ala Thr Gly Asn Leu Ala Ile Gly Leu Phe Gln
    130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
            180                 185                 190

Ala Arg Phe Arg Val Ala Val Glu Lys Leu Gly Tyr Glu Pro Gly Pro
        195                 200                 205

Val Leu Lys His Gly Asn Phe Glu Ala Arg Gly Ile Ser Arg Glu Gln
    210                 215                 220

Val Met Ala Phe Ser Thr Arg Arg Lys Glu Val Leu Glu Ala Arg Arg
225                 230                 235                 240

Gly Pro Gly Leu Asp Ala Gly Arg Ile Ala Ala Leu Asp Thr Arg Ala
                245                 250                 255

Ser Lys Glu Gly Ile Glu Asp Arg Ala Thr Leu Ser Lys Gln Trp Ser
            260                 265                 270

Glu Ala Ala Gln Ser Ile Gly Leu Asp Leu Lys Pro Leu Val Asp Arg
        275                 280                 285

Ala Arg Thr Lys Ala Leu Gly Gln Gly Met Glu Ala Thr Arg Ile Gly
    290                 295                 300

Ser Leu Val Glu Arg Gly Arg Ala Trp Leu Ser Arg Phe Ala Ala His
305                 310                 315                 320

Val Arg Gly Asp Pro Ala Asp Pro Leu Val Pro Pro Ser Val Leu Lys
                325                 330                 335

Gln Asp Arg Gln Thr Ile Ala Ala Ala Gln Ala Val Ala Ser Ala Val
            340                 345                 350

Arg His Leu Ser Gln Arg Glu Ala Ala Phe Glu Arg Thr Ala Leu Tyr
        355                 360                 365

Lys Ala Ala Leu Asp Phe Gly Leu Pro Thr Thr Ile Ala Asp Val Glu
    370                 375                 380

Lys Arg Thr Arg Ala Leu Val Arg Ser Gly Asp Leu Ile Ala Gly Lys
385                 390                 395                 400

Gly Glu His Lys Gly Trp Leu Ala Ser Arg Asp Ala Val Val Thr Glu
                405                 410                 415

Gln Arg Ile Leu Ser Glu Val Ala Ala Gly Lys Gly Asp Ser Ser Pro
            420                 425                 430

Ala Ile Thr Pro Gln Lys Ala Ala Ala Ser Val Gln Ala Ala Ala Leu
        435                 440                 445

Thr Gly Gln Gly Phe Arg Leu Asn Glu Gly Gln Leu Ala Ala Ala Arg
    450                 455                 460

Leu Ile Leu Ile Ser Lys Asp Arg Thr Ile Ala Val Gln Gly Ile Ala
465                 470                 475                 480

Gly Ala Gly Lys Ser Ser Val Leu Lys Pro Val Ala Glu Val Leu Arg
                485                 490                 495
```

```
Asp Glu Gly His Pro Val Ile Gly Leu Ala Ile Gln Asn Thr Leu Val
            500                 505                 510

Gln Met Leu Glu Arg Asp Thr Gly Ile Gly Ser Gln Thr Leu Ala Arg
        515                 520                 525

Phe Leu Gly Gly Trp Asn Lys Leu Leu Asp Asp Pro Gly Asn Val Ala
    530                 535                 540

Leu Arg Ala Glu Ala Gln Ala Ser Leu Lys Asp His Val Leu Val Leu
545                 550                 555                 560

Asp Glu Ala Ser Met Val Ser Asn Glu Asp Lys Glu Lys Leu Val Arg
                565                 570                 575

Leu Ala Asn Leu Ala Gly Val His Arg Leu Val Leu Ile Gly Asp Arg
            580                 585                 590

Lys Gln Leu Gly Ala Val Asp Ala Gly Lys Pro Phe Ala Leu Leu Gln
        595                 600                 605

Arg Ala Gly Ile Ala Arg Ala Glu Met Ala Thr Asn Leu Arg Ala Arg
    610                 615                 620

Asp Pro Val Val Arg Glu Ala Gln Ala Ala Ala Gln Ala Gly Asp Val
625                 630                 635                 640

Arg Lys Ala Leu Arg His Leu Lys Ser His Thr Val Glu Ala Arg Gly
                645                 650                 655

Asp Gly Ala Gln Val Ala Ala Glu Thr Trp Leu Ala Leu Asp Lys Glu
            660                 665                 670

Thr Arg Ala Arg Thr Ser Ile Tyr Ala Ser Gly Arg Ala Ile Arg Ser
        675                 680                 685

Ala Val Asn Ala Ala Val Gln Gln Gly Leu Leu Ala Ser Arg Glu Ile
    690                 695                 700

Gly Pro Ala Lys Met Lys Leu Glu Val Leu Asp Arg Val Asn Thr Thr
705                 710                 715                 720

Arg Glu Glu Leu Arg His Leu Pro Ala Tyr Arg Ala Gly Arg Val Leu
                725                 730                 735

Glu Val Ser Arg Lys Gln Gln Ala Leu Gly Leu Phe Ile Gly Glu Tyr
            740                 745                 750

Arg Val Ile Gly Gln Asp Arg Lys Gly Lys Leu Val Glu Val Glu Asp
        755                 760                 765

Lys Arg Gly Lys Arg Phe Arg Phe Asp Pro Ala Arg Ile Arg Ala Gly
    770                 775                 780

Lys Gly Asp Asp Asn Leu Thr Leu Leu Glu Pro Arg Lys Leu Glu Ile
785                 790                 795                 800

His Glu Gly Asp Arg Ile Arg Trp Thr Arg Asn Asp His Arg Arg Gly
                805                 810                 815

Leu Phe Asn Ala Asp Gln Ala Arg Val Val Glu Ile Ala Asn Gly Lys
            820                 825                 830

Val Thr Phe Glu Thr Ser Lys Gly Asp Leu Val Glu Leu Lys Lys Asp
        835                 840                 845

Asp Pro Met Leu Lys Arg Ile Asp Leu Ala Tyr Ala Leu Asn Val His
    850                 855                 860

Met Ala Gln Gly Leu Thr Ser Asp Arg Gly Ile Ala Val Met Asp Ser
865                 870                 875                 880

Arg Glu Arg Asn Leu Ser Asn Gln Lys Thr Phe Leu Val Thr Val Thr
                885                 890                 895

Arg Leu Arg Asp His Leu Thr Leu Val Val Asp Ser Ala Asp Lys Leu
            900                 905                 910

Gly Ala Ala Val Ala Arg Asn Lys Gly Glu Lys Ala Ser Ala Ile Glu
```

```
        915                 920                 925

Val Thr Gly Ser Val Lys Pro Thr Ala Thr Lys Gly Ser Gly Val Asp
    930                 935                 940

Gln Pro Lys Ser Val Glu Ala Asn Lys Ala Glu Lys Glu Leu Thr Arg
945                 950                 955                 960

Ser Lys Ser Lys Thr Leu Asp Phe Gly Ile
                965                 970


<210> SEQ ID NO 26
<211> LENGTH: 11
<212> TYPE: PRT
<213> ORGANISM: Mycobacterium smegmatis

<400> SEQUENCE: 26

Trp Ser Leu Gly Val Gly Ile Asn Phe Ser Tyr
1               5                   10


<210> SEQ ID NO 27
<211> LENGTH: 11
<212> TYPE: PRT
<213> ORGANISM: Mycobacterium smegmatis

<400> SEQUENCE: 27

Pro Gly Val Ser Ile Ser Ala Asp Leu Gly Asn
1               5                   10


<210> SEQ ID NO 28
<211> LENGTH: 12
<212> TYPE: DNA
<213> ORGANISM: Artificial Sequence
<220> FEATURE:
<223> OTHER INFORMATION: Synthetic Polynucleotide

<400> SEQUENCE: 28

tttttttttt tt                                                         12


<210> SEQ ID NO 29
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 29

ggttgtttct gttggtgctg atattgc                                         27


<210> SEQ ID NO 30
<211> LENGTH: 3635
<212> TYPE: DNA
<213> ORGANISM: Artificial Sequence
<220> FEATURE:
<223> OTHER INFORMATION: Synthetic Polynucleotide

<400> SEQUENCE: 30

gccatcagat tgtgtttgtt agtcgctgcc atcagattgt gtttgttagt cgcttttttt      60

ttttggaatt ttttttttgg aatttttttt ttgcgctaac aacctcctgc cgttttgccc     120

gtgcatatcg gtcacgaaca aatctgatta ctaaacacag tagcctggat ttgttctatc     180

agtaatcgac cttattccta attaaataga gcaaatcccc ttattggggg taagacatga     240

agatgccaga aaaacatgac ctgttggccg ccattctcgc ggcaaaggaa caaggcatcg     300

gggcaatcct tgcgtttgca atggcgtacc ttcgcggcag atataatggc ggtgcgttta     360
```

```
caaaaacagt aatcgacgca acgatgtgcg ccattatcgc ctagttcatt cgtgaccttc    420
tcgacttcgc cggactaagt agcaatctcg cttatataac gagcgtgttt atcggctaca    480
tcggtactga ctcgattggt tcgcttatca aacgcttcgc tgctaaaaaa gccggagtag    540
aagatggtag aaatcaataa tcaacgtaag gcgttcctcg atatgctggc gtggtcggag    600
ggaactgata acggacgtca gaaaaccaga aatcatggtt atgacgtcat tgtaggcgga    660
gagctattta ctgattactc cgatcaccct cgcaaacttg tcacgctaaa cccaaaactc    720
aaatcaacag gcgccggacg ctaccagctt ctttcccgtt ggtgggatgc ctaccgcaag    780
cagcttggcc tgaaagactt ctctccgaaa agtcaggacg ctgtggcatt gcagcagatt    840
aaggagcgtg gcgctttacc tatgattgat cgtggtgata tccgtcaggc aatcgaccgt    900
tgcagcaata tctgggcttc actgccgggc gctggttatg gtcagttcga gcataaggct    960
gacagcctga ttgcaaaatt caaagaagcg ggcggaacgg tcagagagat tgatgtatga   1020
gcagagtcac cgcgattatc tccgctctgg ttatctgcat catcgtctgc ctgtcatggg   1080
ctgttaatca ttaccgtgat aacgccatta cctacaaagc ccagcgcgac aaaaatgcca   1140
gagaactgaa gctggcgaac gcggcaatta ctgacatgca gatgcgtcag cgtgatgttg   1200
ctgcgctcga tgcaaaatac acgaaggagt tagctgatgc taaagctgaa aatgatgctc   1260
tgcgtgatga tgttgccgct ggtcgtcgtc ggttgcacat caaagcagtc tgtcagtcag   1320
tgcgtgaagc caccaccgcc tccggcgtgg ataatgcagc ctccccccga ctggcagaca   1380
ccgctgaacg ggattatttc accctcagag agaggctgat cactatgcaa aaacaactgg   1440
aaggaaccca gaagtatatt aatgagcagt gcagatagag ttgcccatat cgatgggcaa   1500
ctcatgcaat tattgtgagc aatacacacg cgcttccagc ggagtataaa tgcctaaagt   1560
aataaaaccg agcaatccat ttacgaatgt ttgctgggtt tctgttttaa caacattttc   1620
tgcgccgcca caaattttgg ctgcatcgac agttttcttc tgcccaattc cagaaacgaa   1680
gaaatgatgg gtgatggttt cctttggtgc tactgctgcc ggtttgtttt gaacagtaaa   1740
cgtctgttga gcacatcctg taataagcag ggccagcgca gtagcgagta gcattttttt   1800
catggtgtta ttcccgatgc tttttgaagt tcgcagaatc gtatgtgtag aaaattaaac   1860
aaaccctaaa caatgagttg aaatttcata ttgttaatat ttattaatgt atgtcaggtg   1920
cgatgaatcg tcattgtatt cccggattaa ctatgtccac agccctgacg gggaacttct   1980
ctgcgggagt gtccgggaat aattaaaacg atgcacacag ggtttagcgc gtacacgtat   2040
tgcattatgc caacgccccg gtgctgacac ggaagaaacc ggacgttatg atttagcgtg   2100
gaaagatttg tgtagtgttc tgaatgctct cagtaaatag taatgaatta tcaaaggtat   2160
agtaatatct tttatgttca tggatatttg taacccatcg gaaaactcct gctttagcaa   2220
gattttccct gtattgctga aatgtgattt ctcttgattt caacctatca taggacgttt   2280
ctataagatg cgtgtttctt gagaatttaa catttacaac ctttttaagt ccttttatta   2340
acacggtgtt atcgttttct aacacgatgt gaatattatc tgtggctaga tagtaaatat   2400
aatgtgagac gttgtgacgt tttagttcag aataaaacaa ttcacagtct aaatcttttc   2460
gcacttgatc gaatatttct ttaaaaatgg caacctgagc cattggtaaa accttccatg   2520
tgatacgagg gcgcgtagtt tgcattatcg tttttatcgt ttcaatctgg tctgacctcc   2580
ttgtgttttg ttgatgattt atgtcaaata ttaggaatgt tttcacttaa tagtattggt   2640
tgcgtaacaa agtgcggtcc tgctggcatt ctggagggaa atacaaccga cagatgtatg   2700
taaggccaac gtgctcaaat cttcatacag aaagatttga agtaatattt taaccgctag   2760
```

```
atgaagagca agcgcatgga gcgacaaaat gaataaagaa caatctgctg atgatccctc   2820

cgtggatctg attcgtgtaa aaaatatgct taatagcacc atttctatga gttaccctga   2880

tgttgtaatt gcatgtatag aacataaggt gtctctggaa gcattcagag caattgaggc   2940

agcgttggtg aagcacgata ataatatgaa ggattattcc ctggtggttg actgatcacc   3000

ataactgcta atcattcaaa ctatttagtc tgtgacagag ccaacacgca gtctgtcact   3060

gtcaggaaag tggtaaaact gcaactcaat tactgcaatg ccctcgtaat taagtgaatt   3120

tacaatatcg tcctgttcgg agggaagaac gcgggatgtt cattcttcat cacttttaat   3180

tgatgtatat gctctctttt ctgacgttag tctccgacgg caggcttcaa tgacccaggc   3240

tgagaaattc ccggaccctt tttgctcaag agcgatgtta atttgttcaa tcatttggtt   3300

aggaaagcgg atgttgcggg ttgttgttct gcgggttctg ttcttcgttg acatgaggtt   3360

gccccgtatt cagtgtcgct gatttgtatt gtctgaagtt gtttttacgt taagttgatg   3420

cagatcaatt aatacgatac ctgcgtcata attgattatt tgacgtggtt tgatggcctc   3480

cacgcacgtt gtgatatgta gatgataatc attatcactt tacgggtcct ttccggtgaa   3540

aaaaaaggta ccaaaaaaaa catcgtcgtg agtagtgaac cgtaagccgt tctgtttatg   3600

tttcttggac actgattgac acggtttagt agaac                              3635
```

<210> SEQ ID NO 31
<211> LENGTH: 3636
<212> TYPE: DNA
<213> ORGANISM: Artificial Sequence
<220> FEATURE:
<223> OTHER INFORMATION: Synthetic Polynucleotide

<400> SEQUENCE: 31

```
ttttttttt ttttttttt tttttttca agaaacataa acagaacgtg cttacggttc     60

actactcacg acgatgtttt ttttggtacc tttttttca ccggaaagga cccgtaaagt    120

gataatgatt atcatctaca tatcacaacg tgcgtggagg ccatcaaacc acgtcaaata    180

atcaattatg acgcaggtat cgtattaatt gatctgcatc aacttaacgt aaaaacaact    240

tcagacaata caaatcagcg acactgaata cggggcaacc tcatgtcaac gaagaacaga    300

acccgcagaa caacaacccg caacatccgc tttcctaacc aaatgattga acaaattaac    360

atcgctcttg agcaaaaagg gtccgggaat ttctcagcct gggtcattga agcctgccgt    420

cggagactaa cgtcagaaaa gagagcatat acatcaatta aaagtgatga agaatgaaca    480

tcccgcgttc ttccctccga acaggacgat attgtaaatt cacttaatta cgagggcatt    540

gcagtaattg agttgcagtt ttaccacttt cctgacagtg acagactgcg tgttggctct    600

gtcacagact aaatagtttg aatgattagc agttatggtg atcagtcaac caccagggaa    660

taatccttca tattattatc gtgcttcacc aacgctgcct caattgctct gaatgcttcc    720

agagacacct tatgttctat acatgcaatt acaacatcag ggtaactcat agaaatggtg    780

ctattaagca tattttttac acgaatcaga tccacggagg gatcatcagc agattgttct    840

ttattcattt tgtcgctcca tgcgcttgct cttcatctag cggttaaaat attacttcaa    900

atctttctgt atgaagattt gagcacgttg gccttacata catctgtcgg ttgtatttcc    960

ctccagaatg ccagcaggac cgcactttgt tacgcaacca atactattaa gtgaaaacat   1020

tcctaatatt tgacataaat catcaacaaa acacaaggag gtcagaccag attgaaacga   1080

taaaaacgat aatgcaaact acgcgccctc gtatcacatg gaaggtttta ccaatggctc   1140
```

```
aggttgccat ttttaaagaa atattcgatc aagtgcgaaa agatttagac tgtgaattgt   1200
tttattctga actaaaacgt cacaacgtct cacattatat ttactatcta gccacagata   1260
atattcacat cgtgttagaa aacgataaca ccgtgttaat aaaaggactt aaaaaggttg   1320
taaatgttaa attctcaaga aacacgcatc ttatagaaac gtcctatgat aggttgaaat   1380
caagagaaat cacatttcag caatacaggg aaaatcttgc taaagcagga gttttccgat   1440
gggttacaaa tatccatgaa cataaaagat attactatac ctttgataat tcattactat   1500
ttactgagag cattcagaac actacacaaa tctttccacg ctaaatcata acgtccggtt   1560
tcttccgtgt cagcaccggg gcgttggcat aatgcaatac gtgtacgcgc taaaccctgt   1620
gtgcatcgtt ttaattattc ccggacactc ccgcagagaa gttccccgtc agggctgtgg   1680
acatagttaa tccgggaata caatgacgat tcatcgcacc tgacatacat taataaatat   1740
taacaatatg aaatttcaac tcattgttta gggtttgttt aattttctac acatacgatt   1800
ctgcgaactt caaaaagcat cgggaataac accatgaaaa aaatgctact cgctactgcg   1860
ctggccctgc ttattacagg atgtgctcaa cagacgttta ctgttcaaaa caaaccggca   1920
gcagtagcac caaaggaaac catcacccat catttcttcg tttctggaat tgggcagaag   1980
aaaactgtcg atgcagccaa aatttgtggc ggcgcagaaa atgttgttaa aacagaaacc   2040
cagcaaacat tcgtaaatgg attgctcggt tttattactt taggcattta tactccgctg   2100
gaagcgcgtg tgtattgctc acaataattg catgagttgc ccatcgatat gggcaactct   2160
atctgcactg ctcattaata tacttctggg ttccttccag ttgtttttgc atagtgatca   2220
gcctctctct gagggtgaaa taatcccgtt cagcggtgtc tgccagtcgg ggggaggctg   2280
cattatccac gccggaggcg gtggtggctt cacgcactga ctgacagact gctttgatgt   2340
gcaaccgacg acgaccagcg gcaacatcat cacgcagagc atcattttca gctttagcat   2400
cagctaactc cttcgtgtat tttgcatcga gcgcagcaac atcacgctga cgcatctgca   2460
tgtcagtaat tgccgcgttc gccagcttca gttctctggc atttttgtcg cgctgggctt   2520
tgtaggtaat ggcgttatca cggtaatgat taacagccca tgacaggcag acgatgatgc   2580
agataaccag agcggagata atcgcggtga ctctgctcat acatcaatct ctctgaccgt   2640
tccgcccgct tctttgaatt ttgcaatcag gctgtcagcc ttatgctcga actgaccata   2700
accagcgccc ggcagtgaag cccagatatt gctgcaacgg tcgattgcct gacggatatc   2760
accacgatca atcataggta aagcgccacg ctccttaatc tgctgcaatg ccacagcgtc   2820
ctgacttttc ggagagaagt ctttcaggcc aagctgcttg cggtaggcat cccaccaacg   2880
ggaaagaagc tggtagcgtc cggcgcctgt tgatttgagt tttgggttta gcgtgacaag   2940
tttgcgaggg tgatcggagt aatcagtaaa tagctctccg cctacaatga cgtcataacc   3000
atgatttctg gttttctgac gtccgttatc agttccctcc gaccacgcca gcatatcgag   3060
gaacgcctta cgttgattat tgatttctac catcttctac tccggctttt ttagcagcga   3120
agcgtttgat aagcgaacca atcgagtcag taccgatgta gccgataaac acgctcgtta   3180
tataagcgag attgctactt agtccggcga agtcgagaag gtcacgaatg aactaggcga   3240
taatggcgca catcgttgcg tcgattactg tttttgtaaa cgcaccgcca ttatatctgc   3300
cgcgaaggta cgccattgca aacgcaagga ttgccccgat gccttgttcc tttgccgcga   3360
gaatggcggc caacaggtca tgtttttctg gcatcttcat gtcttacccc caataagggg   3420
atttgctcta tttaattagg aataaggtcg attactgata gaacaaatcc aggctactgt   3480
gtttagtaat cagatttgtt cgtgaccgat atgcacgggc aaaacggcag gaggttgtta   3540
```

gcgcaaaaaa aaaattccaa aaaaaaaatt ccaaaaaaaa aaagcgacta acaaacacaa 3600
tctgatggca gcgactaaca aacacaatct gatggc 3636

<210> SEQ ID NO 32
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 32
gcaatatcag caccaacaga aacaacct 28

<210> SEQ ID NO 33
<211> LENGTH: 46
<212> TYPE: DNA
<213> ORGANISM: Artificial Sequence
<220> FEATURE:
<223> OTHER INFORMATION: Synthetic Polynucelotide

<400> SEQUENCE: 33
tttttttttt tttttttttt tttttttttt tttttttttt tttttt 46

<210> SEQ ID NO 34
<211> LENGTH: 7240
<212> TYPE: DNA
<213> ORGANISM: Artificial Sequence
<220> FEATURE:
<223> OTHER INFORMATION: Synthetic Polynucleotide

<400> SEQUENCE: 34
gccatcagat tgtgtttgtt agtcgctgcc atcagattgt gtttgttagt cgcttttttt 60
ttttggaatt ttttttttgg aatttttttt ttgcgctaac aacctcctgc cgttttgccc 120
gtgcatatcg gtcacgaaca aatctgatta ctaaacacag tagcctggat ttgttctatc 180
agtaatcgac cttattccta attaaataga gcaaatcccc ttattggggg taagacatga 240
agatgccaga aaaacatgac ctgttggccg ccattctcgc ggcaaaggaa caaggcatcg 300
gggcaatcct tgcgtttgca atggcgtacc ttcgcggcag atataatggc ggtgcgttta 360
caaaaacagt aatcgacgca acgatgtgcg ccattatcgc ctagttcatt cgtgaccttc 420
tcgacttcgc cggactaagt agcaatctcg cttatataac gagcgtgttt atcggctaca 480
tcggtactga ctcgattggt tcgcttatca aacgcttcgc tgctaaaaaa gccggagtag 540
aagatggtag aaatcaataa tcaacgtaag gcgttcctcg atatgctggc gtggtcggag 600
ggaactgata acggacgtca gaaaaccaga aatcatggtt atgacgtcat tgtaggcgga 660
gagctattta ctgattactc cgatcaccct cgcaaacttg tcacgctaaa cccaaaactc 720
aaatcaacag gcgccggacg ctaccagctt ctttcccgtt ggtgggatgc ctaccgcaag 780
cagcttggcc tgaaagactt ctctccgaaa agtcaggacg ctgtggcatt gcagcagatt 840
aaggagcgtg gcgctttacc tatgattgat cgtggtgata tccgtcaggc aatcgaccgt 900
tgcagcaata tctgggcttc actgccgggc gctggttatg gtcagttcga gcataaggct 960
gacagcctga ttgcaaaatt caaagaagcg ggcggaacgg tcagagagat tgatgtatga 1020
gcagagtcac cgcgattatc tccgctctgg ttatctgcat catcgtctgc ctgtcatggg 1080
ctgttaatca ttaccgtgat aacgccatta cctacaaagc ccagcgcgac aaaaatgcca 1140
gagaactgaa gctggcgaac gcggcaatta ctgacatgca gatgcgtcag cgtgatgttg 1200

```
ctgcgctcga tgcaaaatac acgaaggagt tagctgatgc taaagctgaa aatgatgctc   1260
tgcgtgatga tgttgccgct ggtcgtcgtc ggttgcacat caaagcagtc tgtcagtcag   1320
tgcgtgaagc caccaccgcc tccggcgtgg ataatgcagc ctccccccga ctggcagaca   1380
ccgctgaacg ggattatttc accctcagag agaggctgat cactatgcaa aaacaactgg   1440
aaggaaccca gaagtatatt aatgagcagt gcagatagag ttgcccatat cgatgggcaa   1500
ctcatgcaat tattgtgagc aatacacacg cgcttccagc ggagtataaa tgcctaaagt   1560
aataaaaccg agcaatccat ttacgaatgt ttgctgggtt tctgttttaa caacattttc   1620
tgcgccgcca caaattttgg ctgcatcgac agttttcttc tgcccaattc cagaaacgaa   1680
gaaatgatgg gtgatggttt cctttggtgc tactgctgcc ggtttgtttt gaacagtaaa   1740
cgtctgttga gcacatcctg taataagcag ggccagcgca gtagcgagta gcattttttt   1800
catggtgtta ttcccgatgc tttttgaagt tcgcagaatc gtatgtgtag aaaattaaac   1860
aaaccctaaa caatgagttg aaatttcata ttgttaatat ttattaatgt atgtcaggtg   1920
cgatgaatcg tcattgtatt cccggattaa ctatgtccac agccctgacg gggaacttct   1980
ctgcgggagt gtccgggaat aattaaaacg atgcacacag ggtttagcgc gtacacgtat   2040
tgcattatgc caacgccccg gtgctgacac ggaagaaacc ggacgttatg atttagcgtg   2100
gaaagatttg tgtagtgttc tgaatgctct cagtaaatag taatgaatta tcaaaggtat   2160
agtaatatct tttatgttca tggatatttg taacccatcg gaaaactcct gctttagcaa   2220
gattttccct gtattgctga aatgtgattt ctcttgattt caacctatca taggacgttt   2280
ctataagatg cgtgtttctt gagaatttaa catttacaac ctttttaagt ccttttatta   2340
acacggtgtt atcgttttct aacacgatgt gaatattatc tgtggctaga tagtaaatat   2400
aatgtgagac gttgtgacgt tttagttcag aataaaacaa ttcacagtct aaatcttttc   2460
gcacttgatc gaatatttct ttaaaaatgg caacctgagc cattggtaaa accttccatg   2520
tgatacgagg gcgcgtagtt tgcattatcg tttttatcgt ttcaatctgg tctgacctcc   2580
ttgtgttttg ttgatgattt atgtcaaata ttaggaatgt tttcacttaa tagtattggt   2640
tgcgtaacaa agtgcggtcc tgctggcatt ctggagggaa atacaaccga cagatgtatg   2700
taaggccaac gtgctcaaat cttcatacag aaagatttga agtaatattt taaccgctag   2760
atgaagagca agcgcatgga gcgacaaaat gaataaagaa caatctgctg atgatccctc   2820
cgtggatctg attcgtgtaa aaaatatgct taatagcacc atttctatga gttaccctga   2880
tgttgtaatt gcatgtatag aacataaggt gtctctggaa gcattcagag caattgaggc   2940
agcgttggtg aagcacgata ataatatgaa ggattattcc ctggtggttg actgatcacc   3000
ataactgcta atcattcaaa ctatttagtc tgtgacagag ccaacacgca gtctgtcact   3060
gtcaggaaag tggtaaaact gcaactcaat tactgcaatg ccctcgtaat taagtgaatt   3120
tacaatatcg tcctgttcgg agggaagaac gcgggatgtt cattcttcat cacttttaat   3180
tgatgtatat gctctctttt ctgacgttag tctccgacgg caggcttcaa tgacccaggc   3240
tgagaaattc ccggaccctt tttgctcaag agcgatgtta atttgttcaa tcatttggtt   3300
aggaaagcgg atgttgcggg ttgttgttct gcgggttctg ttcttcgttg acatgaggtt   3360
gccccgtatt cagtgtcgct gatttgtatt gtctgaagtt gtttttacgt taagttgatg   3420
cagatcaatt aatacgatac ctgcgtcata attgattatt tgacgtggtt tgatggcctc   3480
cacgcacgtt gtgatatgta gatgataatc attatcactt tacgggtcct ttccggtgaa   3540
aaaaaaggta ccaaaaaaaa catcgtcgtg agtagtgaac cgtaagcacg ttctgtttat   3600
```

```
gtttcttgtt tgttagcctt ttggctaaca aacaagaaac ataaacagaa cgtgcttacg   3660

gttcactact cacgacgatg ttttttttgg tacctttttt ttcaccggaa aggacccgta   3720

aagtgataat gattatcatc tacatatcac aacgtgcgtg gaggccatca aaccacgtca   3780

aataatcaat tatgacgcag gtatcgtatt aattgatctg catcaactta acgtaaaaac   3840

aacttcagac aatacaaatc agcgacactg aatacggggc aacctcatgt caacgaagaa   3900

cagaacccgc agaacaacaa cccgcaacat ccgctttcct aaccaaatga ttgaacaaat   3960

taacatcgct cttgagcaaa aagggtccgg gaatttctca gcctgggtca ttgaagcctg   4020

ccgtcggaga ctaacgtcag aaaagagagc atatacatca attaaaagtg atgaagaatg   4080

aacatcccgc gttcttccct ccgaacagga cgatattgta aattcactta attacgaggg   4140

cattgcagta attgagttgc agttttacca ctttcctgac agtgacagac tgcgtgttgg   4200

ctctgtcaca gactaaatag tttgaatgat tagcagttat ggtgatcagt caaccaccag   4260

ggaataatcc ttcatattat tatcgtgctt caccaacgct gcctcaattg ctctgaatgc   4320

ttccagagac accttatgtt ctatacatgc aattacaaca tcagggtaac tcatagaaat   4380

ggtgctatta agcatatttt ttacacgaat cagatccacg gagggatcat cagcagattg   4440

ttctttattc attttgtcgc tccatgcgct tgctcttcat ctagcggtta aaatattact   4500

tcaaatcttt ctgtatgaag atttgagcac gttggcctta catacatctg tcggttgtat   4560

ttccctccag aatgccagca ggaccgcact ttgttacgca accaatacta ttaagtgaaa   4620

acattcctaa tatttgacat aaatcatcaa caaaacacaa ggaggtcaga ccagattgaa   4680

acgataaaaa cgataatgca aactacgcgc cctcgtatca catggaaggt tttaccaatg   4740

gctcaggttg ccatttttaa agaaatattc gatcaagtgc gaaaagattt agactgtgaa   4800

ttgttttatt ctgaactaaa acgtcacaac gtctcacatt atatttacta tctagccaca   4860

gataatattc acatcgtgtt agaaaacgat aacaccgtgt taataaaagg acttaaaaag   4920

gttgtaaatg ttaaattctc aagaaacacg catcttatag aaacgtccta tgataggttg   4980

aaatcaagag aaatcacatt tcagcaatac agggaaaatc ttgctaaagc aggagttttc   5040

cgatgggtta caaatatcca tgaacataaa agatattact atacctttga taattcatta   5100

ctatttactg agagcattca gaacactaca caaatctttc cacgctaaat cataacgtcc   5160

ggtttcttcc gtgtcagcac cggggcgttg gcataatgca atacgtgtac gcgctaaacc   5220

ctgtgtgcat cgttttaatt attcccggac actcccgcag agaagttccc cgtcagggct   5280

gtggacatag ttaatccggg aatacaatga cgattcatcg cacctgacat acattaataa   5340

atattaacaa tatgaaattt caactcattg tttagggttt gtttaatttt ctacacatac   5400

gattctgcga acttcaaaaa gcatcgggaa taacaccatg aaaaaaatgc tactcgctac   5460

tgcgctggcc ctgcttatta caggatgtgc tcaacagacg tttactgttc aaaacaaacc   5520

ggcagcagta gcaccaaagg aaaccatcac ccatcatttc ttcgtttctg gaattgggca   5580

gaagaaaact gtcgatgcag ccaaaatttg tggcggcgca gaaaatgttg ttaaaacaga   5640

aacccagcaa acattcgtaa atggattgct cggttttatt actttaggca tttatactcc   5700

gctggaagcg cgtgtgtatt gctcacaata attgcatgag ttgcccatcg atatgggcaa   5760

ctctatctgc actgctcatt aatatacttc tgggttcctt ccagttgttt ttgcatagtg   5820

atcagcctct ctctgagggt gaaataatcc cgttcagcgg tgtctgccag tcgggggggag   5880

gctgcattat ccacgccgga ggcggtggtg gcttcacgca ctgactgaca gactgctttg   5940
```

```
atgtgcaacc gacgacgacc agcggcaaca tcatcacgca gagcatcatt ttcagcttta   6000
gcatcagcta actccttcgt gtattttgca tcgagcgcag caacatcacg ctgacgcatc   6060
tgcatgtcag taattgccgc gttcgccagc ttcagttctc tggcattttt gtcgcgctgg   6120
gctttgtagg taatggcgtt atcacggtaa tgattaacag cccatgacag gcagacgatg   6180
atgcagataa ccagagcgga gataatcgcg gtgactctgc tcatacatca atctctctga   6240
ccgttccgcc cgcttctttg aattttgcaa tcaggctgtc agccttatgc tcgaactgac   6300
cataaccagc gcccggcagt gaagcccaga tattgctgca acggtcgatt gcctgacgga   6360
tatcaccacg atcaatcata ggtaaagcgc cacgctcctt aatctgctgc aatgccacag   6420
cgtcctgact tttcggagag aagtctttca ggccaagctg cttgcggtag gcatcccacc   6480
aacgggaaag aagctggtag cgtccggcgc ctgttgattt gagttttggg tttagcgtga   6540
caagtttgcg agggtgatcg gagtaatcag taaatagctc tccgcctaca atgacgtcat   6600
aaccatgatt tctggttttc tgacgtccgt tatcagttcc ctccgaccac gccagcatat   6660
cgaggaacgc cttacgttga ttattgattt ctaccatctt ctactccggc ttttttagca   6720
gcgaagcgtt tgataagcga accaatcgag tcagtaccga tgtagccgat aaacacgctc   6780
gttatataag cgagattgct acttagtccg gcgaagtcga gaaggtcacg aatgaactag   6840
gcgataatgg cgcacatcgt tgcgtcgatt actgtttttg taaacgcacc gccattatat   6900
ctgccgcgaa ggtacgccat tgcaaacgca aggattgccc cgatgccttg ttcctttgcc   6960
gcgagaatgg cggccaacag gtcatgtttt tctggcatct tcatgtctta cccccaataa   7020
ggggatttgc tctatttaat taggaataag gtcgattact gatagaacaa atccaggcta   7080
ctgtgtttag taatcagatt tgttcgtgac cgatatgcac gggcaaaacg gcaggaggtt   7140
gttagcgcaa aaaaaaaatt ccaaaaaaaa aattccaaaa aaaaaaagcg actaacaaac   7200
acaatctgat ggcagcgact aacaaacaca atctgatggc                         7240
```

<210> SEQ ID NO 35
<211> LENGTH: 897
<212> TYPE: DNA
<213> ORGANISM: Eisenia fetida

<400> SEQUENCE: 35

```
atgagtgcga aggctgctga aggttatgaa caaatcgaag ttgatgtggt tgctgtgtgg     60
aaggaaggtt atgtgtatga aaatcgtggt agtacctccg tggatcaaaa aattaccatc    120
acgaaaggca tgaagaacgt taatagcgaa acccgtacgg tcaccgcgac gcattctatt    180
ggcagtacca tctccacggg tgacgccttt gaaatcggct ccgtggaagt ttcatattcg    240
catagccacg aagaatcaca agtttcgatg accgaaacgg aagtctacga atcaaaagtg    300
attgaacaca ccattacgat cccgccgacc tcgaagttca cgcgctggca gctgaacgca    360
gatgtcggcg gtgctgacat tgaatatatg tacctgatcg atgaagttac cccgattggc    420
ggtacgcaga gtattccgca agtgatcacc tcccgtgcaa aaattatcgt tggtcgccag    480
attatcctgg gcaagaccga aattcgtatc aaacatgctg aacgcaagga atatatgacc    540
gtggttagcc gtaaatcttg gccggcggcc acgctgggtc acagtaaact gtttaagttc    600
gtgctgtacg aagattgggg cggttttcgc atcaaaaccc tgaatacgat gtattctggt    660
tatgaatacg cgtatagctc tgaccagggc ggtatctact tcgatcaagg caccgacaac    720
ccgaaacagc gttgggccat taataagagc ctgccgctgc gccatggtga tgtcgtgacc    780
tttatgaaca aatacttcac gcgttctggt ctgtgctatg atgacggccc ggcgaccaat    840
```

-continued

```
gtgtattgtc tggataaacg cgaagacaag tggattctgg aagttgtcgg ctaatga       897


<210> SEQ ID NO 36
<211> LENGTH: 297
<212> TYPE: PRT
<213> ORGANISM: Eisenia fetida

<400> SEQUENCE: 36

Met Ser Ala Lys Ala Ala Glu Gly Tyr Glu Gln Ile Glu Val Asp Val
1               5                   10                  15

Val Ala Val Trp Lys Glu Gly Tyr Val Tyr Glu Asn Arg Gly Ser Thr
            20                  25                  30

Ser Val Asp Gln Lys Ile Thr Ile Thr Lys Gly Met Lys Asn Val Asn
        35                  40                  45

Ser Glu Thr Arg Thr Val Thr Ala Thr His Ser Ile Gly Ser Thr Ile
    50                  55                  60

Ser Thr Gly Asp Ala Phe Glu Ile Gly Ser Val Glu Val Ser Tyr Ser
65                  70                  75                  80

His Ser His Glu Glu Ser Gln Val Ser Met Thr Glu Thr Glu Val Tyr
                85                  90                  95

Glu Ser Lys Val Ile Glu His Thr Ile Thr Ile Pro Pro Thr Ser Lys
            100                 105                 110

Phe Thr Arg Trp Gln Leu Asn Ala Asp Val Gly Gly Ala Asp Ile Glu
        115                 120                 125

Tyr Met Tyr Leu Ile Asp Glu Val Thr Pro Ile Gly Gly Thr Gln Ser
    130                 135                 140

Ile Pro Gln Val Ile Thr Ser Arg Ala Lys Ile Ile Val Gly Arg Gln
145                 150                 155                 160

Ile Ile Leu Gly Lys Thr Glu Ile Arg Ile Lys His Ala Glu Arg Lys
                165                 170                 175

Glu Tyr Met Thr Val Val Ser Arg Lys Ser Trp Pro Ala Ala Thr Leu
            180                 185                 190

Gly His Ser Lys Leu Phe Lys Phe Val Leu Tyr Glu Asp Trp Gly Gly
        195                 200                 205

Phe Arg Ile Lys Thr Leu Asn Thr Met Tyr Ser Gly Tyr Glu Tyr Ala
    210                 215                 220

Tyr Ser Ser Asp Gln Gly Gly Ile Tyr Phe Asp Gln Gly Thr Asp Asn
225                 230                 235                 240

Pro Lys Gln Arg Trp Ala Ile Asn Lys Ser Leu Pro Leu Arg His Gly
                245                 250                 255

Asp Val Val Thr Phe Met Asn Lys Tyr Phe Thr Arg Ser Gly Leu Cys
            260                 265                 270

Tyr Asp Asp Gly Pro Ala Thr Asn Val Tyr Cys Leu Asp Lys Arg Glu
        275                 280                 285

Asp Lys Trp Ile Leu Glu Val Val Gly
    290                 295
```